US 8,575,217 B2
Nov. 5, 2013

(12) United States Patent
Mian et al.

(10) Patent No.: US 8,575,217 B2
(45) Date of Patent: *Nov. 5, 2013

(54) ANTI-INFLAMMATORY AND ANTIOXIDANT CONJUGATES USEFUL FOR TREATING METABOLIC DISORDERS

(75) Inventors: Alec Mian, Barcelona (ES); Luc Marti Clauzel, Barcelona (ES); Eric Mayoux, Eschau (FR); Silvia Garcia-Vicente, Sant Feliu de Llobregat (ES); Marta Serrano Munoz, Barcelona (ES); Antonio Zorzano Olarte, Barcelona (ES); Julio Cesar Castro Palomino Laria, Premia de Mar (ES)

(73) Assignee: Genmedica Therapeutics SL, Barcelona (ES)

(*) Notice: Subject to any disclaimer, the term of this patent is extended or adjusted under 35 U.S.C. 154(b) by 305 days.

This patent is subject to a terminal disclaimer.

(21) Appl. No.: 12/724,892

(22) Filed: Mar. 16, 2010

(65) Prior Publication Data

US 2010/0234452 A1    Sep. 16, 2010

Related U.S. Application Data

(60) Provisional application No. 61/160,642, filed on Mar. 16, 2009, provisional application No. 61/177,958, filed on May 13, 2009, provisional application No. 61/227,620, filed on Jul. 22, 2009.

(51) Int. Cl.
*A01N 37/12*    (2006.01)
*A01N 37/44*    (2006.01)
*A01N 37/00*    (2006.01)
*A61K 31/195*    (2006.01)
*A61K 31/185*    (2006.01)
*A61K 31/21*    (2006.01)

(52) U.S. Cl.
USPC ............ 514/562; 514/513; 514/576; 562/426

(58) Field of Classification Search
None
See application file for complete search history.

(56) References Cited

U.S. PATENT DOCUMENTS

| | | | |
|---|---|---|---|
| 4,181,719 A | 1/1980 | Margetts et al. |
| 4,563,443 A | 1/1986 | Gobetti |
| 4,567,163 A | 1/1986 | Ponchiroli |
| 5,061,710 A | 10/1991 | Haslanger |
| 5,610,180 A | 3/1997 | Fariss |
| 5,656,620 A | 8/1997 | Ismail |
| 5,871,769 A | 2/1999 | Fleming et al. |
| 5,972,986 A | 10/1999 | Seibert et al. |
| 6,008,249 A | 12/1999 | Gajdos et al. |
| 6,013,663 A | 1/2000 | Fujita et al. |
| 6,121,319 A | 9/2000 | Somers |
| 6,201,028 B1 | 3/2001 | Shiff et al. |
| 6,258,848 B1 | 7/2001 | Fantus |
| 6,309,663 B1 | 10/2001 | Patel et al. |
| 6,313,164 B1 | 11/2001 | Fujita |
| 6,355,666 B1 | 3/2002 | Lai et al. |
| 6,365,176 B1 | 4/2002 | Bell et al. |
| 6,369,098 B1 | 4/2002 | Pershadsingh et al. |
| 6,429,223 B1 | 8/2002 | Lai et al. |
| 6,566,401 B2 | 5/2003 | Herzenberg et al. |
| 6,646,013 B1 | 11/2003 | Barker et al. |
| 6,649,591 B2 | 11/2003 | Lai |
| 6,669,955 B2 | 12/2003 | Chungi et al. |
| 6,852,760 B1 | 2/2005 | Fine et al. |
| 6,852,878 B2 | 2/2005 | Meng et al. |
| 6,896,899 B2 | 5/2005 | Demopolos et al. |
| 6,909,012 B2 | 6/2005 | Hung |
| 6,914,075 B2 | 7/2005 | Nakano et al. |
| 7,078,064 B2 | 7/2006 | Zabrecky |
| 7,118,762 B2 | 10/2006 | Byrd |
| 7,122,537 B2 | 10/2006 | Malfroy-Camine et al. |
| 7,148,211 B2 | 12/2006 | Mazess et al. |
| 7,241,461 B2 | 7/2007 | Myhill et al. |
| 7,271,274 B2 | 9/2007 | Meng et al. |
| 7,345,178 B2 | 3/2008 | Nunes et al. |
| 7,371,895 B2 | 5/2008 | Meng |
| 7,375,252 B2 | 5/2008 | Meng |
| 7,378,412 B2 | 5/2008 | Del Soldato |
| 7,378,437 B2 | 5/2008 | Soldato |
| 7,417,034 B2 | 8/2008 | Susilo |
| 7,666,898 B2 | 2/2010 | Chang |
| 8,093,292 B2 | 1/2012 | Pacioretty |
| 2001/0051184 A1 | 12/2001 | Heng |
| 2002/0037855 A1 | 3/2002 | Stanislaus |
| 2002/0045580 A1 | 4/2002 | Sacks et al. |

(Continued)

FOREIGN PATENT DOCUMENTS

CN    1439632    9/2003
DE    4327462    2/1995

(Continued)

OTHER PUBLICATIONS

Stenstrom et al. "Latent Autoimmune Diabetes in Adults", Diabetes, 2005, vol. 54, supplement 2, pp. S68-S72.*
Bailey et al., "The Reduction of Experimentally Induced Inflammation by Sulfhydryl Compounds." Biochemical Pharmacology, 1967, 16:1175-1182.
Kopke et al., "Reduction of noise-induced hearing loss using L-NAC and salicylate in the chinchilla." Hearing Research, 2000, 149: 138-146.
Kowluru et al., "Abnormalities of retinal metabolism in diabetes and experimental galactosemia: VII. Effect of long-term administration of antioxidants on the development of retinopathy." Diabetes, 2001, 50: 1938-1942.
Xiao et al., "Oral taurine but not N-acetylcysteine ameliorates NEFA-Induced Impairment in insulin sensitivity and beta cell function in obese and overweight, non-diabetic men." Diabetologia, 2008, 51: 139-146.

(Continued)

*Primary Examiner* — James D Anderson
*Assistant Examiner* — Stephanie Springer
(74) *Attorney, Agent, or Firm* — McDonnell Boehnen Hulbert & Berghoff LLP

(57) ABSTRACT

The present invention is directed to methods for treating metabolic disorders with compounds that are conjugates. The conjugates of the present invention are comprised of salicylic acid, triflusal, diflusinal, salsalate, IMD-0354, ibuprofen, diclofenac, licofelone, or HTB, and one or more antioxidants.

12 Claims, 27 Drawing Sheets

(56) References Cited

U.S. PATENT DOCUMENTS

| | | | |
|---|---|---|---|
| 2002/0098247 A1 | 7/2002 | Komorowski et al. | |
| 2002/0155163 A1 | 10/2002 | Benjamin et al. | |
| 2003/0088111 A1 | 5/2003 | Lai | |
| 2003/0100486 A1 | 5/2003 | Ridker et al. | |
| 2003/0119909 A1 | 6/2003 | Stanislaus | |
| 2003/0191064 A1 | 10/2003 | Kopke | |
| 2003/0220468 A1 | 11/2003 | Lai | |
| 2004/0023290 A1 | 2/2004 | Griffin et al. | |
| 2004/0023890 A1 | 2/2004 | Soldato | |
| 2004/0097593 A1* | 5/2004 | Neogi et al. | 514/584 |
| 2004/0106591 A1 | 6/2004 | Pacioretty et al. | |
| 2004/0146551 A1 | 7/2004 | Mannino et al. | |
| 2005/0008690 A1 | 1/2005 | Miller | |
| 2005/0019399 A1 | 1/2005 | Fischer | |
| 2005/0020654 A1 | 1/2005 | Pershadsingh et al. | |
| 2005/0059706 A1 | 3/2005 | Smith et al. | |
| 2005/0143356 A1 | 6/2005 | Breyer | |
| 2005/0271661 A1 | 12/2005 | Manivasakam et al. | |
| 2006/0041009 A1 | 2/2006 | Soto Peredo | |
| 2006/0069161 A1* | 3/2006 | Lee et al. | 514/570 |
| 2006/0135460 A1 | 6/2006 | Widder et al. | |
| 2006/0135489 A1 | 6/2006 | Matuszczak et al. | |
| 2006/0160867 A1 | 7/2006 | Freedman | |
| 2006/0166901 A1 | 7/2006 | Yu | |
| 2006/0172012 A1 | 8/2006 | Finley et al. | |
| 2006/0241017 A1 | 10/2006 | Chandran | |
| 2006/0270635 A1 | 11/2006 | Wallace et al. | |
| 2006/0276416 A1 | 12/2006 | Sinclair et al. | |
| 2007/0042062 A1 | 2/2007 | Pushpangadan et al. | |
| 2007/0149466 A1 | 6/2007 | Milburn et al. | |
| 2007/0231273 A1 | 10/2007 | Wu | |
| 2007/0248590 A1 | 10/2007 | Milne et al. | |
| 2007/0248705 A1 | 10/2007 | Shimura et al. | |
| 2007/0254055 A1 | 11/2007 | Meydani | |
| 2008/0015251 A1 | 1/2008 | Tirosh et al. | |
| 2008/0033027 A1 | 2/2008 | Bascomb et al. | |
| 2008/0038316 A1 | 2/2008 | Wong et al. | |
| 2008/0044399 A1 | 2/2008 | Levy | |
| 2008/0114065 A1 | 5/2008 | Pacioretty et al. | |
| 2008/0118584 A1 | 5/2008 | Olalde Rangel | |
| 2008/0139525 A1 | 6/2008 | Loscalzo | |
| 2008/0176822 A1 | 7/2008 | Chen | |
| 2008/0213319 A1 | 9/2008 | Kang et al. | |
| 2008/0213785 A1 | 9/2008 | Levy | |
| 2008/0220092 A1 | 9/2008 | Dipierro et al. | |
| 2008/0234380 A1 | 9/2008 | Shapiro | |
| 2009/0018136 A1 | 1/2009 | Oppenheimer et al. | |
| 2009/0036516 A1 | 2/2009 | Scherrer et al. | |
| 2009/0169497 A1 | 7/2009 | Horwitz | |
| 2009/0215852 A1 | 8/2009 | Bascomb | |
| 2009/0234011 A1 | 9/2009 | Goldstein | |
| 2009/0298923 A1 | 12/2009 | Mian | |
| 2009/0325975 A1 | 12/2009 | Buschmann | |
| 2010/0239552 A1 | 9/2010 | Mian et al. | |

FOREIGN PATENT DOCUMENTS

| | | |
|---|---|---|
| EP | 0052910 | 6/1982 |
| EP | 0080229 | 6/1983 |
| EP | 0 103 320 | 3/1984 |
| EP | 0 144 519 | 6/1985 |
| EP | 0144519 | 6/1985 |
| EP | 0255164 | 2/1988 |
| EP | 1184366 | 3/2002 |
| EP | 1 219 304 | 7/2002 |
| EP | 1219304 | 7/2002 |
| EP | 1767219 | 3/2007 |
| ES | 549540 | 9/1986 |
| ES | 554853 | 11/1987 |
| FR | 2 550 530 | 2/1985 |
| FR | 2835433 | 8/2003 |
| JP | 43003293 | 2/1968 |
| JP | 56018952 | 2/1981 |
| RU | 2054936 | 2/1996 |
| WO | WO9747270 | 12/1997 |
| WO | WO 98/43630 | 10/1998 |
| WO | WO2006001549 | 10/2000 |
| WO | WO0200167 | 1/2002 |
| WO | WO0204434 | 1/2002 |
| WO | WO 02/30866 | 4/2002 |
| WO | WO 02/30867 | 4/2002 |
| WO | WO0236202 | 5/2002 |
| WO | WO 2004/096256 | 11/2004 |
| WO | 2005/032505 | 4/2005 |
| WO | WO2005032505 | 4/2005 |
| WO | 2005/065667 | 7/2005 |
| WO | WO 2005/112949 | 12/2005 |
| WO | WO 2006/037623 | 4/2006 |
| WO | 2006/066894 | 6/2006 |
| WO | WO2006066894 | 6/2006 |
| WO | WO 2007/011958 | 1/2007 |
| WO | 2007/063095 | 6/2007 |
| WO | WO2007063095 | 6/2007 |
| WO | WO2007117048 | 10/2007 |
| WO | 2007/127913 | 11/2007 |
| WO | WO2007127913 | 11/2007 |
| WO | 2008/012603 | 1/2008 |
| WO | WO2008012603 | 1/2008 |
| WO | 2008/089212 | 7/2008 |
| WO | 2009/089011 | 7/2009 |
| WO | WO2009108297 | 9/2009 |
| WO | WO2009124371 | 10/2009 |
| WO | 2009/138437 | 11/2009 |
| WO | WO2009137827 | 11/2009 |
| WO | WO2009138437 | 11/2009 |

OTHER PUBLICATIONS

Xie et al., "Salicylic Acid Induces Rapid Inhibition of Mitochondrial Electron Transport and Oxidative Phosphorylation in Tobacco Cells." Plant Physiology, 1999, 120: 217-225.

Dannan H. et al.: "S-Acylation of cysteine by 0-acetylsalicylic anhydride: A possible mechanism for aspirin hypersensitivity?" Journal of Pharmaceutical Sciences 1986 US, vol. 75, No. 11, 1986, pp. 1081-1084.

Anonymous, "G-201—Salnacedin (197388)." Prous Science Integrity (Drug Data Report), 1994, URL http://integrity.prous.com/integrity/servlet/xmlxsl/pk_ref_list.xml_related_ref_to?p_id197388&p_origen=PRO&p_tsearch=#link, retrieved on Jul. 13, 2009.

Nomura et al., "Design, synthesis, and evaluation of substituted phenylpropanoic acid derivatives as human peroxisome proliferator activated receptor activators. Discovery of potent and human peroxisome proliferator activated receptor alpha subtype-selective activators." J. Med. Chem., 2003, 46(17): 3581-99.

Tsunoda et al., "KRP-101: A potent PPAR alpha agonist ameliorates fat-induced insulin resistance with suppression of adiposity in dogs." Diabetes, 2007, 56(Suppl. 1): A137-8.

Netea et al., "The effect of salicylates on insulin sensitivity." J. Clin. Invest., 2001, 108(11): 1723-4.

Fernandez-Real et al., "Salicylates increase insulin secretion in healthy obese subjects." Journal of Clinical Endocrinology and Metabolism, 2008, 93(7): 2523-30.

Zu et al., "Salicylate blocks lipolytic actions of tumor necrosis factor-alpha in primary rat adipocytes." Molecular Pharmacology, 2008, 73(1): 215-23.

Moller et al., "Novel 5-aminosalicylic acid NSAID conjugates: synthesis; pharmacological and toxicological properties." Eur. J. Med. Chem., 1989, 24(5): 463-9.

Hideaki et al., "Beneficial effects of antioxidants in diabetes: Possible protection of pancreatic beta-cells against glucose toxicity," Diabetes, vol. 48, No. 12, Dec. 1999, pp. 2398-2406.

Winiarska et al, "Hypoglycaemic, antioxidative and nephroprotective effects of taurine in alloxan diabetic rabbits," Biochimie, Masson, Paris, FR (Feb. 1, 2009), vol. 91, No. 2, pp. 261-270.

Arany et al, "Taurine supplement in early life altered islet morphology, decreased insulitis and delayed the onset of diabetes in non-obese diabetic mice," Diabetologia, vol. 47, No. 10, Oct. 2004, pp. 1831-1837.

Gorogawa et al, "Probucol preserves pancreatic beta-cell function through reduction of oxidative stress in type 2 diabetes," Diabetes Research and Clinical Practice, vol. 57, No. 1, Jul. 2002, pp. 1-10.

(56) References Cited

OTHER PUBLICATIONS

Yan et al, "The study of insulin resistance and leptin resistance on the model of simplicity obesity rats by curcumin," Zhonghua Yufang Yixue Zazhi, Zhonghua Yixuehu, Beijing, CN, vol. 42, No. 11, (Nov. 1, 2008), pp. 818-822.

Maedler et al, "Pioglitazone and sodium salicylate protect human beta-cells against glucose- and IL-beta-induced apoptosis and impaired function," Diabetes, vol. 53, No. Suppl. 2, (Jun. 2004), p. A376.

Bundesverband Der Pharmazeutischen Industrie: "Rote Liste 2004," Jan. 1, 2004, Editio Cantor Verlag Aulendorf, pp. 05420-05433 Aspirin plus C etc.

Hsu et al, "Five Cysteine-Containing Compounds Delay Diabetic Deterioration in Balb/cA Mice," 2004, Journal of Nutrition, vol. 134, pp. 3245-3249.

Riess et al, "Pharmacokinetics and metabolism of the antiinflammatory agent voltaren," Scandinavian Journal of Rheumatology, Supplement (1978), 22(Diclofenac Sodium: Antirheum., Anti-Inflammatory, Analg. Agent), 17-29.

Stierlin et al, Biotransformation of diclofenac sodium (Voltaren) in animals and in man. I. Isolation and identification of principal metabolites, Xenobiotica (1979), 9(10), 601-10.

Tsuchiya et al, "Disposition and enterohepatic circulation of diclofenac in dogs," Arzneimittel-Forschung (1980) 30 (10) 1650-3.

Baillie et al, "Taurine conjugation of ibuprofen in humans and in rat liver in vitro. Relationship to metabolic chiral inversion," J Pharmacol Exp Ther, Jun. 1994, 269:1166-1175.

Araya et al, "The Novel Formulation Design of Self-emulsifying Drug Delivery Systems (SEDDS) Type O/W Microemulsion III: The Permeation Mechanism of a Poorly Water Soluble Drug Entrapped O/W Microemulsion in Rat Isolated Intestinal Membrane by the Ussing Chamber Method," Drug Metab. Pharmacokinet. 21(1) 45:53 (2006).

Hoffer et al, "N-Acetylcysteine enhances the action of anti-inflammatory drugs as suppressors of prostaglandin production in monocytes," Mediators of Inflammation, 11, 321-323 (2002).

Efrati et al, "N-acetylcysteine attenuates NSAID-induced rat renal failure by restoring intrarenal prostaglandin synthesis," Nephrol Dial Transplant (2007) 22:1873-1881.

International Search Report for PCT/EP2010/053418 filed Mar. 16, 2010.

Copending U.S. Appl. No. 12/724,756, filed Mar. 16, 2010 (Published as US 2010/0239552).

Copending U.S. Appl. No. 13/235,031, filed Sep. 16, 2011.

Copending U.S. Appl. No. 12/465,201, filed May 13, 2009 (published as US 2009/0298923).

International Search Report for PCT/EP2010/053419 filed Mar. 16, 2010.

International Search Report for PCT/EP2011/072819 filed Dec. 14, 2011.

CAS Registry No. 87573-01-1, STN Entry Date Nov. 16, 1984.

Oskay et al., "Analgesic and anti-inflammatory effects of some benzanilides." Journal of Pharmaceutical Sciences, 1989, 78(6): 460-1.

Shen et al., "Diabetes and cardiovascular diseases—fundamental and clinic," Shanghai Shiji Publication Col. Ltd, 53-56 (2006) (with translation of relevant portion).

Kaneto et al., "Beneficial Effects of Antioxidants in Diabetes—Possible Protection of Pancreatic Beta Cells Against Glucose Toxicity," Diabetes, vol. 48, 2398-2406 (1999).

Copending U.S. Appl. No. 12/465,201, filed May 13, 2009, Excerpts dated Jan. 18, 2011 to Oct. 30, 2012.

\* cited by examiner

Chemical Stability of Salicylate-NAC (GMC-3a), Diflunisal-NAC (GMC-3b, and dexibuprofen-NAC (GMC-3d) Conjugates

| | | Phosphate buffer saline (PBS) | | | |
|---|---|---|---|---|---|
| | | neutral pH | | Acidic pH | Basic pH (9) |
| | | RT | | RT | RT |
| | | t=0h | t=14h  t=72h | 3 h | 3h |
| GMC-3a | free acid (+NaOH) | stable | 10%   50% | stable | 5% |
| | lysine salt | stable | | | |

| | | neutral pH | | acidic pH | Basic pH (9) |
|---|---|---|---|---|---|
| | | 4ºC   RT | 4ºC | RT | RT |
| | | 3 h | 24 h | 3 h | 3h |
| | free acid | stable | Stable | | |
| GMC-3b | free acid in MeOH/H2O | stable  stable | 3%    stable | precipitate | 18% |
| | lysine salt | 20% | 70% | | |
| | Lysine salt in MeOH/H2O | Stable  Stable | Stable  stable | | stable |
| GMC-3d | free acid | Stable | Stable | | |
| | lysine salt | | | | |
| | MeOH/H2O free acid | | | | |

Figure 1

Rat Plasma Levels of Salicylate, Diflunisal, and (L) N-acetyl cysteine Following Oral Administration (20mg/kg) of Conjugates Salicylate-NAC (GMC-1.3a) and Diflunisal-NAC (GMC-1.3b)

- 6 weeks-old db/db mice
- 4.5-week daily treatment
- Route: Oral
- Groups: (n = 7-8 mice per group).

| Treatments | Oral daily dose (at 4 pm) | Corresponding dose of NSAID | Corresponding dose of NAC |
|---|---|---|---|
| PBS (vehicle) | | | |
| PBS-lysine (conjugate vehicle) | 1.5 mmol/kg/day (lysine alone) | | |
| GMC-1.5-lysine salt | 1.5 mmol/kg/day (2-fold greater than dose used by Yuan et al. 2001) | 240 mg/kg | 245 mg/kg |
| GMC-0.5-lysine salt | 0.5 mmol/kg/day (66% of dose by Yuan et al 2001) | 125 mg/kg | 82 mg/kg |

- Measurement of glycemia, body weight, water and food intake during 4 weeks.
- 3rd week: Insulin Tolerance Test (ITT)
- 4th week: Glucose Tolerance Test (OGTT)
- Mice killed at day 34. Samples: Blood, plasma, WAT, Pancreas, Liver, GI tract

Figure 14

| | Conjugate Structure | Chemical stability | In vitro cleavage | | In vivo cleavage | In vivo acute effect | In vivo chronic effect |
|---|---|---|---|---|---|---|---|
| | | | Human Plasma cleavage | Human liver microsomes | PK/Oral admin. in mice/rat | Alloxan model i.p. administration | db/db (anti-diabetic effect) |
| GMC-250 | Dexibuprofen-NAC | S | B | B | B | B | C |
| GMC-264 | Lipoic-diflunisal-O-Me | S | B | A | A | C | C |
| GMC-265 | Lipoic-diflunisal-O-Bn | S | B | A | B | C | C |
| GMC-266 | Lipoic-diflunisal-O-tBu | S | B | B | B | C | C |
| GMC-271 | Diflunisal-NAC-O-Me | S | A | A | A | C | C |
| GMC-272 | Diflunisal-NAC-O-Et | S | A | A | A | C | C |
| GMC-232 | Salicylate-NAC | S | A | A | A | A | A |
| GMC-252 | Diflunisal-NAC | S | A | A | A | A | A |

A : increased activity
B : decreased activity
C : not tested
S : stable

Figure 15

GMC-264 is the conjugate lipoic acid-difunisal.

ANTI-INFLAMMATORY AND ANTIOXIDANT CONJUGATES USEFUL FOR TREATING METABOLIC DISORDERS

This application claims the benefit of U.S. Provisional Application No. 61/160,642 filed Mar. 16, 2009; U.S. Provisional Application No. 61/177,958 filed May 13, 2009; and U.S. Provisional Application No. 61/227,620 filed Jul. 22, 2009.

BACKGROUND

Oxidative stress and inflammation are implicated in the pathogenesis of metabolic diseases, diabetes, obesity, dyslipidemia and their associated cardiovascular complications. For example, oxidative stress is a common pathogenic factor leading to insulin resistance, β-cell dysfunction, impaired glucose tolerance, and type 2 diabetes mellitus. With regard to inflammation, clinical studies suggest that acute hyperglycemia results in elevated levels of circulating inflammatory cytokines such as TNFα, IL6, and IL18.

During hyperglycemia and/or hyperlipidemia, mitochondria generate cellular energy through TCA cycle activity and the associated electron transport chain of the inner mitochondrial membrane. However, while mitochondria generate elevated ATP production, mitochondria can also generate significant reactive oxygen species (ROS) and reactive nitrogen species (RNS). Cells are equipped with several antioxidant enzymes to neutralize ROS and RNS. For example, superoxide anions are enzymatically converted to hydrogen peroxide by a manganese superoxide dismutase (MnSOD) within mitochondria. Hydrogen peroxide can then be rapidly removed by the mitochondrial enzyme glutathione (GSH) peroxidase. A further antioxidant enzyme, catalase, is the hydrogen peroxide detoxifying enzyme founded exclusively in peroxisomes. Glutathione (GSH) is probably the most important defense with which the cell is equipped, for scavenging ROS generated by mitochondria metabolism and excess free radicals produced secondary to hyperglycemia and hyperlipidemia.

However, while cells have a number of available antioxidant mechanisms, damage most likely occurs when the ROS is excessive and/or anti-oxidant pathways are overwhelmed as is frequently the case in diabetes. In diabetic patients, the levels of antioxidant enzymes responsible for scavenging free radicals are diminished. Glutathione pools become depleted in diabetic patients following frequent and severe hyperglycemic episodes. It is now widely accepted that overproduction of reactive oxygen species (ROS) contributes to cell and tissue dysfunction and damage caused by glucolipotoxicity in diabetes, insulin resistance, and obesity.

In particular, compared to several other cells of the body, pancreatic β-cells have relatively low levels of free radical detoxification and redox regulating enzymes such as superoxide dismutase, glutathione peroxidase, catalase and thioredoxin. The consequence of limited scavenging systems is that ROS concentration in β-cells may increase rapidly, damaging the β-cells. Thus, under hyperglycemic conditions, the production of ROS, and subsequent oxidative stress, contributes to β-cell deterioration observed in type 2 diabetes.

ROS is also considered a strong stimulus for the release of cytokines and increased superoxide can promote inflammation through NF-kB activation. Thus the role of oxidative stress and associated activation of NF-kB leading to chronic inflammation and insulin resistance is essential in the processes implicated in the pathogenesis of diabetes and its progression. Administration of glutathione, a powerful antioxidant, completely suppresses cytokine elevation, providing further support that an oxidative stress mechanism mediates the inflammatory effects of hyperglycemia in humans.

Salicylates, or aspirin-like drugs, are some of the most commonly used anti-inflammatory agents. For more than two decades, the anti-inflammatory properties of aspirin have been almost exclusively attributed to blocking prostaglandin synthesis via inhibition of cyclo-oxygenase activity. Recently, aspirin and sodium salicylate have been found to inhibit the activation of the transcription factor NF-kB. High doses of salicylate are thought to inhibit NF-kB and its upstream activator, the IKB kinase β (IKKβ).

Also, high doses of salicylic acid lower blood glucose levels. Recent studies report that diabetic animals given salicylates or salsalate showed a decrease in IKKβ activity, accompanied by improvement in insulin sensitivity. High doses of Salicylate (120 mg/kg/day) administered by subcutaneous infusion in Zucker fa/fa rats or ob/ob mice for 3-4 weeks exhibited anti-diabetic effects, reduction in fasting blood glucose, and glucose tolerance improvement. Beneficial effects of high doses of salicylic acid have been recently reported in human diabetic patients treated with 4.5 g/day of salsalate. However, at this high dose, side effects, such as tinnitus, are enhanced by 66% and the long term risk of gastric bleeding and ulceration is also increased.

Thus, there remains a need in the art for compounds for treating metabolic disorders by way of ameliorating the inflammatory and oxidative processes associated with such disorders, particularly diabetes.

SUMMARY OF THE INVENTION

The present invention relates to conjugates comprised of an anti-inflammatory agent and an anti-oxidant agent. The conjugates of the present invention are useful for treating atherosclerosis, neuropathy, nephropathy, retinopathy, inflammatory disorders, Chronic Obstructive Pulmonary Disease (COPD), cardiovascular diseases, and metabolic disorders, such as any form of diabetes mellitus including type I and type II diabetes and Latent Autoimmune Diabetes of Adulthood (LADA), metabolic syndrome, hyperglycemia, and insulin sensitivity. The conjugates are also useful for reducing advanced glycated end products (AGEs), ROS, lipid peroxidation, tissue and plasma TNFα and IL6 levels, and for delaying or preventing cardiovascular complications associated with atherosclerosis. Also, the conjugates of the present invention are useful for protecting pancreatic β-cells, preventing their impairment or failure and subsequent lower insulin secretion. The anti-inflammatory agent and antioxidant agent as provided herein are covalently bonded directly to each other or covalently bonded directly to the same linker. In particular, the present invention is exemplified by the use of conjugates comprised of salicylic acid and N-acetylcysteine (NAC) or diflunisal and NAC, for treating the disorders disclosed herein.

The compounds of the present invention, in particular Example 1 (salnacedin) and Example 13 (conjugate comprised of diflunisal and NAC), show additive or synergistic effects relative to treatment with an antioxidant agent alone or an anti-inflammatory agent alone. The additive or synergistic effect improves the anti-diabetic effect while reducing side effects associated with monotherapy. In particular, treatment with Example 1 or Example 13 improves anti-diabetic effects while lowering the risk of gastric bleeding, associated with salicylic acid, and/or tinnitus, associated with N-acetylcysteine.

The present invention provides compounds of Formula (I)-(XXII), as defined herein. In another aspect, the present invention provides pharmaceutical compositions comprised of a compound of Formula (I)-(XXII) and at least one pharmaceutically acceptable carrier. The compounds of Formula (I)-(XXII) and the pharmaceutical compositions comprised of Formula (I)-(IX) and at least one pharmaceutically acceptable carrier are useful for treating atherosclerosis, neuropathy, nephropathy, retinopathy, inflammatory disorders, Chronic Obstructive Pulmonary Disease (COPD), cardiovascular diseases, metabolic disorders, type I diabetes mellitus, type II diabetes mellitus, Latent Autoimmune Diabetes of Adulthood (LADA), metabolic syndrome, dyslipidemia, hyperglycemia, or insulin resistance. The compounds and pharmaceutical compositions of the present invention are useful for protecting pancreatic β-cells, preventing their impairment or failure and subsequent lower insulin secretion. Also, the compounds and pharmaceutical compositions of the present invention are also useful for reducing free fatty acids (FFA), triglycerides, advanced glycated end products (AGEs), ROS, lipid peroxidation, tissue and plasma TNFα and IL6 levels, or for delaying or preventing cardiovascular complications associated with atherosclerosis.

In another aspect, the present invention provides methods for treating atherosclerosis, neuropathy, nephropathy, retinopathy, inflammatory disorders, Chronic Obstructive Pulmonary Disease (COPD), cardiovascular diseases, metabolic disorders, type I diabetes mellitus, type II diabetes mellitus, Latent Autoimmune Diabetes of Adulthood (LADA), metabolic syndrome, dyslipidemia, hyperglycemia, or insulin resistance in a mammal or human patient comprising administering to the mammal or human patient in need of such treatment a therapeutically effective amount of a compound of Formula (I)-(IX) or a pharmaceutical composition comprised of a compound of Formula (I)-(IX) and at least one pharmaceutically acceptable carrier. The present invention also provides methods for reducing free fatty acids (FFA), triglycerides, advanced glycated end products (AGEs), ROS, lipid peroxidation, tissue and plasma TNFα and IL6 levels, or for delaying or preventing cardiovascular complications associated with atherosclerosis in a mammal or human patient comprising administering to the mammal or human patient in need of such treatment a therapeutically effective amount of a compound of Formula (I)-(XXII) or a pharmaceutical composition comprised of a compound of Formula (I)-(XXII) and at least one pharmaceutically acceptable carrier. Also, the present invention provides methods for protecting pancreatic β-cells, preventing their impairment or failure and subsequent lower insulin secretion in a mammal or human patient comprising administering to the mammal or human patient in need of such treatment a therapeutically effective amount of a compound of Formula (I)-(XXII) or a pharmaceutical composition comprised of a compound of Formula (I)-(XXII) and at least one pharmaceutically acceptable carrier.

In another aspect, the present invention provides uses for compounds of Formula (I)-(XXII), or pharmaceutical compositions comprised of a compound of Formula (I)-(XXII) and at least one pharmaceutically acceptable carrier, for preparing, or for the manufacture of, a medicament for treating atherosclerosis, neuropathy, nephropathy, retinopathy, inflammatory disorders, Chronic Obstructive Pulmonary Disease (COPD), cardiovascular diseases, metabolic disorders, type I diabetes mellitus, type II diabetes mellitus, Latent Autoimmune Diabetes of Adulthood (LADA), metabolic syndrome, dyslipidemia, hyperglycemia, or insulin resistance in a mammal or human patient. The present invention also provides uses for compounds of Formula (I)-(XXII), or pharmaceutical compositions comprised of a compound of Formula (I)-(XXII) and at least one pharmaceutically acceptable carrier, for preparing, or for the manufacture of, a medicament for reducing free fatty acids (FFA), triglycerides, advanced glycated end products (AGEs), ROS, lipid peroxidation, tissue and plasma TNFα and IL6 levels, or for delaying or preventing cardiovascular complications associated with atherosclerosis in a mammal or human patient. The present invention also provides uses for compounds of Formula (I)-(XXII), or pharmaceutical compositions comprised of a compound of Formula (I)-(XXII) and at least one pharmaceutically acceptable carrier, for preparing, or for the manufacture of, a medicament for protecting pancreatic β-cells, preventing their impairment or failure and subsequent lower insulin secretion, in a mammal or human patient.

Specific embodiments of the present invention will become evident from the following more detailed description of certain preferred embodiments and the claims.

BRIEF DESCRIPTION OF THE DRAWINGS

FIG. 1 is directed to the chemical stability of conjugates of the present invention in neutral, acidic, and basic solutions. The conjugates were tested in their free acid form and as lysine salts and include: salicylic acid-(L) N-acetyl cysteine (GMC-3a), diflunisal-(L) N-acetyl cysteine (GMC-3b), and dexibuprofen-(L) N-acetyl cysteine (GMC-3d).

FIG. 14 illustrates the protocol used in FIGS. 8, 9, 10, 11, 12, and 13.

FIG. 15 is a graphical illustration of in vitro and in vivo cleavage data for several conjugates where lighter colors indicate positive results (white indicates not tested).

FIG. 19B illustrates the reduction of glycemia during the insulin tolerance test (ITT). FIG. 19C illustrates the reduction of glycemia during the glucose tolerance test (GTT).

DETAILED DESCRIPTION

Figure 2:
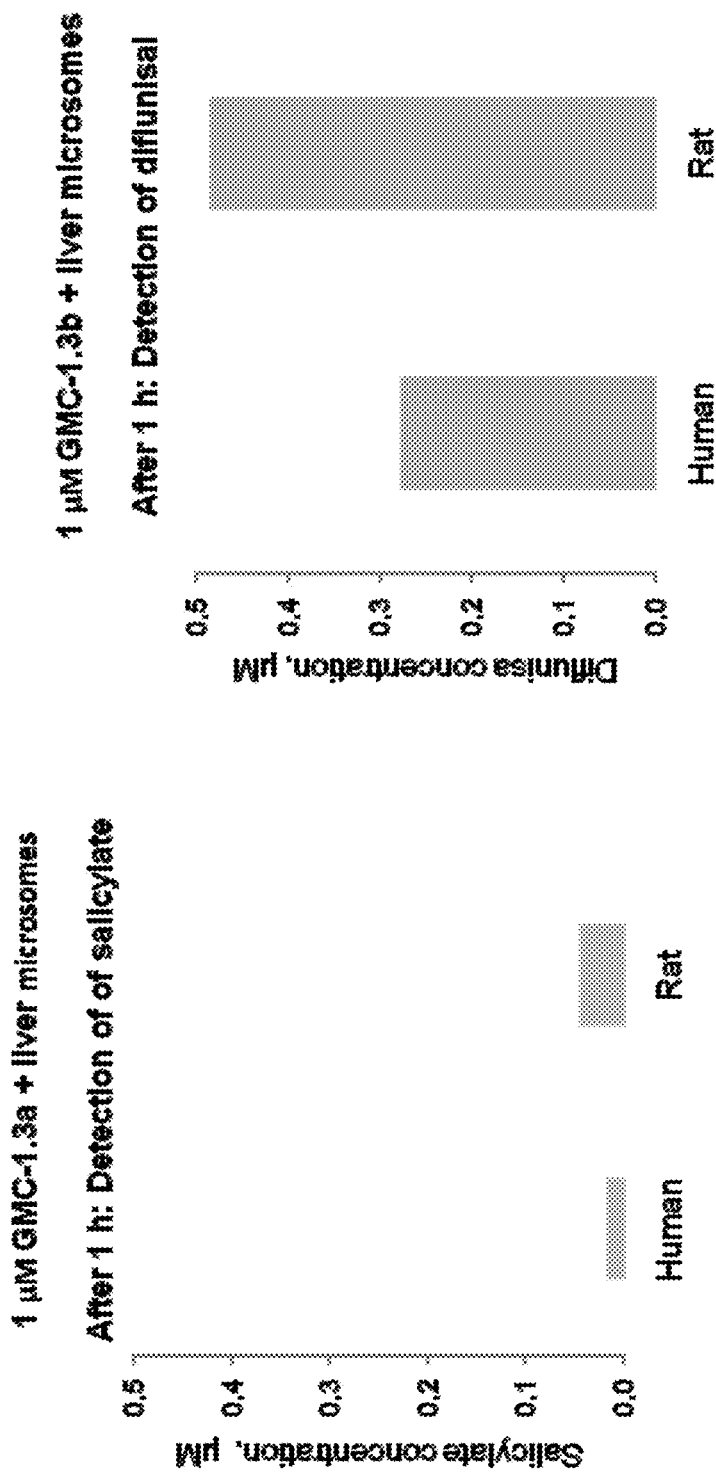
FIGS. 2-4 are graphical illustrations of the cleavage efficiency for salicylic acid-(L) N-acetyl cysteine (GMC-3a) and diflunisal-(L) N-acetyl cysteine (GMC-3b) in rat and human.

The present invention provides compounds, reagents, pharmaceutical compositions and methods for treating atherosclerosis, neuropathy, nephropathy, retinopathy, inflammatory disorders, Chronic Obstructive Pulmonary Disease (COPD), cardiovascular diseases, and metabolic disorders in a mammal or patient comprising administering to the mammal or patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); and $R_7$, $R_8$, $R_9$, $X_1$, and L are as defined in Formula (I) of the Summary section.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood (LADA), in a patient comprising administering to the patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); and $R_7$, $R_8$, $R_9$, $X_1$, and L are as defined in Formula (I) of the Summary section.

In certain embodiments, the present invention provides methods for reducing advanced glycated end products and/or lipid peroxidation including, but not limited to, oxidation of low-density lipoproteins in a mammal or patient comprising administering to the mammal or patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); and $R_7$, $R_8$, $R_9$, $X_1$, and L are as defined in Formula (I) of the Summary section.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood (LADA), in a patient comprising administering to the patient in need of such treatment a therapeutically effective amount of a pharmaceutical composition comprising at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); and $R_7$, $R_8$, $R_9$, $X_1$, and L are as defined in Formula (I) of the Summary section.

In certain embodiments, the present invention provides methods for reducing advanced glycated end products and lipid peroxidation including, but not limited to, oxidation of low-density lipoproteins, in a patient comprising administering to the patient in need of such treatment a therapeutically effective amount of a pharmaceutical composition comprising at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); and $R_7$, $R_8$, $R_9$, $X_1$, and L are as defined in Formula (I) of the Summary section.

In another aspect of the present invention, a method is provided for treating atherosclerosis, neuropathy, nephropathy, retinopathy, inflammatory disorders, Chronic Obstructive Pulmonary Disease (COPD), cardiovascular diseases, and metabolic disorders in a mammal or patient which includes the step of administering to the mammal or patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); $R_7$ is $(C_1-C_6)$alkoxy, hydroxy, or $NZ_9Z_{10}$ wherein $Z_9$ and $Z_{10}$ are hydrogen; $R_8$ is hydrogen; $R_9$ is $(C_1-C_6)$alkylcarbonyl; $X_1$ is S; and L is $CH_2$.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood (LADA), in a patient comprising administering to the patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); $R_7$ is $(C_1-C_6)$alkoxy, hydroxy, or $NZ_9Z_{10}$ wherein $Z_9$ and $Z_{10}$ are hydrogen; $R_8$ is hydrogen; $R_9$ is $(C_1-C_6)$alkylcarbonyl; $X_1$ is S; and L is $CH_2$.

In certain embodiments, the present invention provides methods for reducing advanced glycated end products and/or lipid peroxidation including, but not limited to, oxidation of low-density lipoproteins in a mammal or patient comprising administering to the mammal or patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); $R_7$ is $(C_1-C_6)$alkoxy, hydroxy, or $NZ_9Z_{10}$ wherein $Z_9$ and $Z_{10}$ are hydrogen; $R_8$ is hydrogen; $R_9$ is $(C_1-C_6)$alkylcarbonyl; $X_1$ is S; and L is $CH_2$.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood (LADA), in a patient comprising administering to the patient in need of such treatment a therapeutically effective amount of a pharmaceutical composition comprising at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); $R_7$ is $(C_1-C_6)$alkoxy, hydroxy, or $NZ_9Z_{10}$ wherein $Z_9$ and $Z_{10}$ are hydrogen; $R_8$ is hydrogen; $R_9$ is $(C_1-C_6)$alkylcarbonyl; $X_1$ is S; and L is $CH_2$.

In certain embodiments, the present invention provides methods for reducing advanced glycated end products and lipid peroxidation including, but not limited to, oxidation of low-density lipoproteins, in a patient comprising administering to the patient in need of such treatment a therapeutically effective amount of a pharmaceutical composition comprising at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); $R_7$ is $(C_1-C_6)$alkoxy, hydroxy, or $NZ_9Z_{10}$ wherein $Z_9$ and $Z_{10}$ are hydrogen; $R_8$ is hydrogen; $R_9$ is $(C_1-C_6)$alkylcarbonyl; $X_1$ is S; and L is $CH_2$.

In another aspect of the present invention, a method is provided for treating atherosclerosis, neuropathy, nephropathy, retinopathy, inflammatory disorders, Chronic Obstructive Pulmonary Disease, cardiovascular diseases, and metabolic disorders in a mammal or patient which includes the step of administering to the mammal or patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); $R_7$ is amino, ethoxy, methoxy, or hydroxy; $R_8$ is hydrogen; $R_9$ is acetyl; $X_1$ is S; and L is $CH_2$.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); $R_7$ is amino, ethoxy, methoxy, or hydroxy; $R_8$ is hydrogen; $R_9$ is acetyl; $X_1$ is S; and L is $CH_2$.

In certain embodiments, the present invention provides methods for reducing advanced glycated end products and/or lipid peroxidation including, but not limited to, oxidation of low-density lipoproteins in a mammal or patient comprising administering to the mammal or patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); $R_7$ is amino, ethoxy, methoxy, or hydroxy; $R_8$ is hydrogen; $R_9$ is acetyl; $X_1$ is S; and L is $CH_2$.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a pharmaceutical composition comprising at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); $R_7$ is amino, ethoxy, methoxy, or hydroxy; $R_8$ is hydrogen; $R_9$ is acetyl; $X_1$ is S; and L is $CH_2$.

In certain embodiments, the present invention provides methods for reducing advanced glycated end products and lipid peroxidation including, but not limited to, oxidation of low-density lipoproteins, in a patient comprising administering to the patient in need of such treatment a therapeutically effective amount of a pharmaceutical composition comprising at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); $R_7$ is amino, ethoxy, methoxy, or hydroxy; $R_8$ is hydrogen; $R_9$ is acetyl; $X_1$ is S; and L is $CH_2$.

In accordance with the present invention, a method is provided for treating atherosclerosis, neuropathy, nephropathy, retinopathy, inflammatory disorders, Chronic Obstructive Pulmonary Disease, cardiovascular diseases, and metabolic disorders in a mammal or patient which includes the step of administering to the mammal or patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; and $R_6$ is (L) N-acetylcysteine.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; and $R_6$ is (L) N-acetylcysteine.

In certain embodiments, the present invention provides methods for reducing advanced glycated end products and/or lipid peroxidation including, but not limited to, oxidation of low-density lipoproteins in a mammal or patient comprising administering to the mammal or patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; and $R_6$ is (L) N-acetylcysteine.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a pharmaceutical composition comprising at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; and $R_6$ is (L) N-acetylcysteine.

In certain embodiments, the present invention provides methods for reducing advanced glycated end products and lipid peroxidation including, but not limited to, oxidation of low-density lipoproteins, in a patient comprising administering to the patient in need of such treatment a therapeutically effective amount of a pharmaceutical composition comprising at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; and $R_6$ is (L) N-acetylcysteine.

In accordance with the present invention, a method is provided for treating atherosclerosis, neuropathy, nephropathy, retinopathy, inflammatory disorders, Chronic Obstructive Pulmonary Disease, cardiovascular diseases, and metabolic disorders in a mammal or patient which includes the step of administering to the mammal or patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is hydrogen, ($C_1$-$C_6$)alkyl, ($C_1$-$C_6$)alkylcarbonyl, phenyl, phenyl($CH_2$)—, or phenyl($CH_2$)$_2$—, wherein the phenyl is optionally substituted with 1, 2, 3, 4, or 5 groups that are independently ($C_1$-$C_6$)alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, —$NZ_7Z_8$, or ($NZ_7Z_8$)carbonyl; and $Z_7$ and $Z_8$ are independently hydrogen, ($C_1$-$C_6$)alkyl, or ($C_1$-$C_6$)alkylcarbonyl.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is hydrogen, ($C_1$-$C_6$)alkyl, ($C_1$-$C_6$)alkylcarbonyl, phenyl, phenyl($CH_2$)—, or phenyl($CH_2$)$_2$—, wherein the phenyl is optionally substituted with 1, 2, 3, 4, or 5 groups that are independently ($C_1$-$C_6$)alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, —$NZ_7Z_8$, or ($NZ_7Z_8$)carbonyl; and $Z_7$ and $Z_8$ are independently hydrogen, ($C_1$-$C_6$)alkyl, or ($C_1$-$C_6$)alkylcarbonyl.

In certain embodiments, the present invention provides methods for reducing advanced glycated end products and/or lipid peroxidation including, but not limited to, oxidation of low-density lipoproteins in a mammal or patient comprising administering to the mammal or patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is hydrogen, ($C_1$-$C_6$) alkyl, ($C_1$-$C_6$)alkylcarbonyl, phenyl, phenyl($CH_2$)—, or phenyl($CH_2$)$_2$—, wherein the phenyl is optionally substituted with 1, 2, 3, 4, or 5 groups that are independently ($C_1$-$C_6$) alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, —$NZ_7Z_8$, or ($NZ_7Z_8$)carbonyl; and $Z_7$ and $Z_8$ are independently hydrogen, ($C_1$-$C_6$)alkyl, or ($C_1$-$C_6$)alkylcarbonyl.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a pharmaceutical composition comprising at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is hydrogen, ($C_1$-$C_6$) alkyl, ($C_1$-$C_6$)alkylcarbonyl, phenyl, phenyl($CH_2$)—, or phenyl($CH_2$)$_2$—, wherein the phenyl is optionally substituted with 1, 2, 3, 4, or 5 groups that are independently ($C_1$-$C_6$) alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, —$NZ_7Z_8$, or ($NZ_7Z_8$)carbonyl; and $Z_7$ and $Z_8$ are independently hydrogen, ($C_1$-$C_6$)alkyl, or ($C_1$-$C_6$)alkylcarbonyl.

In certain embodiments, the present invention provides methods for reducing advanced glycated end products and lipid peroxidation including, but not limited to, oxidation of low-density lipoproteins, in a patient comprising administering to the patient in need of such treatment a therapeutically effective amount of a pharmaceutical composition comprising at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is hydrogen, ($C_1$-$C_6$)alkyl, ($C_1$-$C_6$)alkylcarbonyl, phenyl, phenyl($CH_2$)—, or phenyl($CH_2$)$_2$—, wherein the phenyl is optionally substituted with 1, 2, 3, 4, or 5 groups that are independently ($C_1$-$C_6$)alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, —$NZ_7Z_8$, or ($NZ_7Z_8$)carbonyl; and $Z_7$ and $Z_8$ are independently hydrogen, ($C_1$-$C_6$)alkyl, or ($C_1$-$C_6$)alkylcarbonyl.

The present invention further provides methods for treating atherosclerosis, neuropathy, nephropathy, retinopathy, inflammatory disorders, Chronic Obstructive Pulmonary Disease, cardiovascular diseases, and metabolic disorders in a mammal or patient which includes the step of administering to the mammal or patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is hydrogen, ($C_1$-$C_6$)alkyl, ($C_1$-$C_6$)alkylcarbonyl.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is hydrogen, ($C_1$-$C_6$)alkyl, ($C_1$-$C_6$)alkylcarbonyl.

In certain embodiments, the present invention provides methods for reducing advanced glycated end products and/or lipid peroxidation including, but not limited to, oxidation of low-density lipoproteins in a mammal or patient comprising administering to the mammal or patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is hydrogen, ($C_1$-$C_6$)alkyl, ($C_1$-$C_6$)alkylcarbonyl. In certain embodiments, the inventive methods include treating dyslipidemia, insulin resistance, elevated fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a pharmaceutical composition comprising at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is hydrogen, ($C_1$-$C_6$)alkyl, ($C_1$-$C_6$)alkylcarbonyl.

In certain embodiments, the present invention provides methods for reducing advanced glycated end products and lipid peroxidation including, but not limited to, oxidation of low-density lipoproteins, in a patient comprising administering to the patient in need of such treatment a therapeutically effective amount of a pharmaceutical composition comprising at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is hydrogen, ($C_1$-$C_6$) alkyl, ($C_1$-$C_6$)alkylcarbonyl.

The present invention additionally provides methods for treating atherosclerosis, neuropathy, nephropathy, retinopathy, inflammatory disorders, Chronic Obstructive Pulmonary Disease, cardiovascular diseases, and metabolic disorders in a mammal or patient which includes the step of administering to the mammal or patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is —$NZ_5Z_6$; $Z_5$ is hydrogen; and $Z_6$ is hydrogen.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is —$NZ_5Z_6$; $Z_5$ is hydrogen; and $Z_6$ is hydrogen.

In certain embodiments, the present invention provides methods for reducing advanced glycated end products and/or lipid peroxidation including, but not limited to, oxidation of low-density lipoproteins in a mammal or patient comprising administering to the mammal or patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is —$NZ_5Z_6$; $Z_5$ is hydrogen; and $Z_6$ is hydrogen.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a pharmaceutical composition comprising at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is —$NZ_5Z_6$; $Z_5$ is hydrogen; and $Z_6$ is hydrogen.

In certain embodiments, the present invention provides methods for reducing advanced glycated end products and lipid peroxidation including, but not limited to, oxidation of low-density lipoproteins, in a patient comprising administering to the patient in need of such treatment a therapeutically effective amount of a pharmaceutical composition comprising at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is —$NZ_5Z_6$; $Z_5$ is hydrogen; and $Z_6$ is hydrogen.

The present invention also provides methods for treating atherosclerosis, neuropathy, nephropathy, retinopathy, inflammatory disorders, Chronic Obstructive Pulmonary Disease, cardiovascular diseases, and metabolic disorders in a mammal or patient which includes the step of administering to the mammal or patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is phenyl, wherein the phenyl is optionally substituted with 1, 2, 3, 4, or 5 groups that are independently ($C_1$-$C_6$)alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, —$NZ_7Z_8$, or ($NZ_7Z_8$)carbonyl; and $Z_7$ and $Z_8$ are independently hydrogen, ($C_1$-$C_6$)alkyl, or ($C_1$-$C_6$)alkylcarbonyl.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, halo ($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is phenyl, wherein the phenyl is optionally substituted with 1, 2, 3, 4, or 5 groups that are independently ($C_1$-$C_6$)alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, —$NZ_7Z_8$, or ($NZ_7Z_8$)carbonyl; and $Z_7$ and $Z_8$ are independently hydrogen, ($C_1$-$C_6$)alkyl, or ($C_1$-$C_6$)alkylcarbonyl.

In certain embodiments, the present invention provides methods for reducing advanced glycated end products and/or lipid peroxidation including, but not limited to, oxidation of low-density lipoproteins in a mammal or patient comprising administering to the mammal or patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is phenyl, wherein the phenyl is optionally substituted with 1, 2, 3, 4, or 5 groups that are independently ($C_1$-$C_6$)alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, —$NZ_7Z_8$, or ($NZ_7Z_8$)carbonyl; and $Z_7$ and $Z_8$ are independently hydrogen, ($C_1$-$C_6$)alkyl, or ($C_1$-$C_6$)alkylcarbonyl.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a pharmaceutical composition comprising at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is phenyl, wherein the phenyl is optionally substituted with 1, 2, 3, 4, or 5 groups that are independently ($C_1$-$C_6$)alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, —$NZ_7Z_8$, or ($NZ_7Z_8$)carbonyl; and $Z_7$ and $Z_8$ are independently hydrogen, ($C_1$-$C_6$)alkyl, or ($C_1$-$C_6$)alkylcarbonyl.

In certain embodiments, the present invention provides methods for reducing advanced glycated end products and lipid peroxidation including, but not limited to, oxidation of low-density lipoproteins, in a patient comprising administering to the patient in need of such treatment a therapeutically effective amount of a pharmaceutical composition comprising at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is phenyl, wherein the phenyl is optionally substituted with 1, 2, 3, 4, or 5 groups that are independently ($C_1$-$C_6$)alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, —$NZ_7Z_8$, or ($NZ_7Z_8$)carbonyl; and $Z_7$ and $Z_8$ are independently hydrogen, ($C_1$-$C_6$)alkyl, or ($C_1$-$C_6$)alkylcarbonyl.

The present invention provides methods for treating atherosclerosis, neuropathy, nephropathy, retinopathy, inflammatory disorders, Chronic Obstructive Pulmonary Disease, cardiovascular diseases, and metabolic disorders in a mammal or patient which includes the step of administering to the mammal or patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, halo ($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is phenyl, wherein the phenyl is optionally substituted with 1 or 2 groups that are independently halo($C_1$-$C_6$)alkyl or halogen.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, halo $(C_1$-$C_6)$alkyl, or phenyl wherein the phenyl is optionally substituted with 1 or 2 halogens; $R_6$ is —$NZ_5Z_6$; $Z_5$ is hydrogen; $Z_6$ is phenyl, wherein the phenyl is optionally substituted with 1 or 2 groups that are independently halo$(C_1$-$C_6)$alkyl or halogen.

In certain embodiments, the present invention provides methods for reducing advanced glycated end products and/or lipid peroxidation including, but not limited to, oxidation of low-density lipoproteins in a mammal or patient comprising administering to the mammal or patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, halo$(C_1$-$C_6)$alkyl, or phenyl wherein the phenyl is optionally substituted with 1 or 2 halogens; $R_6$ is —$NZ_5Z_6$; $Z_5$ is hydrogen; $Z_6$ is phenyl, wherein the phenyl is optionally substituted with 1 or 2 groups that are independently halo$(C_1$-$C_6)$alkyl or halogen.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a pharmaceutical composition comprising at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, halo$(C_1$-$C_6)$alkyl, or phenyl wherein the phenyl is optionally substituted with 1 or 2 halogens; $R_6$ is —$NZ_5Z_6$; $Z_5$ is hydrogen; $Z_6$ is phenyl, wherein the phenyl is optionally substituted with 1 or 2 groups that are independently halo$(C_1$-$C_6)$alkyl or halogen.

In certain embodiments, the present invention provides methods for reducing advanced glycated end products and lipid peroxidation including, but not limited to, oxidation of low-density lipoproteins, in a patient comprising administering to the patient in need of such treatment a therapeutically effective amount of a pharmaceutical composition comprising at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, halo$(C_1$-$C_6)$alkyl, or phenyl wherein the phenyl is optionally substituted with 1 or 2 halogens; $R_6$ is —$NZ_5Z_6$; $Z_5$ is hydrogen; $Z_6$ is phenyl, wherein the phenyl is optionally substituted with 1 or 2 groups that are independently halo$(C_1$-$C_6)$alkyl or halogen.

In accordance with the present invention, methods are provided for treating atherosclerosis, neuropathy, nephropathy, retinopathy, inflammatory disorders, Chronic Obstructive Pulmonary Disease, cardiovascular diseases, and metabolic disorders in a mammal or patient which includes the step of administering to the mammal or patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2-4,difluorophenyl; $R_6$ is —$NZ_5Z_6$; $Z_5$ is hydrogen; $Z_6$ is phenyl, wherein the phenyl is optionally substituted with 1 or 2 groups that are independently trifluoromethyl or Cl.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2-4,difluorophenyl; $R_6$ is —$NZ_5Z_6$; $Z_5$ is hydrogen; $Z_6$ is phenyl, wherein the phenyl is optionally substituted with 1 or 2 groups that are independently trifluoromethyl or Cl.

In certain embodiments, the present invention provides methods for reducing advanced glycated end products and/or lipid peroxidation including, but not limited to, oxidation of low-density lipoproteins in a mammal or patient comprising administering to the mammal or patient in need of such treatment a therapeutically effective amount of a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2-4,difluorophenyl; $R_6$ is —$NZ_5Z_6$; $Z_5$ is hydrogen; $Z_6$ is phenyl, wherein the phenyl is optionally substituted with 1 or 2 groups that are independently trifluoromethyl or Cl.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a pharmaceutical composition comprising at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2-4,difluorophenyl; $R_6$ is —$NZ_5Z_6$; $Z_5$ is hydrogen; $Z_6$ is phenyl, wherein the phenyl is optionally substituted with 1 or 2 groups that are independently trifluoromethyl or Cl.

In certain embodiments, the present invention provides methods for reducing advanced glycated end products and lipid peroxidation including, but not limited to, oxidation of low-density lipoproteins, in a patient comprising administering to the patient in need of such treatment a therapeutically effective amount of a pharmaceutical composition comprising at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2-4,difluorophenyl; $R_6$ is —$NZ_5Z_6$; $Z_5$ is hydrogen; $Z_6$ is phenyl, wherein the phenyl is optionally substituted with 1 or 2 groups that are independently trifluoromethyl or Cl.

In accordance with the present invention, methods are provided for treating atherosclerosis, neuropathy, nephropathy, retinopathy, inflammatory disorders, Chronic Obstructive Pulmonary Disease, cardiovascular diseases, and metabolic disorders in a mammal or patient which includes the step of administering to the mammal or patient in need of such treatment a therapeutically effective amount of a conjugate of Formula (I) or Formula (IV), or a pharmaceutically acceptable salt thereof, wherein the conjugate of Formula (I) or Formula (IV) is N-(3,5-bis(trifluoromethyl)phenyl)-5- chloro-2-hydroxybenzamide or 2-(3,5-bis(trifluoromethyl)phenylcarbamoyl)-4-chlorophenyl acetate.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a conjugate of Formula (I) or Formula (IV), or a pharmaceutically acceptable salt thereof, wherein the conjugate of Formula (I) or Formula (IV) is N-(3,5-bis(trifluoromethyl)phenyl)-5-chloro-2-hydroxybenzamide or 2-(3,5-bis(trifluoromethyl)phenylcarbamoyl)-4-chlorophenyl acetate.

In certain embodiments, the present invention provides methods for reducing advanced glycated end products and/or lipid peroxidation including, but not limited to, oxidation of low-density lipoproteins in a mammal or patient comprising administering to the mammal or patient in need of such treatment a therapeutically effective amount of a conjugate of Formula (I) or Formula (IV), or a pharmaceutically acceptable salt thereof, wherein the conjugate of Formula (I) or Formula (IV) is N-(3,5-bis(trifluoromethyl)phenyl)-5-chloro-2-hydroxybenzamide or 2-(3,5-bis(trifluoromethyl)phenylcarbamoyl)-4-chlorophenyl acetate.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a pharmaceutical composition comprising at least one pharmaceutically acceptable carrier and a conjugate of Formula (I) or Formula (IV), or a pharmaceutically acceptable salt thereof, wherein the conjugate of Formula (I) or Formula (IV) is N-(3,5-bis(trifluoromethyl)phenyl)-5-chloro-2-hydroxybenzamide or 2-(3,5-bis(trifluoromethyl)phenylcarbamoyl)-4-chlorophenyl acetate.

In certain embodiments, the present invention provides methods for reducing advanced glycated end products and lipid peroxidation including, but not limited to, oxidation of low-density lipoproteins, in a patient comprising administering to the patient in need of such treatment a therapeutically effective amount of a pharmaceutical composition comprising at least one pharmaceutically acceptable carrier and a conjugate of Formula (I) or Formula (IV), or a pharmaceutically acceptable salt thereof, wherein the conjugate of Formula (I) or Formula (IV) is N-(3,5-bis(trifluoromethyl)phenyl)-5-chloro-2-hydroxybenzamide or 2-(3,5-bis(trifluoromethyl)phenylcarbamoyl)-4-chlorophenyl acetate.

In another aspect, the present invention provides methods for treating atherosclerosis, neuropathy, nephropathy, retinopathy, inflammatory disorders, Chronic Obstructive Pulmonary Disease, cardiovascular diseases, and metabolic disorders in a mammal or patient that comprises administering to the mammal or patient in need of such treatment a therapeutically effective amount of a compound selected from Example 1, 2, 3, 4, 5, 6, 7, 8, 9, 10, 11, 12, 13, 14, 15, 16, 17, or 18.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a compound selected from Example 1, 2, 3, 4, 5, 6, 7, 8, 9, 10, 11, 12, 13, 14, 15, 16, 17, or 18.

In certain embodiments, the present invention provides methods for reducing advanced glycated end products and/or lipid peroxidation including, but not limited to, oxidation of low-density lipoproteins in a mammal or patient comprising administering to the mammal or patient in need of such treatment a therapeutically effective amount of a compound selected from Example 1, 2, 3, 4, 5, 6, 7, 8, 9, 10, 11, 12, 13, 14, 15, 16, 17, or 18.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a pharmaceutical composition comprising at least one pharmaceutically acceptable carrier and a compound selected from Example 1, 2, 3, 4, 5, 6, 7, 8, 9, 10, 11, 12, 13, 14, 15, 16, 17, or 18.

In certain embodiments, the present invention provides methods for reducing advanced glycated end products and lipid peroxidation including, but not limited to, oxidation of low-density lipoproteins, in a patient comprising administering to the patient in need of such treatment a therapeutically effective amount of a pharmaceutical composition comprising at least one pharmaceutically acceptable carrier and a compound selected from Example 1, 2, 3, 4, 5, 6, 7, 8, 9, 10, 11, 12, 13, 14, 15, 16, 17, or 18.

In another aspect, the present invention provides methods for treating atherosclerosis, neuropathy, nephropathy, retinopathy, inflammatory disorders, Chronic Obstructive Pulmonary Disease, cardiovascular diseases, and metabolic disorders in a mammal or patient that comprises administering to the mammal or patient in need of such treatment a therapeutically effective amount of Example 1 (salnacedin).

In certain embodiments, the inventive methods include treating dyslipidemia, insulin resistance, metabolic syndrome, and any form of diabetes mellitus including type I and type II diabetes and Latent Autoimmune Diabetes of Adulthood, in a patient comprising administering to the patient in need of such treatment a therapeutically effective amount of Example 1.

In certain embodiments, the present invention provides methods for treating β-cell dysfunction in a patient comprising administering to the patient in need of such treatment a therapeutically effective amount of Example 1 (salnacedin).

In certain embodiments, the present invention provides methods for treating hyperglycemia in a patient comprising administering to the patient in need of such treatment a therapeutically effective amount of Example 1 (salnacedin).

In certain embodiments, the present invention provides methods for reducing free fatty acids in a patient comprising administering to the patient in need of such treatment a therapeutically effective amount of Example 1 (salnacedin).

In certain embodiments, the present invention provides methods for reducing triglycerides in a patient comprising administering to the patient in need of such treatment a therapeutically effective amount of Example 1 (salnacedin).

In certain embodiments, the present invention provides methods for reducing advanced glycated end products and/or lipid peroxidation including, but not limited to, oxidation of low-density lipoproteins in a mammal or patient comprising administering to the mammal or patient in need of such treatment a therapeutically effective amount of Example 1.

In certain embodiments, the inventive methods include treating dyslipidemia, insulin resistance, metabolic syndrome, and any form of diabetes mellitus including type I and type II diabetes and Latent Autoimmune Diabetes of Adulthood, in a patient comprising administering to the patient in need of such treatment a therapeutically effective amount of a pharmaceutical composition comprising at least one pharmaceutically acceptable carrier and Example 1.

In certain embodiments, the present invention includes methods for treating β-cell dysfunction in a patient comprising administering to the patient in need of such treatment a therapeutically effective amount of a pharmaceutical composition comprising at least one pharmaceutically acceptable carrier and Example 1 (salnacedin).

In certain embodiments, the present invention includes methods for treating hyperglycemia in a patient comprising administering to the patient in need of such treatment a therapeutically effective amount of a pharmaceutical composition comprising at least one pharmaceutically acceptable carrier and Example 1 (salnacedin).

In certain embodiments, the present invention includes methods for reducing free fatty acids in a patient comprising administering to the patient in need of such treatment a therapeutically effective amount of a pharmaceutical composition comprising at least one pharmaceutically acceptable carrier and Example 1 (salnacedin).

In certain embodiments, the present invention includes methods for reducing triglycerides in a patient comprising administering to the patient in need of such treatment a therapeutically effective amount of a pharmaceutical composition comprising at least one pharmaceutically acceptable carrier and Example 1 (salnacedin).

In certain embodiments, the present invention provides methods for reducing advanced glycated end products and lipid peroxidation including, but not limited to, oxidation of low-density lipoproteins, in a patient comprising administering to the patient in need of such treatment a therapeutically effective amount of a pharmaceutical composition comprising administering to the patient in need of such treatment a therapeutically effective amount of a pharmaceutical composition comprising at least one pharmaceutically acceptable carrier and Example 1.

In another aspect, the present invention provides methods for treating atherosclerosis, neuropathy, nephropathy, retinopathy, inflammatory disorders, Chronic Obstructive Pulmonary Disease, cardiovascular diseases, and metabolic disorders in a mammal or patient that comprises administering to the mammal or patient in need of such treatment a therapeutically effective amount of Example 4.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of Example 4.

In certain embodiments, the present invention provides methods for reducing advanced glycated end products and/or lipid peroxidation including, but not limited to, oxidation of low-density lipoproteins in a mammal or patient comprising administering to the mammal or patient in need of such treatment a therapeutically effective amount of Example 4.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a pharmaceutical composition comprising at least one pharmaceutically acceptable carrier and Example 4.

In certain embodiments, the present invention provides methods for reducing advanced glycated end products and lipid peroxidation including, but not limited to, oxidation of low-density lipoproteins, in a patient comprising administering to the patient in need of such treatment a therapeutically effective amount of a pharmaceutical composition comprising administering to the patient in need of such treatment a therapeutically effective amount of a pharmaceutical composition comprising at least one pharmaceutically acceptable carrier and Example 4.

In another aspect, the present invention provides methods for treating atherosclerosis, neuropathy, nephropathy, retinopathy, inflammatory disorders, Chronic Obstructive Pulmonary Disease, cardiovascular diseases, and metabolic disorders in a mammal or patient that comprises administering to the mammal or patient in need of such treatment a therapeutically effective amount of Example 7. In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of Example 7.

In certain embodiments, the present invention provides methods for reducing advanced glycated end products and/or lipid peroxidation including, but not limited to, oxidation of low-density lipoproteins in a mammal or patient comprising administering to the mammal or patient in need of such treatment a therapeutically effective amount of Example 7.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a pharmaceutical composition comprising at least one pharmaceutically acceptable carrier and Example 7.

In certain embodiments, the present invention provides methods for reducing advanced glycated end products and lipid peroxidation including, but not limited to, oxidation of low-density lipoproteins, in a patient comprising administering to the patient in need of such treatment a therapeutically effective amount of a pharmaceutical composition comprising administering to the patient in need of such treatment a therapeutically effective amount of a pharmaceutical composition comprising at least one pharmaceutically acceptable carrier and Example 7.

In another aspect, the present invention provides methods for treating atherosclerosis, neuropathy, nephropathy, retinopathy, inflammatory disorders, Chronic Obstructive Pulmonary Disease, cardiovascular diseases, and metabolic disorders in a mammal or patient that comprises administering to the mammal or patient in need of such treatment a therapeutically effective amount of Example 10.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of Example 10.

In certain embodiments, the present invention provides methods for reducing advanced glycated end products and/or lipid peroxidation including, but not limited to, oxidation of low-density lipoproteins in a mammal or patient comprising administering to the mammal or patient in need of such treatment a therapeutically effective amount of Example 10.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a pharmaceutical composition comprising at least one pharmaceutically acceptable carrier and Example 10.

In certain embodiments, the present invention provides methods for reducing advanced glycated end products and lipid peroxidation including, but not limited to, oxidation of low-density lipoproteins, in a patient comprising administering to the patient in need of such treatment a therapeutically effective amount of a pharmaceutical composition comprising administering to the patient in need of such treatment a therapeutically effective amount of a pharmaceutical composition comprising at least one pharmaceutically acceptable carrier and Example 10.

In another aspect, the present invention provides methods for treating atherosclerosis, neuropathy, nephropathy, retinopathy, inflammatory disorders, Chronic Obstructive Pulmonary Disease, cardiovascular diseases, and metabolic disorders in a mammal or patient that comprises administering to the mammal or patient in need of such treatment a therapeutically effective amount of Example 13.

In certain embodiments, the inventive methods include treating dyslipidemia, insulin resistance, metabolic syndrome, and any form of diabetes mellitus including type I and type II diabetes and Latent Autoimmune Diabetes of Adulthood, and any form of diabetes mellitus including type I and type II diabetes, in a patient comprising administering to the patient in need of such treatment a therapeutically effective amount of Example 13.

In certain embodiments, the present invention provides methods for reducing advanced glycated end products and/or lipid peroxidation including, but not limited to, oxidation of low-density lipoproteins in a mammal or patient comprising administering to the mammal or patient in need of such treatment a therapeutically effective amount of Example 13.

In another aspect, the present invention provides methods for treating β-cell dysfunction in a patient comprising administering to the patient in need of such treatment a therapeutically effective amount of Example 13.

In another aspect, the present invention provides methods for treating hyperglycemia in a patient comprising administering to the patient in need of such treatment a therapeutically effective amount of Example 13.

In another aspect, the present invention provides methods for reducing free fatty acids in a patient comprising administering to the patient in need of such treatment a therapeutically effective amount of Example 13.

In another aspect, the present invention provides methods for reducing triglycerides in a patient comprising administering to the patient in need of such treatment a therapeutically effective amount of Example 13.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a pharmaceutical composition comprising at least one pharmaceutically acceptable carrier and Example 13.

In certain embodiments, the present invention provides methods for reducing advanced glycated end products and lipid peroxidation including, but not limited to, oxidation of low-density lipoproteins, in a patient comprising administering to the patient in need of such treatment a therapeutically effective amount of a pharmaceutical composition comprising administering to the patient in need of such treatment a therapeutically effective amount of a pharmaceutical composition comprising at least one pharmaceutically acceptable carrier and Example 13.

In certain embodiments, present invention includes methods for treating β-cell dysfunction in a patient comprising administering to the patient in need of such treatment a therapeutically effective amount of a pharmaceutical composition comprising at least one pharmaceutically acceptable carrier and Example 13.

In certain embodiments, present invention includes methods for treating hyperglycemia in a patient comprising administering to the patient in need of such treatment a therapeutically effective amount of a pharmaceutical composition comprising at least one pharmaceutically acceptable carrier and Example 13.

In certain embodiments, present invention includes methods for reducing free fatty acids in a patient comprising administering to the patient in need of such treatment a therapeutically effective amount of a pharmaceutical composition comprising at least one pharmaceutically acceptable carrier and Example 13.

In certain embodiments, present invention includes methods for reducing triglycerides in a patient comprising administering to the patient in need of such treatment a therapeutically effective amount of a pharmaceutical composition comprising at least one pharmaceutically acceptable carrier and Example 13.

In another aspect, the present invention provides methods for treating atherosclerosis, neuropathy, nephropathy, retinopathy, inflammatory disorders, Chronic Obstructive Pulmonary Disease, cardiovascular diseases, and metabolic disorders in a mammal or patient that comprises administering to the mammal or patient in need of such treatment a therapeutically effective amount of Example 16.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, and any form of diabetes mellitus including type I and type II diabetes, in a patient comprising administering to the patient in need of such treatment a therapeutically effective amount of Example 16.

In certain embodiments, the present invention provides methods for reducing advanced glycated end products and/or lipid peroxidation including, but not limited to, oxidation of low-density lipoproteins in a mammal or patient comprising administering to the mammal or patient in need of such treatment a therapeutically effective amount of Example 16.

In certain embodiments, the inventive methods include treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient comprising administering to the patient in need of such treatment a therapeutically effective amount of a pharmaceutical composition comprising at least one pharmaceutically acceptable carrier and Example 16.

In certain embodiments, the present invention provides methods for reducing advanced glycated end products and lipid peroxidation including, but not limited to, oxidation of low-density lipoproteins, in a patient comprising administering to the patient in need of such treatment a therapeutically effective amount of a pharmaceutical composition comprising administering to the patient in need of such treatment a therapeutically effective amount of a pharmaceutical composition comprising at least one pharmaceutically acceptable carrier and Example 16.

In another aspect, the present invention provides uses for conjugates of Formula (I) for preparing, or for the manufacture of, a medicament for treating atherosclerosis, neuropathy, nephropathy, retinopathy, inflammatory disorders, Chronic Obstructive Pulmonary Disease, cardiovascular diseases, and metabolic disorders in a mammal or patient, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); and $R_7$, $R_8$, $R_9$, $X_1$, and L are as defined in Formula (I) of the Summary section.

In certain embodiments, the present invention provides uses for conjugates of Formula (I) for preparing, or for the manufacture of, a medicament for treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); and $R_7$, $R_8$, $R_9$, $X_1$, and L are as defined in Formula (I) of the Summary section.

In certain embodiments, the present invention provides uses for conjugates of Formula (I) for preparing, or for the manufacture of, a medicament for reducing advanced glycated end products and/or lipid peroxidation including, but not limited to, oxidation of low-density lipoproteins in a patient, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); and $R_7$, $R_8$, $R_9$, $X_1$, and L are as defined in Formula (I) of the Summary section.

In certain embodiments, the present invention provides uses for pharmaceutical compositions for preparing, or for the manufacture of, a medicament for treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein the pharmaceutical composition comprises at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); and $R_7$, $R_8$, $R_9$, $X_1$, and L are as defined in Formula (I) of the Summary section.

In certain embodiments, the present invention provides uses for pharmaceutical compositions for preparing, or for the manufacture of, a medicament for reducing advanced glycated end products and/or lipid peroxidation including, but not limited to, oxidation of low-density lipoproteins in a patient, wherein the pharmaceutical composition comprises at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); and $R_7$, $R_8$, $R_9$, $X_1$, and L are as defined in Formula (I) of the Summary section.

In another aspect, the present invention provides uses for conjugates of Formula (I) for preparing, or for the manufacture of, a medicament for treating atherosclerosis, neuropathy, nephropathy, retinopathy, inflammatory disorders, Chronic Obstructive Pulmonary Disease, cardiovascular diseases, and metabolic disorders in a mammal or patient, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); $R_7$ is $(C_1$-$C_6)$alkoxy, hydroxy, or $NZ_9Z_{10}$ wherein $Z_9$ and $Z_{10}$ are hydrogen; $R_8$ is hydrogen; $R_9$ is $(C_1$-$C_6)$alkylcarbonyl; $X_1$ is S; and L is $CH_2$.

In certain embodiments, the present invention provides uses for conjugates of Formula (I) for preparing, or for the manufacture of, a medicament for treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); $R_7$ is $(C_1$-$C_6)$alkoxy, hydroxy, or $NZ_9Z_{10}$ wherein $Z_9$ and $Z_{10}$ are hydrogen; $R_8$ is hydrogen; $R_9$ is $(C_1$-$C_6)$alkylcarbonyl; $X_1$ is S; and L is $CH_2$.

In certain embodiments, the present invention provides uses for conjugates of Formula (I) for preparing, or for the manufacture of, a medicament for reducing advanced glycated end products and/or lipid peroxidation including, but not limited to, oxidation of low-density lipoproteins in a patient, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); $R_7$ is $(C_1$-$C_6)$alkoxy, hydroxy, or $NZ_9Z_{10}$ wherein $Z_9$ and $Z_{10}$ are hydrogen; $R_8$ is hydrogen; $R_9$ is $(C_1$-$C_6)$alkylcarbonyl; $X_1$ is S; and L is $CH_2$.

In certain embodiments, the present invention provides uses for pharmaceutical compositions for preparing, or for the manufacture of, a medicament for treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein the pharmaceutical composition comprises at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); $R_2$ is $(C_1$-$C_6)$alkoxy, hydroxy, or $NZ_9Z_{10}$ wherein $Z_9$ and $Z_{10}$ are hydrogen; $R_8$ is hydrogen; $R_9$ is $(C_1$-$C_6)$alkylcarbonyl; $X_1$ is S; and L is $CH_2$.

In certain embodiments, the present invention provides uses for pharmaceutical compositions for preparing, or for the manufacture of, a medicament for reducing advanced glycated end products and/or lipid peroxidation including, but not limited to, oxidation of low-density lipoproteins in a patient, wherein the pharmaceutical composition comprises at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); $R_2$ is ($C_1$-$C_6$)alkoxy, hydroxy, or $NZ_9Z_{10}$ wherein $Z_9$ and $Z_{10}$ are hydrogen; $R_8$ is hydrogen; $R_9$ is ($C_1$-$C_6$)alkylcarbonyl; $X_1$ is S; and L is $CH_2$.

In another aspect, the present invention provides uses for conjugates of Formula (I) for preparing, or for the manufacture of, a medicament for treating atherosclerosis, neuropathy, nephropathy, retinopathy, inflammatory disorders, Chronic Obstructive Pulmonary Disease, cardiovascular diseases, and metabolic disorders in a mammal or patient, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); $R_2$ is amino, ethoxy, methoxy, or hydroxy; $R_8$ is hydrogen; $R_9$ is acetyl; $X_1$ is S; and L is $CH_2$.

In certain embodiments, the present invention provides uses for conjugates of Formula (I) for preparing, or for the manufacture of, a medicament for treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); $R_2$ is amino, ethoxy, methoxy, or hydroxy; $R_8$ is hydrogen; $R_9$ is acetyl; $X_1$ is S; and L is $CH_2$.

In certain embodiments, the present invention provides uses for conjugates of Formula (I) for preparing, or for the manufacture of, a medicament for reducing advanced glycated end products and/or lipid peroxidation including, but not limited to, oxidation of low-density lipoproteins in a patient, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); $R_7$ is amino, ethoxy, methoxy, or hydroxy; $R_8$ is hydrogen; $R_9$ is acetyl; $X_1$ is S; and L is $CH_2$.

In certain embodiments, the present invention provides uses for pharmaceutical compositions for preparing, or for the manufacture of, a medicament for treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein the pharmaceutical composition comprises at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); $R_7$ is amino, ethoxy, methoxy, or hydroxy; $R_8$ is hydrogen; $R_9$ is acetyl; $X_1$ is S; and L is $CH_2$.

In certain embodiments, the present invention provides uses for pharmaceutical compositions for preparing, or for the manufacture of, a medicament for reducing advanced glycated end products and/or lipid peroxidation including, but not limited to, oxidation of low-density lipoproteins in a patient, wherein the pharmaceutical composition comprises at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is formula (i); $R_7$ is amino, ethoxy, methoxy, or hydroxy; $R_8$ is hydrogen; $R_9$ is acetyl; $X_1$ is S; and L is $CH_2$.

In another aspect, the present invention provides uses for conjugates of Formula (I) for preparing, or for the manufacture of, a medicament for treating atherosclerosis, neuropathy, nephropathy, retinopathy, inflammatory disorders, Chronic Obstructive Pulmonary Disease, cardiovascular diseases, and metabolic disorders in a mammal or patient, wherein $R_1$ is hydrogen or acetyl; $R_2$, $R_3$, $R_4$, and $R_5$ are independently hydrogen, trifluoromethyl, or 2,4-difluorophenyl; and $R_6$ is (L) N-acetylcysteine.

In certain embodiments, the present invention provides uses for conjugates of Formula (I) for preparing, or for the manufacture of, a medicament for treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, and any form of diabetes mellitus including type I and type II diabetes, in a patient, wherein $R_1$ is hydrogen or acetyl; $R_2$, $R_3$, $R_4$, and $R_5$ are independently hydrogen, trifluoromethyl, or 2,4-difluorophenyl; and $R_6$ is (L) N-acetylcysteine.

In certain embodiments, the present invention provides uses for conjugates of Formula (I) for preparing, or for the manufacture of, a medicament for reducing advanced glycated end products and/or lipid peroxidation including, but not limited to, oxidation of low-density lipoproteins in a patient, wherein $R_1$ is hydrogen or acetyl; $R_2$, $R_3$, $R_4$, and $R_5$ are independently hydrogen, trifluoromethyl, or 2,4-difluorophenyl; and $R_6$ is (L) N-acetylcysteine.

In certain embodiments, the present invention provides uses for pharmaceutical compositions for preparing, or for the manufacture of, a medicament for treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein the pharmaceutical composition comprises at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; and $R_6$ is (L) N-acetylcysteine.

In certain embodiments, the present invention provides uses for pharmaceutical compositions for preparing, or for the manufacture of, a medicament for reducing advanced glycated end products and/or lipid peroxidation including, but not limited to, oxidation of low-density lipoproteins in a patient, wherein the pharmaceutical composition comprises at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; and $R_6$ is (L) N-acetylcysteine.

In another aspect, the present invention provides uses for conjugates of Formula (I) for preparing, or for the manufacture of, a medicament for treating atherosclerosis, neuropathy, nephropathy, retinopathy, inflammatory disorders, Chronic Obstructive Pulmonary Disease, cardiovascular diseases, and metabolic disorders in a mammal or patient, wherein the conjugate of Formula (I) is selected from Example 1, 2, 3, 4, 5, 6, 7, 8, 9, 10, 11, 12, 13, 14, 15, 16, 17, or 18.

In certain embodiments, the present invention provides uses for conjugates of Formula (I) for preparing, or for the manufacture of, a medicament for treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein the conjugate of Formula (I) is selected from Example 1, 2, 3, 4, 5, 6, 7, 8, 9, 10, 11, 12, 13, 14, 15, 16, 17, or 18.

In certain embodiments, the present invention provides uses for conjugates of Formula (I) for preparing, or for the manufacture of, a medicament for reducing advanced glycated end products and/or lipid peroxidation including, but not limited to, oxidation of low-density lipoproteins in a patient, wherein the conjugate of Formula (I) is selected from Example 1, 2, 3, 4, 5, 6, 7, 8, 9, 10, 11, 12, 13, 14, 15, 16, 17, or 18.

In certain embodiments, the present invention provides uses for pharmaceutical compositions for preparing, or for the manufacture of, a medicament for treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein the pharmaceutical composition comprises at least one pharmaceutically acceptable carrier and a conjugate of Formula (I), or a pharmaceutically acceptable salt thereof, wherein the conjugate of Formula (I) is selected from Example 1, 2, 3, 4, 5, 6, 7, 8, 9, 10, 11, 12, 13, 14, 15, 16, 17, or 18.

In certain embodiments, the present invention provides uses for pharmaceutical compositions for preparing, or for the manufacture of, a medicament for reducing advanced glycated end products and/or lipid peroxidation including, but not limited to, oxidation of low-density lipoproteins in a patient, wherein the pharmaceutical composition comprises at least one pharmaceutically acceptable carrier and a conjugate of Formula (I), or a pharmaceutically acceptable salt thereof, wherein the conjugate of Formula (I) is selected from Example 1, 2, 3, 4, 5, 6, 7, 8, 9, 10, 11, 12, 13, 14, 15, 16, 17, or 18.

In another aspect, the present invention provides uses for conjugates of Formula (I) for preparing, or for the manufacture of, a medicament for treating atherosclerosis, neuropathy, nephropathy, retinopathy, inflammatory disorders, Chronic Obstructive Pulmonary Disease, cardiovascular diseases, and metabolic disorders in a mammal or patient, wherein the conjugate of Formula (I) is Example 1 (salnacedin).

In certain embodiments, the present invention provides uses for conjugates of Formula (I) for preparing, or for the manufacture of, a medicament for treating dyslipidemia, insulin resistance, β-cell dysfunction, metabolic syndrome, and any form of diabetes mellitus including type I and type II diabetes and Latent Autoimmune Diabetes of Adulthood, in a patient, wherein the conjugate of Formula (I) is Example 1 (salnacedin).

In certain embodiments, the present invention provides uses for conjugates of Formula (I) for preparing, or for the manufacture of, a medicament for treating hyperglycemia in a patient, wherein the conjugate of Formula (I) is Example 1 (salnacedin).

In certain embodiments, the present invention provides uses for conjugates of Formula (I) for preparing, or for the manufacture of, a medicament for reducing free free fatty acids in a patient, wherein the conjugate of Formula (I) is Example 1 (salnacedin).

In certain embodiments, the present invention provides uses for conjugates of Formula (I) for preparing, or for the manufacture of, a medicament for reducing triglycerides in a patient, wherein the conjugate of Formula (I) is Example 1 (salnacedin).

In certain embodiments, the present invention provides uses for conjugates of Formula (I) for preparing, or for the manufacture of, a medicament for reducing advanced glycated end products and/or lipid peroxidation including, but not limited to, oxidation of low-density lipoproteins in a patient, wherein the conjugate of Formula (I) is Example 1 (salnacedin).

In certain embodiments, the present invention provides uses for pharmaceutical compositions for preparing, or for the manufacture of, a medicament for treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein the pharmaceutical composition comprises at least one pharmaceutically acceptable carrier and a conjugate of Formula (I), or a pharmaceutically acceptable salt thereof, wherein the conjugate of Formula (I) is Example 1 (salnacedin).

In certain embodiments, the present invention provides uses for pharmaceutical compositions for preparing, or for the manufacture of, a medicament for treating hyperglycemia in a patient, wherein the pharmaceutical composition comprises at least one pharmaceutically acceptable carrier and a conjugate of Formula (I), or a pharmaceutically acceptable salt thereof, wherein the conjugate of Formula (I) is Example 1 (salnacedin).

In certain embodiments, the present invention provides uses for pharmaceutical compositions for preparing, or for the manufacture of, a medicament for reducing free fatty acids in a patient, wherein the pharmaceutical composition comprises at least one pharmaceutically acceptable carrier and a conjugate of Formula (I), or a pharmaceutically acceptable salt thereof, wherein the conjugate of Formula (I) is Example 1 (salnacedin).

In certain embodiments, the present invention provides uses for pharmaceutical compositions for preparing, or for the manufacture of, a medicament for reducing triglycerides in a patient, wherein the pharmaceutical composition comprises at least one pharmaceutically acceptable carrier and a conjugate of Formula (I), or a pharmaceutically acceptable salt thereof, wherein the conjugate of Formula (I) is Example 1 (salnacedin).

In certain embodiments, the present invention provides uses for pharmaceutical compositions for preparing, or for the manufacture of, a medicament for reducing advanced glycated end products and/or lipid peroxidation including, but not limited to, oxidation of low-density lipoproteins in a patient, wherein the pharmaceutical composition comprises at least one pharmaceutically acceptable carrier and a conjugate of Formula (I), or a pharmaceutically acceptable salt thereof, wherein the conjugate of Formula (I) is Example 1 (salnacedin).

In another aspect, the present invention provides uses for conjugates of Formula (I) for preparing, or for the manufacture of, a medicament for treating atherosclerosis, neuropathy, nephropathy, retinopathy, inflammatory disorders, Chronic Obstructive Pulmonary Disease, cardiovascular diseases, and metabolic disorders in a mammal or patient, wherein the conjugate of Formula (I) is Example 4.

In certain embodiments, the present invention provides uses for conjugates of Formula (I) for preparing, or for the manufacture of, a medicament for treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein the conjugate of Formula (I) is Example 4.

In certain embodiments, the present invention provides uses for conjugates of Formula (I) for preparing, or for the manufacture of, a medicament for reducing advanced glycated end products and/or lipid peroxidation including, but not limited to, oxidation of low-density lipoproteins in a patient, wherein the conjugate of Formula (I) is Example 4.

In certain embodiments, the present invention provides uses for pharmaceutical compositions for preparing, or for the manufacture of, a medicament for treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein the pharmaceutical composition comprises at least one pharmaceutically acceptable carrier and a conjugate of Formula (I), or a pharmaceutically acceptable salt thereof, wherein the conjugate of Formula (I) is Example 4.

In certain embodiments, the present invention provides uses for pharmaceutical compositions for preparing, or for the manufacture of, a medicament for reducing advanced glycated end products and/or lipid peroxidation including, but not limited to, oxidation of low-density lipoproteins in a patient, wherein the pharmaceutical composition comprises at least one pharmaceutically acceptable carrier and a conjugate of Formula (I), or a pharmaceutically acceptable salt thereof, wherein the conjugate of Formula (I) is Example 4.

In another aspect, the present invention provides the uses for conjugates of Formula (I) for preparing, or for the manufacture of, a medicament for treating atherosclerosis, neuropathy, nephropathy, retinopathy, inflammatory disorders, Chronic Obstructive Pulmonary Disease, cardiovascular diseases, and metabolic disorders in a mammal or patient, wherein the conjugate of Formula (I) is Example 7.

In certain embodiments, the present invention provides uses for conjugates of Formula (I) for preparing, or for the manufacture of, a medicament for treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein the conjugate of Formula (I) is Example 7.

In certain embodiments, the present invention provides uses for conjugates of Formula (I) for preparing, or for the manufacture of, a medicament for reducing advanced glycated end products and/or lipid peroxidation including, but not limited to, oxidation of low-density lipoproteins in a patient, wherein the conjugate of Formula (I) is Example 7.

In certain embodiments, the present invention provides uses for pharmaceutical compositions for preparing, or for the manufacture of, a medicament for treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein the pharmaceutical composition comprises at least one pharmaceutically acceptable carrier and a conjugate of Formula (I), or a pharmaceutically acceptable salt thereof, wherein the conjugate of Formula (I) is Example 7.

In certain embodiments, the present invention provides uses for pharmaceutical compositions for preparing, or for the manufacture of, a medicament for reducing advanced glycated end products and/or lipid peroxidation including, but not limited to, oxidation of low-density lipoproteins in a patient, wherein the pharmaceutical composition comprises at least one pharmaceutically acceptable carrier and a conjugate of Formula (I), or a pharmaceutically acceptable salt thereof, wherein the conjugate of Formula (I) is Example 7.

In another aspect, the present invention provides uses for conjugates of Formula (I) for preparing, or for the manufacture of, a medicament for treating atherosclerosis, neuropathy, nephropathy, retinopathy, inflammatory disorders, Chronic Obstructive Pulmonary Disease, cardiovascular diseases, and metabolic disorders in a mammal or patient, wherein the conjugate of Formula (I) is Example 10.

In certain embodiments, the present invention provides uses for conjugates of Formula (I) for preparing, or for the manufacture of, a medicament for reducing advanced glycated end products and/or lipid peroxidation including, but not limited to, oxidation of low-density lipoproteins in a patient, wherein the conjugate of Formula (I) is Example 10.

In certain embodiments, the present invention provides uses for conjugates of Formula (I) for preparing, or for the manufacture of, a medicament for treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein the conjugate of Formula (I) is Example 10.

In certain embodiments, the present invention provides uses for pharmaceutical compositions for preparing, or for the manufacture of, a medicament for treating dyslipidemia, insulin resistance, elevated free fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein the pharmaceutical composition comprises at least one pharmaceutically acceptable carrier and a conjugate of Formula (I), or a pharmaceutically acceptable salt thereof, wherein the conjugate of Formula (I) is Example 10.

In certain embodiments, the present invention provides uses for pharmaceutical compositions for preparing, or for the manufacture of, a medicament for reducing advanced glycated end products and/or lipid peroxidation including, but not limited to, oxidation of low-density lipoproteins in a patient, wherein the pharmaceutical composition comprises at least one pharmaceutically acceptable carrier and a conjugate of Formula (I), or a pharmaceutically acceptable salt thereof, wherein the conjugate of Formula (I) is Example 10.

In another aspect, the present invention provides uses for conjugates of Formula (I) for preparing, or for the manufacture of, a medicament for treating atherosclerosis, neuropathy, nephropathy, retinopathy, inflammatory disorders, Chronic Obstructive Pulmonary Disease, cardiovascular diseases, and metabolic disorders in a mammal or patient, wherein the conjugate of Formula (I) is Example 13.

In certain embodiments, the present invention provides uses for conjugates of Formula (I) for preparing, or for the manufacture of, a medicament for treating dyslipidemia, insulin resistance, β-cell dysfunction, metabolic syndrome, and any form of diabetes mellitus including type I and type II diabetes, in a patient, wherein the conjugate of Formula (I) is Example 13.

In certain embodiments, the present invention provides uses for conjugates of Formula (I) for preparing, or for the manufacture of, a medicament for treating hyperglycemia in a patient, wherein the conjugate of Formula (I) is Example 13.

In certain embodiments, the present invention provides uses for conjugates of Formula (I) for preparing, or for the manufacture of, a medicament for reducing free fatty acids in a patient, wherein the conjugate of Formula (I) is Example 13.

In certain embodiments, the present invention provides uses for conjugates of Formula (I) for preparing, or for the manufacture of, a medicament for reducing triglycerides in a patient, wherein the conjugate of Formula (I) is Example 13.

In certain embodiments, the present invention provides uses for conjugates of Formula (I) for preparing, or for the manufacture of, a medicament for reducing advanced glycated end products and/or lipid peroxidation including, but not limited to, oxidation of low-density lipoproteins in a patient, wherein the conjugate of Formula (I) is Example 13.

In certain embodiments, the present invention provides uses for pharmaceutical compositions for preparing, or for the manufacture of, a medicament for treating dyslipidemia, insulin resistance, β-cell dysfunction, metabolic syndrome, and any form of diabetes mellitus including type I and type II diabetes and Latent Autoimmune Diabetes of Adulthood, in a patient, wherein the pharmaceutical composition comprises at least one pharmaceutically acceptable carrier and a conjugate of Formula (I), or a pharmaceutically acceptable salt thereof, wherein the conjugate of Formula (I) is Example 13.

In certain embodiments, the present invention provides uses for pharmaceutical compositions for preparing, or for the manufacture of, a medicament for treating hyperglycemia in a patient, wherein the pharmaceutical composition comprises at least one pharmaceutically acceptable carrier and a conjugate of Formula (I), or a pharmaceutically acceptable salt thereof, wherein the conjugate of Formula (I) is Example 13.

In certain embodiments, the present invention provides uses for pharmaceutical compositions for preparing, or for the manufacture of, a medicament for reducing free fatty acids in a patient, wherein the pharmaceutical composition comprises at least one pharmaceutically acceptable carrier and a conjugate of Formula (I), or a pharmaceutically acceptable salt thereof, wherein the conjugate of Formula (I) is Example 13.

In certain embodiments, the present invention provides uses for pharmaceutical compositions for preparing, or for the manufacture of, a medicament for reducing triglycerides in a patient, wherein the pharmaceutical composition comprises at least one pharmaceutically acceptable carrier and a conjugate of Formula (I), or a pharmaceutically acceptable salt thereof, wherein the conjugate of Formula (I) is Example 13.

In certain embodiments, the present invention provides uses for pharmaceutical compositions for preparing, or for the manufacture of, a medicament for reducing advanced glycated end products and/or lipid peroxidation including, but not limited to, oxidation of low-density lipoproteins in a patient, wherein the pharmaceutical composition comprises at least one pharmaceutically acceptable carrier and a conjugate of Formula (I), or a pharmaceutically acceptable salt thereof, wherein the conjugate of Formula (I) is Example 13.

In another aspect, the present invention provides uses for conjugates of Formula (I) for preparing, or for the manufacture of, a medicament for treating atherosclerosis, neuropathy, nephropathy, retinopathy, inflammatory disorders, Chronic Obstructive Pulmonary Disease, cardiovascular diseases, and metabolic disorders in a mammal or patient, wherein the conjugate of Formula (I) is Example 16.

In certain embodiments, the present invention provides uses for conjugates of Formula (I) for preparing, or for the manufacture of, a medicament for treating dyslipidemia, insulin resistance, elevated fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein the conjugate of Formula (I) is Example 16.

In certain embodiments, the present invention provides uses for conjugates of Formula (I) for preparing, or for the manufacture of, a medicament for reducing advanced glycated end products and/or lipid peroxidation including, but not limited to, oxidation of low-density lipoproteins in a patient, wherein the conjugate of Formula (I) is Example 16.

In certain embodiments, the present invention provides uses for pharmaceutical compositions for preparing, or for the manufacture of, a medicament for treating dyslipidemia, insulin resistance, elevated fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein the pharmaceutical composition comprises at least one pharmaceutically acceptable carrier and a conjugate of Formula (I), or a pharmaceutically acceptable salt thereof, wherein the conjugate of Formula (I) is Example 16.

In certain embodiments, the present invention provides uses for pharmaceutical compositions for preparing, or for the manufacture of, a medicament for reducing advanced glycated end products and/or lipid peroxidation including, but not limited to, oxidation of low-density lipoproteins in a patient, wherein the pharmaceutical composition comprises at least one pharmaceutically acceptable carrier and a conjugate of Formula (I), or a pharmaceutically acceptable salt thereof, wherein the conjugate of Formula (I) is Example 16.

In another aspect, the present invention provides uses for conjugates of Formula (I) for preparing, or for the manufacture of, a medicament for treating atherosclerosis, neuropathy, nephropathy, retinopathy, inflammatory disorders, Chronic Obstructive Pulmonary Disease, cardiovascular diseases, and metabolic disorders in a mammal or patient, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is hydrogen, ($C_1$-$C_6$) alkyl, ($C_1$-$C_6$)alkylcarbonyl, phenyl, phenyl($CH_2$)—, or phenyl($CH_2$)$_2$—, wherein the phenyl is optionally substituted with 1, 2, 3, 4, or 5 groups that are independently ($C_1$-$C_6$) alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, —$NZ_7Z_8$, or ($NZ_7Z_8$)carbonyl; and $Z_7$ and $Z_8$ are independently hydrogen, ($C_1$-$C_6$)alkyl, or ($C_1$-$C_6$)alkylcarbonyl.

In certain embodiments, the present invention provides uses for conjugates of Formula (I) for preparing, or for the manufacture of, a medicament for treating dyslipidemia, insulin resistance, elevated fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is hydrogen, ($C_1$-$C_6$) alkyl, ($C_1$-$C_6$)alkylcarbonyl, phenyl, phenyl($CH_2$)—, or phenyl($CH_2$)$_2$—, wherein the phenyl is optionally substituted with 1, 2, 3, 4, or 5 groups that are independently ($C_1$-$C_6$) alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, —$NZ_7Z_8$, or ($NZ_7Z_8$)carbonyl; and $Z_7$ and $Z_8$ are independently hydrogen, ($C_1$-$C_6$)alkyl, or ($C_1$-$C_6$)alkylcarbonyl.

In certain embodiments, the present invention provides uses for conjugates of Formula (I) for preparing, or for the manufacture of, a medicament for reducing advanced glycated end products and/or lipid peroxidation including, but not limited to, oxidation of low-density lipoproteins in a patient, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is hydrogen, ($C_1$-$C_6$)alkyl, ($C_1$-$C_6$)alkylcarbonyl, phenyl, phenyl($CH_2$)—, or phenyl($CH_2$)$_2$—, wherein the phenyl is optionally substituted with 1, 2, 3, 4, or 5 groups that are independently ($C_1$-$C_6$)alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, —$NZ_7Z_8$, or ($NZ_7Z_8$)carbonyl; and $Z_7$ and $Z_8$ are independently hydrogen, ($C_1$-$C_6$)alkyl, or ($C_1$-$C_6$)alkylcarbonyl.

In certain embodiments, the present invention provides uses for pharmaceutical compositions for preparing, or for the manufacture of, a medicament for treating dyslipidemia, insulin resistance, elevated fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein the pharmaceutical composition comprises at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is hydrogen, ($C_1$-$C_6$)alkyl, ($C_1$-$C_6$)alkylcarbonyl, phenyl, phenyl($CH_2$)—, or phenyl($CH_2$)$_2$—, wherein the phenyl is optionally substituted with 1, 2, 3, 4, or 5 groups that are independently ($C_1$-$C_6$)alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, —$NZ_7Z_8$, or ($NZ_7Z_8$)carbonyl; and $Z_7$ and $Z_8$ are independently hydrogen, ($C_1$-$C_6$)alkyl, or ($C_1$-$C_6$)alkylcarbonyl.

In certain embodiments, the present invention provides uses for pharmaceutical compositions for preparing, or for the manufacture of, a medicament for reducing advanced glycated end products and/or lipid peroxidation including, but not limited to, oxidation of low-density lipoproteins in a patient, wherein the pharmaceutical composition comprises at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is hydrogen, ($C_1$-$C_6$)alkyl, ($C_1$-$C_6$)alkylcarbonyl, phenyl, phenyl($CH_2$)—, or phenyl($CH_2$)$_2$—, wherein the phenyl is optionally substituted with 1, 2, 3, 4, or 5 groups that are independently ($C_1$-$C_6$)alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, —$NZ_7Z_8$, or ($NZ_7Z_8$)carbonyl; and $Z_7$ and $Z_8$ are independently hydrogen, ($C_1$-$C_6$)alkyl, or ($C_1$-$C_6$)alkylcarbonyl.

In another aspect, the present invention provides uses for conjugates of Formula (I) for preparing, or for the manufacture of, a medicament for treating atherosclerosis, neuropathy, nephropathy, retinopathy, inflammatory disorders, Chronic Obstructive Pulmonary Disease, cardiovascular diseases, and metabolic disorders in a mammal or patient, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is hydrogen, ($C_1$-$C_6$)alkyl, ($C_1$-$C_6$)alkylcarbonyl. In certain embodiments, the present invention provides uses for conjugates of Formula (I) for preparing, or for the manufacture of, a medicament for treating dyslipidemia, insulin resistance, elevated fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein $R_1$ is hydrogen or acetyl; $R_2$, $R_3$, $R_4$, and $R_5$ are independently hydrogen, halo($C_1$-$C_6$)alkyl, or halogen; $R_6$ is —$NZ_5Z_6$; $Z_5$ is hydrogen; $Z_6$ is hydrogen, ($C_1$-$C_6$)alkyl, ($C_1$-$C_6$)alkylcarbonyl.

In certain embodiments, the present invention provides uses for conjugates of Formula (I) for preparing, or for the manufacture of, a medicament for reducing advanced glycated end products and/or lipid peroxidation including, but not limited to, oxidation of low-density lipoproteins in a patient, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is hydrogen, ($C_1$-$C_6$)alkyl, ($C_1$-$C_6$)alkylcarbonyl.

In certain embodiments, the present invention provides uses for pharmaceutical compositions for preparing, or for the manufacture of, a medicament for treating dyslipidemia, insulin resistance, elevated fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein the pharmaceutical composition comprises at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is hydrogen, ($C_1$-$C_6$)alkyl, ($C_1$-$C_6$)alkylcarbonyl.

In certain embodiments, the present invention provides uses for pharmaceutical compositions for preparing, or for the manufacture of, a medicament for reducing advanced glycated end products and/or lipid peroxidation including, but not limited to, oxidation of low-density lipoproteins in a patient, wherein the pharmaceutical composition comprises at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is hydrogen, ($C_1$-$C_6$)alkyl, ($C_1$-$C_6$)alkylcarbonyl.

In another aspect, the present invention provides uses for conjugates of Formula (I) for preparing, or for the manufacture of, a medicament for treating atherosclerosis, neuropathy, nephropathy, retinopathy, inflammatory disorders, Chronic Obstructive Pulmonary Disease, cardiovascular diseases, and metabolic disorders in a mammal or patient, wherein $R_1$ is hydrogen or acetyl; $R_2$, $R_3$, $R_4$, and $R_5$ are independently hydrogen, trifluoromethyl, or 2,4-difluorophenyl; $R_6$ is $-NZ_5Z_6$; $Z_5$ is hydrogen; and $Z_6$ is hydrogen.

In certain embodiments, the present invention provides uses for conjugates of Formula (I) for preparing, or for the manufacture of, a medicament for treating dyslipidemia, insulin resistance, elevated fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein $R_1$ is hydrogen or acetyl; $R_2$, $R_3$, $R_4$, and $R_5$ are independently hydrogen, trifluoromethyl, or 2,4-difluorophenyl; $R_6$ is $-NZ_5Z_6$; $Z_5$ is hydrogen; and $Z_6$ is hydrogen.

In certain embodiments, the present invention provides uses for conjugates of Formula (I) for preparing, or for the manufacture of, a medicament for reducing advanced glycated end products and/or lipid peroxidation including, but not limited to, oxidation of low-density lipoproteins in a patient, wherein $R_1$ is hydrogen or acetyl; $R_2$, $R_3$, $R_4$, and $R_5$ are independently hydrogen, trifluoromethyl, or 2,4-difluorophenyl; $R_6$ is $-NZ_5Z_6$; $Z_5$ is hydrogen; and $Z_6$ is hydrogen.

In certain embodiments, the present invention provides uses for pharmaceutical compositions for preparing, or for the manufacture of, a medicament for treating dyslipidemia, insulin resistance, elevated fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein the pharmaceutical composition comprises at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is $-NZ_5Z_6$; $Z_5$ is hydrogen; and $Z_6$ is hydrogen.

In certain embodiments, the present invention provides uses for pharmaceutical compositions for preparing, or for the manufacture of, a medicament for reducing advanced glycated end products and/or lipid peroxidation including, but not limited to, oxidation of low-density lipoproteins in a patient, wherein the pharmaceutical composition comprises at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is $-NZ_5Z_6$; $Z_5$ is hydrogen; and $Z_6$ is hydrogen.

In another aspect, the present invention provides uses for conjugates of Formula (I) for preparing, or for the manufacture of, a medicament for treating atherosclerosis, neuropathy, nephropathy, retinopathy, inflammatory disorders, Chronic Obstructive Pulmonary Disease, cardiovascular diseases, and metabolic disorders in a mammal or patient, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is $-NZ_5Z_6$; $Z_5$ is hydrogen; $Z_6$ is phenyl, wherein the phenyl is optionally substituted with 1, 2, 3, 4, or 5 groups that are independently ($C_1$-$C_6$)alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, $-NZ_7Z_8$, or ($NZ_7Z_8$)carbonyl; and $Z_7$ and $Z_8$ are independently hydrogen, ($C_1$-$C_6$)alkyl, or ($C_1$-$C_6$)alkylcarbonyl.

In certain embodiments, the present invention provides uses for conjugates of Formula (I) for preparing, or for the manufacture of, a medicament for treating dyslipidemia, insulin resistance, elevated fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is $-NZ_5Z_6$; $Z_5$ is hydrogen; $Z_6$ is phenyl, wherein the phenyl is optionally substituted with 1, 2, 3, 4, or 5 groups that are independently ($C_1$-$C_6$)alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, $-NZ_7Z_8$, or ($NZ_7Z_8$)carbonyl; and $Z_7$ and $Z_8$ are independently hydrogen, ($C_1$-$C_6$)alkyl, or ($C_1$-$C_6$)alkylcarbonyl.

In certain embodiments, the present invention provides uses for conjugates of Formula (I) for preparing, or for the manufacture of, a medicament for reducing advanced glycated end products and/or lipid peroxidation including, but not limited to, oxidation of low-density lipoproteins in a patient, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is $-NZ_5Z_6$; $Z_5$ is hydrogen; $Z_6$ is phenyl, wherein the phenyl is optionally substituted with 1, 2, 3, 4, or 5 groups that are independently ($C_1$-$C_6$)alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, $-NZ_7Z_8$, or ($NZ_7Z_8$)carbonyl; and $Z_7$ and $Z_8$ are independently hydrogen, ($C_1$-$C_6$)alkyl, or ($C_1$-$C_6$)alkylcarbonyl.

In certain embodiments, the present invention provides uses for pharmaceutical compositions for preparing, or for the manufacture of, a medicament for treating dyslipidemia, insulin resistance, elevated fatty acids, elevated triglycerides, β-cell dysfunction, hyperglycemia, metabolic syndrome, and any form of diabetes mellitus including type I and type II diabetes and Latent Autoimmune Diabetes of Adulthood, wherein the pharmaceutical composition comprises at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is $-NZ_5Z_6$; $Z_5$ is hydrogen; $Z_6$ is phenyl, wherein the phenyl is optionally substituted with 1, 2, 3, 4, or 5 groups that are independently ($C_1$-$C_6$)alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, $-NZ_7Z_8$, or ($NZ_7Z_8$)carbonyl; and $Z_7$ and $Z_8$ are independently hydrogen, ($C_1$-$C_6$)alkyl, or ($C_1$-$C_6$)alkylcarbonyl.

In certain embodiments, the present invention provides uses for pharmaceutical compositions for preparing, or for the manufacture of, a medicament for reducing advanced glycated end products and/or lipid peroxidation including, but not limited to, oxidation of low-density lipoproteins in a patient, wherein the pharmaceutical composition comprises at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is phenyl, wherein the phenyl is optionally substituted with 1, 2, 3, 4, or 5 groups that are independently ($C_1$-$C_6$)alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, —$NZ_7Z_8$, or ($NZ_7Z_8$)carbonyl; and $Z_7$ and $Z_8$ are independently hydrogen, ($C_1$-$C_6$)alkyl, or ($C_1$-$C_6$)alkylcarbonyl.

In another aspect, the present invention provides uses for conjugates of Formula (I) for preparing, or for the manufacture of, a medicament for treating atherosclerosis, neuropathy, nephropathy, retinopathy, inflammatory disorders, Chronic Obstructive Pulmonary Disease, cardiovascular diseases, and metabolic disorders in a mammal or patient, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is phenyl, wherein the phenyl is optionally substituted with 1 or 2 groups that are independently halo($C_1$-$C_6$)alkyl or halogen.

In certain embodiments, the present invention provides uses for conjugates of Formula (I) for preparing, or for the manufacture of, a medicament for treating dyslipidemia, insulin resistance, elevated fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is phenyl, wherein the phenyl is optionally substituted with 1 or 2 groups that are independently halo($C_1$-$C_6$)alkyl or halogen.

In certain embodiments, the present invention provides uses for conjugates of Formula (I) for preparing, or for the manufacture of, a medicament for reducing advanced glycated end products and/or lipid peroxidation including, but not limited to, oxidation of low-density lipoproteins in a patient, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is phenyl, wherein the phenyl is optionally substituted with 1 or 2 groups that are independently halo($C_1$-$C_6$)alkyl or halogen.

In certain embodiments, the present invention provides uses for pharmaceutical compositions for preparing, or for the manufacture of, a medicament for treating dyslipidemia, insulin resistance, elevated fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein the pharmaceutical composition comprises at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is phenyl, wherein the phenyl is optionally substituted with 1 or 2 groups that are independently halo($C_1$-$C_6$)alkyl or halogen.

In certain embodiments, the present invention provides uses for pharmaceutical compositions for preparing, or for the manufacture of, a medicament for reducing advanced glycated end products and/or lipid peroxidation including, but not limited to, oxidation of low-density lipoproteins in a patient, wherein the pharmaceutical composition comprises at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, halo($C_1$-$C_6$)alkyl, or phenyl wherein the phenyl is optionally substituted with 1 or 2 halogens; $R_6$ is —$NZ_5Z_6$; $Z_5$ is hydrogen; $Z_6$ is phenyl, wherein the phenyl is optionally substituted with 1 or 2 groups that are independently halo($C_1$-$C_6$)alkyl or halogen.

In another aspect, the present invention provides uses for conjugates of Formula (I) for preparing, or for the manufacture of, a medicament for treating atherosclerosis, neuropathy, nephropathy, retinopathy, inflammatory disorders, Chronic Obstructive Pulmonary Disease, cardiovascular diseases, and metabolic disorders in a mammal or patient, wherein $R_1$ is hydrogen or acetyl; $R_2$, $R_3$, $R_4$, and $R_5$ are independently hydrogen, trifluoromethyl, or 2,4-difluorophenyl; $R_6$ is —$NZ_5Z_6$; $Z_5$ is hydrogen; $Z_6$ is phenyl, wherein the phenyl is optionally substituted with 1 or 2 groups that are independently trifluoromethyl or Cl.

In certain embodiments, the present invention provides uses for conjugates of Formula (I) for preparing, or for the manufacture of, a medicament for treating dyslipidemia, insulin resistance, elevated fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein $R_1$ is hydrogen or acetyl; $R_2$, $R_3$, $R_4$, and $R_5$ are independently hydrogen, trifluoromethyl, or 2,4-difluorophenyl; $R_6$ is —$NZ_5Z_6$; $Z_5$ is hydrogen; $Z_6$ is phenyl, wherein the phenyl is optionally substituted with 1 or 2 groups that are independently trifluoromethyl or Cl.

In certain embodiments, the present invention provides uses for conjugates of Formula (I) for preparing, or for the manufacture of, a medicament for reducing advanced glycated end products and/or lipid peroxidation including, but not limited to, oxidation of low-density lipoproteins in a patient, wherein $R_1$ is hydrogen or acetyl; $R_2$, $R_3$, $R_4$, and $R_5$ are independently hydrogen, trifluoromethyl, or 2,4-difluorophenyl; $R_6$ is —$NZ_5Z_6$; $Z_5$ is hydrogen; $Z_6$ is phenyl, wherein the phenyl is optionally substituted with 1 or 2 groups that are independently trifluoromethyl or Cl.

In certain embodiments, the present invention provides uses for pharmaceutical compositions for preparing, or for the manufacture of, a medicament for treating dyslipidemia, insulin resistance, elevated fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein the pharmaceutical composition comprises at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is —$NZ_5Z_6$; $Z_5$ is hydrogen; $Z_6$ is phenyl, wherein the phenyl is optionally substituted with 1 or 2 groups that are independently trifluoromethyl or Cl.

In certain embodiments, the present invention provides uses for pharmaceutical compositions for preparing, or for the manufacture of, a medicament for reducing advanced glycated end products and/or lipid peroxidation including, but not limited to, oxidation of low-density lipoproteins in a patient, wherein the pharmaceutical composition comprises at least one pharmaceutically acceptable carrier and a conjugate of Formula (I), or a pharmaceutically acceptable salt thereof, wherein $R_1$ is hydrogen or acetyl; $R_2$, $R_3$, $R_4$, and $R_5$ are independently hydrogen, trifluoromethyl, or 2,4-difluorophenyl; $R_6$ is —$NZ_5Z_6$; $Z_5$ is hydrogen; $Z_6$ is phenyl, wherein the phenyl is optionally substituted with 1 or 2 groups that are independently trifluoromethyl or Cl.

In another aspect, the present invention provides uses for conjugates of Formula (I) or Formula (IV) for preparing, or for the manufacture of, a medicament for treating atherosclerosis, neuropathy, nephropathy, retinopathy, inflammatory disorders, Chronic Obstructive Pulmonary Disease, cardiovascular diseases, and metabolic disorders in a mammal or patient, wherein the conjugate of Formula (I) or Formula (IV) is N-(3,5-bis(trifluoromethyl)phenyl)-5-chloro-2-hydroxybenzamide or 2-(3,5-bis(trifluoromethyl)phenylcarbamoyl)-4-chlorophenyl acetate.

In certain embodiments, the present invention provides uses for conjugates of Formula (I) or Formula (IV) for preparing, or for the manufacture of, a medicament for treating dyslipidemia, insulin resistance, elevated fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein the conjugate of Formula (I) or Formula (IV) is N-(3,5-bis(trifluoromethyl)phenyl)-5-chloro-2-hydroxybenzamide or 2-(3,5-bis(trifluoromethyl)phenylcarbamoyl)-4-chlorophenyl acetate.

In certain embodiments, the present invention provides uses for conjugates of Formula (I) or Formula (IV) for preparing, or for the manufacture of, a medicament for reducing advanced glycated end products and/or lipid peroxidation including, but not limited to, oxidation of low-density lipoproteins in a patient, wherein the conjugate of Formula (I) or Formula (IV) is N-(3,5-bis(trifluoromethyl)phenyl)-5-chloro-2-hydroxybenzamide or 2-(3,5-bis(trifluoromethyl)phenylcarbamoyl)-4-chlorophenyl acetate.

In certain embodiments, the present invention provides uses for pharmaceutical compositions for preparing, or for the manufacture of, a medicament for treating dyslipidemia, insulin resistance, elevated fatty acids, elevated triglycerides, β-cell dysfunction, hyperglycemia, metabolic syndrome, and any form of diabetes mellitus including type I and type II diabetes and Latent Autoimmune Diabetes of Adulthood, in a patient, wherein the pharmaceutical composition comprises at least one pharmaceutically acceptable carrier and a conjugate of Formula (I) or Formula (IV), or a pharmaceutically acceptable salt thereof, wherein the conjugate of Formula (I) or Formula (IV) is N-(3,5-bis(trifluoromethyl)phenyl)-5-chloro-2-hydroxybenzamide or 2-(3,5-bis(trifluoromethyl)phenylcarbamoyl)-4-chlorophenyl acetate.

In certain embodiments, the present invention provides uses for pharmaceutical compositions for preparing, or for the manufacture of, a medicament for reducing advanced glycated end products and/or lipid peroxidation including, but not limited to, oxidation of low-density lipoproteins in a patient, wherein the pharmaceutical composition comprises at least one pharmaceutically acceptable carrier and a conjugate of Formula (I) or Formula (IV), or a pharmaceutically acceptable salt thereof, wherein the conjugate of Formula (I) or Formula (IV) is N-(3,5-bis(trifluoromethyl)phenyl)-5-chloro-2-hydroxybenzamide or 2-(3,5-bis(trifluoromethyl)phenylcarbamoyl)-4-chlorophenyl acetate.

In another aspect, the present invention provides conjugates of Formula (I)

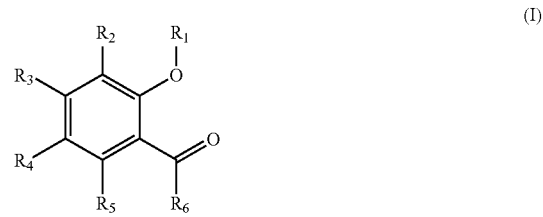

or a pharmaceutically acceptable salt thereof, wherein $R_1$ is hydrogen, $(C_1-C_6)$alkylcarbonyl, or A;

$R_2$, $R_3$, $R_4$, and $R_5$ are independently hydrogen, $(C_1-C_6)$alkoxy, $(C_1-C_6)$alkoxycarbonyl, $(C_1-C_6)$alkoxysulfonyl, $(C_1-C_6)$alkyl, $(C_1-C_6)$alkylcarbonyl, $(C_1-C_6)$alkylcarbonyloxy, $(C_1-C_6)$alkylsulfonyl, $(C_1-C_6)$alkylthio, carboxy, cyano, formyl, halo$(C_1-C_6)$alkoxy, halo$(C_1-C_6)$alkyl, halogen, hydroxy, hydroxy$(C_1-C_6)$alkyl, mercapto, nitro, phenyl, —$NZ_1Z_2$, or $(NZ_1Z_2)$carbonyl, wherein the phenyl is optionally substituted with 1, 2, 3, 4, or 5 groups that are independently $C_1-C_6$)alkoxy, $(C_1-C_6)$alkoxycarbonyl, $(C_1-C_6)$alkoxysulfonyl, $(C_1-C_6)$alkyl, $(C_1-C_6)$alkylcarbonyl, $(C_1-C_6)$alkylcarbonyloxy, $(C_1-C_6)$alkylsulfonyl, $(C_1-C_6)$alkylthio, carboxy, cyano, formyl, halo$(C_1-C_6)$alkoxy, halo$(C_1-C_6)$alkyl, halogen, hydroxy, hydroxy$(C_1-C_6)$alkyl, mercapto, nitro, phenyl, —$NZ_3Z_4$, $(NZ_3Z_4)$carbonyl;

$Z_1$, $Z_2$, $Z_3$, and $Z_4$ are independently hydrogen, $(C_1-C_6)$alkyl, or $(C_1-C_6)$alkylcarbonyl;

$R_6$ is hydroxy, —$NZ_5Z_6$,

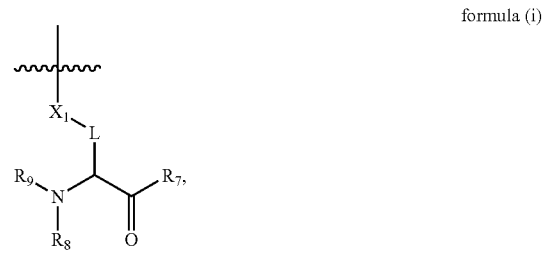

formula (i)

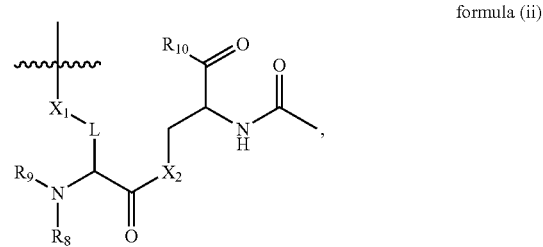

formula (ii)

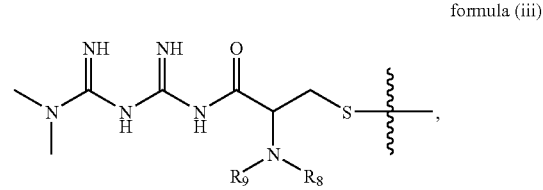

formula (iii)

41
-continued

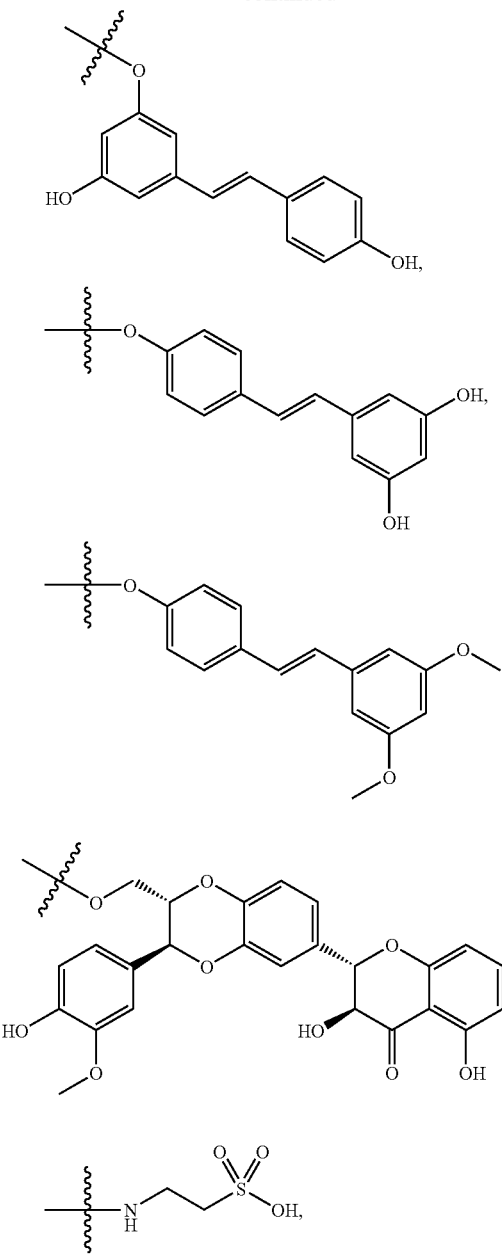

42
-continued

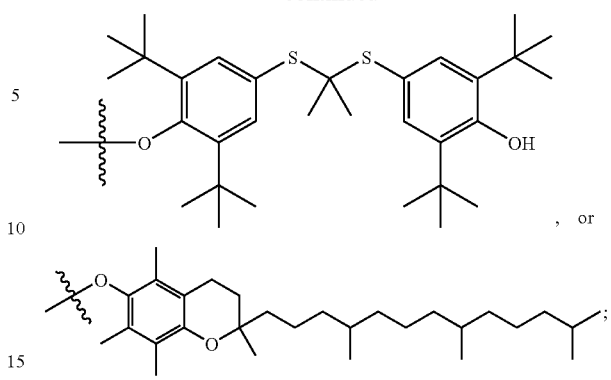
, or

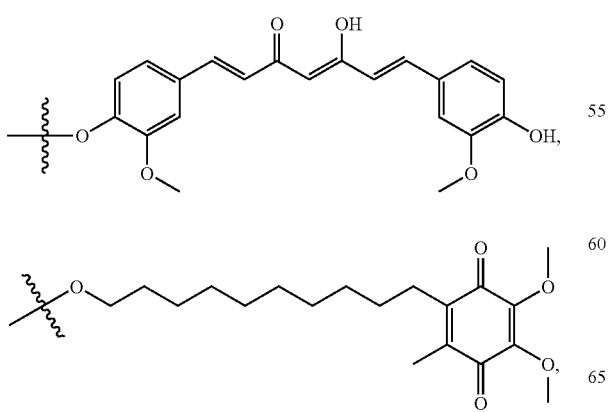
;

provided that when $R_6$ is hydroxy, then $R_1$ is A;

$Z_5$ and $Z_6$ are independently hydrogen, $(C_1-C_6)$alkyl, $(C_1-C_6)$alkylcarbonyl, phenyl, phenyl$(CH_2)$—, or phenyl $(CH_2)_2$—, wherein the phenyl is optionally substituted with 1, 2, 3, 4, or 5 groups that are independently $(C_1-C_6)$alkoxy, $(C_1-C_6)$alkoxycarbonyl, $(C_1-C_6)$alkoxysulfonyl, $(C_1-C_6)$alkyl, $(C_1-C_6)$alkylcarbonyl, $(C_1-C_6)$alkylcarbonyloxy, $(C_1-C_6)$alkylsulfonyl, $(C_1-C_6)$alkylthio, carboxy, cyano, formyl, halo$(C_1-C_6)$alkoxy, halo$(C_1-C_6)$alkyl, halogen, hydroxy, hydroxy$(C_1-C_6)$alkyl, mercapto, nitro, phenyl, —$NZ_7Z_8$, or $(NZ_7Z_8)$carbonyl;

$Z_7$ and $Z_8$ are independently hydrogen, $(C_1-C_6)$alkyl, or $(C_1-C_6)$alkylcarbonyl;

$R_7$ is $(C_1-C_6)$alkoxy, $(C_1-C_6)$alkyl, $(C_1-C_6)$alkylthio, hydroxy, —$NZ_9Z_{10}$, or —O-phenyl, wherein the phenyl is optionally substituted with 1, 2, 3, 4, or 5 groups that are independently $(C_1-C_6)$alkoxy, $(C_1-C_6)$alkoxycarbonyl, $(C_1-C_6)$alkyl, $(C_1-C_6)$alkylcarbonyl, $(C_1-C_6)$alkylcarbonyloxy, carboxy, cyano, formyl, halo$(C_1-C_6)$alkoxy, halo$(C_1-C_6)$alkyl, halogen, hydroxy, or hydroxy$(C_1-C_6)$alkyl;

$R_8$ is hydrogen or $(C_1-C_6)$alkyl;

$R_9$ is hydrogen, $(C_1-C_6)$alkyl, or $(C_1-C_6)$alkylcarbonyl;

$R_{10}$ is $(C_1-C_6)$alkoxy, $(C_1-C_6)$alkyl, $(C_1-C_6)$alkylthio, hydroxy, or —$NZ_9Z_{10}$;

$Z_9$ and $Z_{10}$ are independently hydrogen, $(C_1-C_6)$alkyl, or $(C_1-C_6)$alkylcarbonyl;

$X_1$ and $X_2$ are independently O or S;

L is $(C_1-C_6)$alkylene;

A is

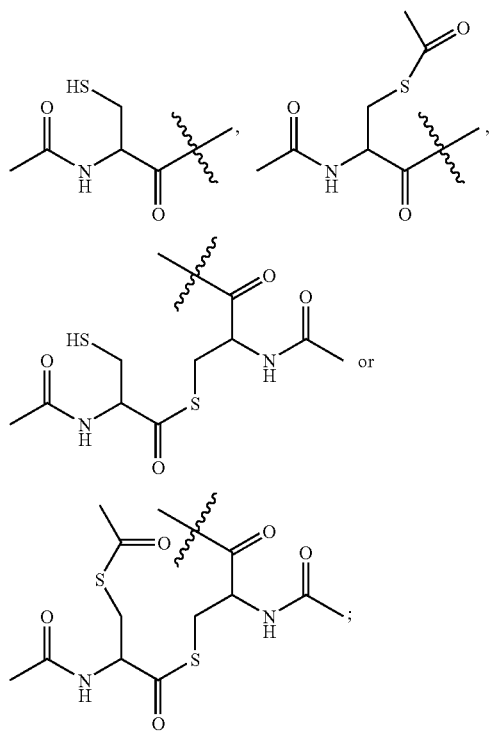

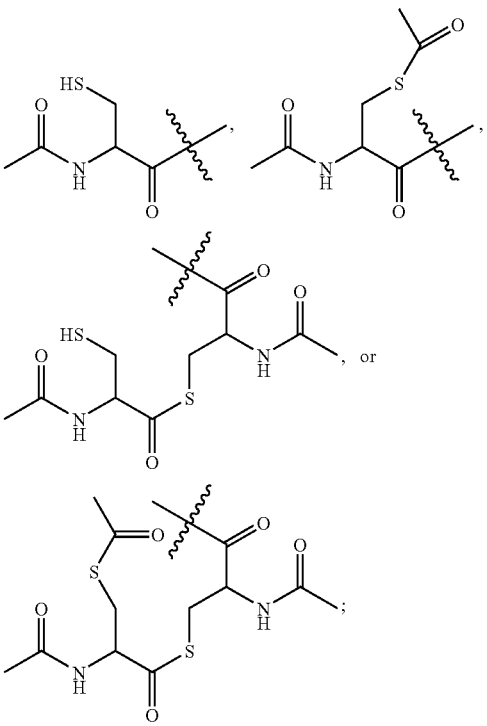

$R_{1a}$ is hydrogen, $(C_1-C_6)$alkylcarbonyl, or B;

$R_{2a}$, $R_{3a}$, $R_{4a}$, and $R_{5a}$ are independently hydrogen, $(C_1-C_6)$alkoxy, $(C_1-C_6)$alkoxycarbonyl, $(C_1-C_6)$alkoxysulfonyl, $(C_1-C_6)$alkyl, $(C_1-C_6)$alkylcarbonyl, $(C_1-C_6)$alkylcarbonyloxy, $(C_1-C_6)$alkylsulfonyl, $(C_1-C_6)$alkylthio, carboxy, cyano, formyl, halo$(C_1-C_6)$alkoxy, halo$(C_1-C_6)$alkyl, halogen, hydroxy, hydroxy$(C_1-C_6)$alkyl, mercapto, nitro, phenyl, —$NZ_{1a}Z_{2a}$, or $(NZ_{1a}Z_{2a})$carbonyl, wherein the phenyl is optionally substituted with 1, 2, 3, 4, or 5 groups that are independently $C_1-C_6$alkoxy, $(C_1-C_6)$alkoxycarbonyl, $(C_1-C_6)$alkoxysulfonyl, $(C_1-C_6)$alkyl, $(C_1-C_6)$alkylcarbonyl, $(C_1-C_6)$alkylcarbonyloxy, $(C_1-C_6)$alkylsulfonyl, $(C_1-C_6)$alkylthio, carboxy, cyano, formyl, halo$(C_1-C_6)$alkoxy, halo$(C_1-C_6)$alkyl, halogen, hydroxy, hydroxy$(C_1-C_6)$alkyl, mercapto, nitro, phenyl, —$NZ_{3a}Z_{4a}$, or $(NZ_{3a}Z_{4a})$carbonyl;

$Z_{1a}$, $Z_{2a}$, $Z_{3a}$, and $Z_{4a}$ are independently hydrogen, $(C_1-C_6)$alkyl, or $(C_1-C_6)$alkylcarbonyl;

B is

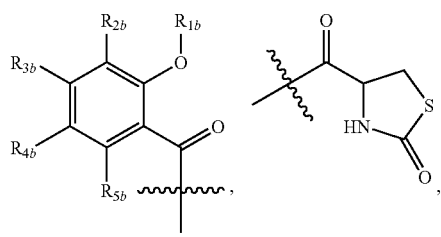

$R_{1b}$ is hydrogen, $(C_1-C_6)$alkylcarbonyl, or C;

$R_{2b}$, $R_{3b}$, $R_{4b}$, and $R_{5b}$ are independently hydrogen, $(C_1-C_6)$alkoxy, $(C_1-C_6)$alkoxycarbonyl, $(C_1-C_6)$alkoxysulfonyl, $(C_1-C_6)$alkyl, $(C_1-C_6)$alkylcarbonyl, $(C_1-C_6)$alkylcarbonyloxy, $(C_1-C_6)$alkylsulfonyl, $(C_1-C_6)$alkylthio, carboxy, cyano, formyl, halo$(C_1-C_6)$alkoxy, halo$(C_1-C_6)$alkyl, halogen, hydroxy, hydroxy$(C_1-C_6)$alkyl, mercapto, nitro, phenyl, —$NZ_{1b}Z_{2b}$, or $(NZ_{1b}Z_{2b})$carbonyl, wherein the phenyl is optionally substituted with 1, 2, 3, 4, or 5 groups that are independently $C_1-C_6$alkoxy, $(C_1-C_6)$alkoxycarbonyl, $(C_1-C_6)$alkoxysulfonyl, $(C_1-C_6)$alkyl, $(C_1-C_6)$alkylcarbonyl, $(C_1-C_6)$alkylcarbonyloxy, $(C_1-C_6)$alkylsulfonyl, $(C_1-C_6)$alkylthio, carboxy, cyano, formyl, halo$(C_1-C_6)$alkoxy, halo$(C_1-C_6)$alkyl, halogen, hydroxy, hydroxy$(C_1-C_6)$alkyl, mercapto, nitro, phenyl, —$NZ_{3b}Z_{4b}$, or $(NZ_{3b}Z_{4b})$carbonyl;

$Z_{1b}$, $Z_{2b}$, $Z_{3b}$, and $Z_{4b}$ are independently hydrogen, $(C_1-C_6)$alkyl, or $(C_1-C_6)$alkylcarbonyl; and C is

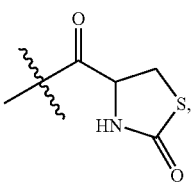

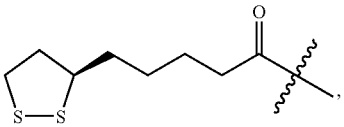

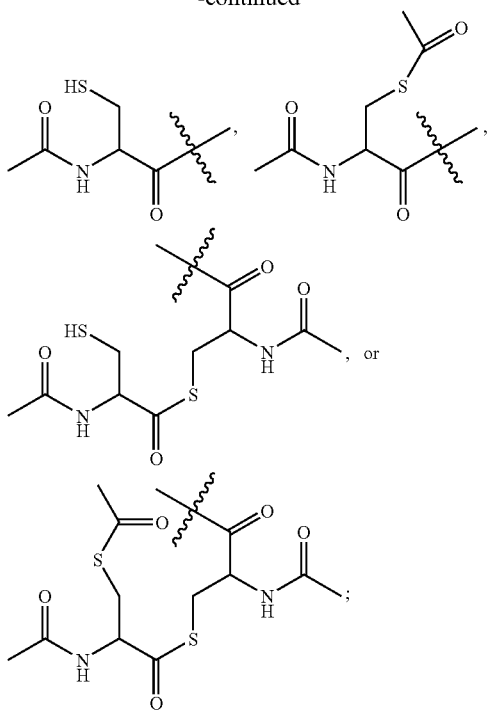

provided that Formula (I) does not encompass $R_1$ is hydrogen or acetyl; $R_2$, $R_3$, $R_4$, and $R_5$ are hydrogen; and $R_6$ is (L) N-acetylcysteine, (D) N-acetylcysteine, or (±) N-acetylcysteine; also provided that Formula (I) does not encompass N-acetyl-S-[(2',4'-difluoro-4-hydroxy[1,1'-biphenyl]-3-yl)carbonyl]-L-cysteine methyl ester; N-acetyl-S-[(2',4'-difluoro-4-hydroxy[1,1'-biphenyl]-3-yl)carbonyl]-L-cysteine ethyl ester; N-acetyl-S-[(2',4'-difluoro-4-acetyloxy[1,1'-biphenyl]-3-yl)carbonyl]-L-cysteine methyl ester; and N-acetyl-S-[(2',4'-difluoro-4-acetyloxy[1,1'-biphenyl]-3-yl)carbonyl]-L-cysteine ethyl ester.

In another aspect, the present invention provides conjugates of Formula (I) wherein $R_1$ is hydrogen or acetyl; $R_2$, $R_3$, $R_4$, and $R_5$ are independently hydrogen, halo($C_1$-$C_6$)alkyl, halogen, or phenyl, wherein the phenyl is optionally substituted with 1, 2, 3, 4, or 5 groups that are independently $C_1$-$C_6$alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, —$NZ_3Z_4$, or ($N_3Z_4$)carbonyl; $R_6$ is formula (i); $R_2$ is ($C_1$-$C_6$)alkoxy, ($C_1$-$C_6$)alkyl, ($C_1$-$C_6$)alkylthio, hydroxy, or —$NZ_9Z_{10}$; $R_8$ is hydrogen or ($C_1$-$C_6$)alkyl; $R_9$ is ($C_1$-$C_6$)alkylcarbonyl; $X_1$ is O or S; L is ($C_1$-$C_6$)alkylene; and $Z_3$, $Z_4$, $Z_9$, and $Z_{10}$ are independently hydrogen, ($C_1$-$C_6$)alkyl, or ($C_1$-$C_6$)alkylcarbonyl; provided that Formula (I) does not encompass $R_1$ is hydrogen or acetyl; $R_2$, $R_3$, $R_4$, and $R_5$ are hydrogen; and $R_6$ is (L) N-acetylcysteine, (D) N-acetylcysteine, or (±) N-acetylcysteine.

In another aspect, the present invention provides conjugates of Formula (I) wherein $R_1$ is hydrogen or acetyl; $R_2$, $R_3$, $R_4$, and $R_5$ are independently hydrogen or phenyl, wherein the phenyl is optionally substituted with 1 or 2 groups that are independently halo($C_1$-$C_6$)alkoxy, halo($C_1$-$C_6$)alkyl, or halogen; $R_6$ is formula (i); $R_2$ is ($C_1$-$C_6$)alkoxy or hydroxy; $R_8$ is hydrogen or ($C_1$-$C_6$)alkyl; $R_9$ is ($C_1$-$C_6$)alkylcarbonyl; $X_1$ is O or S; L is ($C_1$-$C_6$)alkylene; provided that Formula (I) does not encompass $R_1$ is hydrogen or acetyl; $R_2$, $R_3$, $R_4$, and $R_5$ are hydrogen; and $R_6$ is (L) N-acetylcysteine, (D) N-acetylcysteine, or (±) N-acetylcysteine.

In another aspect, the present invention provides conjugates of Formula (I) wherein $R_1$ is hydrogen or acetyl; $R_2$, $R_3$, $R_4$, and $R_5$ are independently hydrogen or phenyl, wherein the phenyl is optionally substituted with 1 or 2 halogen groups; $R_6$ is formula (i); $R_2$ is ethoxy, methoxy, or hydroxy; $R_8$ is hydrogen or methyl; $R_9$ is acetyl; $X_1$ is O or S; and L is $CH_2$; provided that Formula (I) does not encompass $R_1$ is hydrogen or acetyl; $R_2$, $R_3$, $R_4$, and $R_5$ are hydrogen; and $R_6$ is (L) N-acetylcysteine, (D) N-acetylcysteine, or (±) N-acetylcysteine.

In another aspect, the present invention provides conjugates of Formula (I) wherein $R_1$ is hydrogen or acetyl; one of $R_2$, $R_3$, $R_4$, and $R_5$ is 2,4-difluorophenyl and the rest are hydrogen; $R_6$ is formula (i); $R_2$ is hydroxy; $R_8$ is hydrogen; $R_9$ is acetyl; $X_1$ is S; and L is $CH_2$.

In another aspect, the present invention provides conjugates of Formula (I) wherein $R_1$ is hydrogen or acetyl; $R_2$, $R_3$, $R_4$, and $R_5$ are independently hydrogen, halo($C_1$-$C_6$)alkyl, or halogen; $R_6$ is formula (i); $R_7$ is ($C_1$-$C_6$)alkoxy, ($C_1$-$C_6$)alkyl, ($C_1$-$C_6$)alkylthio, hydroxy, or —$NZ_9Z_{10}$; $R_8$ is hydrogen or ($C_1$-$C_6$)alkyl; $R_9$ is ($C_1$-$C_6$)alkylcarbonyl; $X_1$ is O or S; L is ($C_1$-$C_6$)alkylene; and $Z_9$ and $Z_{10}$ are independently hydrogen, ($C_1$-$C_6$)alkyl, or ($C_1$-$C_6$)alkylcarbonyl; provided that Formula (I) does not encompass $R_1$ is hydrogen or acetyl; $R_2$, $R_3$, $R_4$, and $R_5$ are hydrogen; and $R_6$ is N-acetylcysteine, (D) N-acetylcysteine, or (±) N-acetylcysteine.

In another aspect, the present invention provides conjugates of Formula (I) wherein $R_1$ is hydrogen or acetyl; $R_2$, $R_3$, $R_4$, and $R_5$ are independently hydrogen or halo($C_1$-$C_6$)alkyl; $R_6$ is formula (i); $R_7$ is ($C_1$-$C_6$)alkoxy or hydroxy; $R_8$ is hydrogen or ($C_1$-$C_6$)alkyl; $R_9$ is ($C_1$-$C_6$)alkylcarbonyl; $X_1$ is O or S; and L is ($C_1$-$C_6$)alkylene; provided that Formula (I) does not encompass $R_1$ is hydrogen or acetyl; $R_2$, $R_3$, $R_4$, and $R_5$ are hydrogen; and $R_6$ is (L) N-acetylcysteine, (D) N-acetylcysteine, or (±) N-acetylcysteine.

In another aspect, the present invention provides conjugates of Formula (I) wherein $R_1$ is hydrogen or acetyl; $R_2$, $R_3$, $R_4$, and $R_5$ are independently hydrogen or trifluormethyl; $R_6$ is formula (i); $R_7$ is ethoxy, methoxy, or hydroxy; $R_8$ is hydrogen or methyl; $R_9$ is acetyl; $X_1$ is O or S; and L is $CH_2$; provided that Formula (I) does not encompass $R_1$ is hydrogen or acetyl; $R_2$, $R_3$, $R_4$, and $R_5$ are hydrogen; and $R_6$ is N-acetylcysteine, (D) N-acetylcysteine, or (±) N-acetylcysteine.

In another aspect, the present invention provides conjugates of Formula (I) wherein $R_1$ is hydrogen or acetyl; one of $R_2$, $R_3$, $R_4$, and $R_5$ is trifluormethyl and the rest are hydrogen; $R_6$ is formula (i); $R_7$ is hydroxy; $R_8$ is hydrogen; $R_9$ is acetyl; $X_1$ is S; and L is $CH_2$.

In another aspect, the present invention provides conjugates of Formula (I) wherein $R_1$ is hydrogen or acetyl; $R_2$, $R_3$, $R_4$, and $R_5$ are independently hydrogen, halo($C_1$-$C_6$)alkyl, or halogen; $R_6$ is —$NZ_5Z_6$; $Z_5$ is hydrogen; $Z_6$ is hydrogen, ($C_1$-$C_6$)alkyl, ($C_1$-$C_6$)alkylcarbonyl, phenyl, phenyl($CH_2$)—, or phenyl($CH_2$)$_2$—, wherein the phenyl is optionally substituted with 1, 2, 3, 4, or 5 groups that are independently ($C_1$-$C_6$)alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, —$NZ_7Z_8$, or ($NZ_7Z_8$)carbonyl; and $Z_7$ and $Z_8$ are independently hydrogen, ($C_1$-$C_6$)alkyl, or ($C_1$-$C_6$)alkylcarbonyl.

In another aspect, the present invention provides conjugates of Formula (I) wherein $R_1$ is hydrogen or acetyl; $R_2$, $R_3$, $R_4$, and $R_5$ are independently hydrogen, halo($C_1$-$C_6$)alkyl, or halogen; $R_6$ is —$NZ_5Z_6$; $Z_5$ is hydrogen; $Z_6$ is hydrogen, ($C_1$-$C_6$)alkyl, ($C_1$-$C_6$)alkylcarbonyl.

In another aspect, the present invention provides conjugates of Formula (I) wherein $R_1$ is hydrogen or acetyl; $R_2$, $R_3$, $R_4$, and $R_5$ are independently hydrogen, trifluoromethyl, or Cl; $R_6$ is —$NZ_5Z_6$; $Z_5$ is hydrogen; and $Z_6$ is hydrogen.

In another aspect, the present invention provides conjugates of Formula (I) wherein $R_1$ is hydrogen or acetyl; $R_2$, $R_3$, $R_4$, and $R_5$ are independently hydrogen, halo($C_1$-$C_6$)alkyl, or halogen; $R_6$ is —$NZ_5Z_6$; $Z_5$ is hydrogen; $Z_6$ is phenyl, wherein the phenyl is optionally substituted with 1, 2, 3, 4, or 5 groups that are independently ($C_1$-$C_6$)alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylcarbonyloxy, ($C_1$-$C_6$)alkylsulfonyl, ($C_1$-$C_6$)alkylthio, carboxy, cyano, formyl, halo($C_1$-$C_6$)alkoxy, halo($C_1$-$C_6$)alkyl, halogen, hydroxy, hydroxy($C_1$-$C_6$)alkyl, mercapto, nitro, phenyl, —$NZ_7Z_8$, or ($NZ_7Z_8$)carbonyl; and $Z_7$ and $Z_8$ are independently hydrogen, ($C_1$-$C_6$)alkyl, or ($C_1$-$C_6$)alkylcarbonyl.

In another aspect, the present invention provides conjugates of Formula (I) wherein $R_1$ is hydrogen or acetyl; $R_2$, $R_3$, $R_4$, and $R_5$ are independently hydrogen, halo($C_1$-$C_6$)alkyl, or halogen; $R_6$ is —$NZ_5Z_6$; $Z_5$ is hydrogen; $Z_6$ is phenyl, wherein the phenyl is optionally substituted with 1 or 2 groups that are independently halo($C_1$-$C_6$)alkyl or halogen.

In another aspect, the present invention provides conjugates of Formula (I) wherein $R_1$ is hydrogen or acetyl; $R_2$, $R_3$, $R_4$, and $R_5$ are independently hydrogen, trifluoromethyl, or Cl; $R_6$ is —$NZ_5Z_6$; $Z_5$ is hydrogen; $Z_6$ is phenyl, wherein the phenyl is optionally substituted with 1 or 2 groups that are independently trifluoromethyl or Cl.

Representative conjugates of Formula (I) include, but are not limited to, the compounds shown below, wherein $R_1$ is hydrogen or acetyl.

-continued
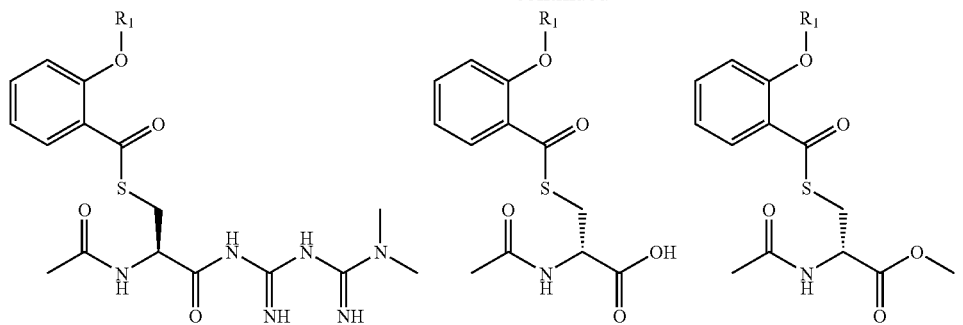
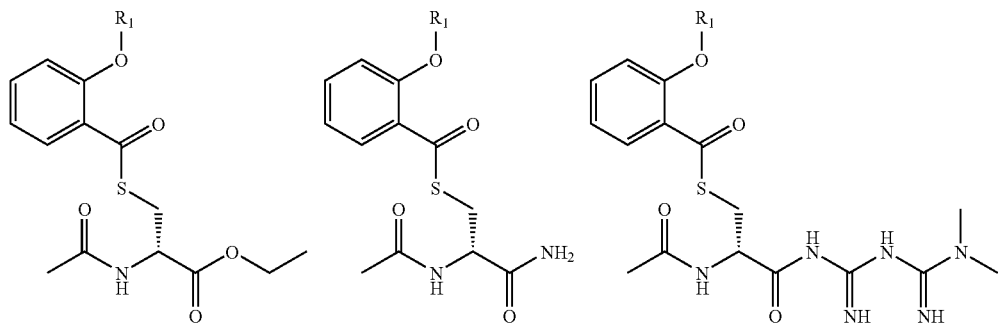
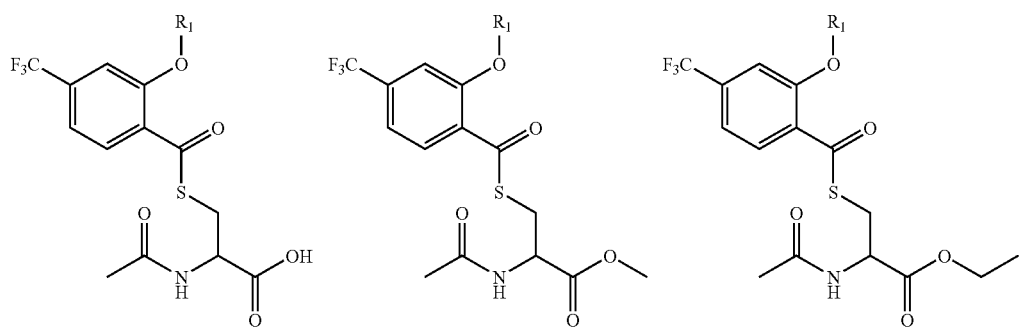
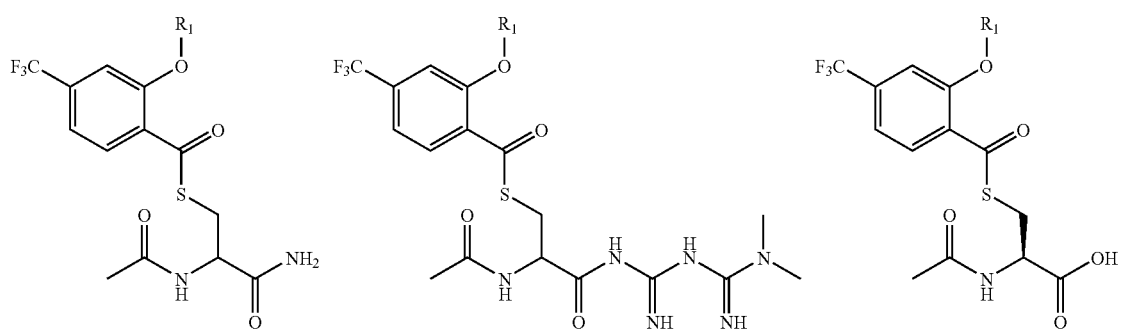
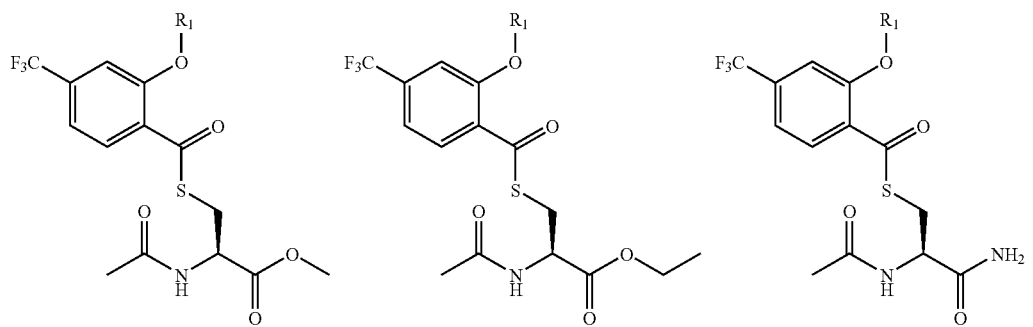

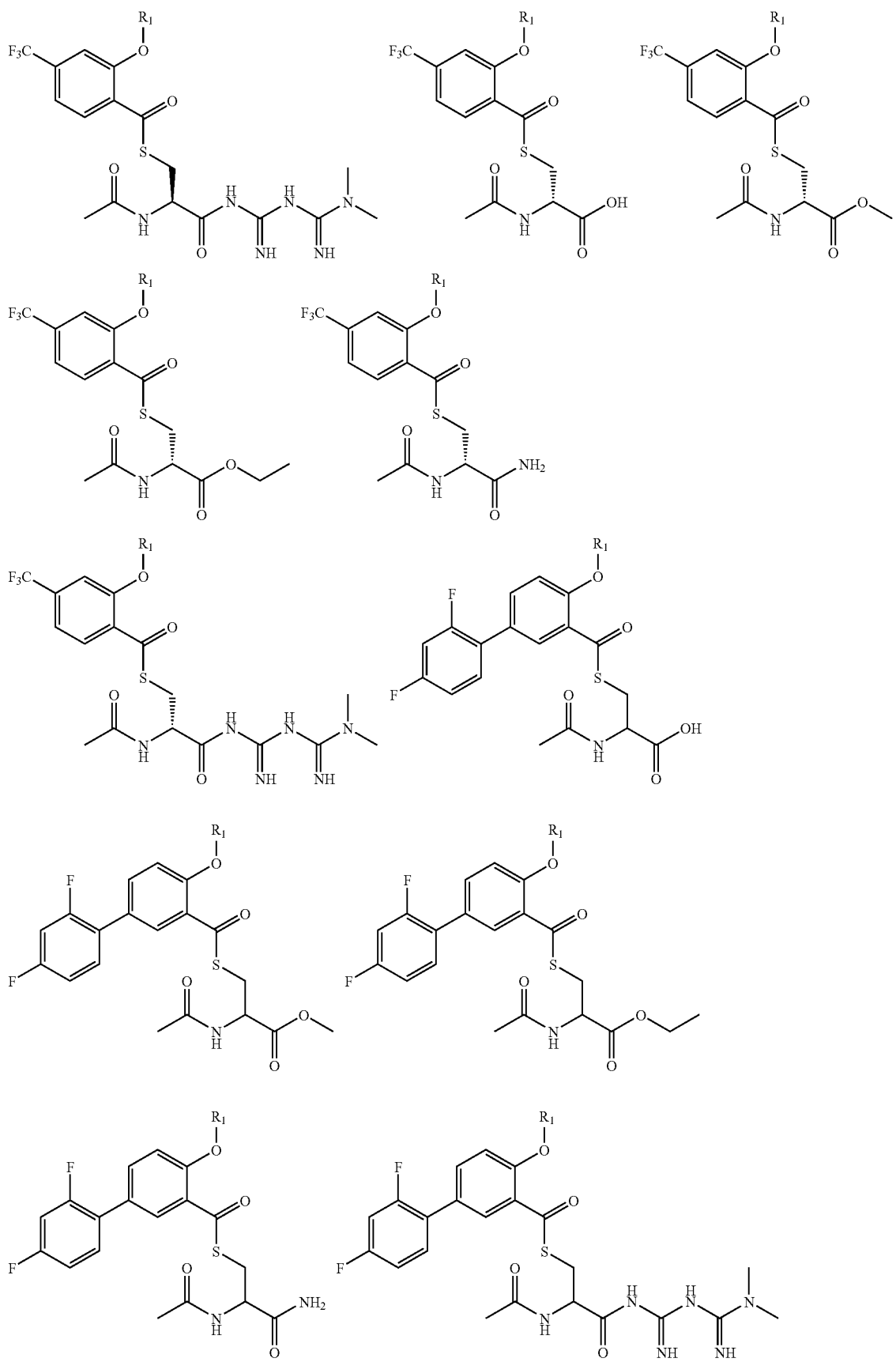

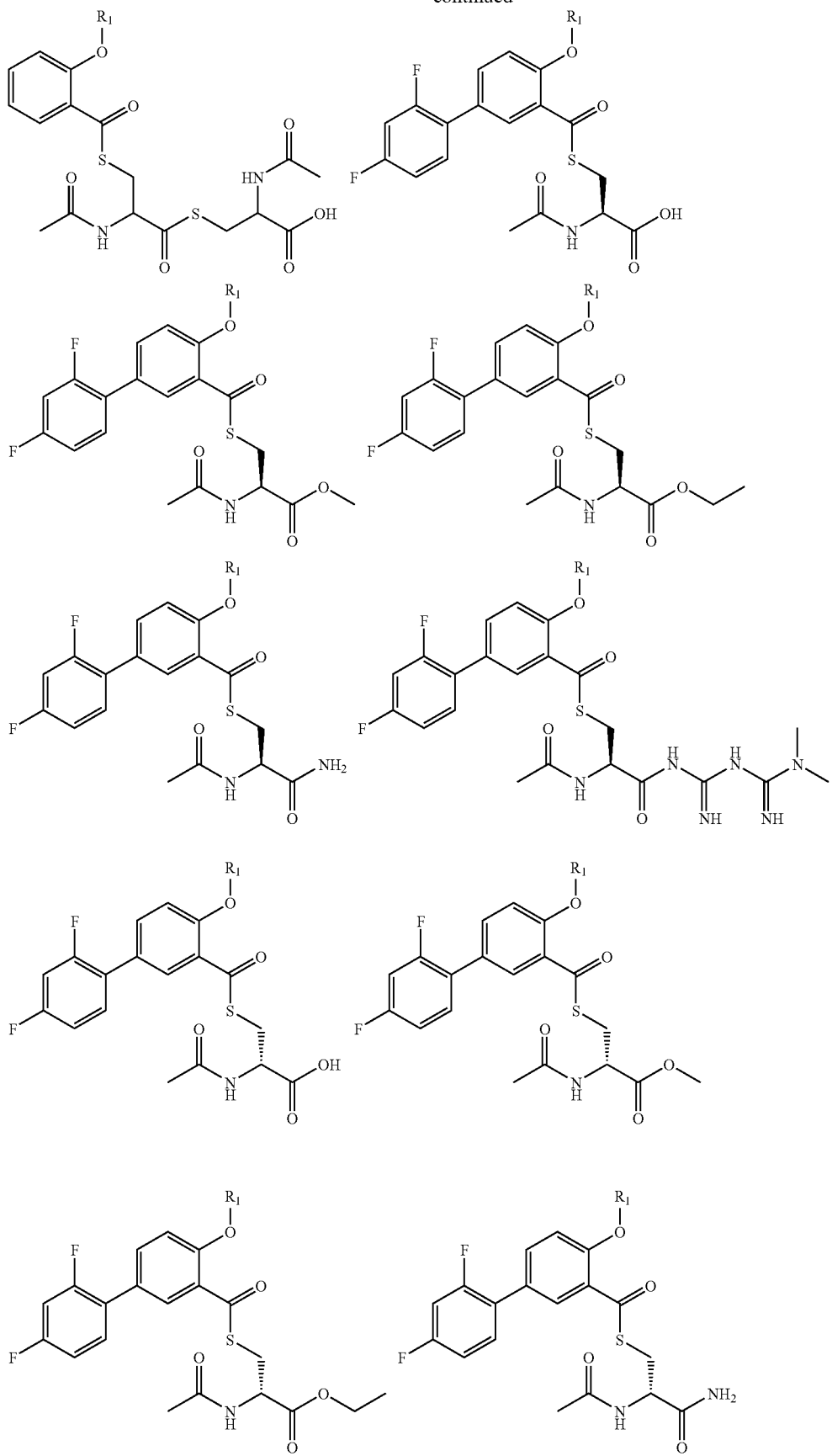

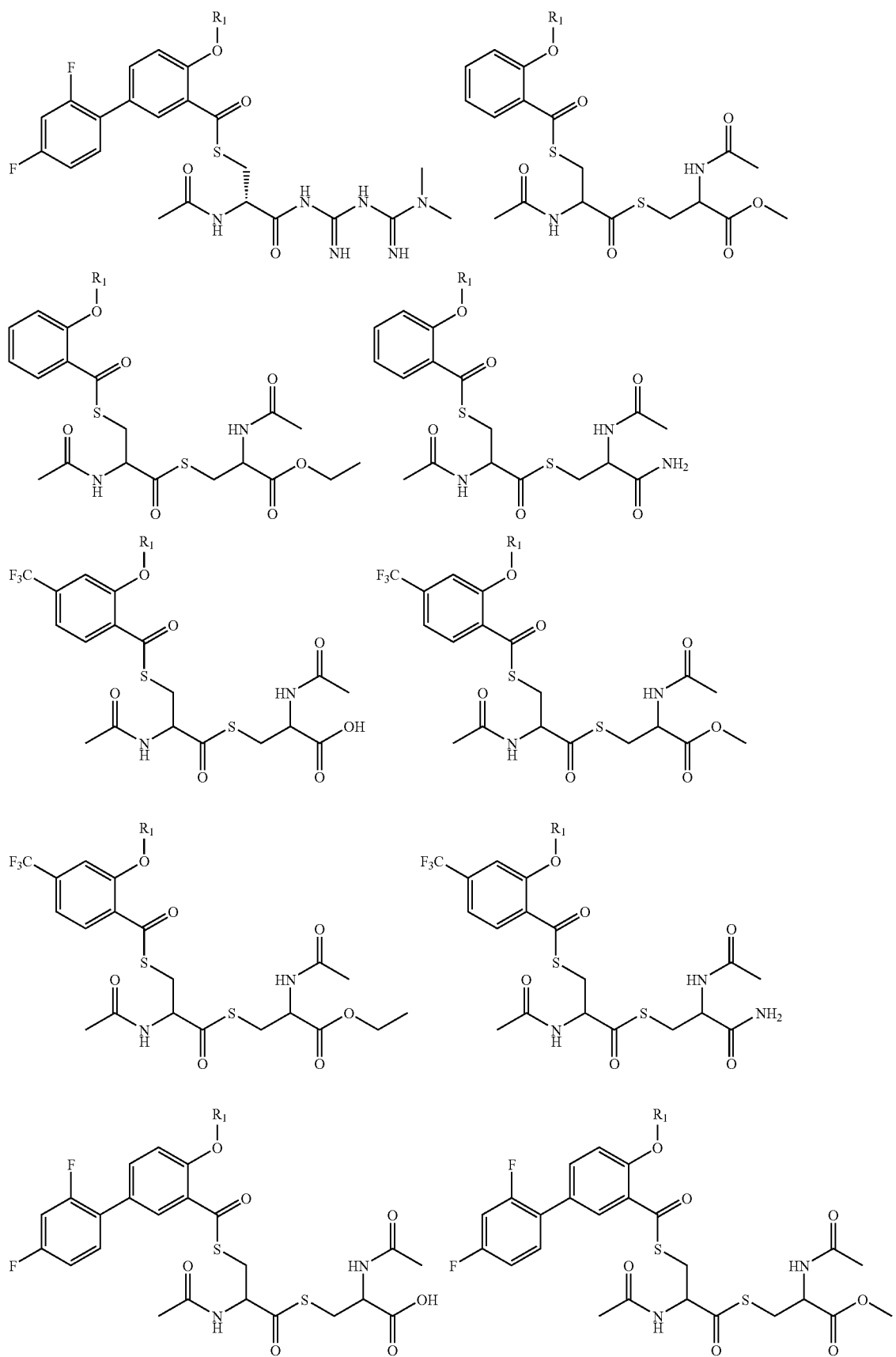

-continued
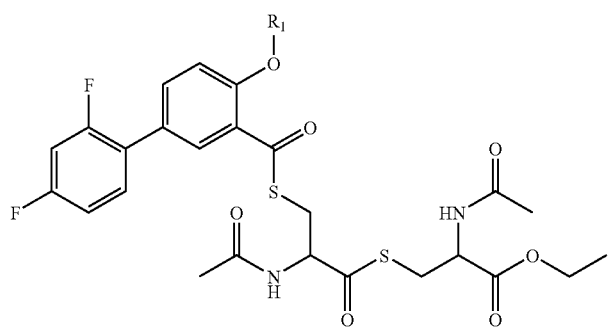
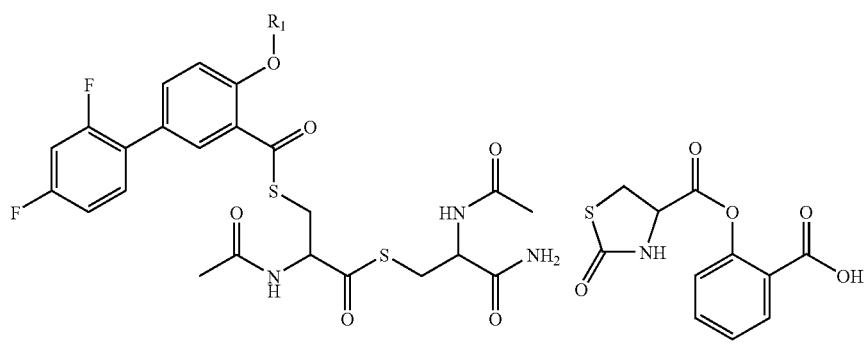
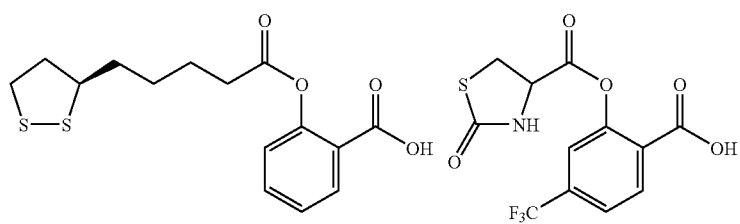
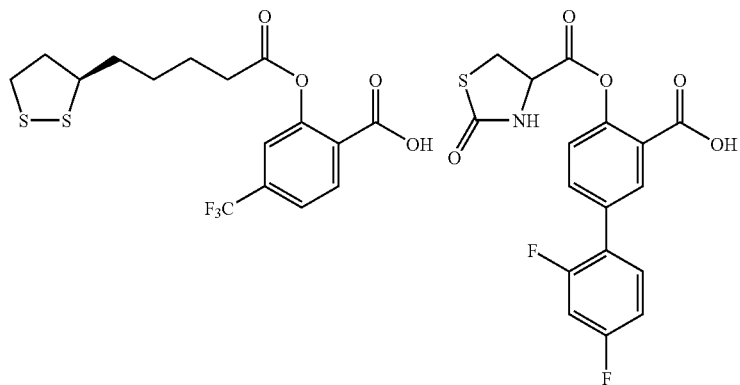
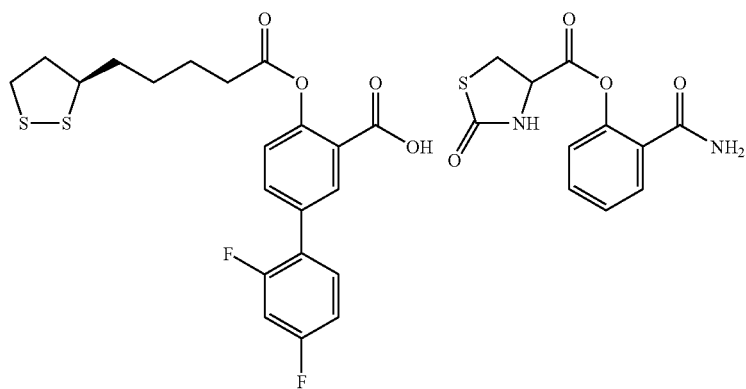

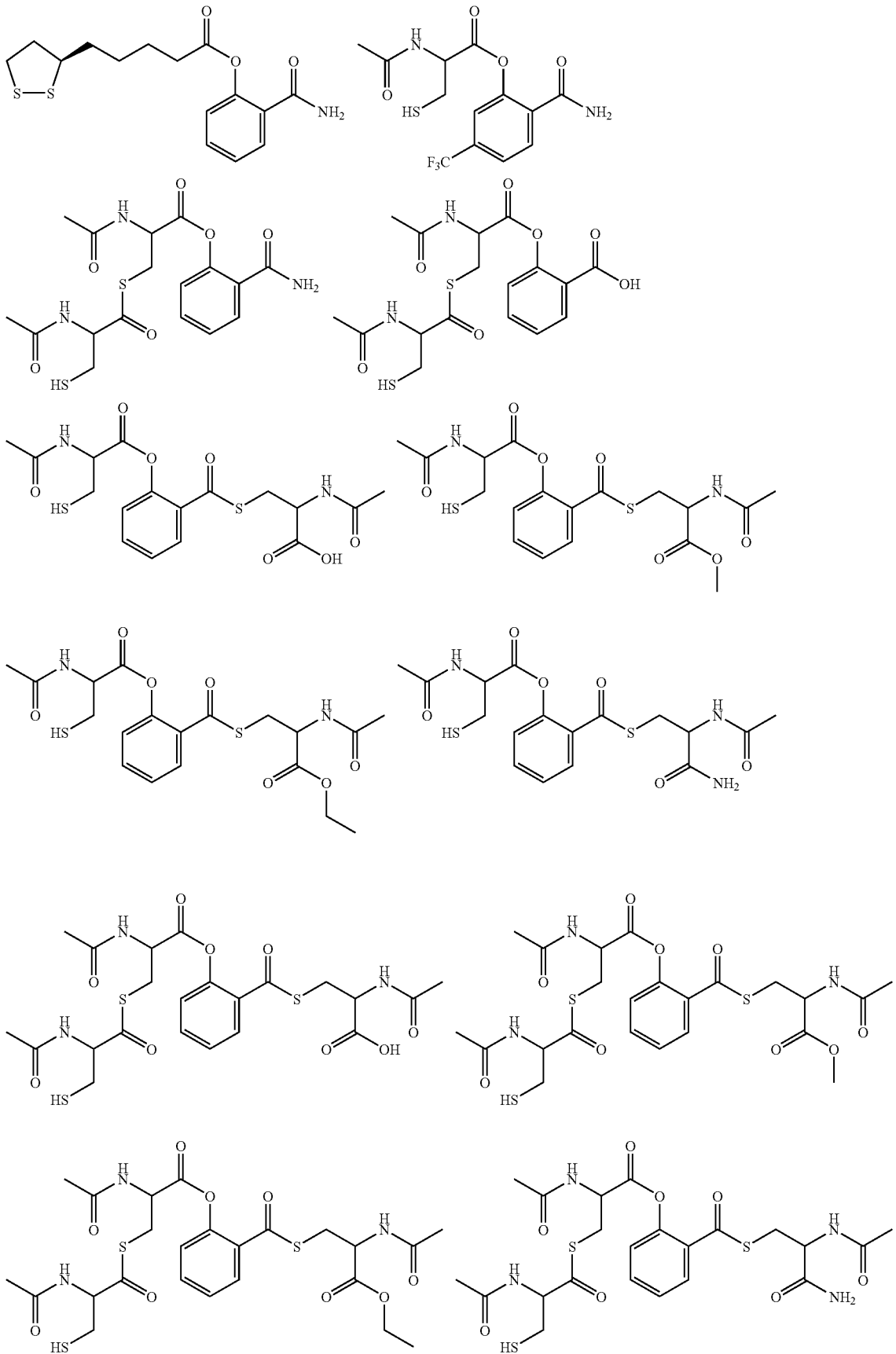

61
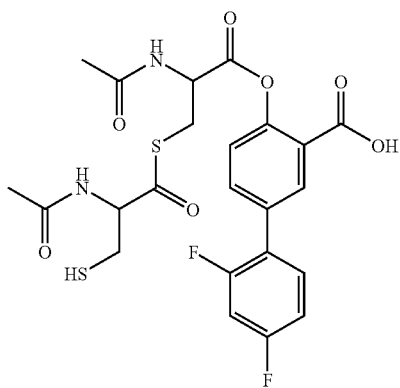
62
-continued
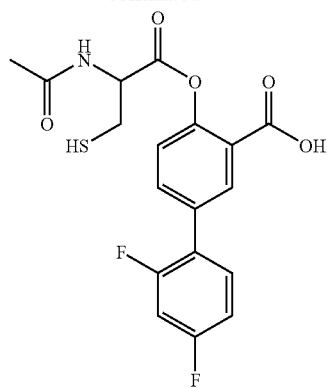
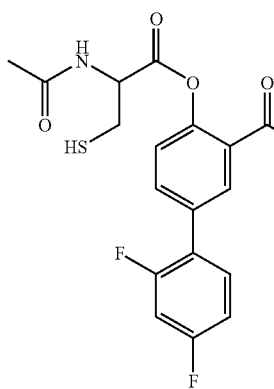
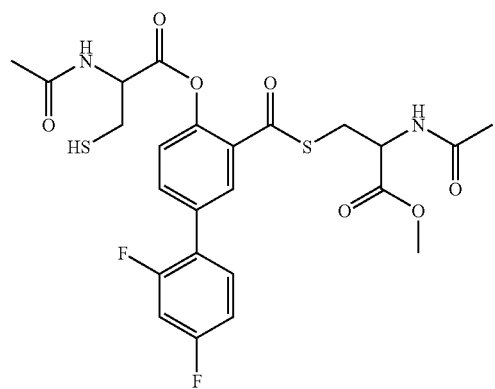
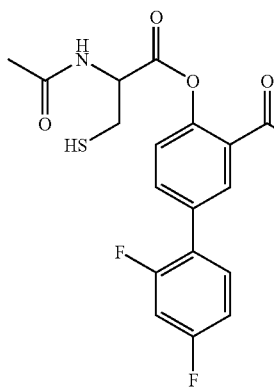
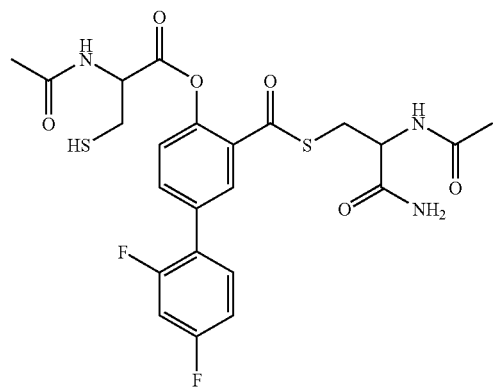
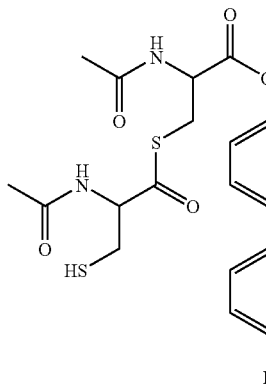
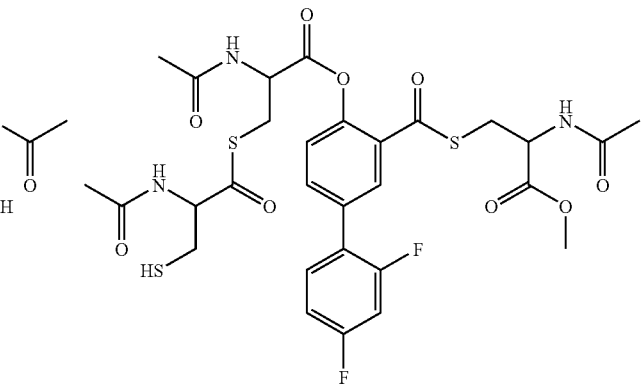

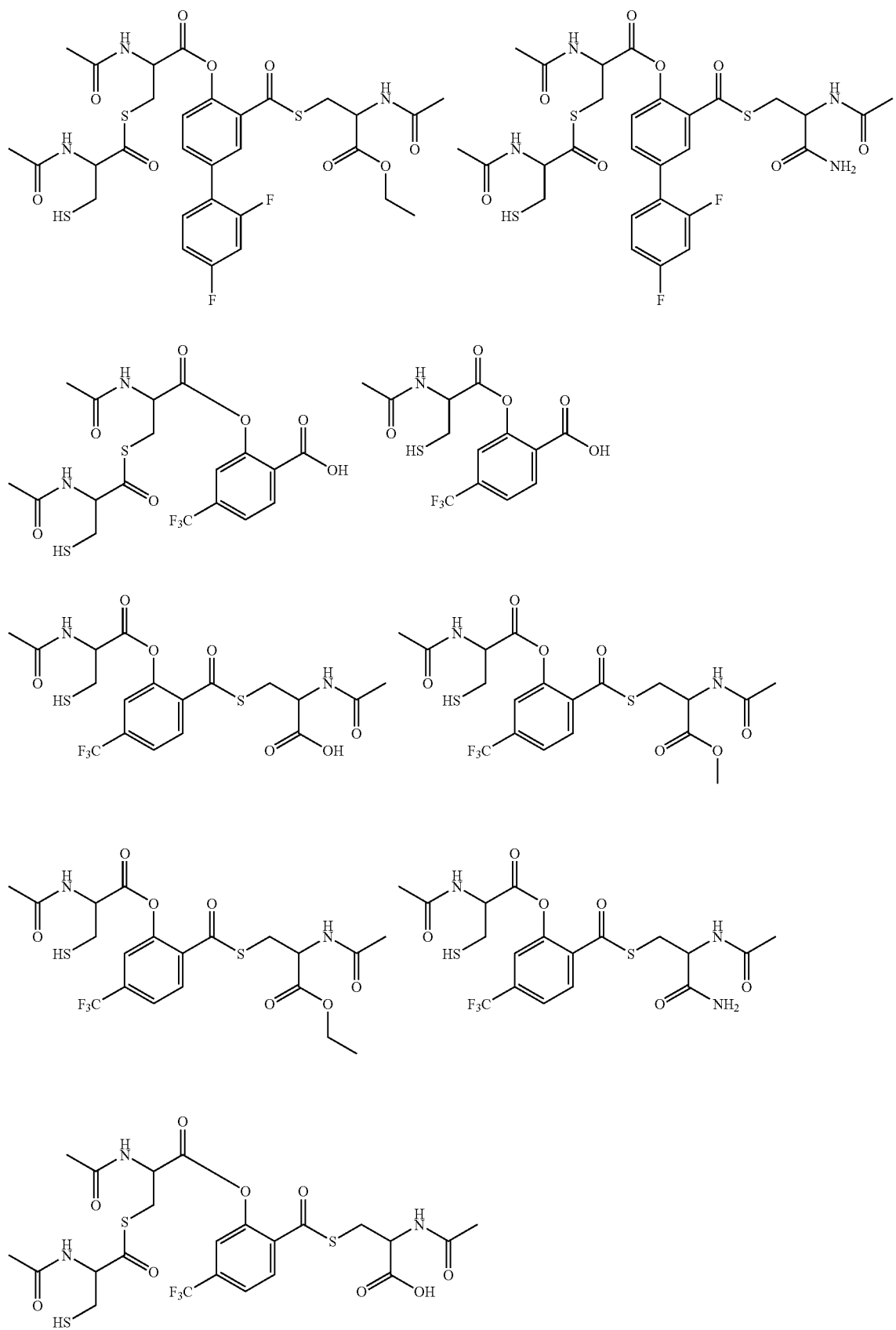

-continued
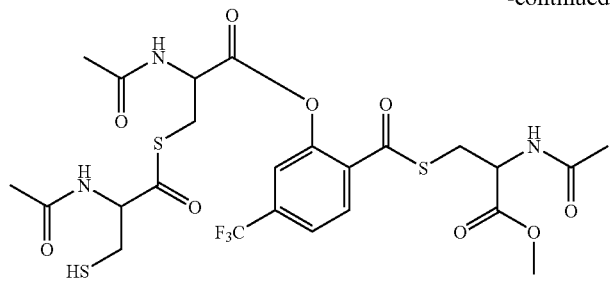
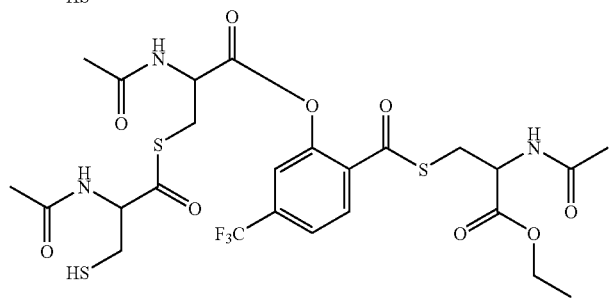
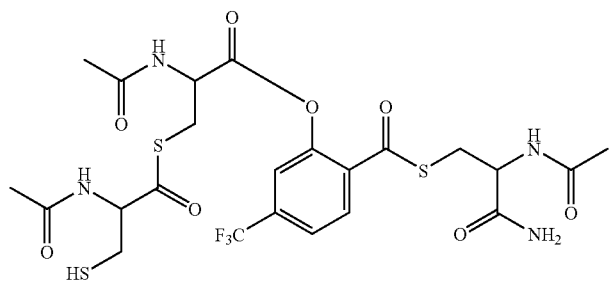
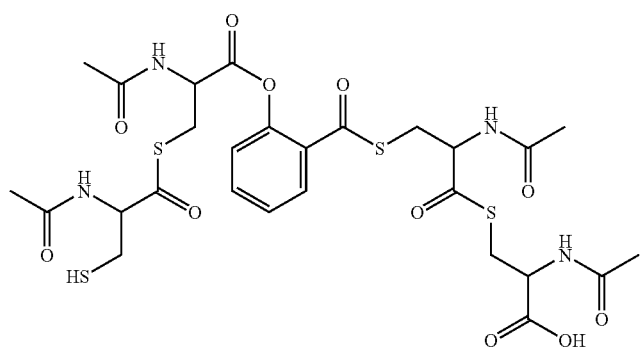
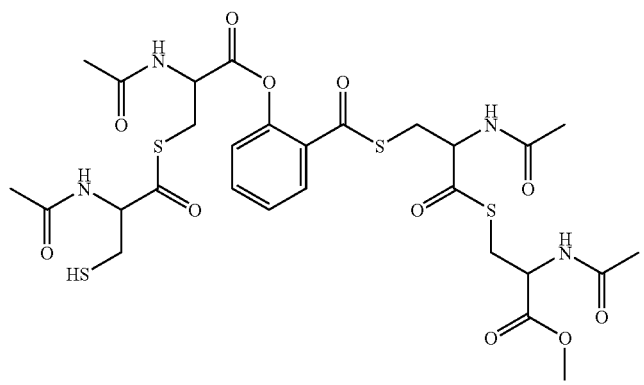

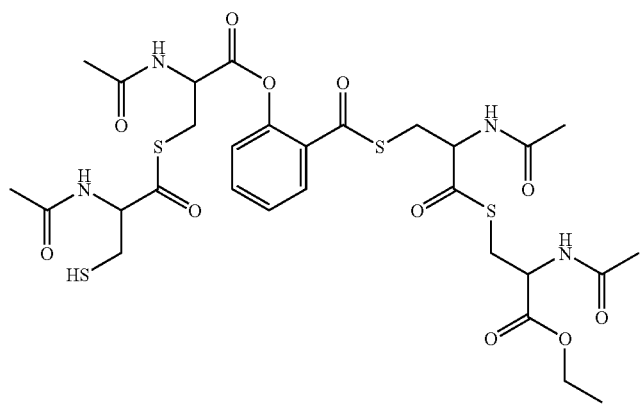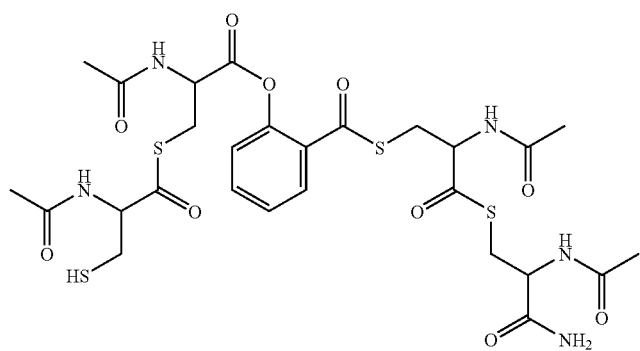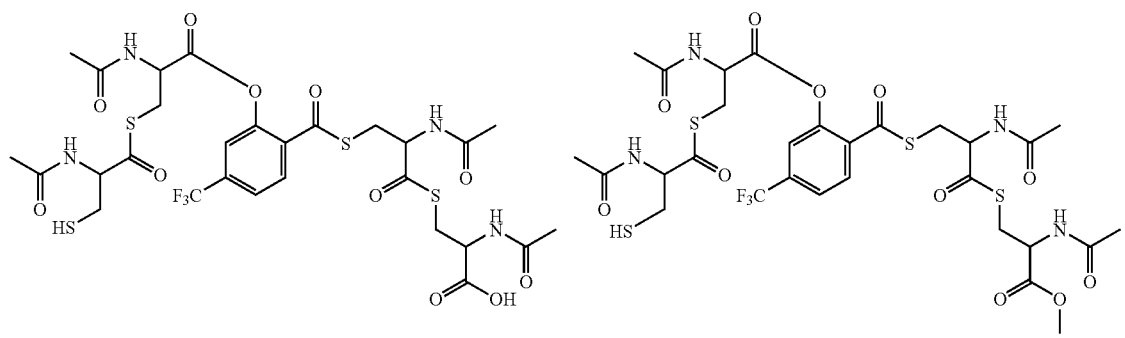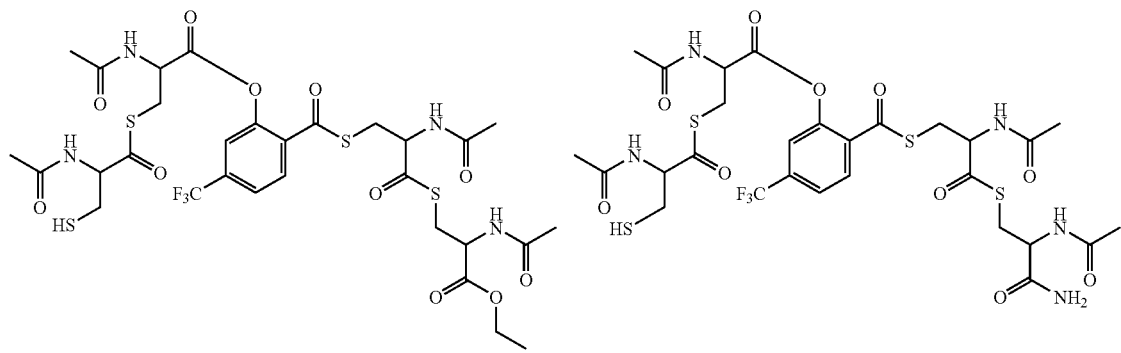

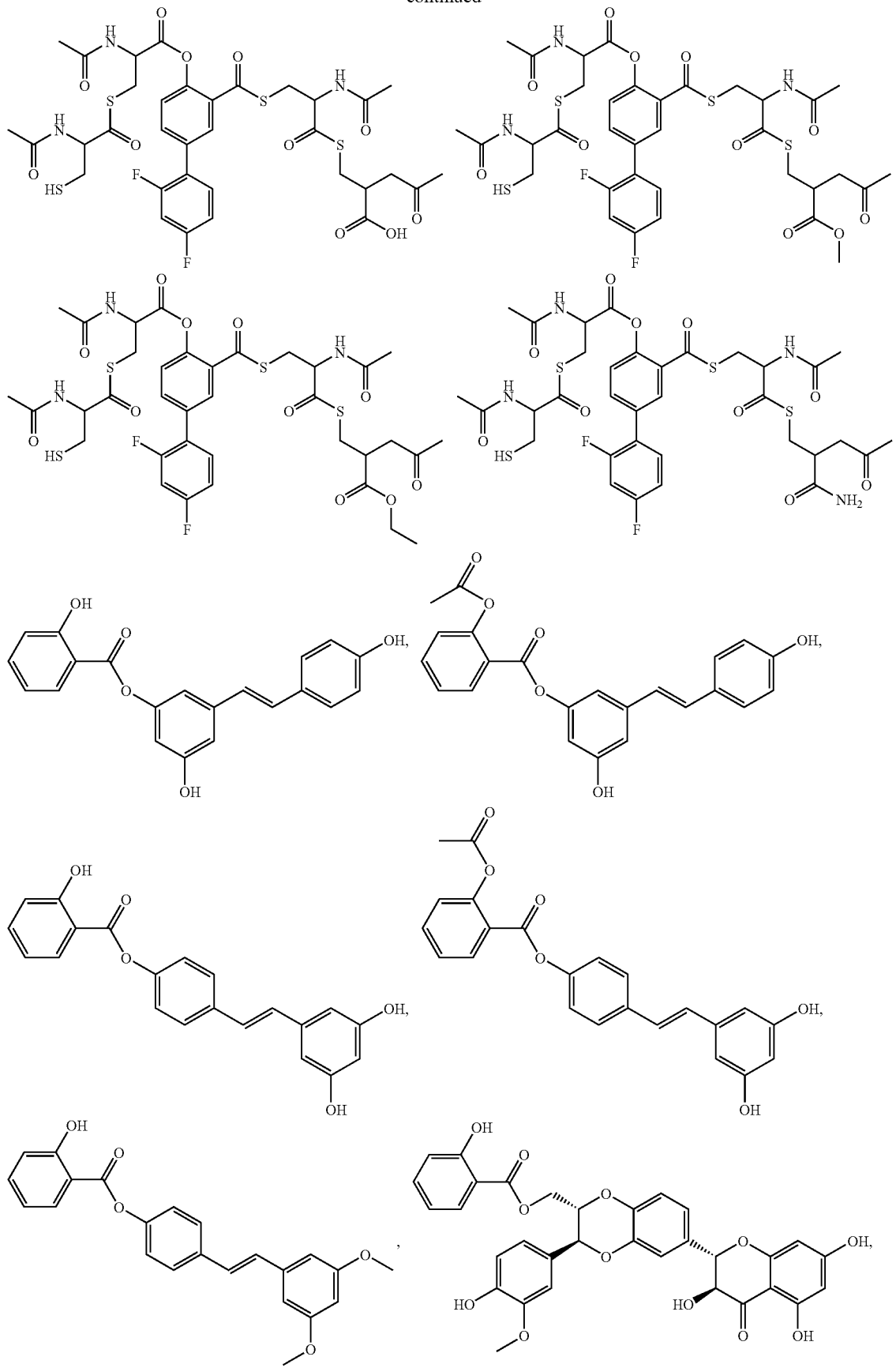

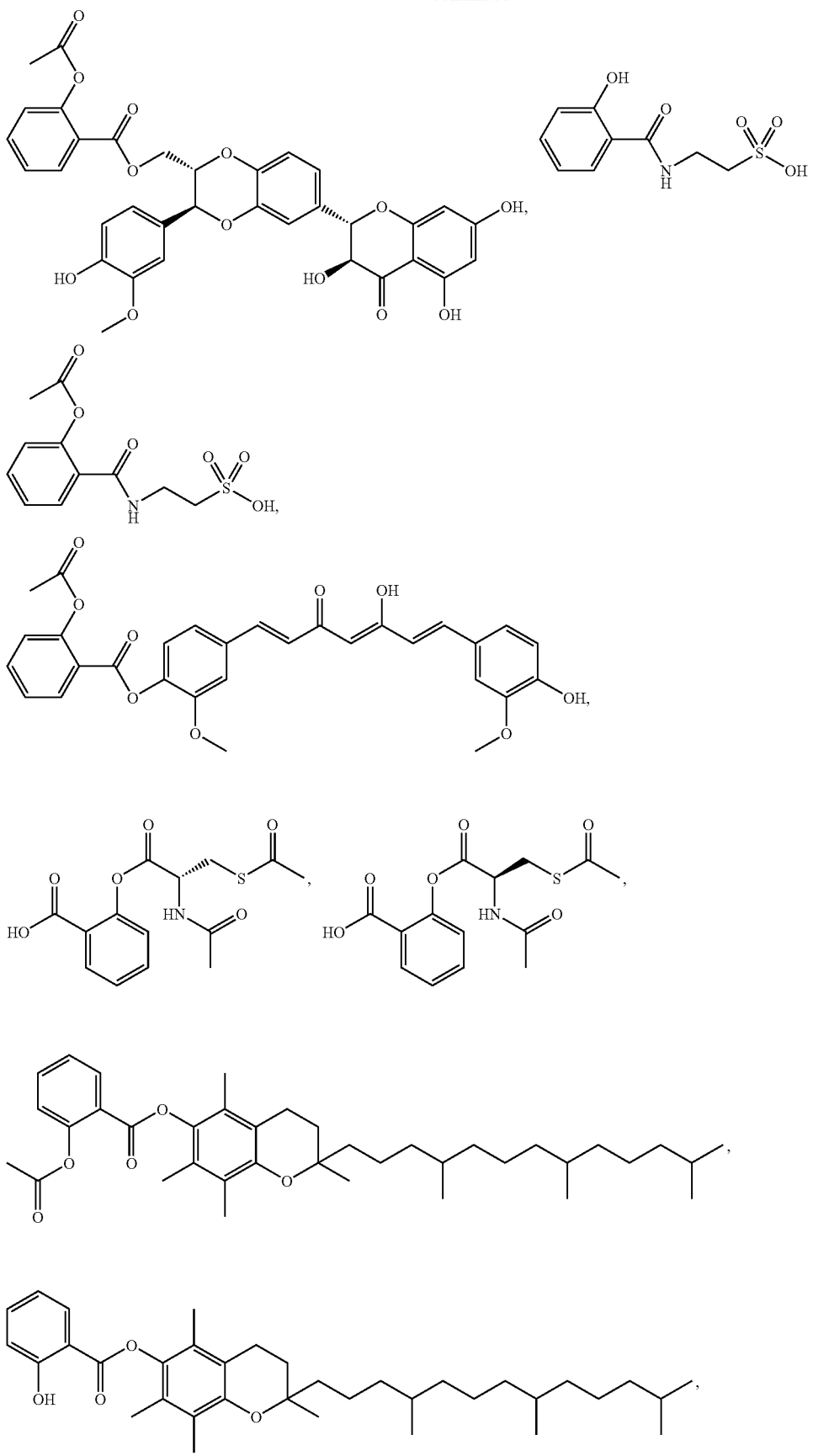

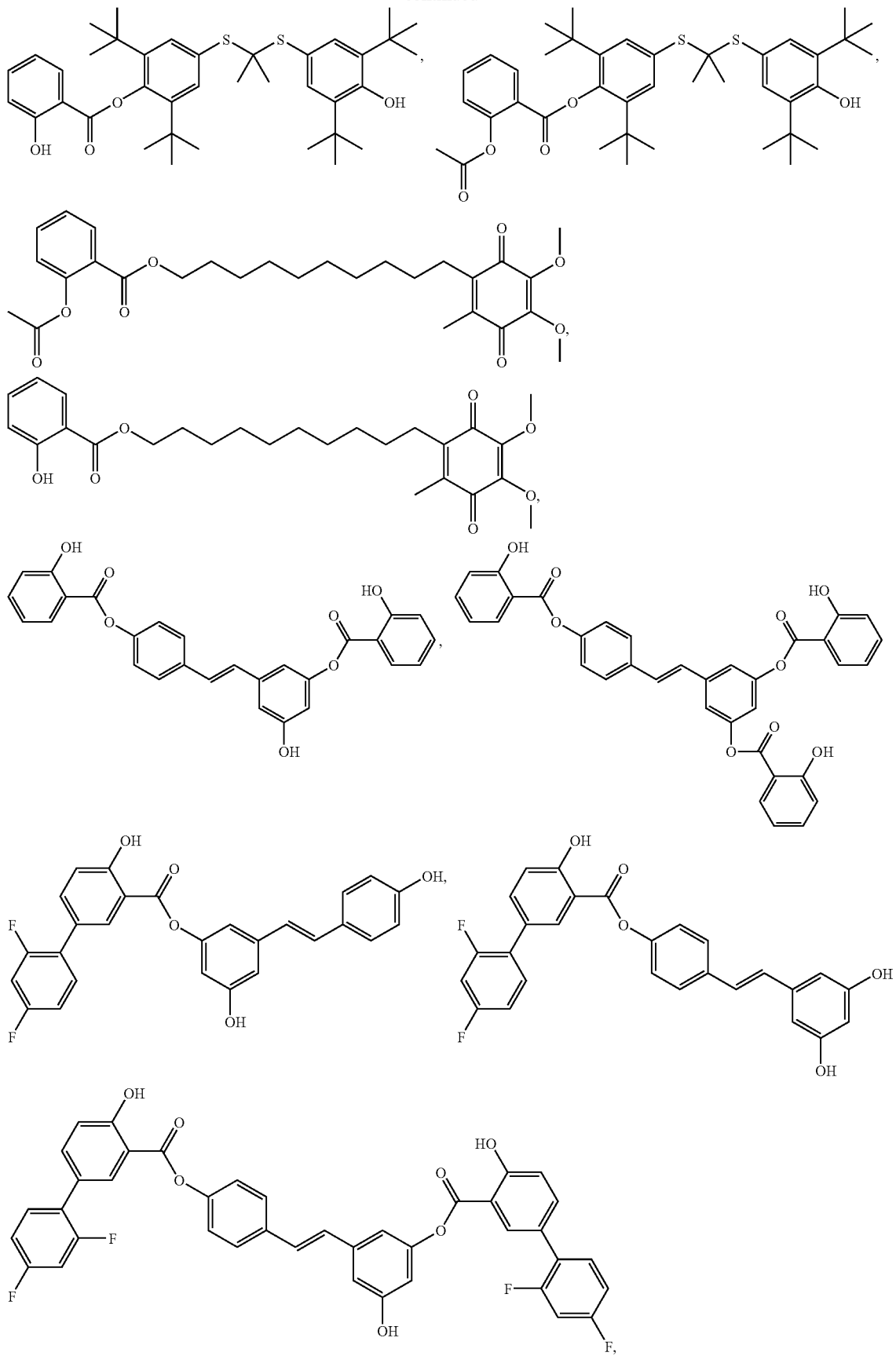

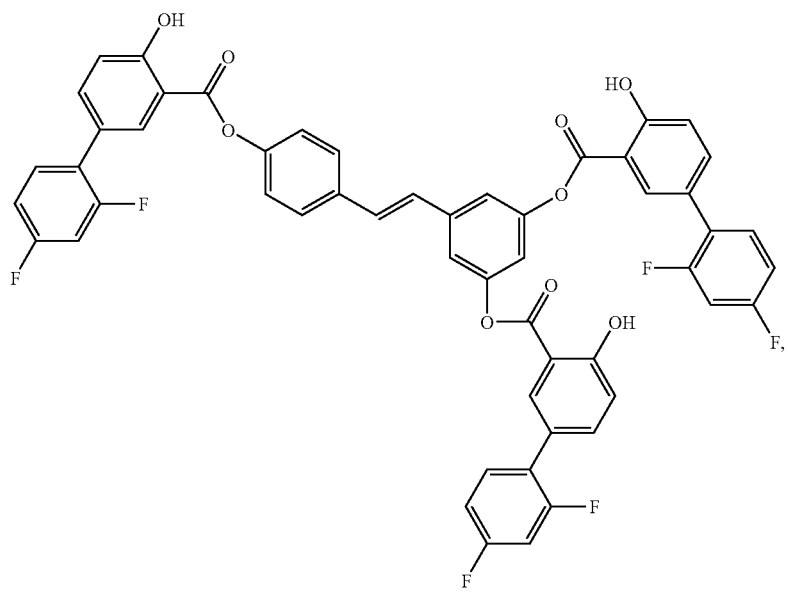
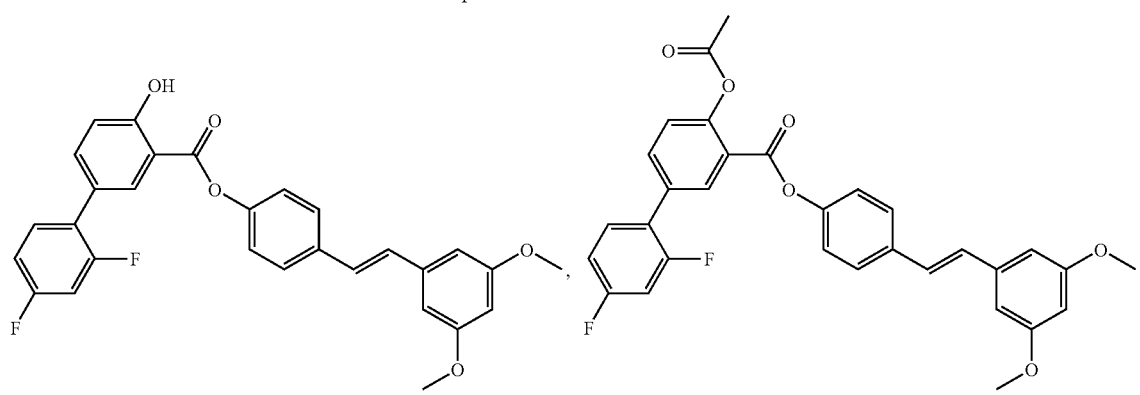
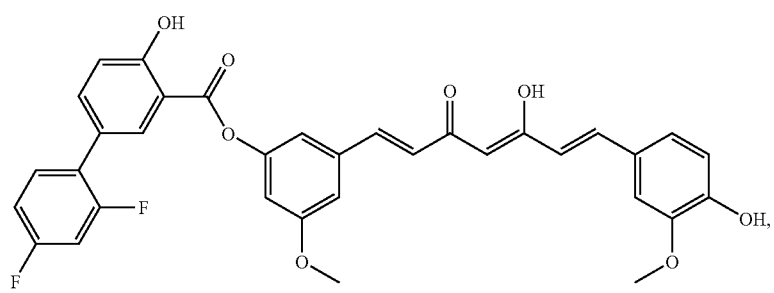
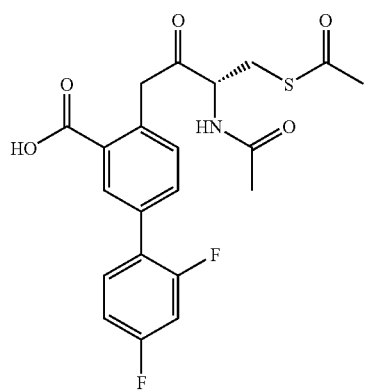

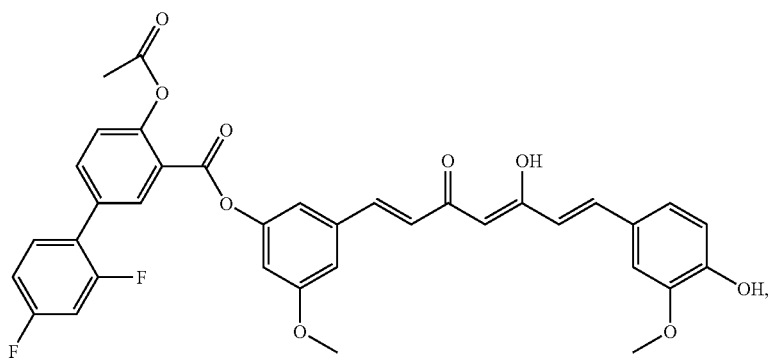
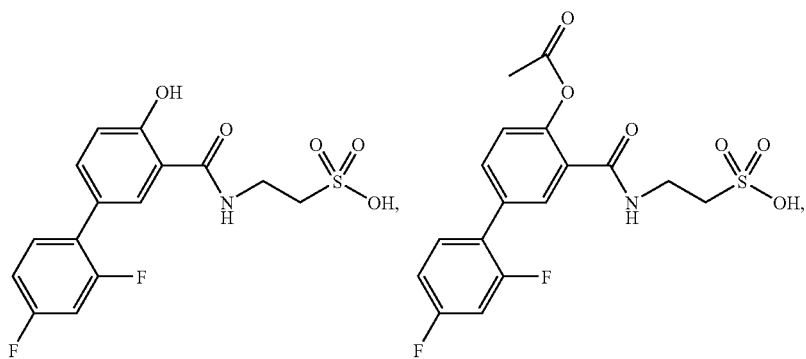
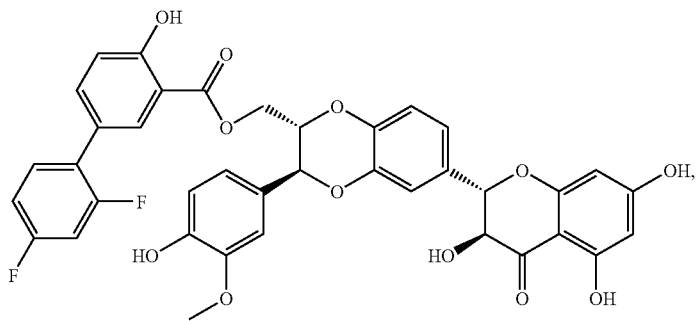
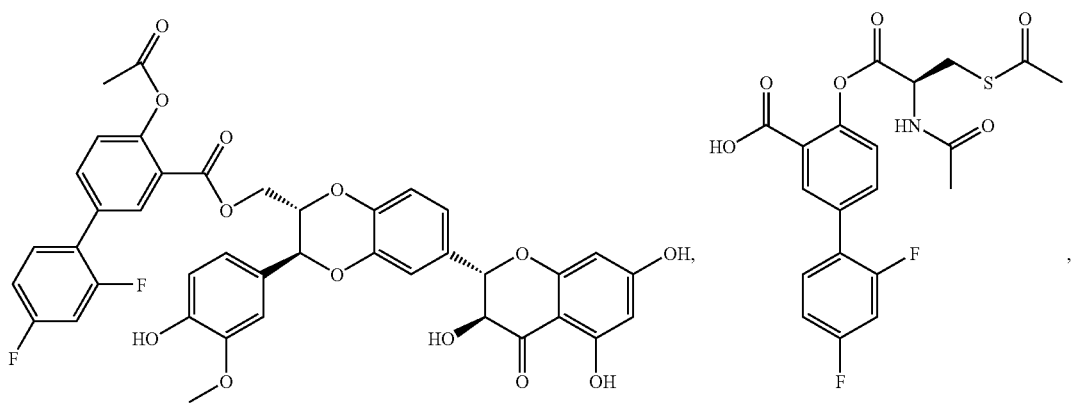

-continued
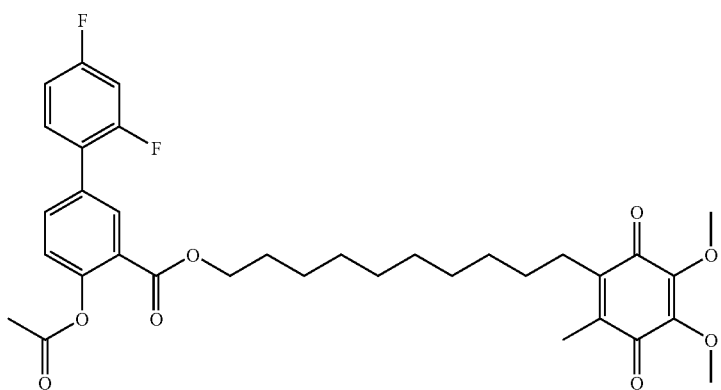
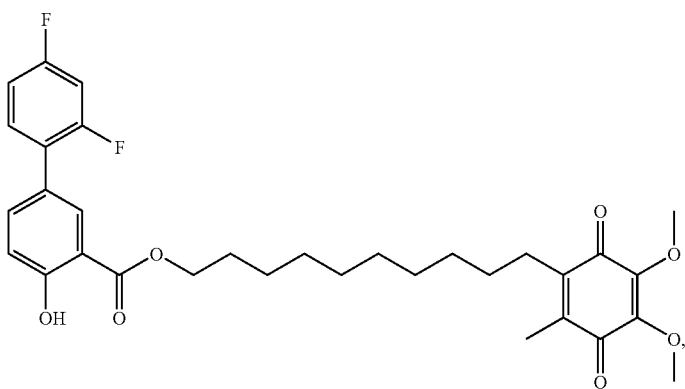
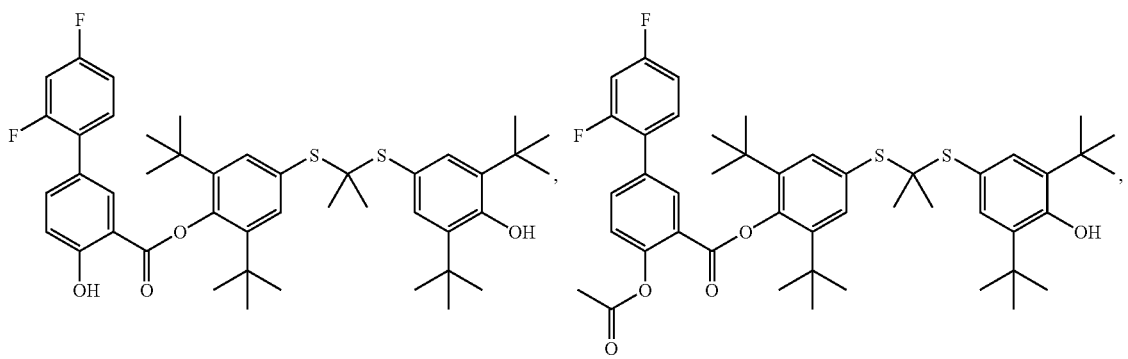
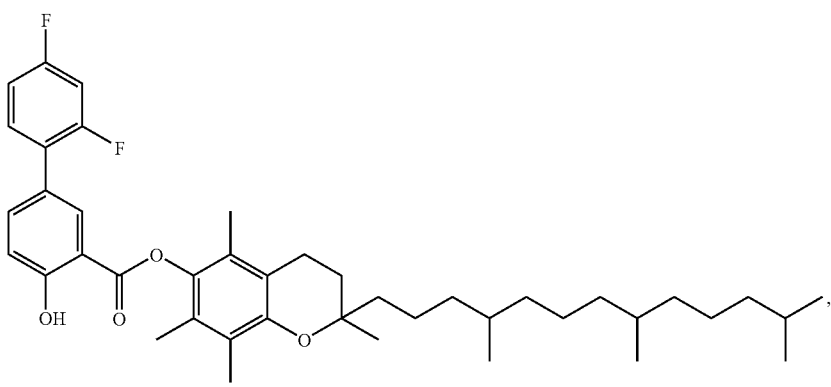

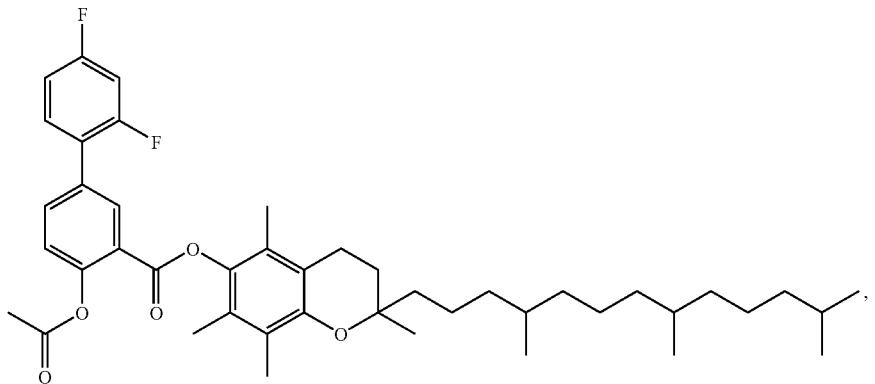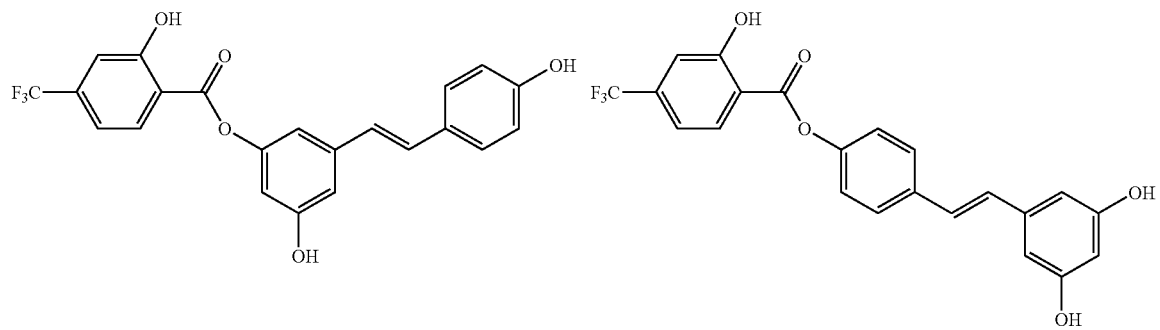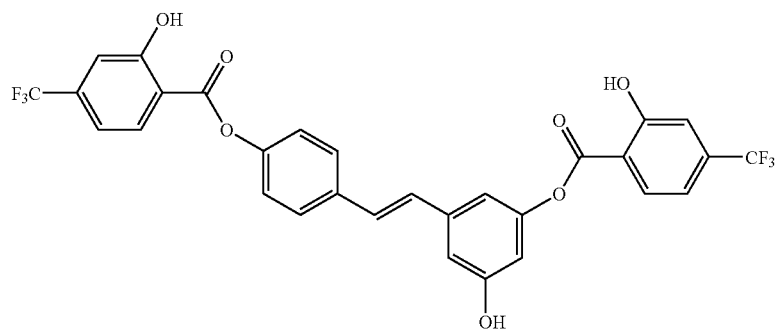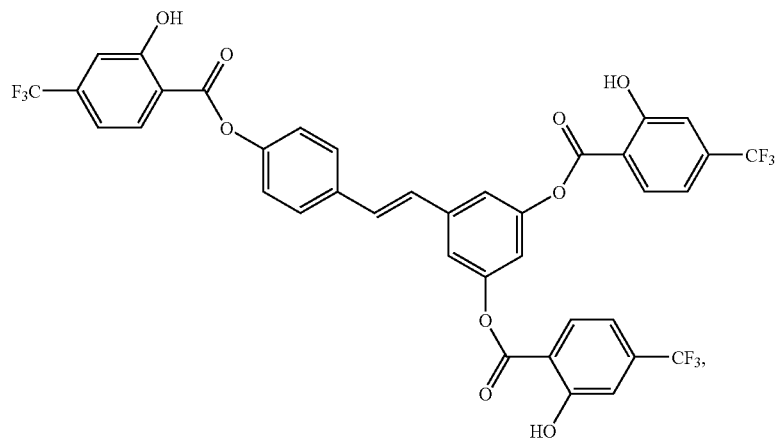

83
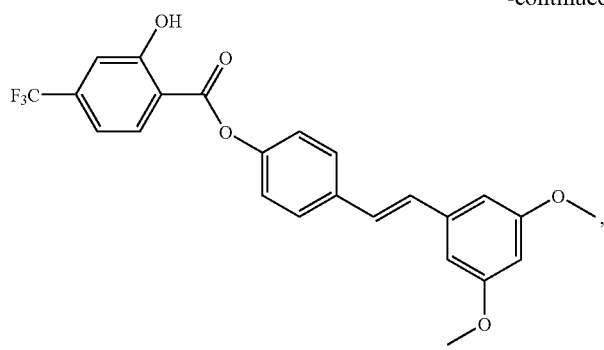
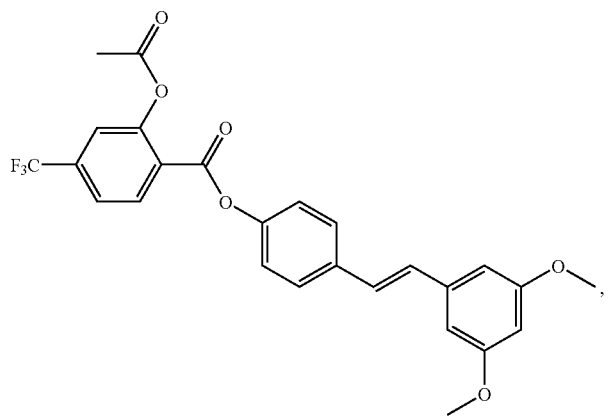
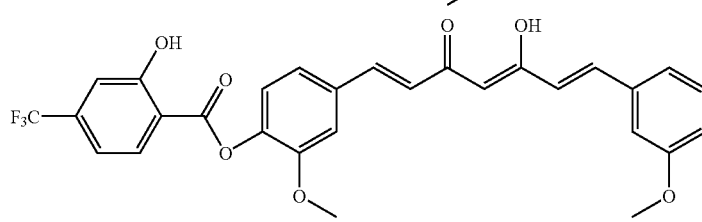
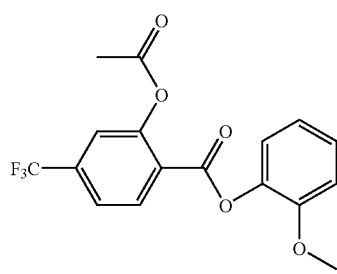
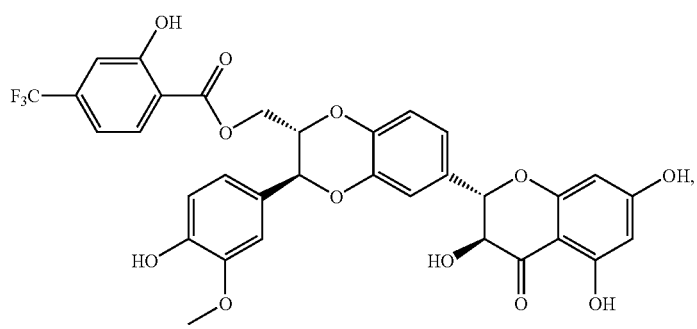
84
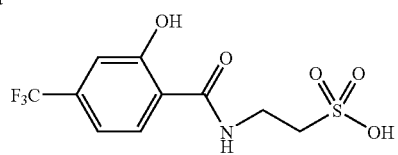
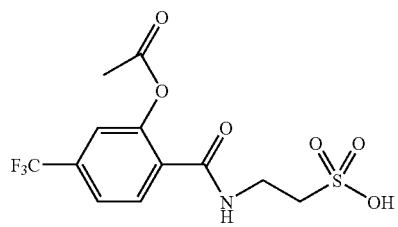
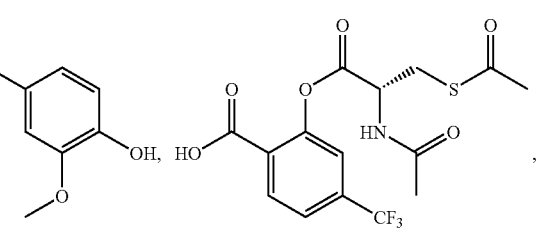
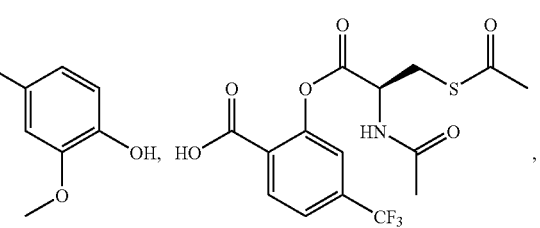

-continued
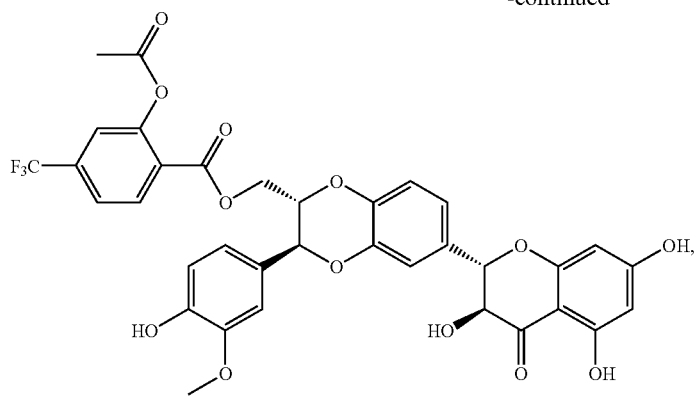
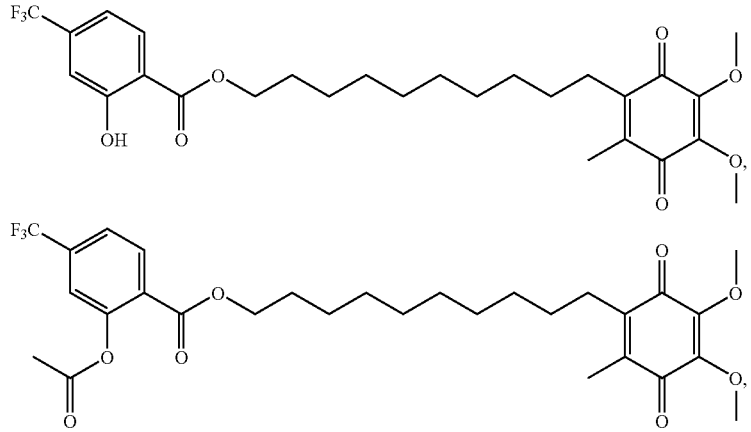
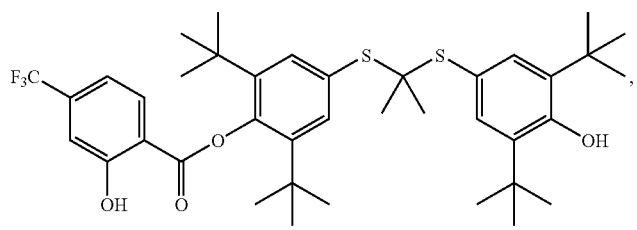
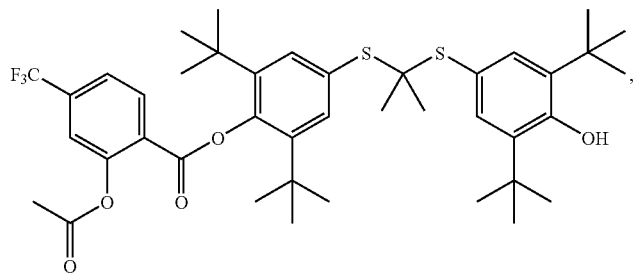
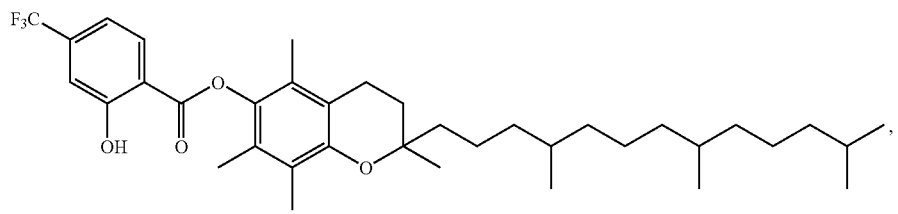

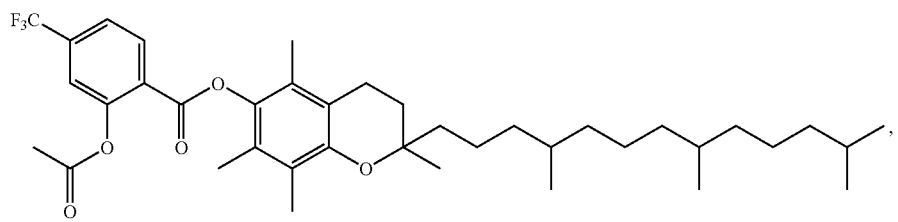
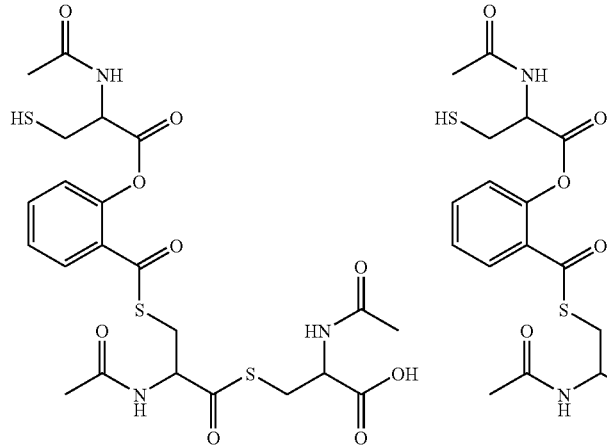
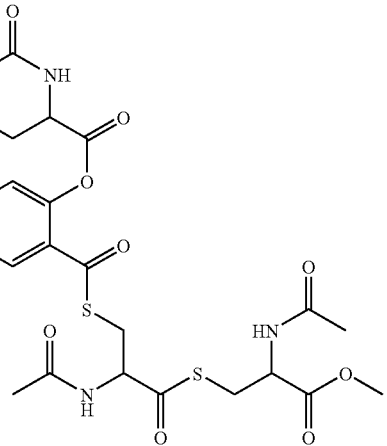
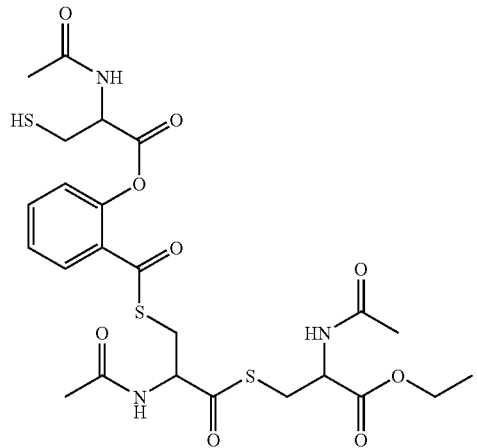
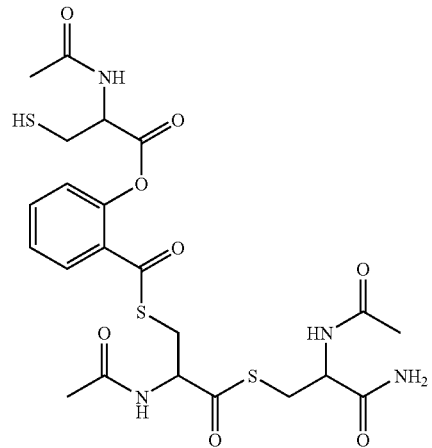
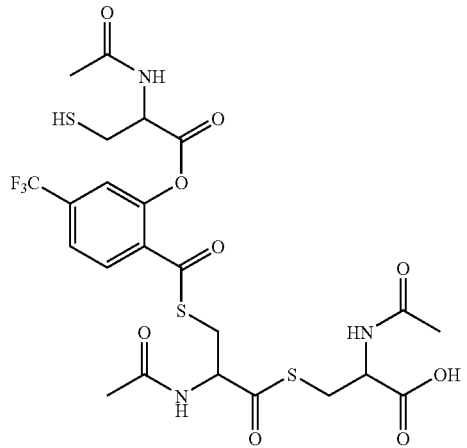
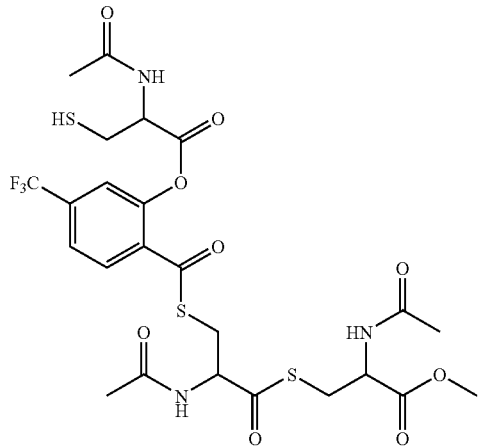

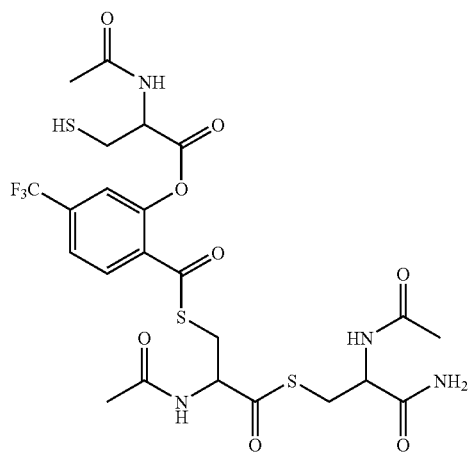
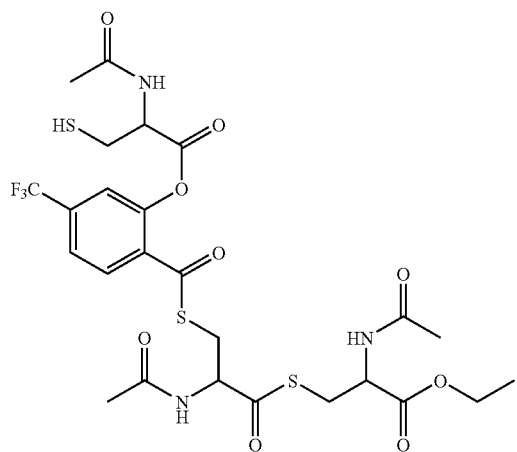
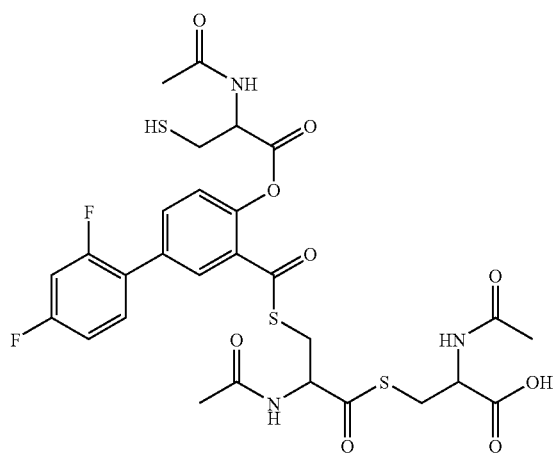
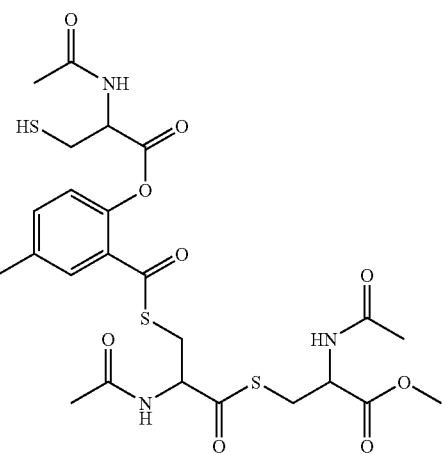
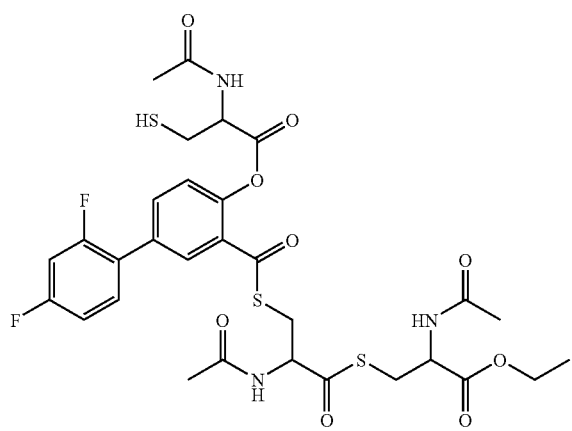
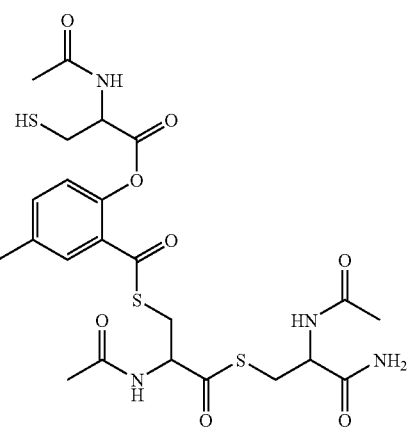

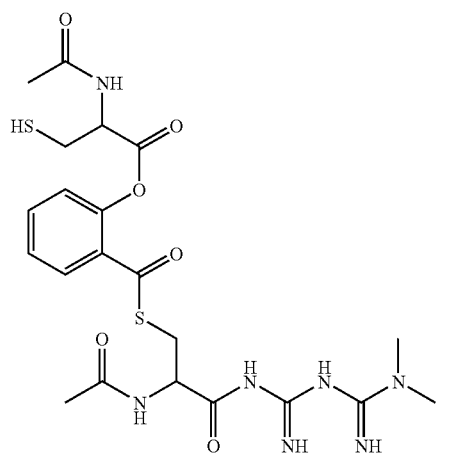
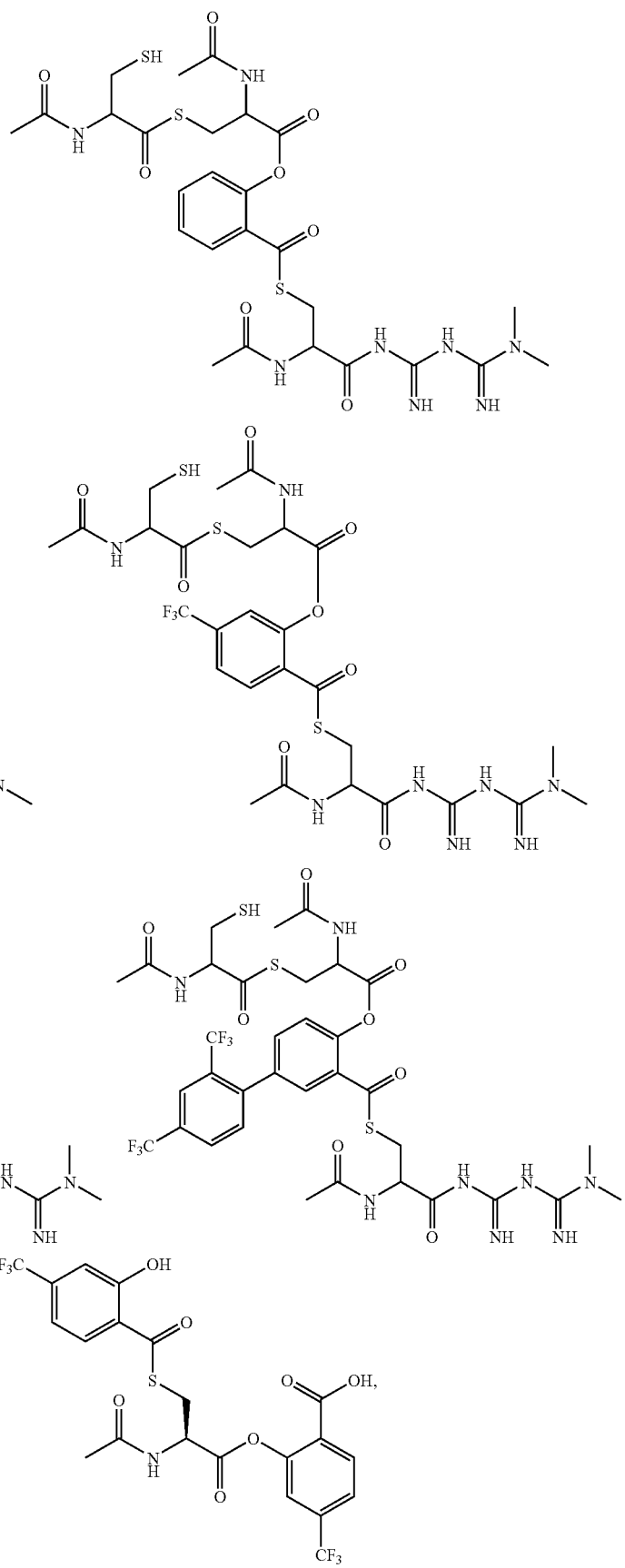

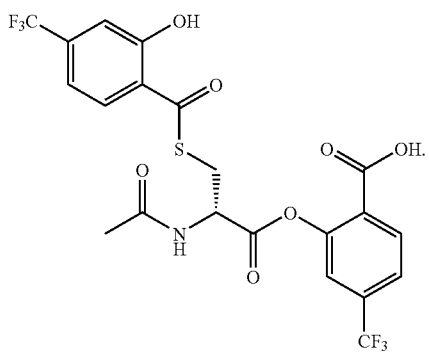

In another aspect, the present invention provides pharmaceutical compositions comprised of a compound of Formula (I), as shown above, and at least one pharmaceutically acceptable carrier.

In another aspect, the present invention provides conjugates of Formula (II)

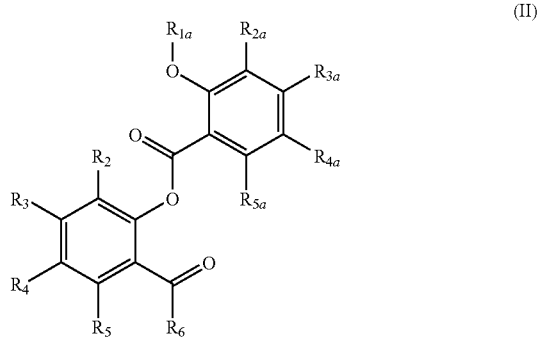

wherein $R_2$, $R_3$, $R_4$, $R_5$, $R_6$, $R_{1a}$, $R_{2a}$, $R_{3a}$, $R_{4a}$, and $R_{5a}$ are as defined in Formula (I) of the Summary section, provided that when $R_6$ is hydroxy then $R_{1a}$ is B, as defined in Formula (I) of the Summary section.

In another aspect, the present invention provides conjugates of Formula (II) wherein $R_2$, $R_3$, $R_4$, $R_5$, are independently hydrogen, trifluoromethyl, or 2,4-difluorophenyl; $R_6$ is as defined in Formula (I) of the Summary section; $R_{1a}$ is hydrogen or acetyl; and $R_{2a}$, $R_{3a}$, $R_{4a}$, and $R_{5a}$, are independently hydrogen, trifluoromethyl, or 2,4-difluorophenyl.

In another aspect, the present invention provides conjugates of Formula (II) wherein $R_2$, $R_3$, $R_4$, $R_5$, are independently hydrogen, trifluoromethyl, or 2,4-difluorophenyl; $R_6$ is N-acetylcysteine, (L) N-acetylcysteine, or (D) N-acetylcysteine; $R_{1a}$ is hydrogen or acetyl; and one of $R_{2a}$, $R_{3a}$, $R_{4a}$, and $R_{5a}$ is C(O)—$R_{6a}$ and the rest are hydrogen; and $R_{6a}$ is as defined in Formula (I).

Representative conjugates of Formula (II) include, but are not limited to, the compounds shown below, wherein $R_{1a}$ is hydrogen or acetyl.

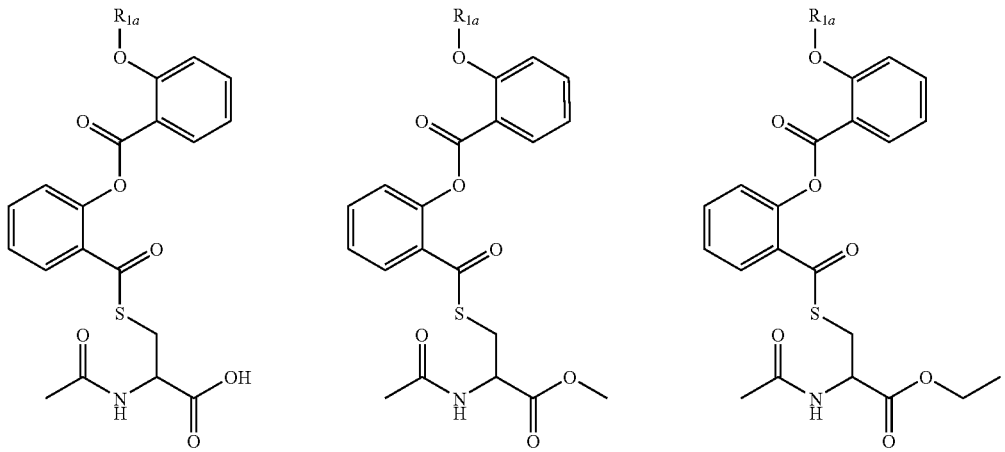

-continued
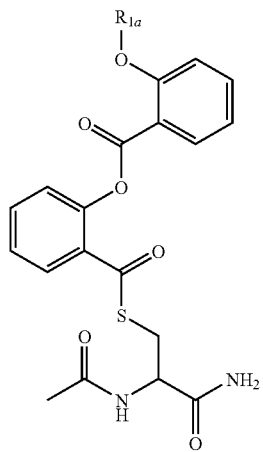 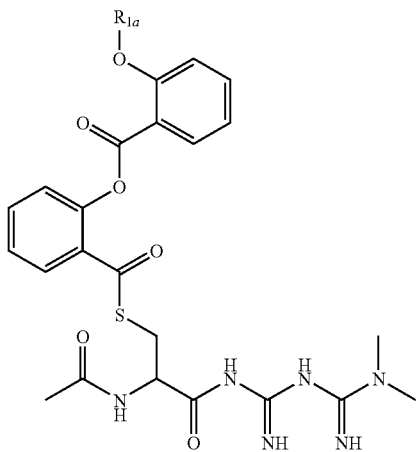 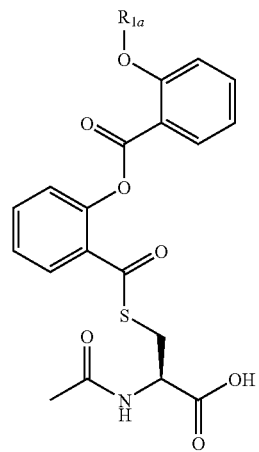
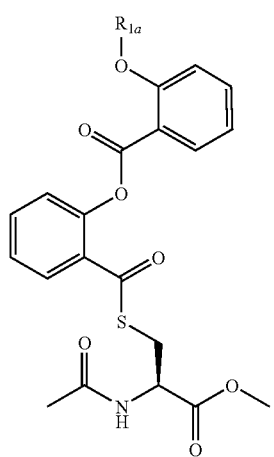 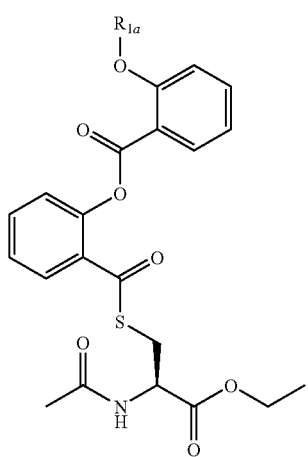 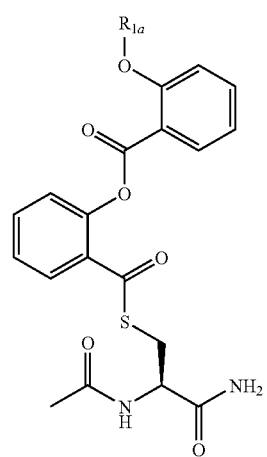
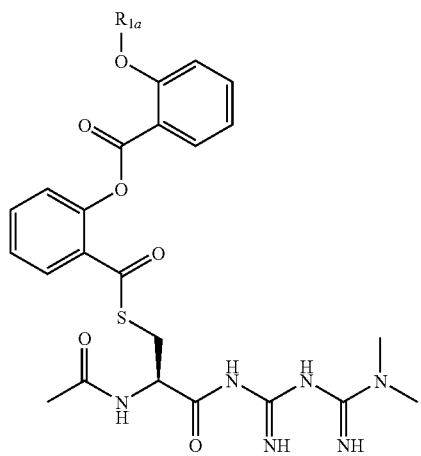 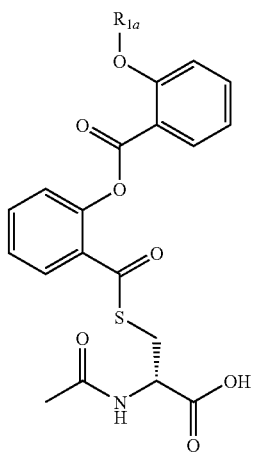 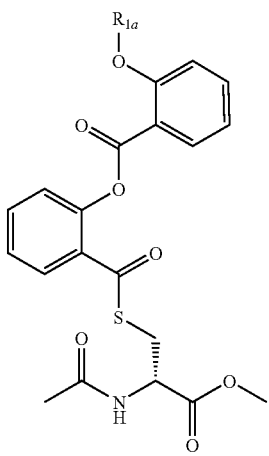

-continued
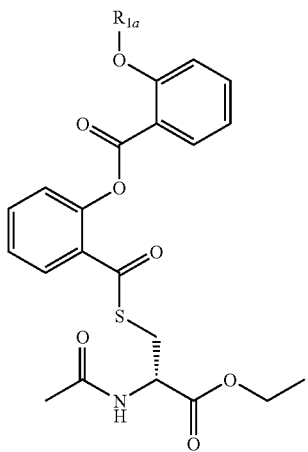
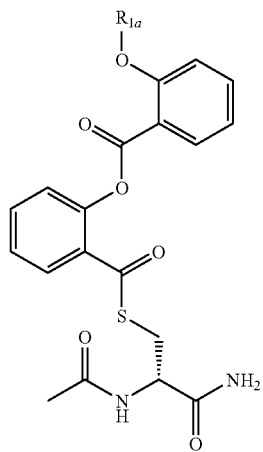
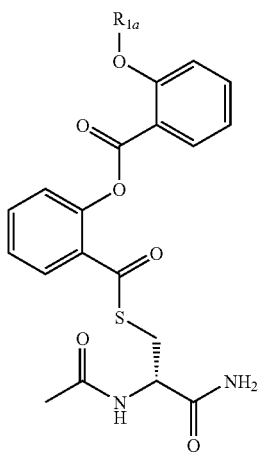
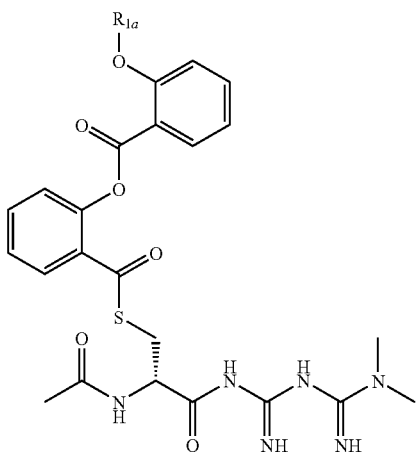
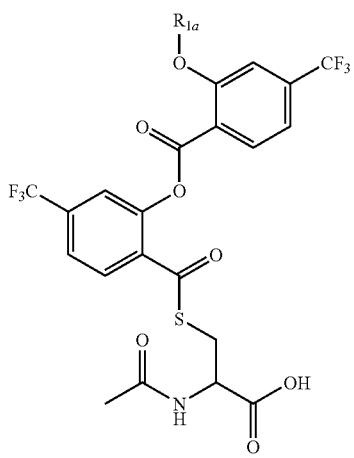
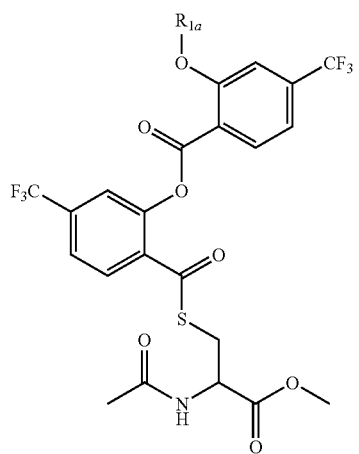

-continued
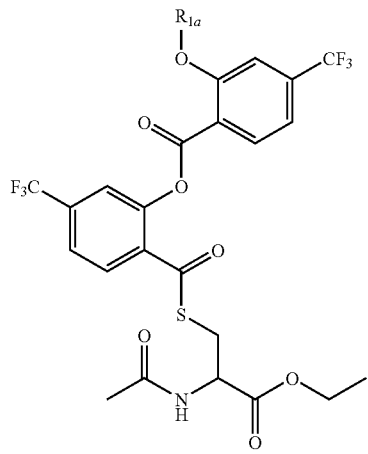
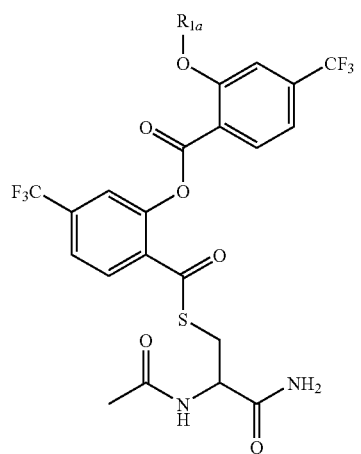
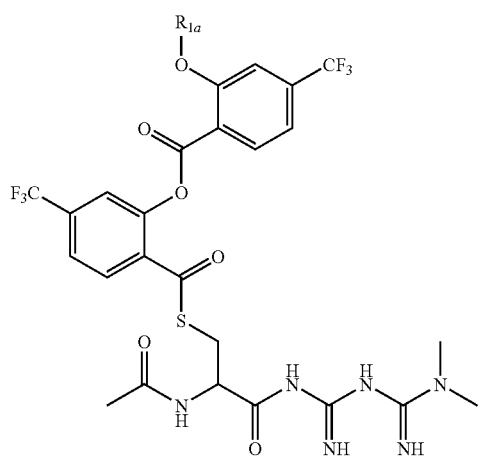
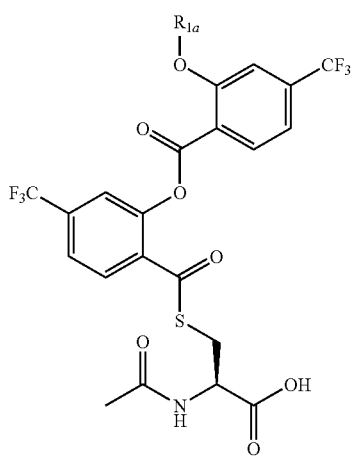
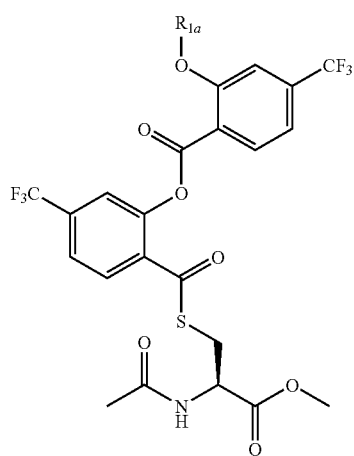
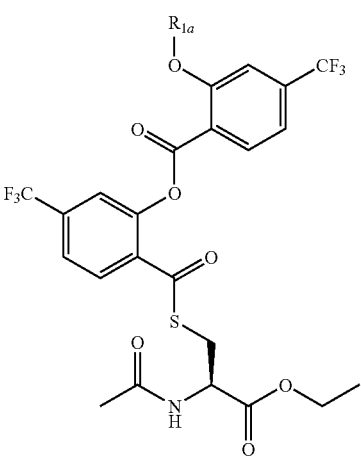

-continued
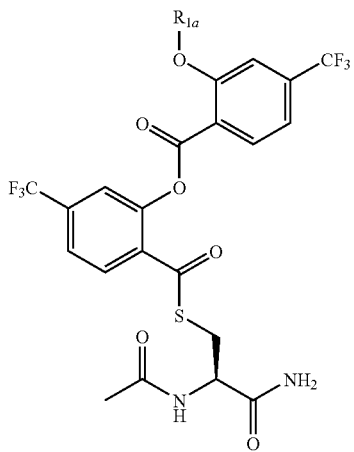
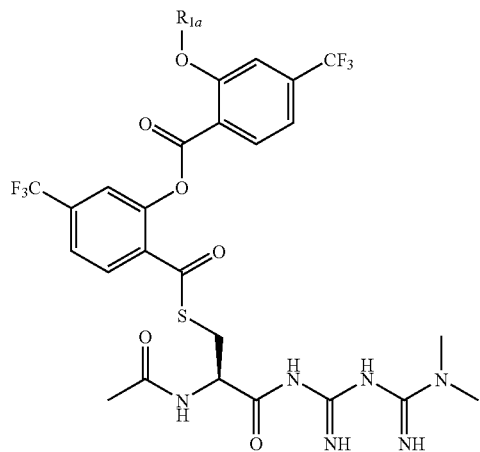
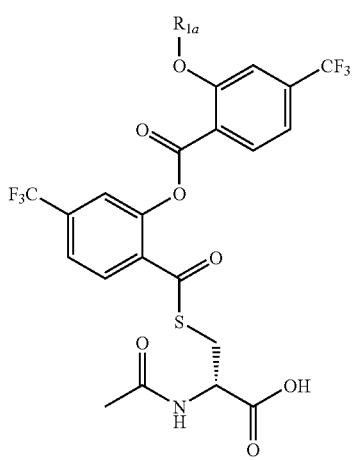
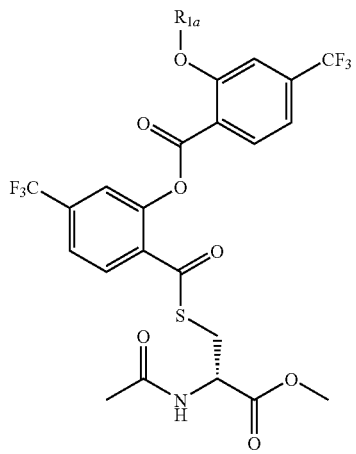
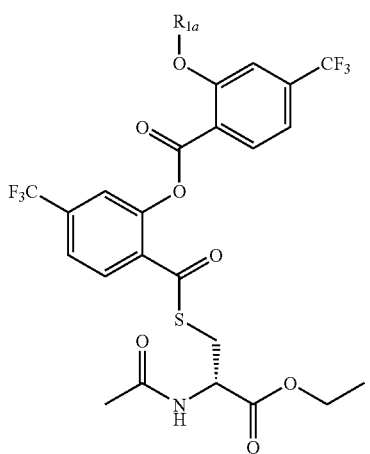
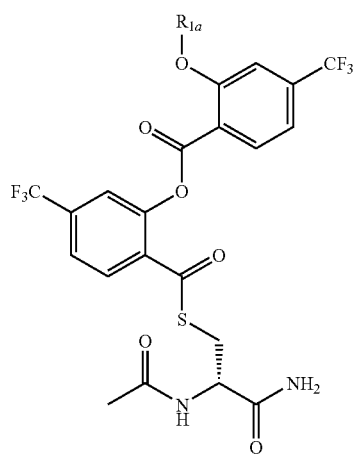

103
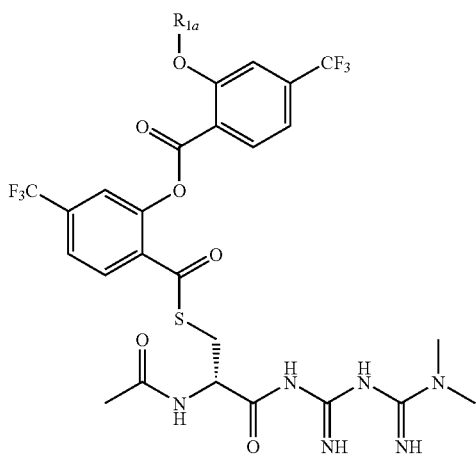
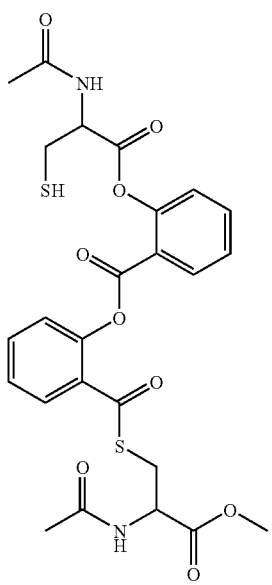
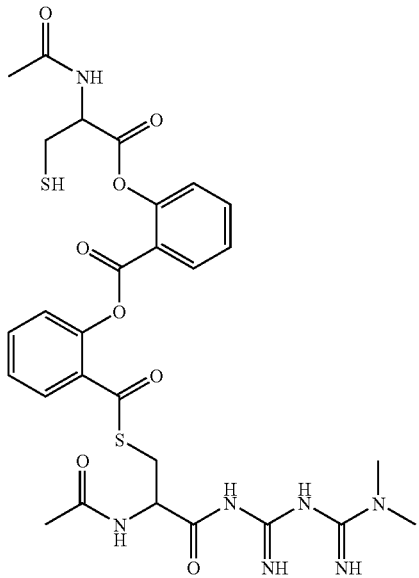
104
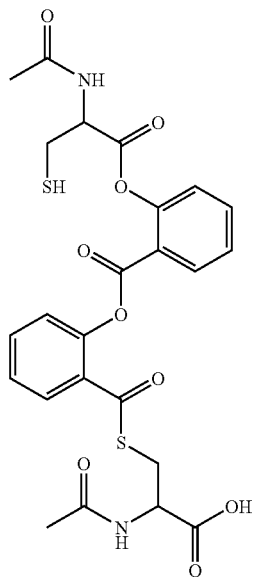
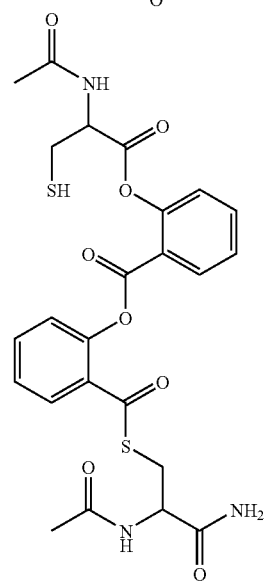
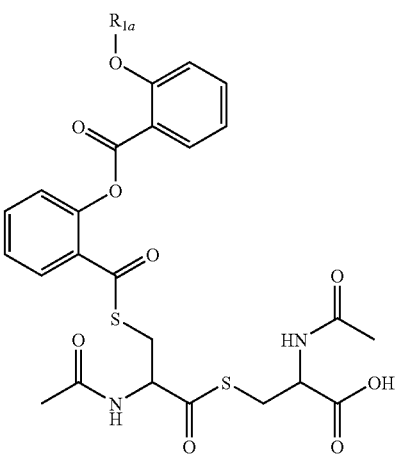

-continued
105
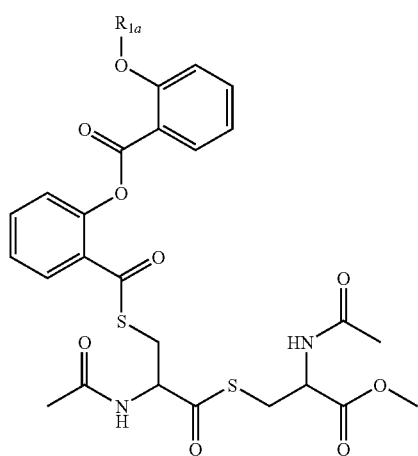
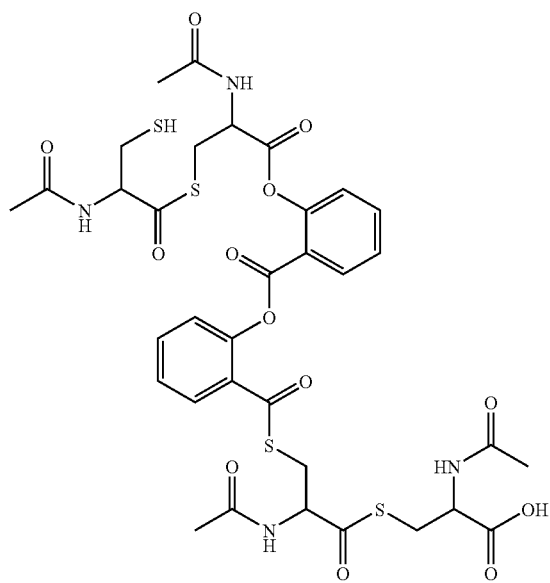
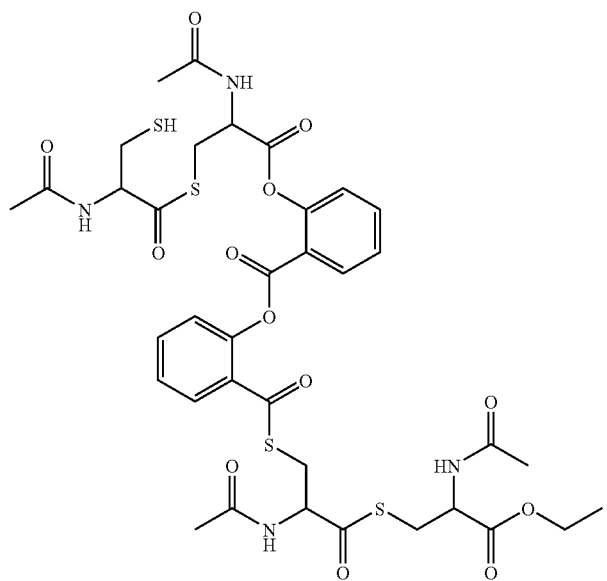
106
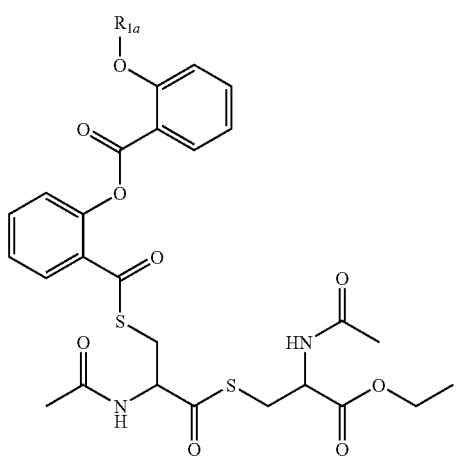
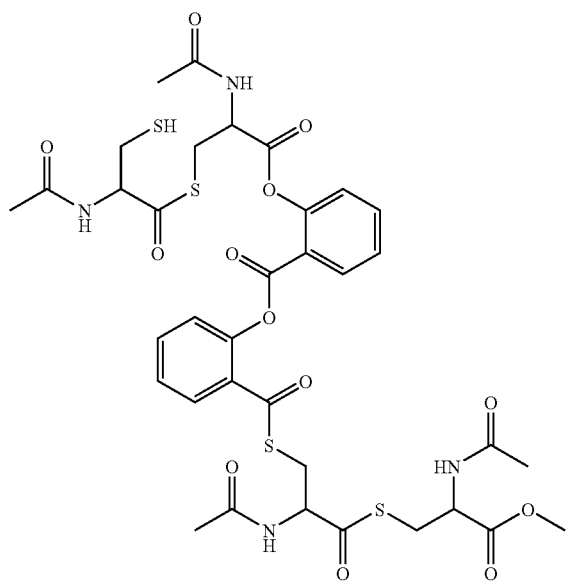

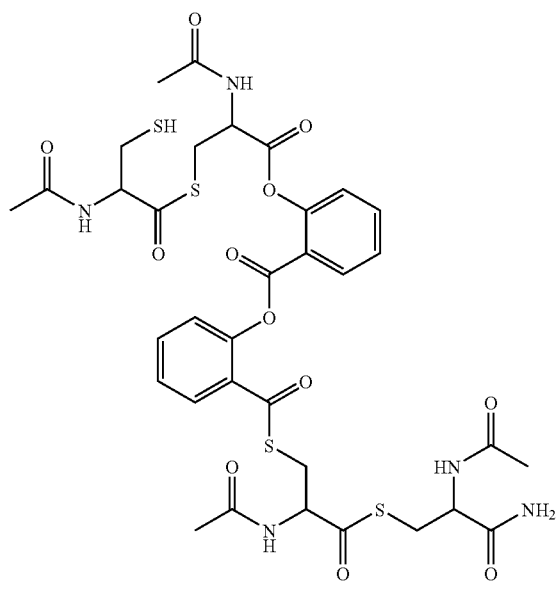
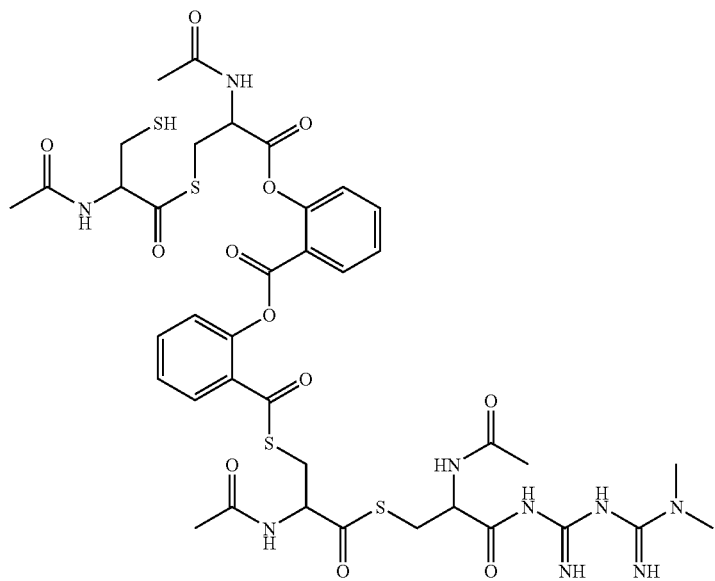
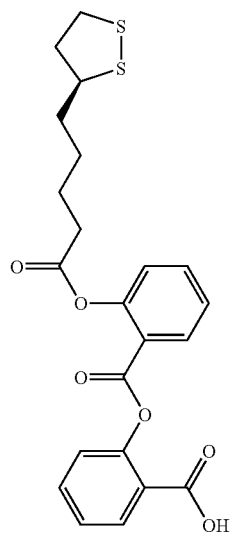
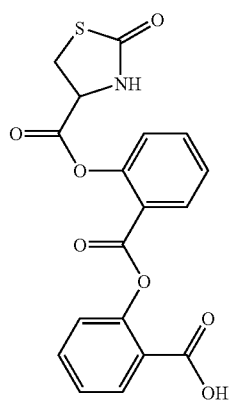
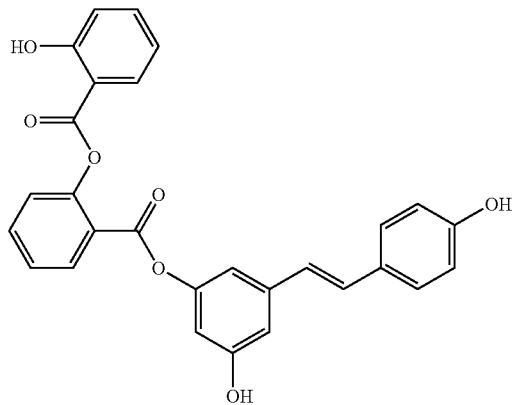

109 110
-continued
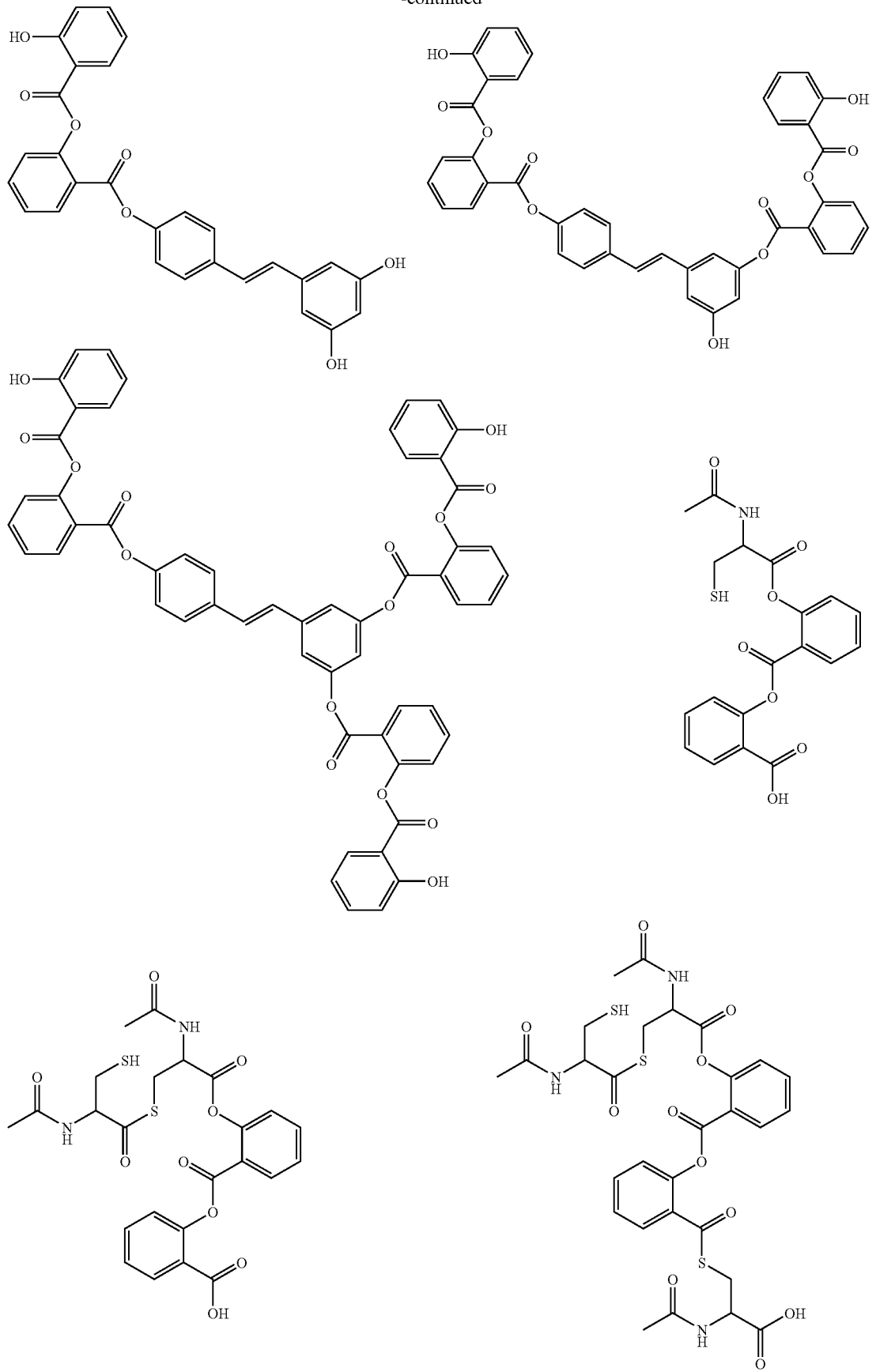

111
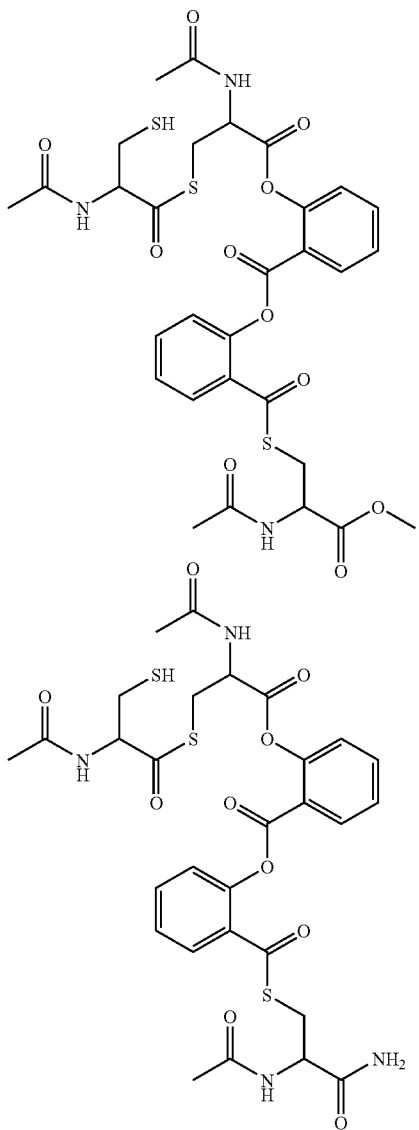
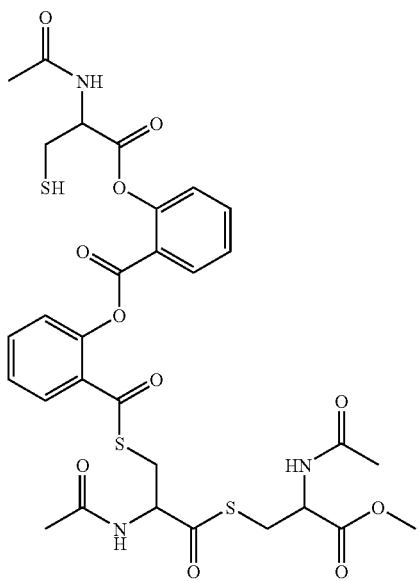
112
-continued
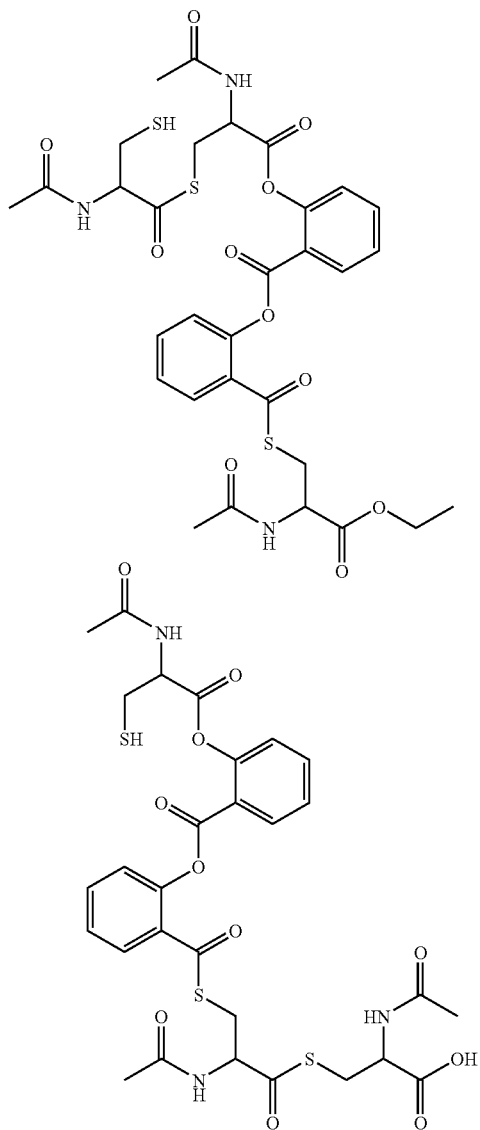
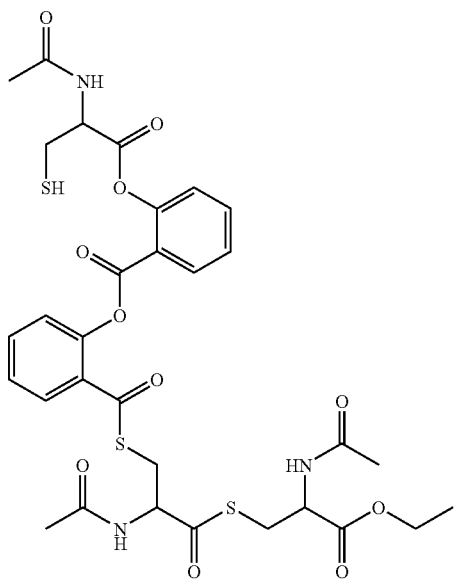

113
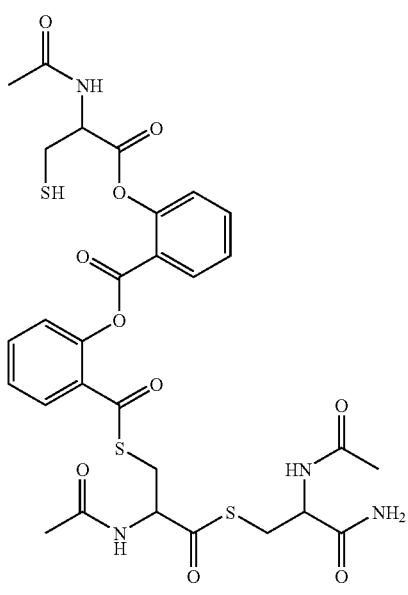
114
-continued
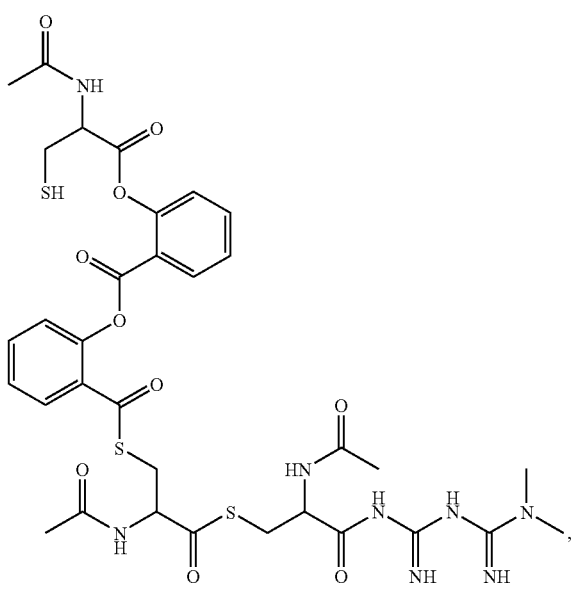
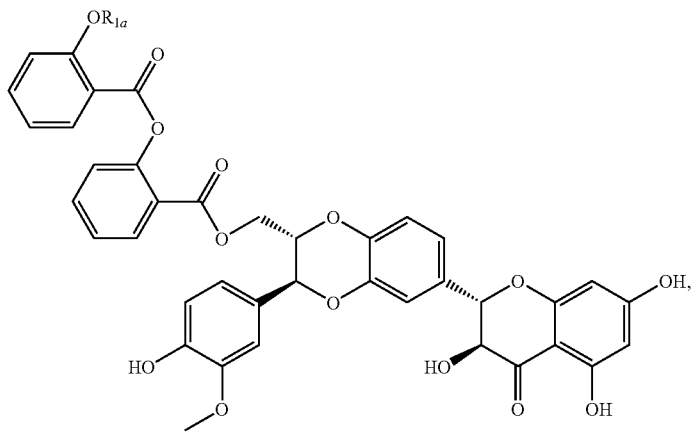
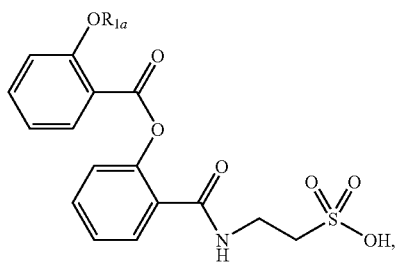
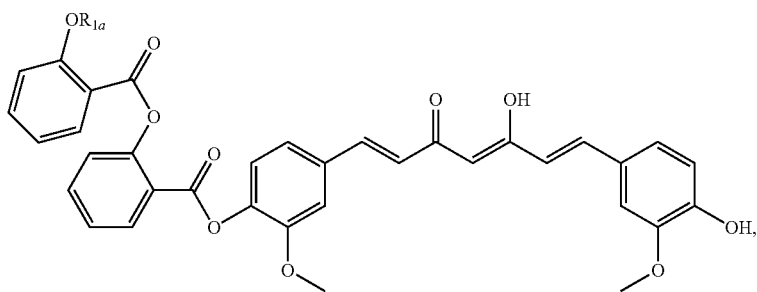

-continued
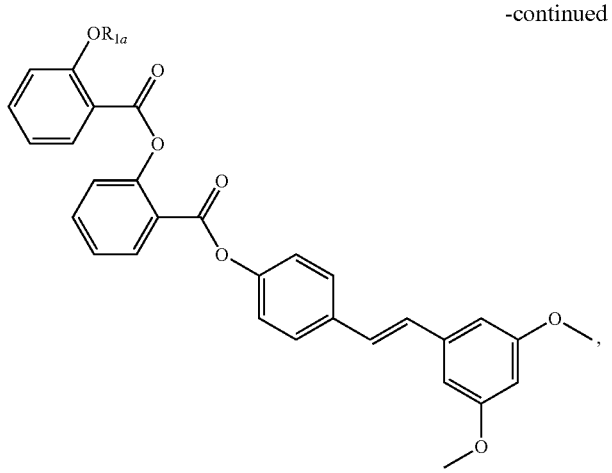
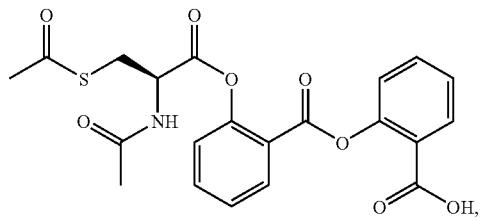
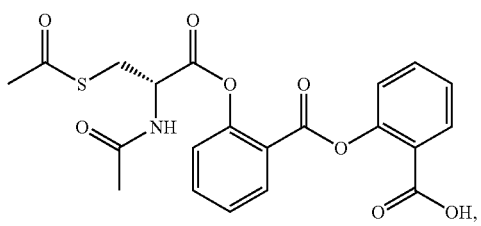
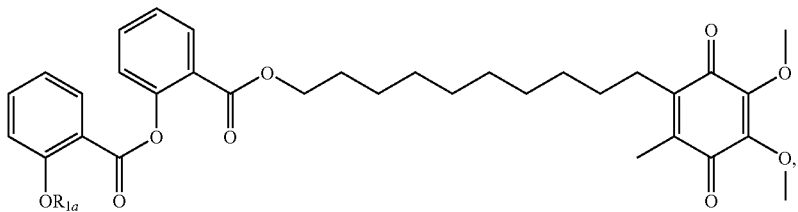
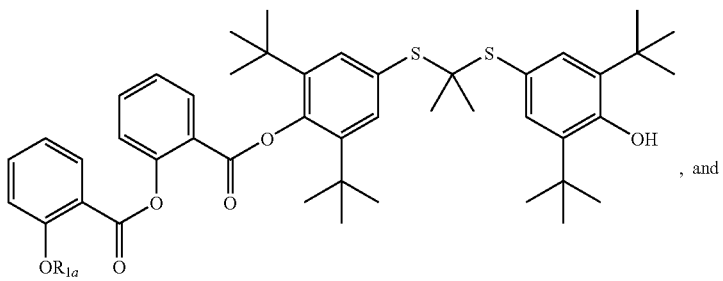
, and
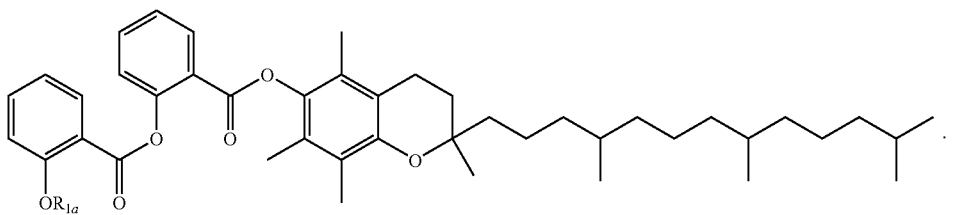

In another aspect, the present invention provides pharmaceutical compositions comprised of a compound of Formula (II), as shown above, and at least one pharmaceutically acceptable carrier.

In another aspect, the present invention provides conjugates of Formula (III)

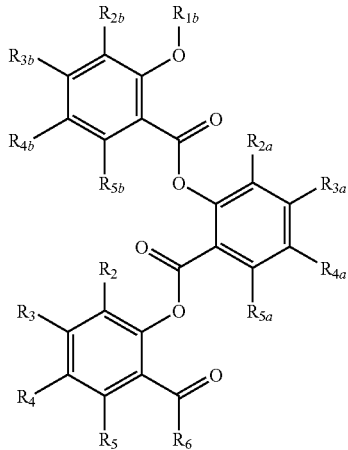

(III)

wherein $R_2$, $R_3$, $R_4$, $R_5$, $R_6$, $R_{2a}$, $R_{3a}$, $R_{4a}$, $R_{5a}$, $R_{1b}$, $R_{2b}$, $R_{3b}$, $R_{4b}$, and $R_{5b}$ are as defined in Formula (I) of the Summary section, provided that when $R_6$ is hydroxy then $R_{1b}$ is C, as defined in Formula (I) of the Summary section.

In another aspect, the present invention provides conjugates of Formula (III) wherein $R_2$, $R_3$, $R_4$, $R_5$, are independently hydrogen, trifluoromethyl, or 2,4-difluorophenyl; $R_6$ is (L) N-acetylcysteine; $R_{2a}$, $R_{3a}$, $R_{4a}$, and $R_{5a}$, are independently hydrogen, trifluoromethyl, or 2,4-difluorophenyl; $R_{2b}$, $R_{3b}$, $R_{4b}$, and $R_{5b}$, are independently hydrogen, trifluoromethyl, or 2,4-difluorophenyl; and $R_{1b}$ is hydrogen or acetyl.

Representative conjugates of Formula (III) include, but are not limited to, the compounds shown below, wherein $R_{1b}$ is hydrogen or acetyl.

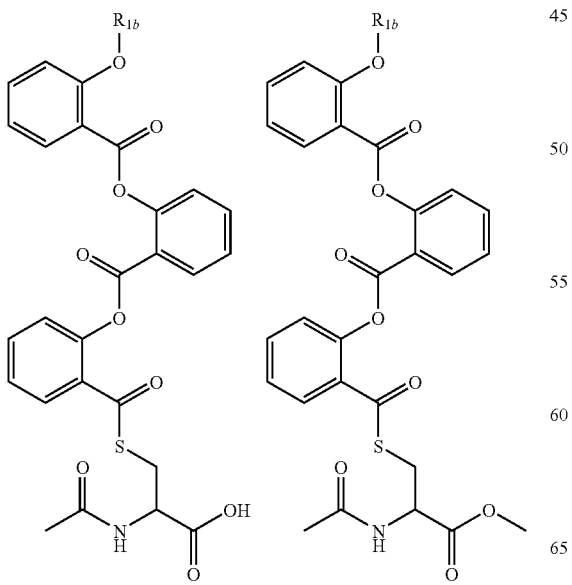

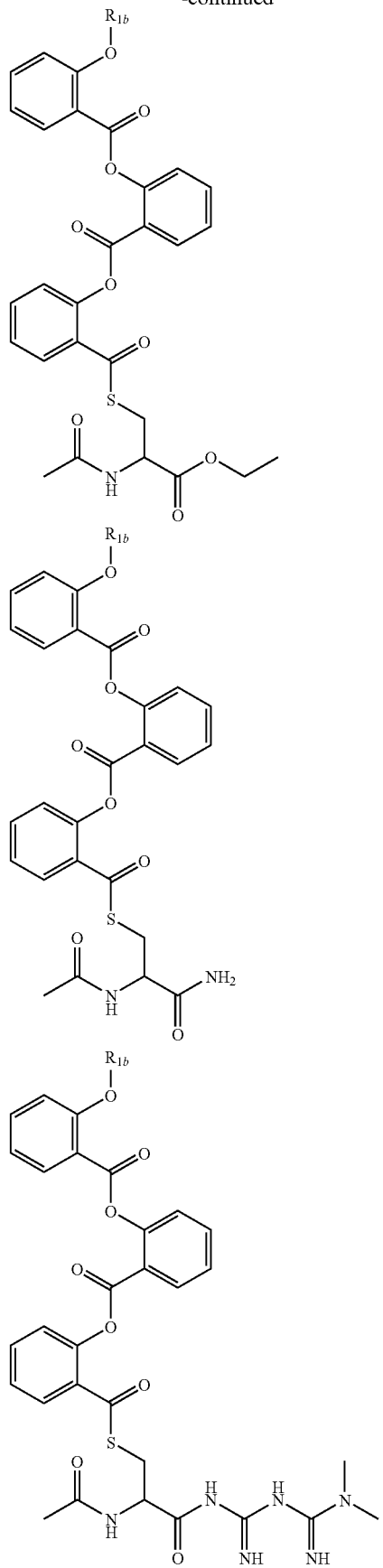

119
-continued
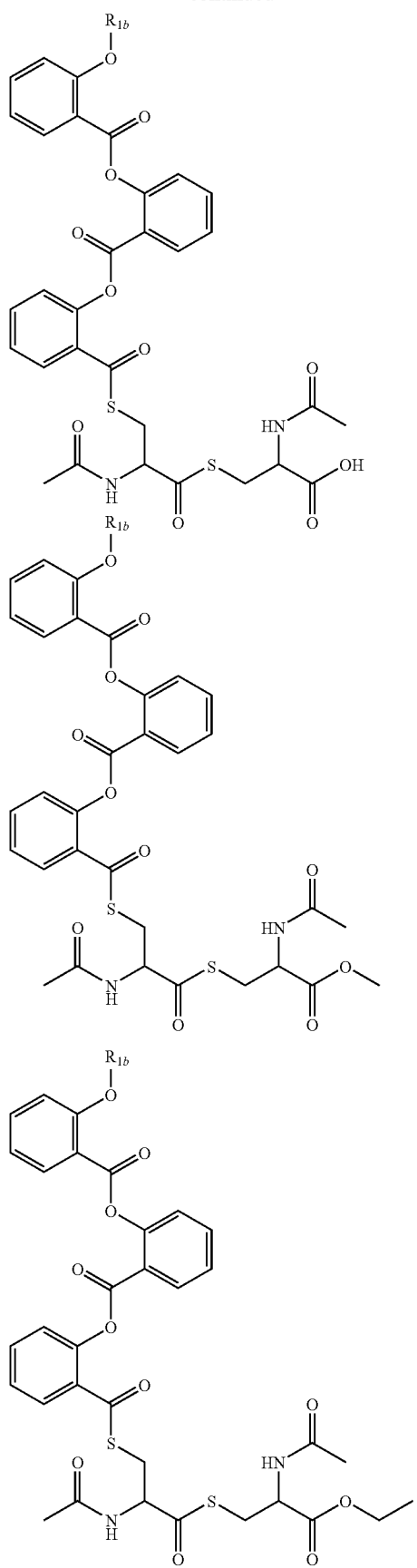
120
-continued
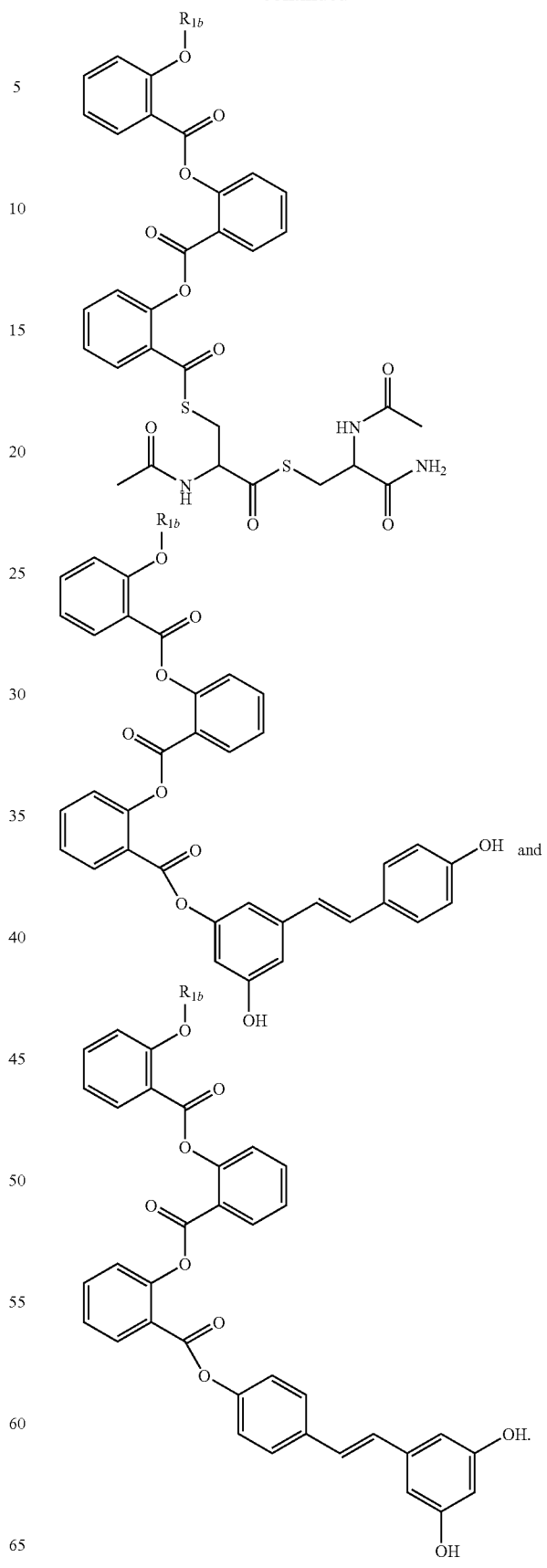
and

In another aspect, the present invention provides pharmaceutical compositions comprised of a compound of Formula (III), as shown above, and at least one pharmaceutically acceptable carrier.

In another aspect, the present invention provides conjugates of Formula (IV)

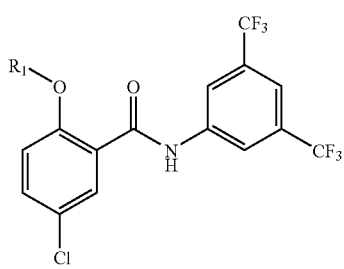

(IV)

wherein $R_1$ is hydrogen, $(C_1-C_6)$alkylcarbonyl,

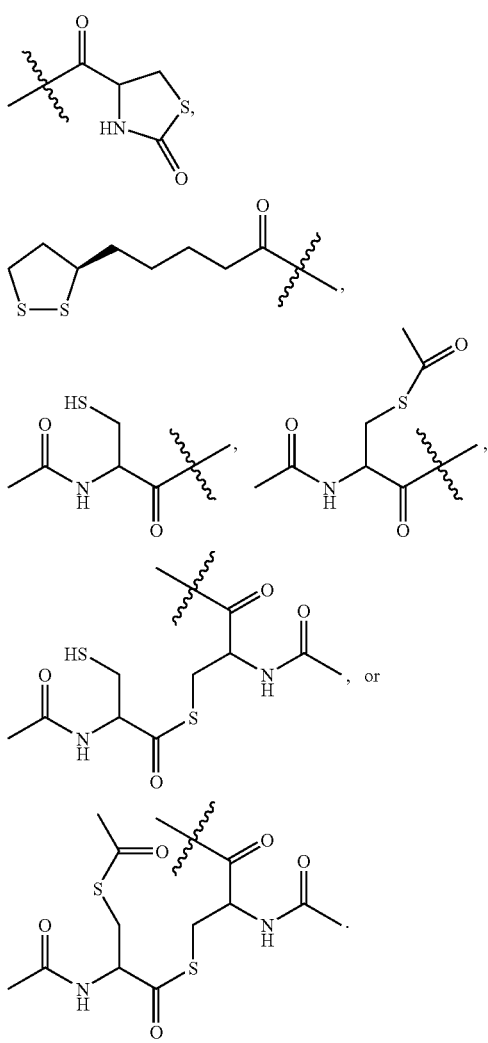

, or

Representative conjugates of Formula (IV) include the compounds shown below, wherein $R_1$ is hydrogen or acetyl.

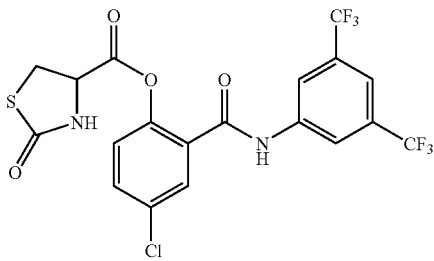

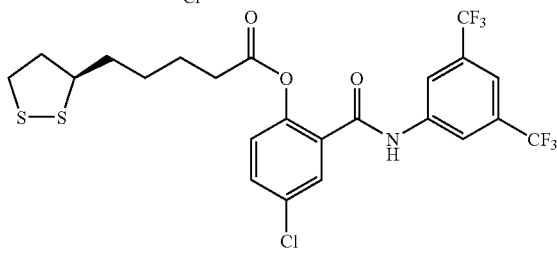

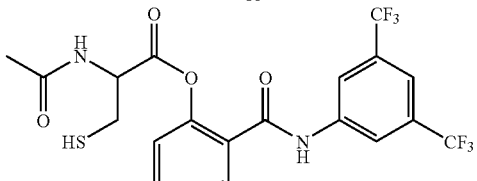

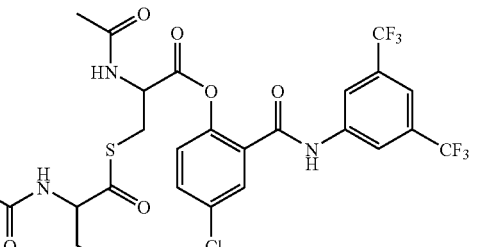

and

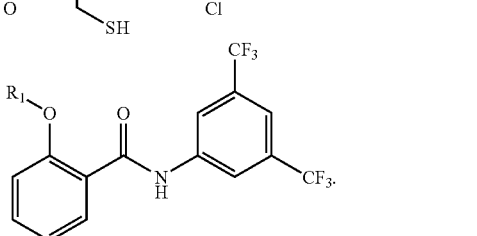

In another aspect, the present invention provides pharmaceutical compositions comprised of a compound of Formula (IV), as shown above, and at least one pharmaceutically acceptable carrier.

In another aspect, the present invention provides conjugates of Formula (V)

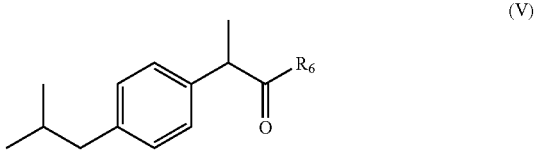

(V)

wherein R₆ is formula (i)
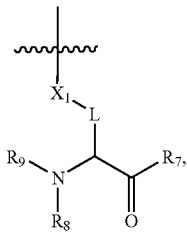

formula (ii)
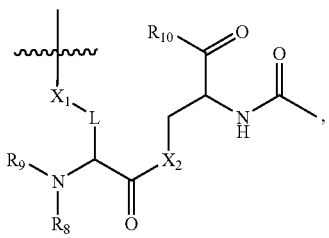

formula (iii)
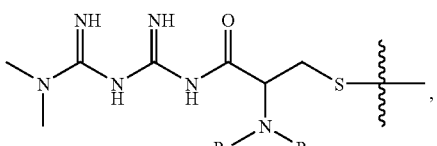

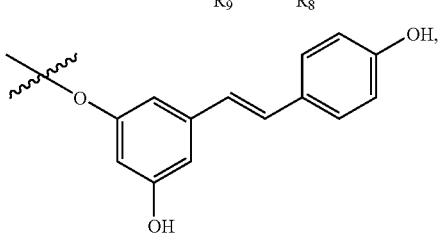

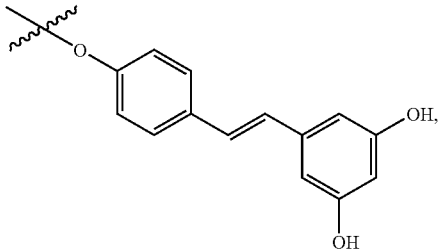

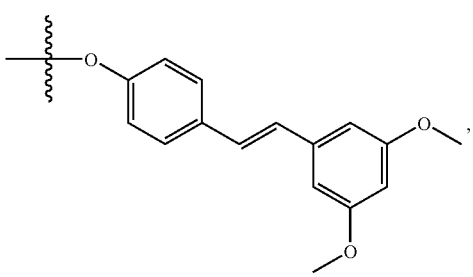

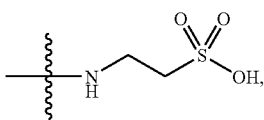

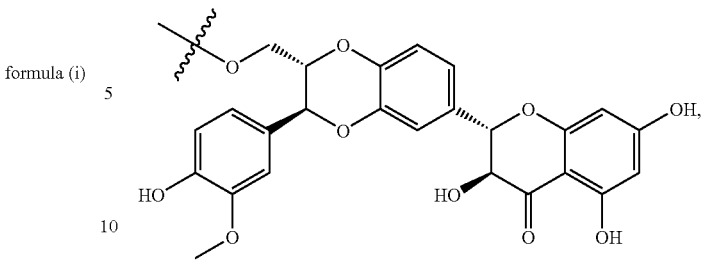

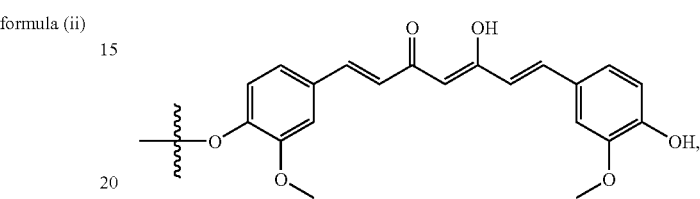

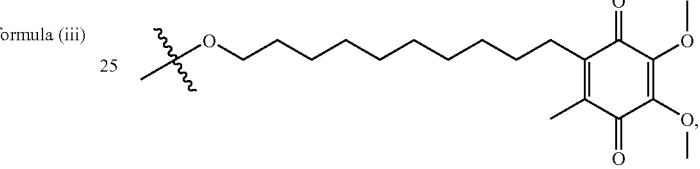

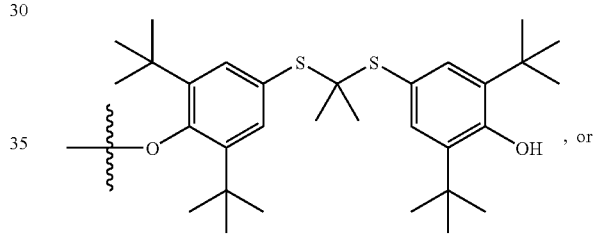, or

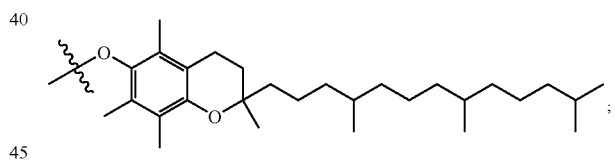;

R₇ is (C₁-C₆)alkoxy, (C₁-C₆)alkyl, (C₁-C₆)alkylthio, hydroxy, —NZ₉Z₁₀, or —O-phenyl, wherein the phenyl is optionally substituted with 1, 2, 3, 4, or 5 groups that are independently (C₁-C₆)alkoxy, (C₁-C₆)alkoxycarbonyl, (C₁-C₆)alkyl, (C₁-C₆)alkylcarbonyl, (C₁-C₆)alkylcarbonyloxy, carboxy, cyano, formyl, halo(C₁-C₆)alkoxy, halo(C₁-C₆)alkyl, halogen, hydroxy, or hydroxy(C₁-C₆)alkyl;

R₈ is hydrogen or (C₁-C₆)alkyl;

R₉ is hydrogen, (C₁-C₆)alkyl, or (C₁-C₆)alkylcarbonyl;

R₁₀ is (C₁-C₆)alkoxy, (C₁-C₆)alkylthio, hydroxy, or —NZ₉Z₁₀;

X₁ and X₂ are independently O or S;

L is (C₁-C₆)alkylene; and

Z₉ and Z₁₀ are independently hydrogen, (C₁-C₆)alkyl, or (C₁-C₆)alkylcarbonyl.

Representative conjugates of Formula (V) include, but are not limited to, the compounds shown below.

125 126
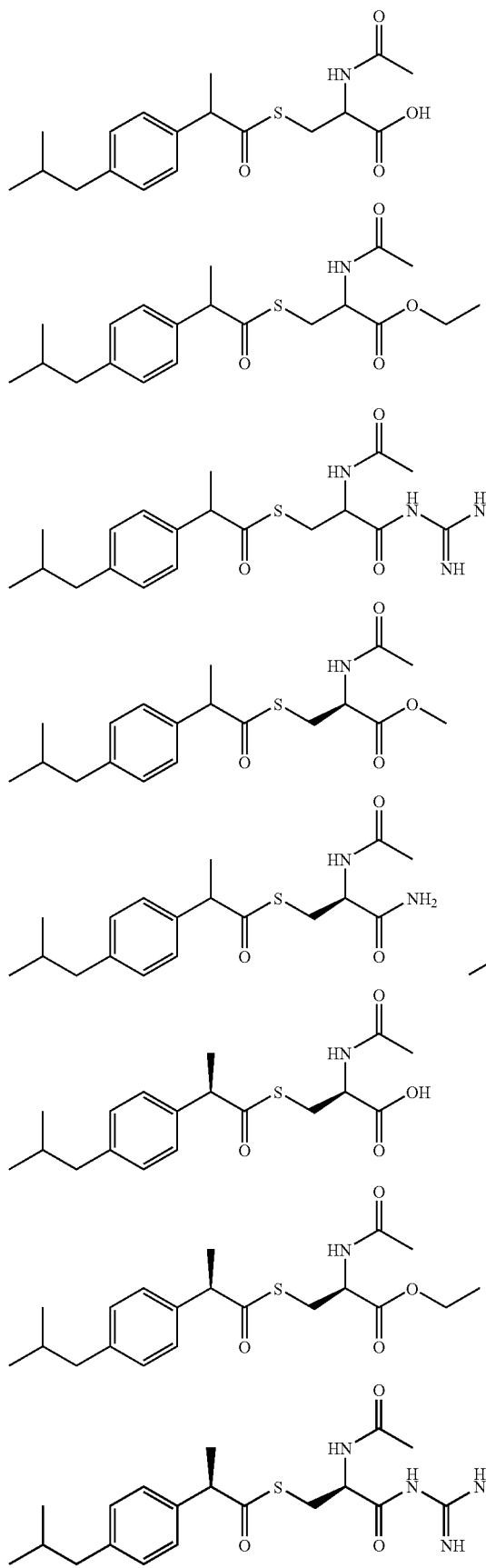

-continued
127
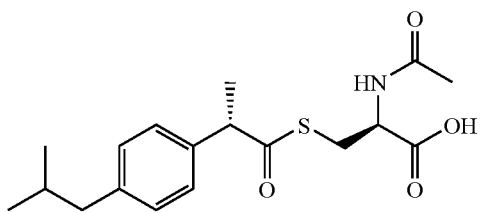
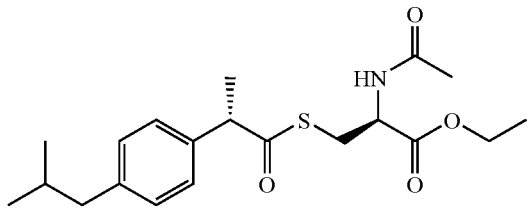
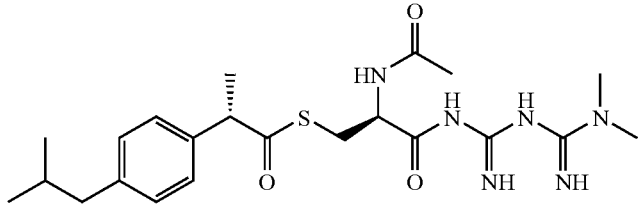
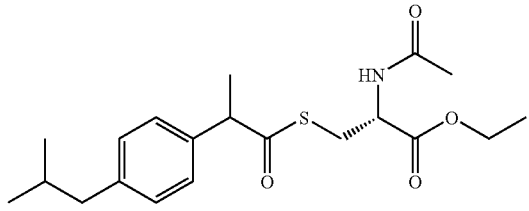
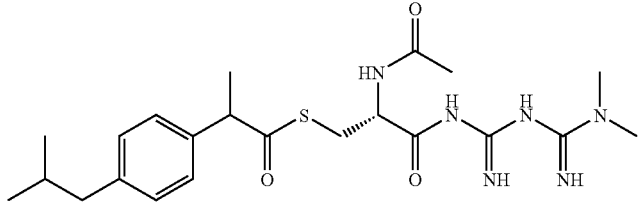
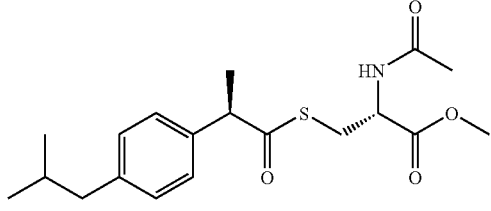
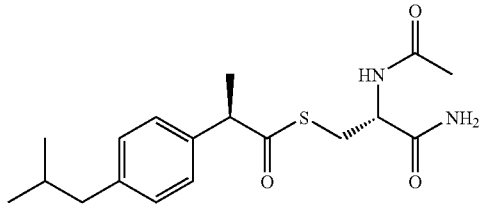
128
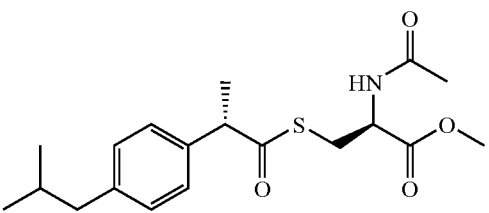
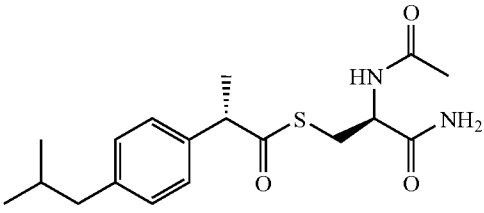
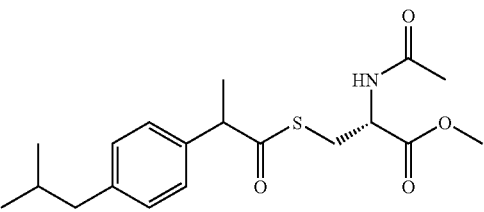
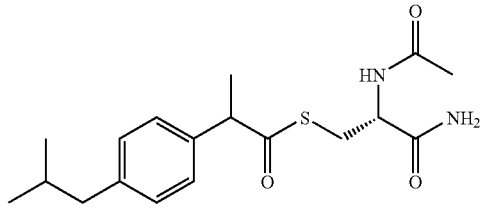
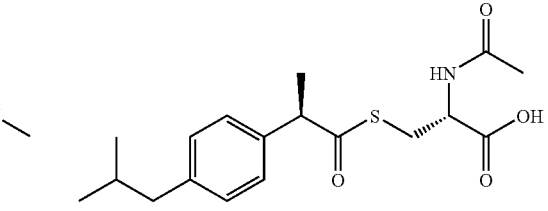
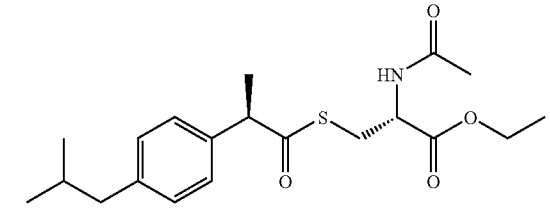
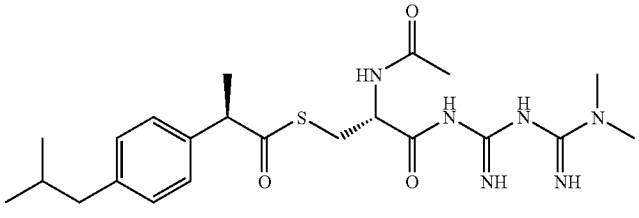

-continued
129
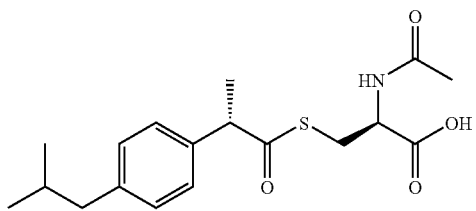
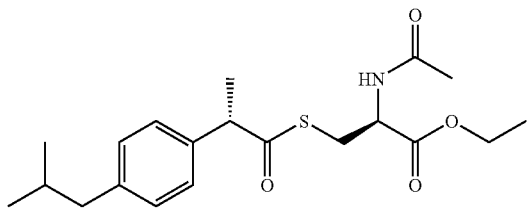
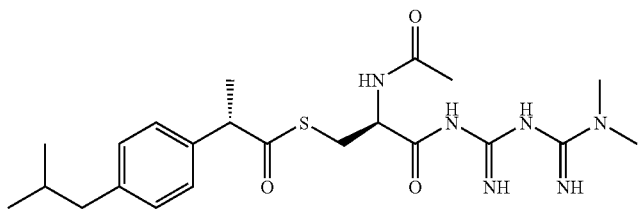
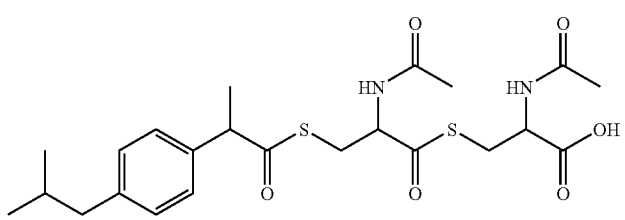
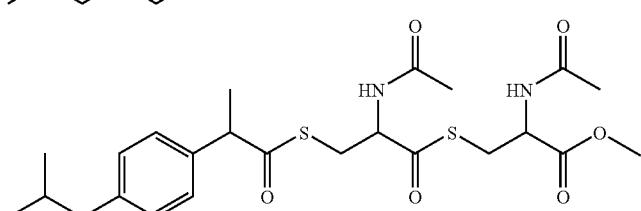
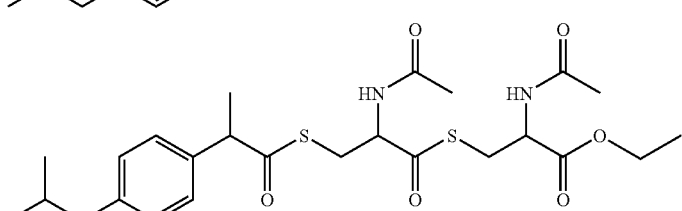
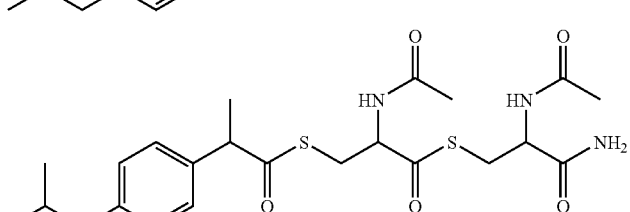
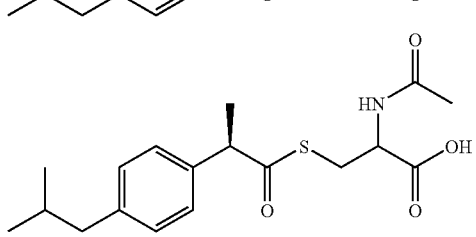
130
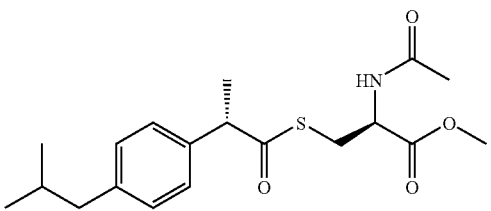
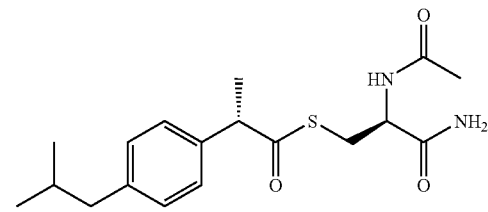
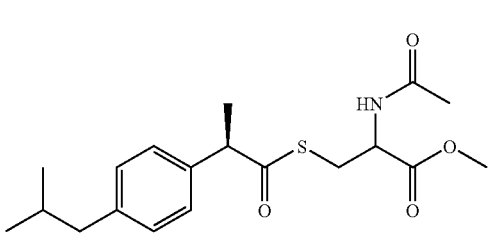

131
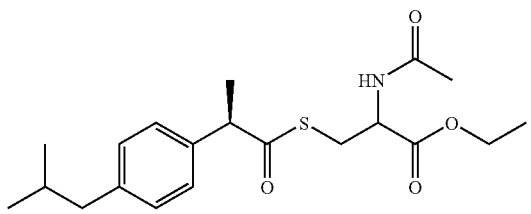
132
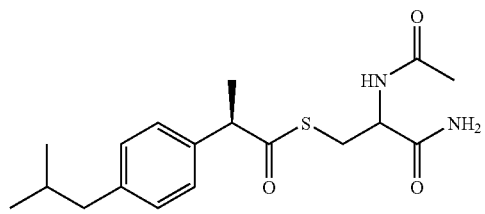
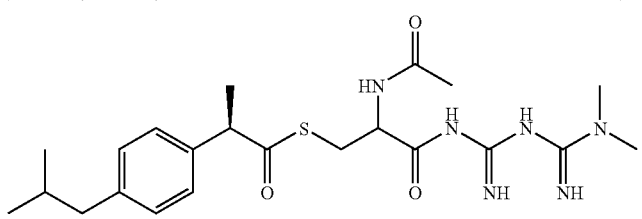
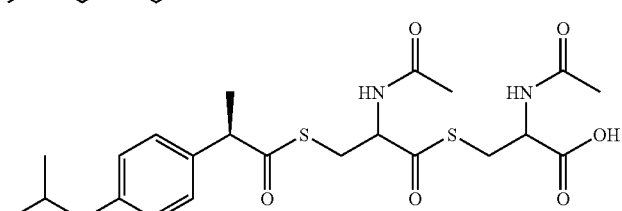
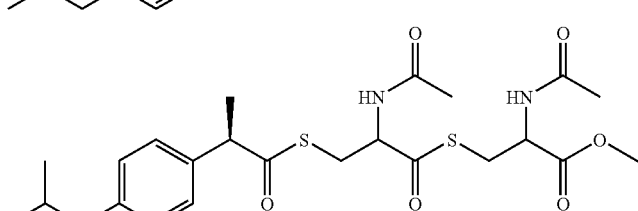
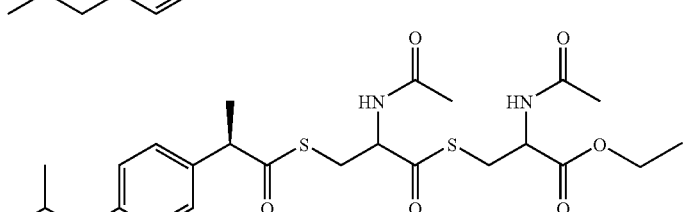
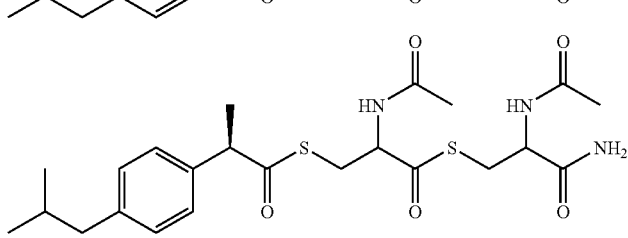
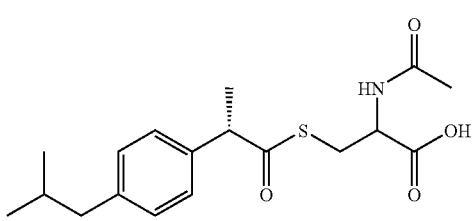
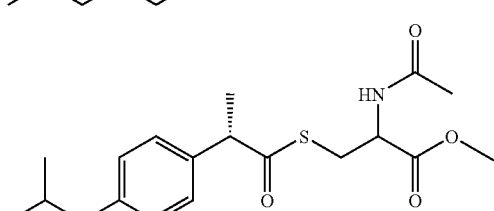
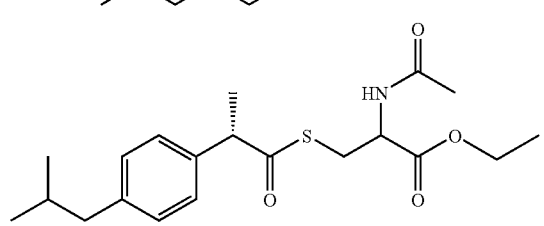
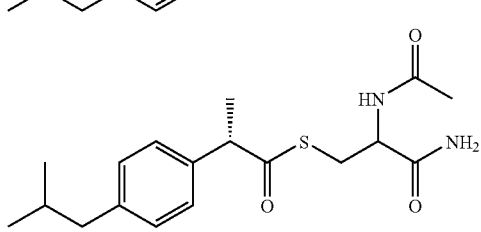

-continued
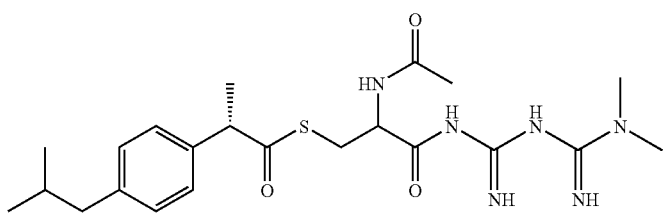
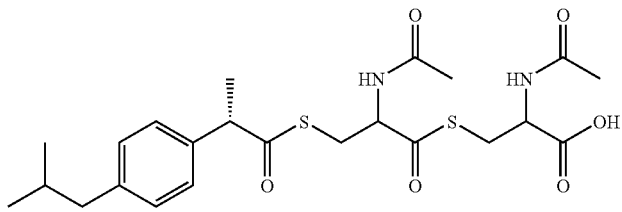
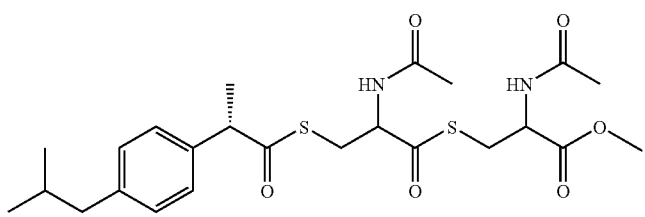
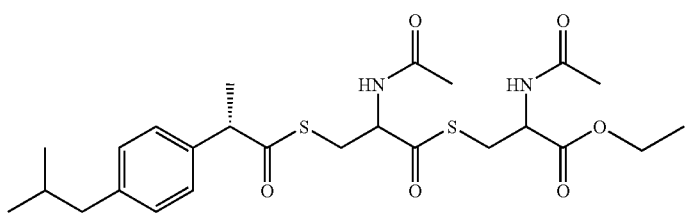
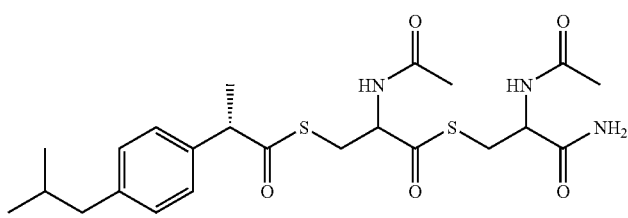
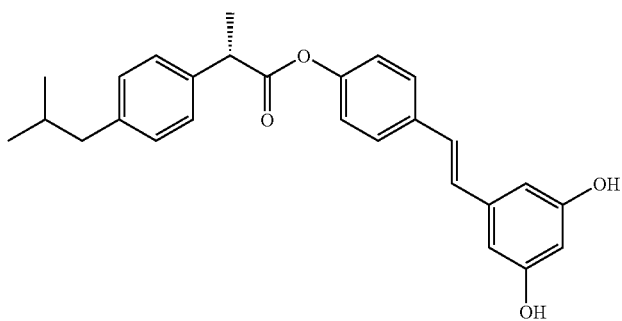
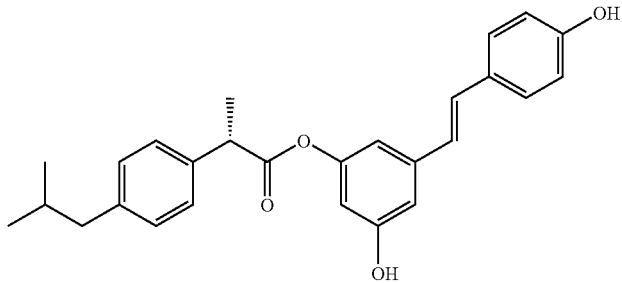

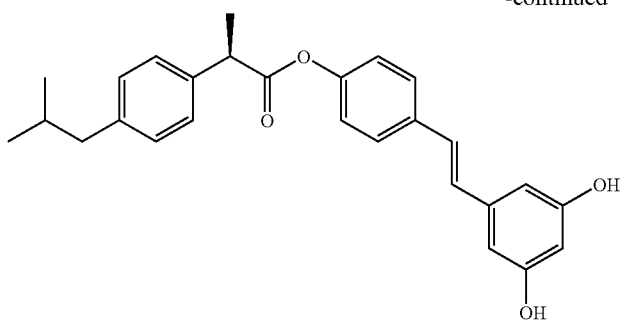
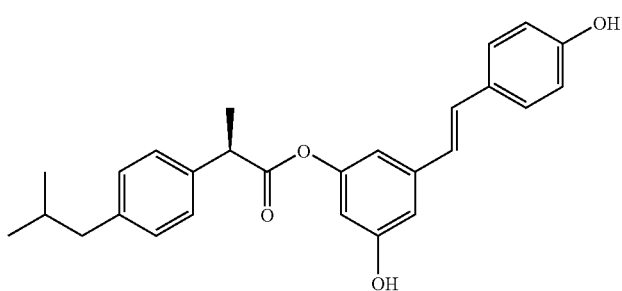
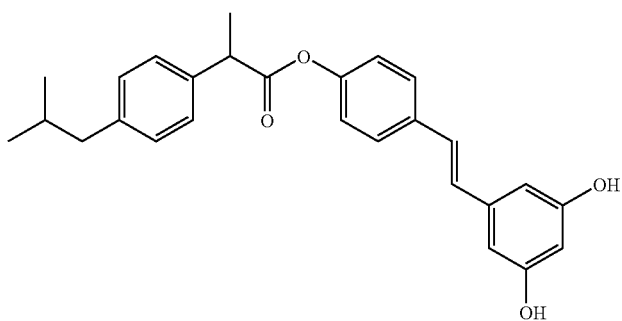
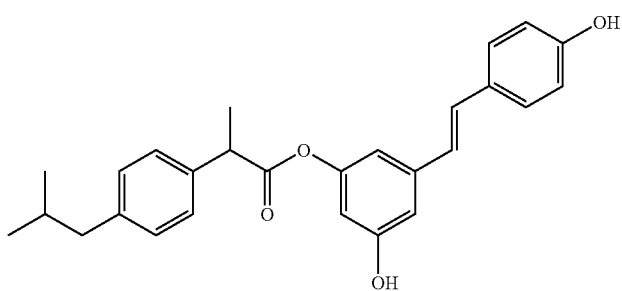
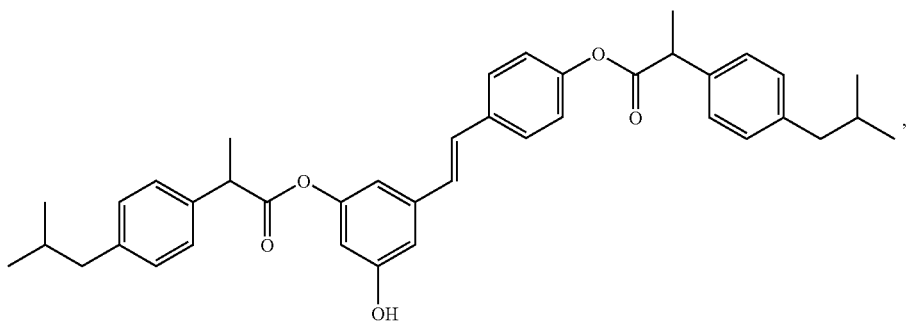

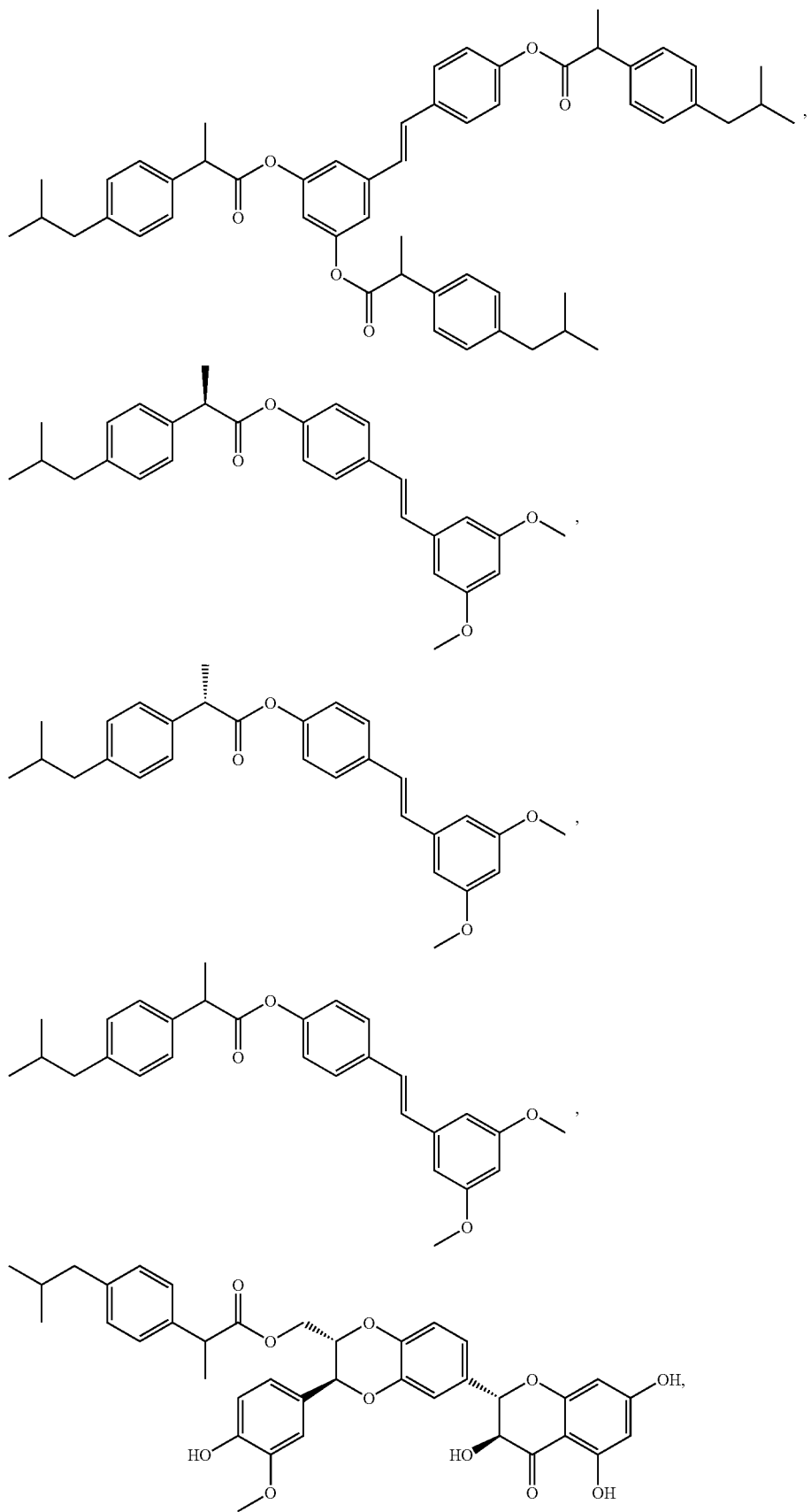

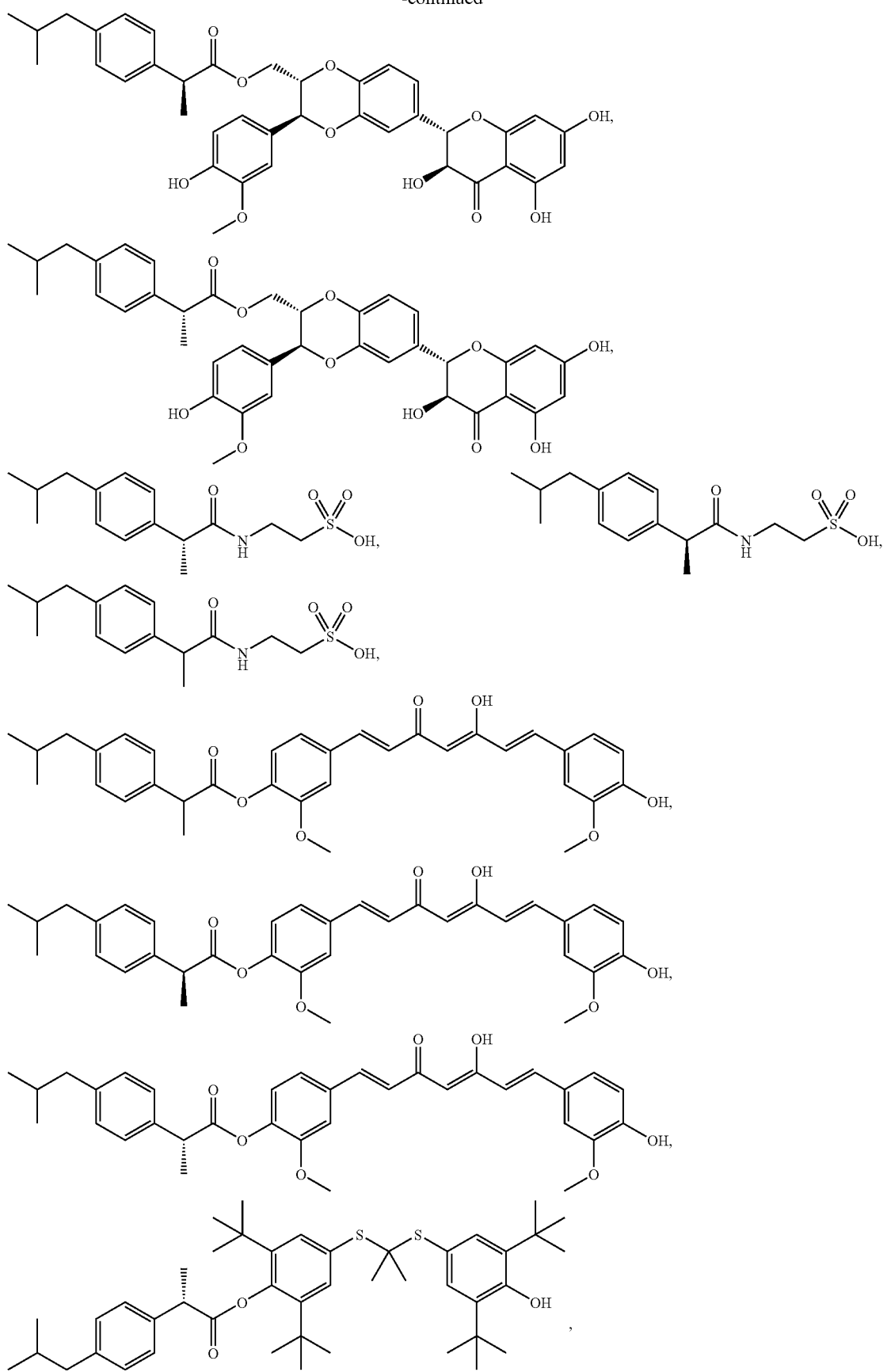

-continued
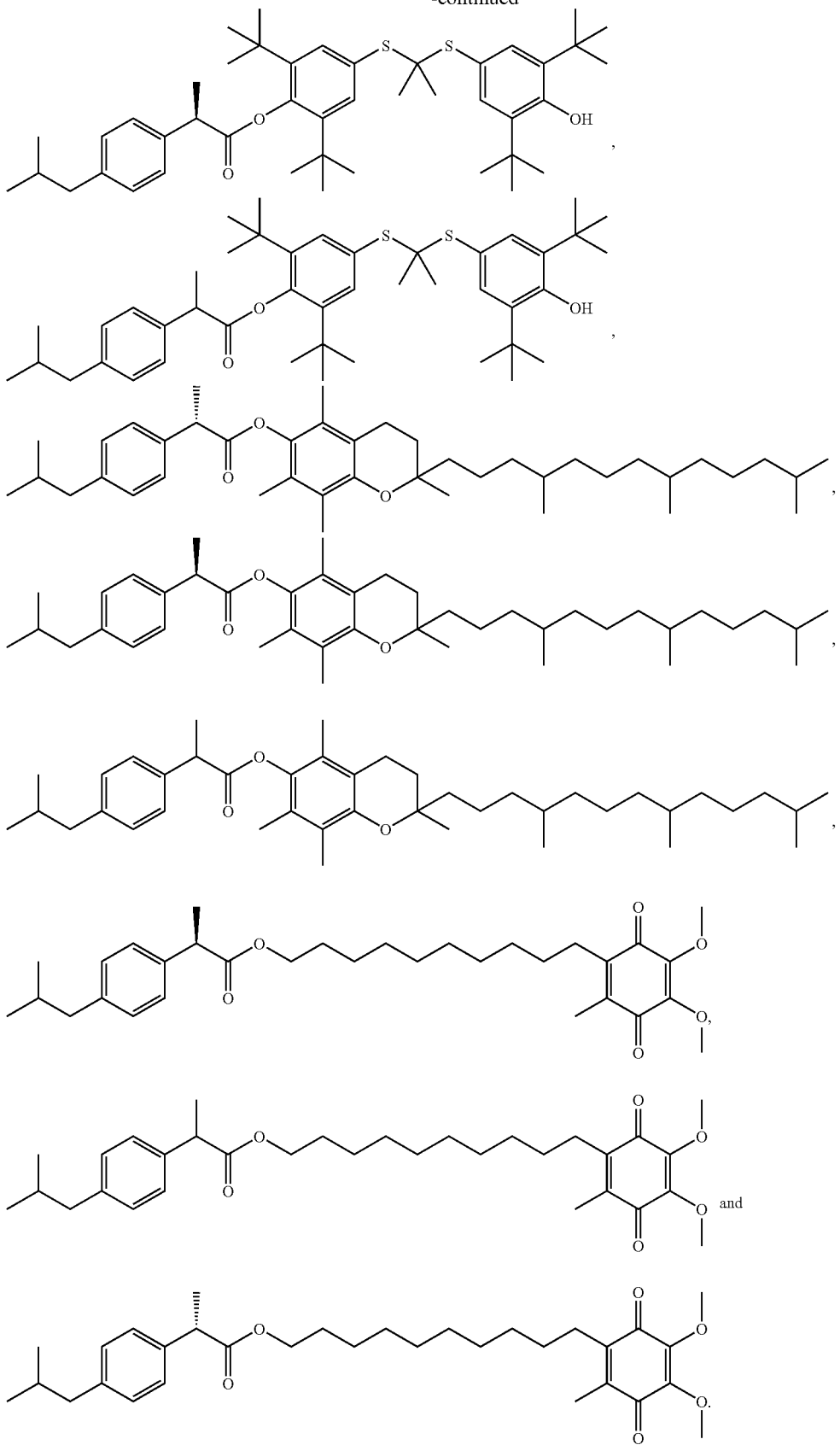

In another aspect, the present invention provides pharmaceutical compositions comprised of a compound of Formula (V), as shown above, and at least one pharmaceutically acceptable carrier.

In another aspect, the present invention provides conjugates of Formula (VI)

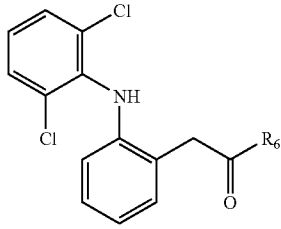
(VI)

wherein $R_6$ is

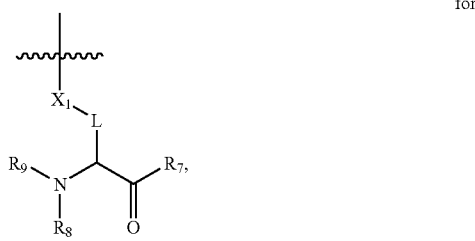
formula (i)

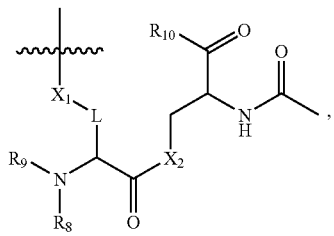
formula (ii)

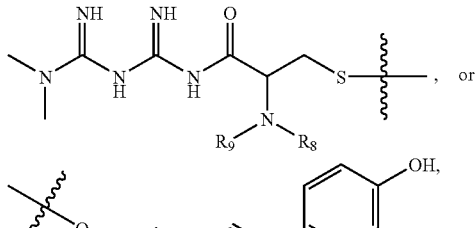
formula (iii)

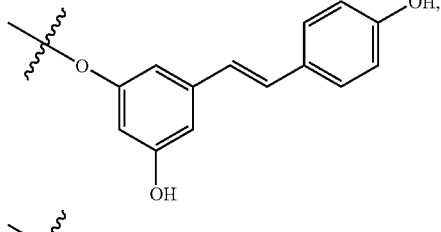

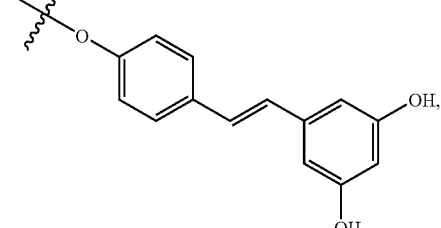

-continued

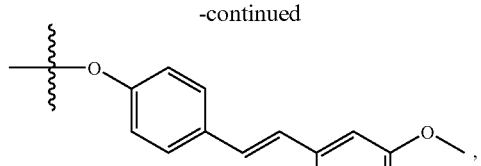

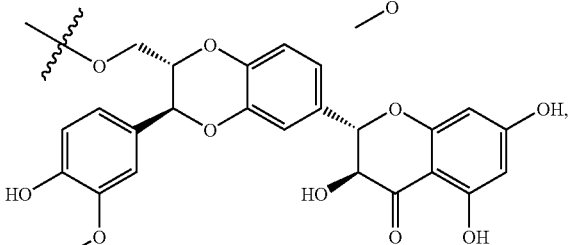

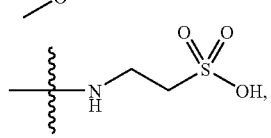

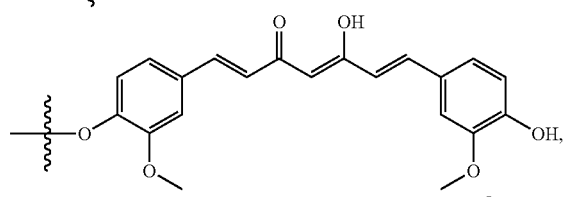

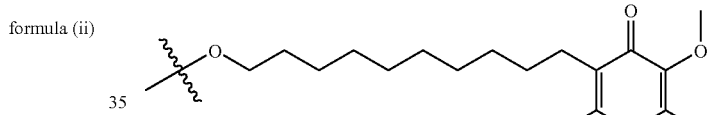

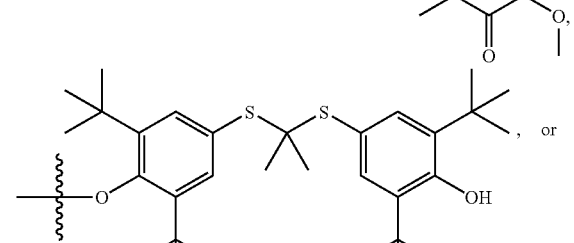

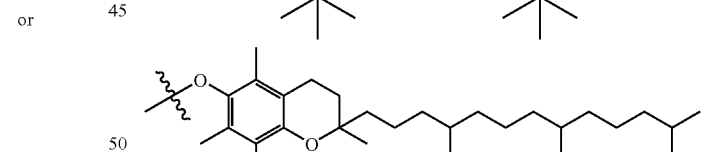

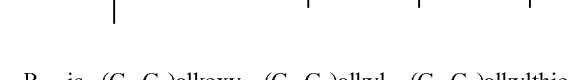
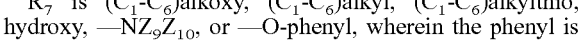

$R_7$ is $(C_1$-$C_6)$alkoxy, $(C_1$-$C_6)$alkyl, $(C_1$-$C_6)$alkylthio, hydroxy, $-NZ_9Z_{10}$, or $-O$-phenyl, wherein the phenyl is optionally substituted with 1, 2, 3, 4, or 5 groups that are independently $(C_1$-$C_6)$alkoxy, $(C_1$-$C_6)$alkoxycarbonyl, $(C_1$-$C_6)$alkyl, $(C_1$-$C_6)$alkylcarbonyl, $(C_1$-$C_6)$alkylcarbonyloxy, carboxy, cyano, formyl, halo$(C_1$-$C_6)$alkoxy, halo$(C_1$-$C_6)$alkyl, halogen, hydroxy, or hydroxy$(C_1$-$C_6)$alkyl;

$R_8$ is hydrogen or $(C_1$-$C_6)$alkyl;

$R_9$ is hydrogen, $(C_1$-$C_6)$alkyl, or $(C_1$-$C_6)$alkylcarbonyl;

$R_{10}$ is $(C_1$-$C_6)$alkoxy, $(C_1$-$C_6)$alkylthio, hydroxy, or $-NZ_9Z_{10}$;

$X_1$ and $X_2$ are independently O or S;

L is $(C_1$-$C_6)$alkylene; and $Z_9$ and $Z_{10}$ are independently hydrogen, $(C_1$-$C_6)$alkyl, or $(C_1$-$C_6)$alkylcarbonyl.

Representative conjugates of Formula (VI) include, but are not limited to, the compounds shown below.
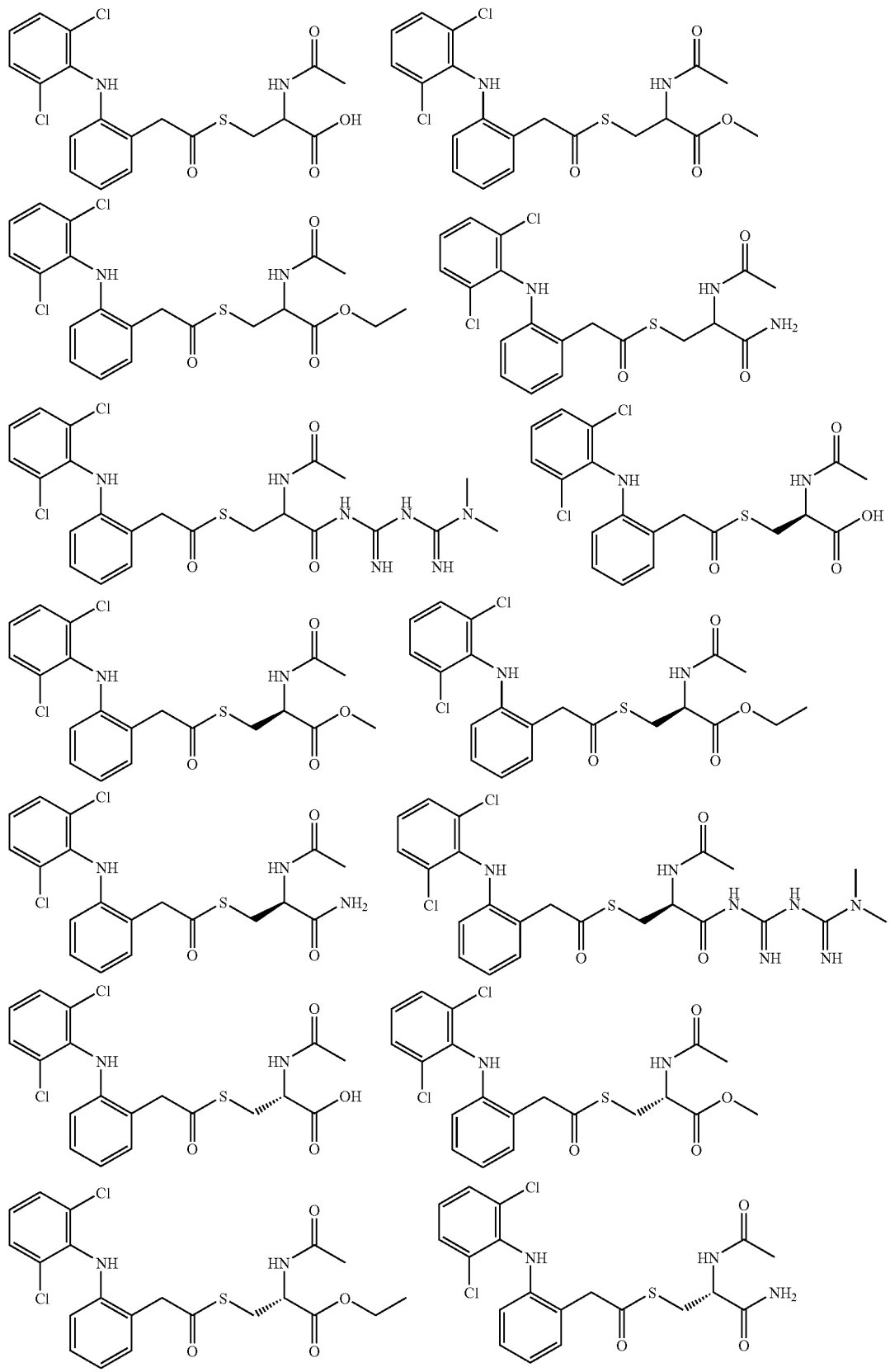

147 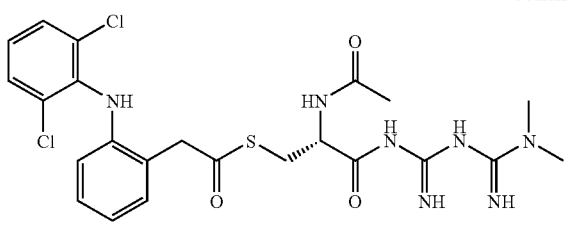 148 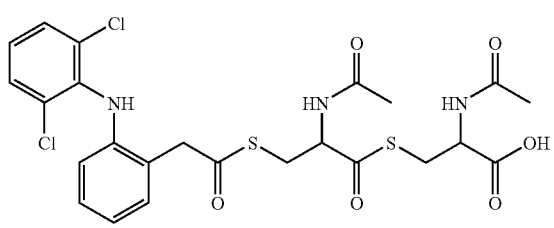
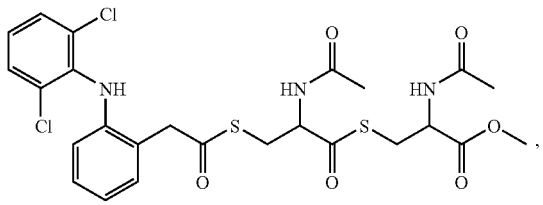 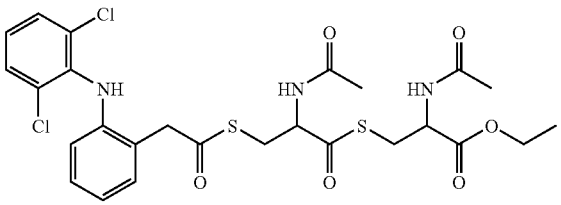
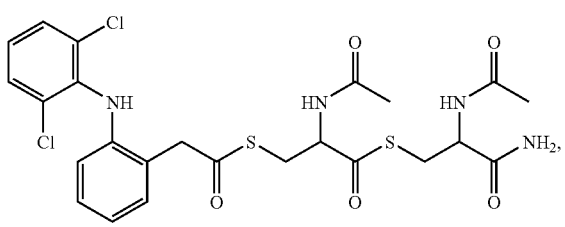 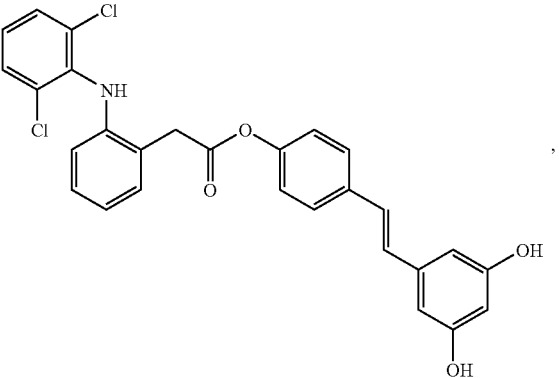
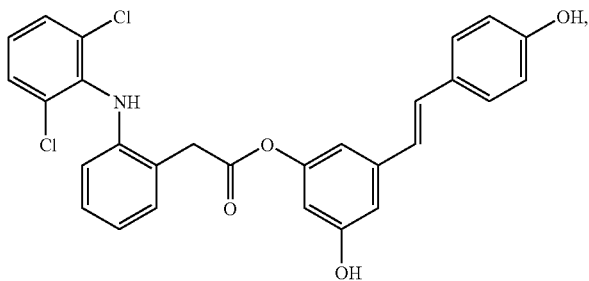
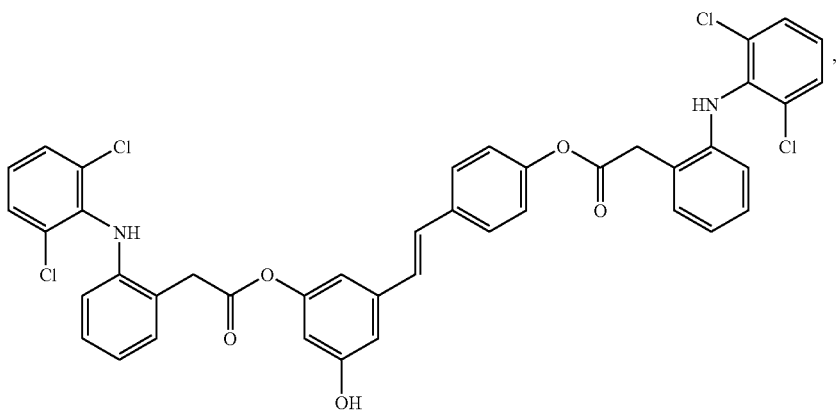

-continued
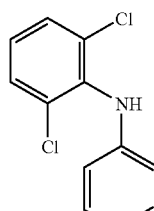 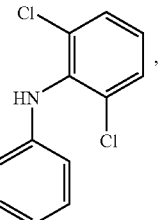 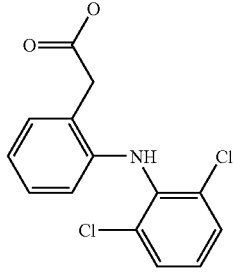
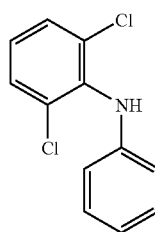
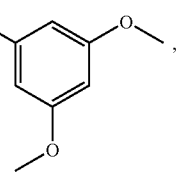
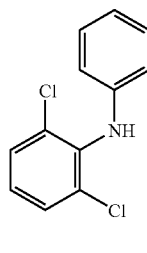 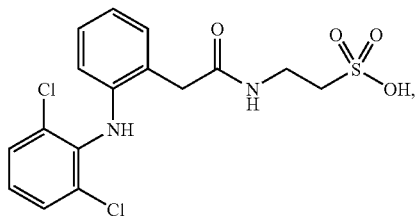
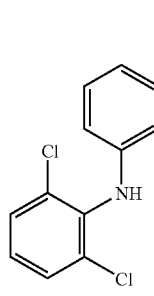 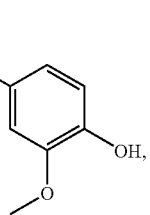

-continued
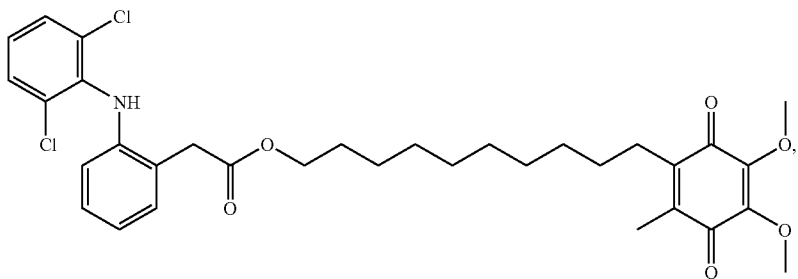
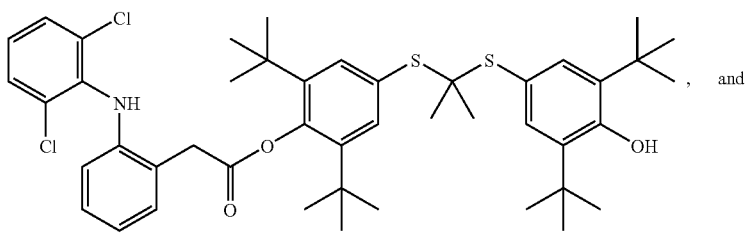
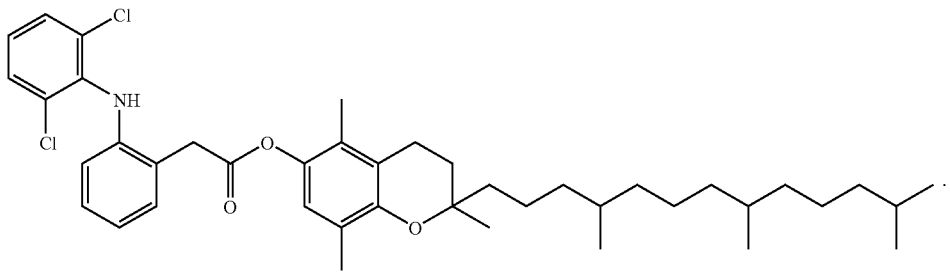
In another aspect, the present invention provides pharmaceutical compositions comprised of a compound of Formula (VI), as shown above, and at least one pharmaceutically acceptable carrier.
In another aspect, the present invention provides conjugates of Formula (VII)
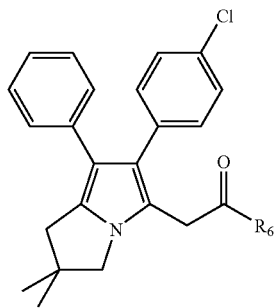
(VII)
wherein $R_6$ is
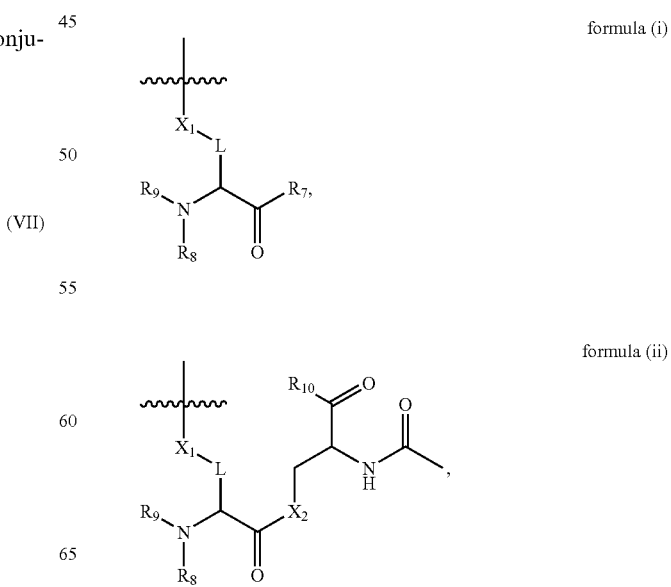
formula (i)
formula (ii)

153
-continued formula (iii)

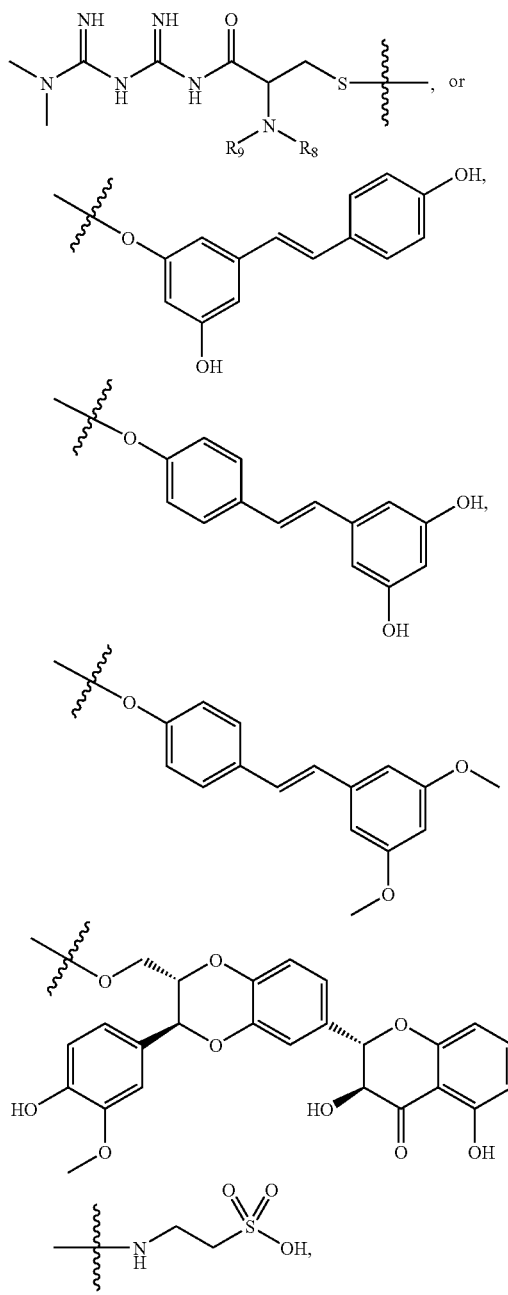

154
-continued

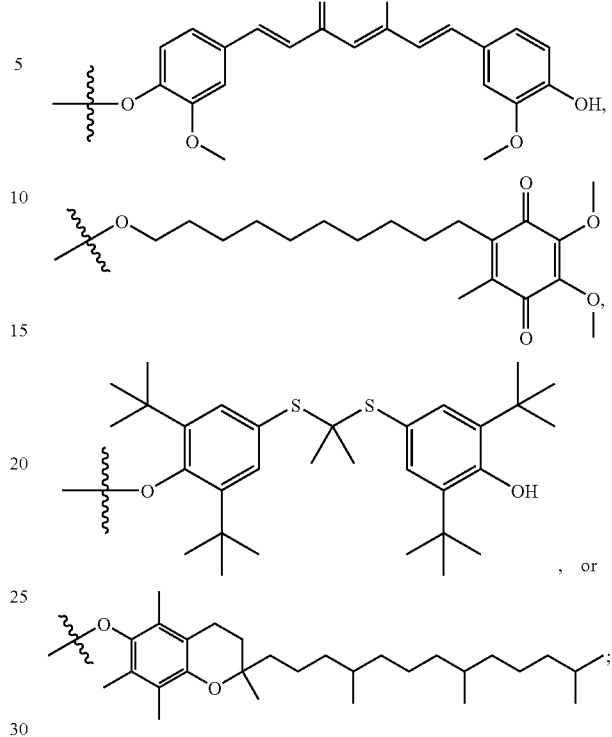

R$_7$ is (C$_1$-C$_6$)alkoxy, (C$_1$-C$_6$)alkyl, (C$_1$-C$_6$)alkylthio, hydroxy, —NZ$_9$Z$_{10}$, or —O-phenyl, wherein the phenyl is optionally substituted with 1, 2, 3, 4, or 5 groups that are independently (C$_1$-C$_6$)alkoxy, (C$_1$-C$_6$)alkoxycarbonyl, (C$_1$-C$_6$)alkyl, (C$_1$-C$_6$)alkylcarbonyl, (C$_1$-C$_6$)alkylcarbonyloxy, carboxy, cyano, formyl, halo(C$_1$-C$_6$)alkoxy, halo(C$_1$-C$_6$)alkyl, halogen, hydroxy, or hydroxy(C$_1$-C$_6$)alkyl;

R$_8$ is hydrogen or (C$_1$-C$_6$)alkyl;

R$_9$ is hydrogen, (C$_1$-C$_6$)alkyl, or (C$_1$-C$_6$)alkylcarbonyl;

R$_{10}$ is (C$_1$-C$_6$)alkoxy, (C$_1$-C$_6$)alkylthio, hydroxy, or —NZ$_9$Z$_{10}$;

X$_1$ and X$_2$ are independently O or S;

L is (C$_1$-C$_6$)alkylene; and

Z$_9$ and Z$_{10}$ are independently hydrogen, (C$_1$-C$_6$)alkyl, or (C$_1$-C$_6$)alkylcarbonyl.

Representative conjugates of Formula (VII) include, but are not limited to, the compounds shown below.

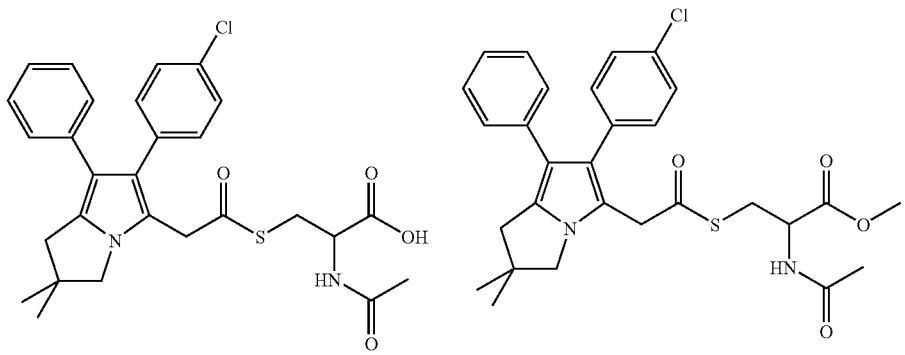

-continued
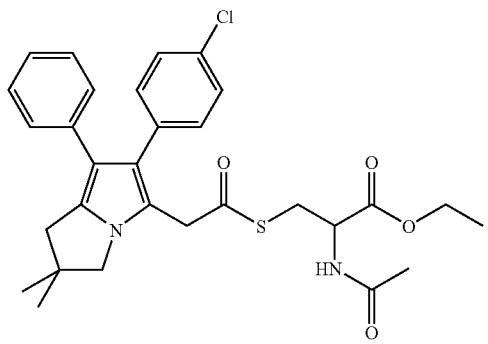
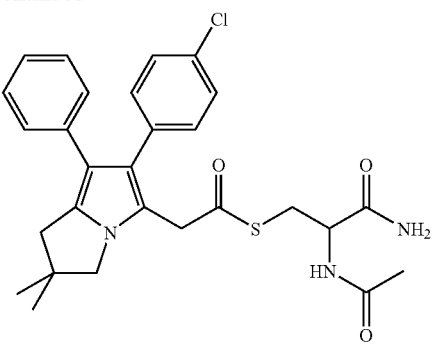
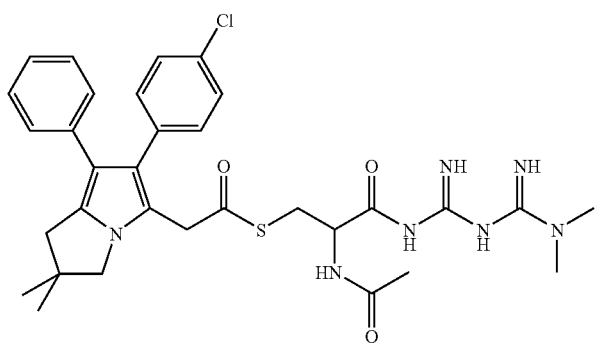
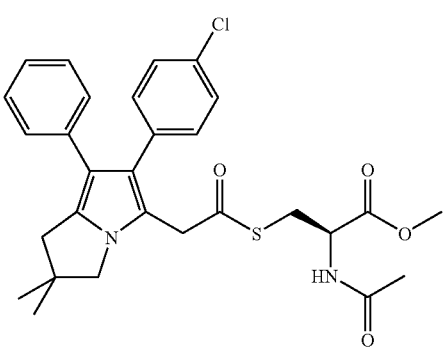
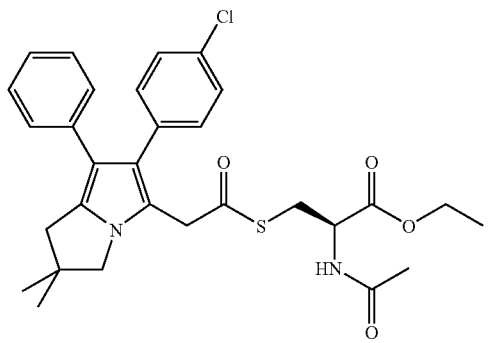
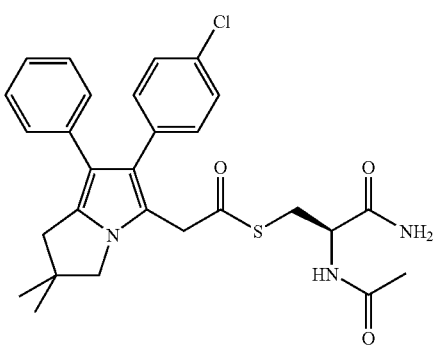
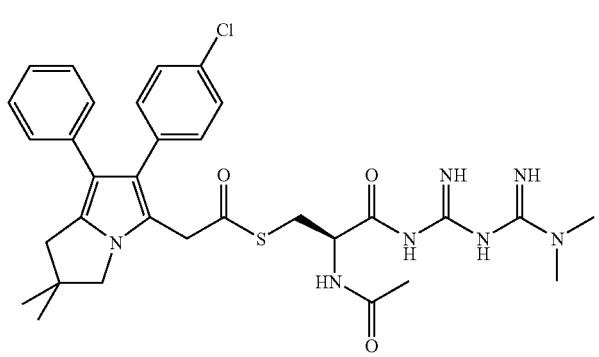
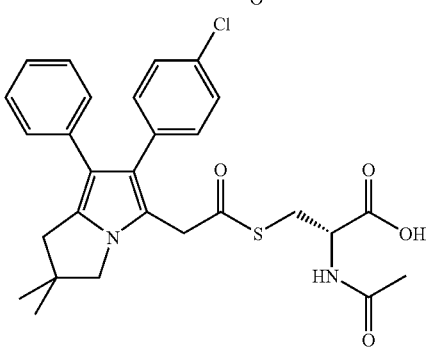

157
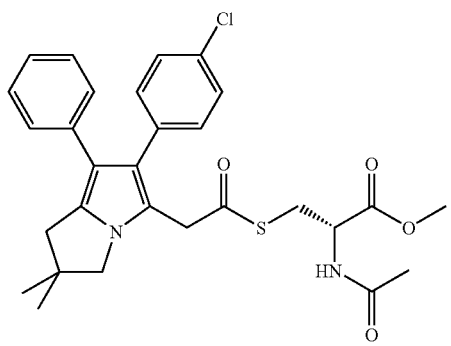
158
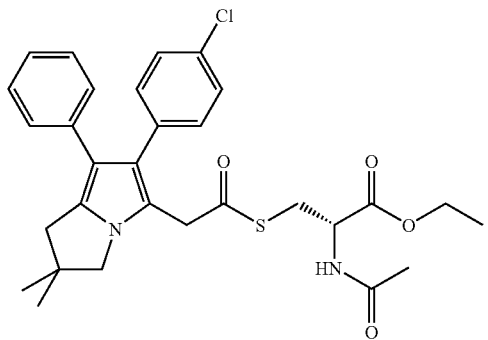
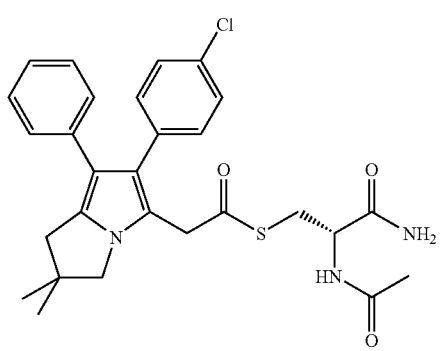
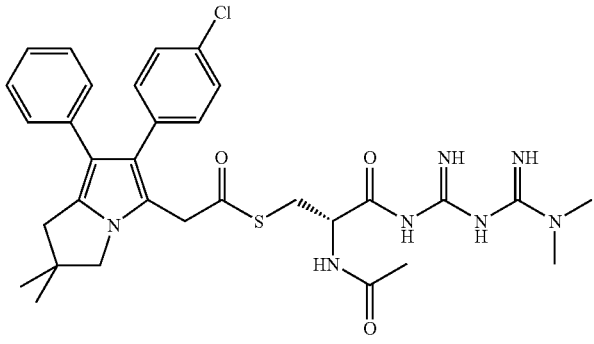
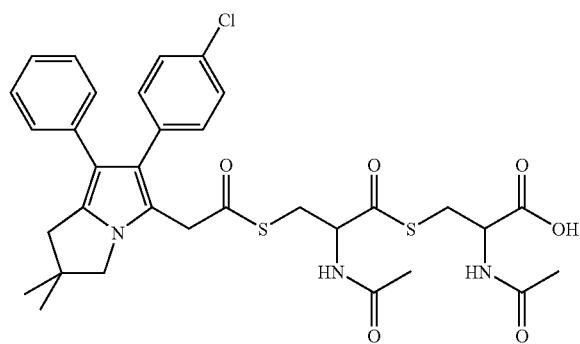
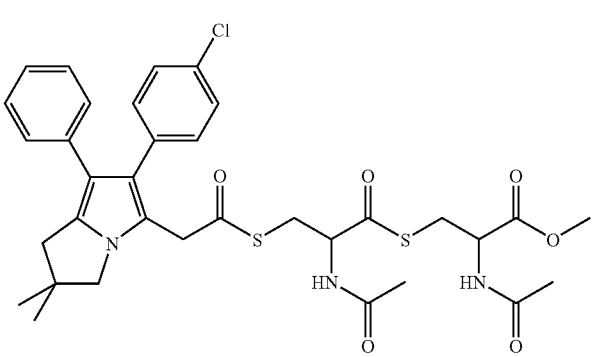
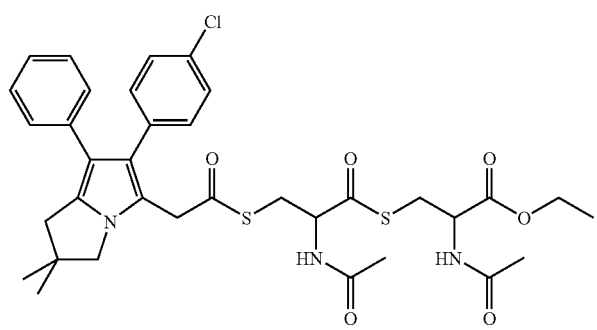
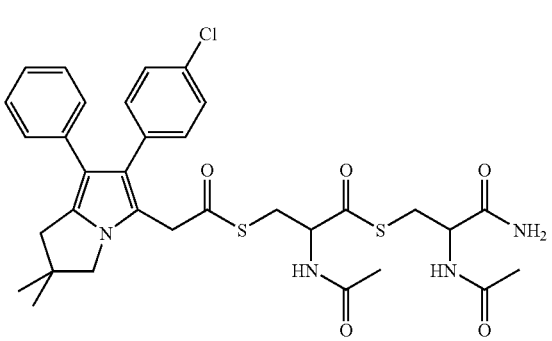

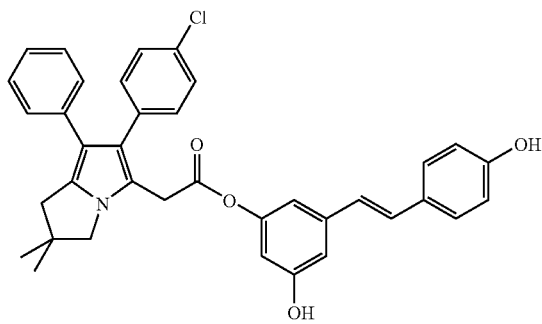
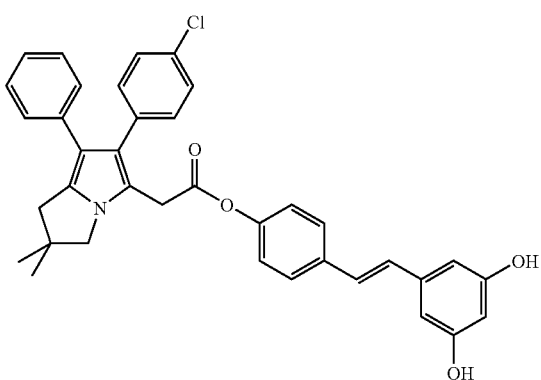
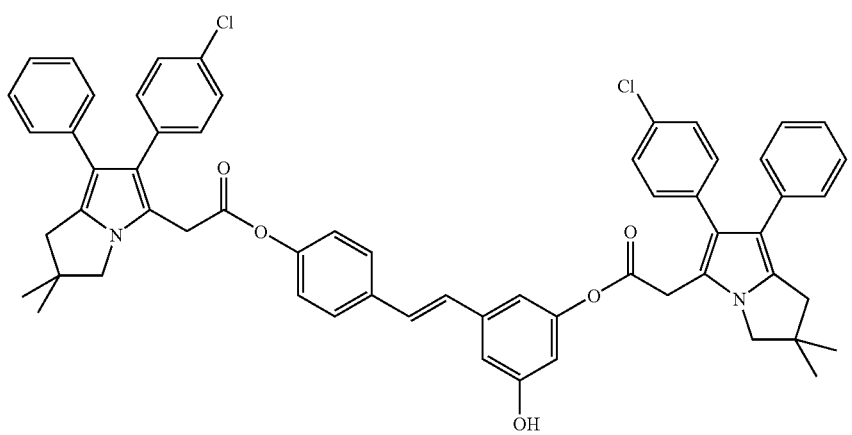
and
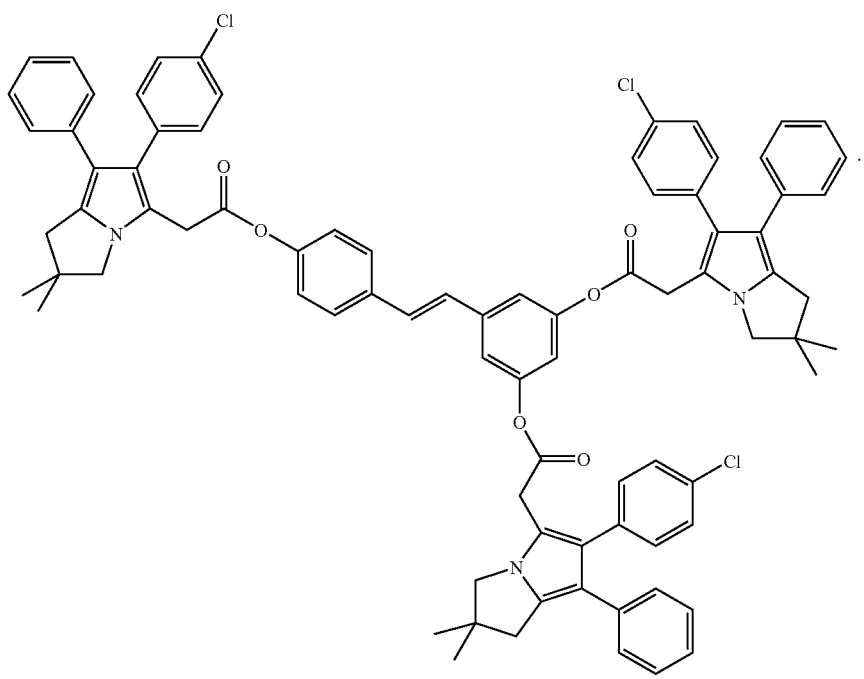

In another aspect, the present invention provides pharmaceutical compositions comprised of a compound of Formula (VII), as shown above, and at least one pharmaceutically acceptable carrier.

In another aspect, the present invention provides conjugates of Formula (X)

(VIII)

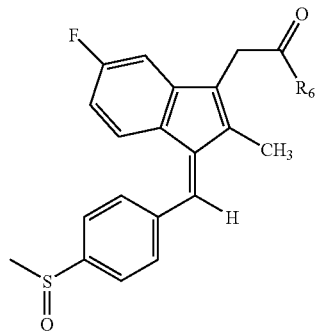

wherein $R_6$ is formula (i)

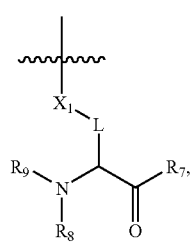

formula (ii)

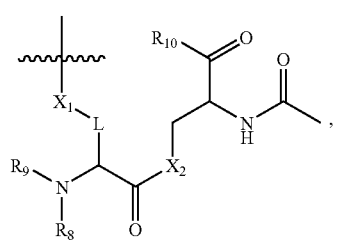

formula (iii)

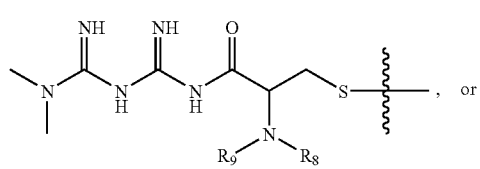

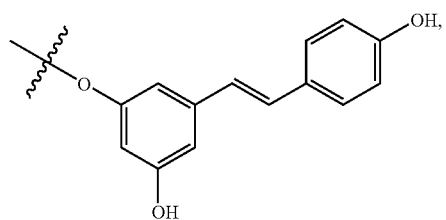

-continued

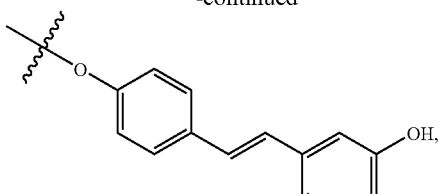

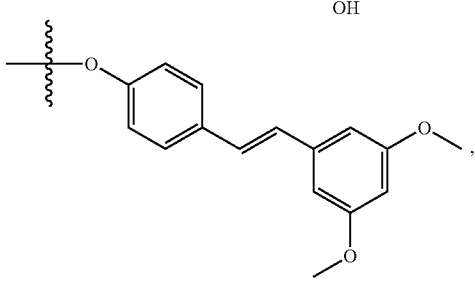

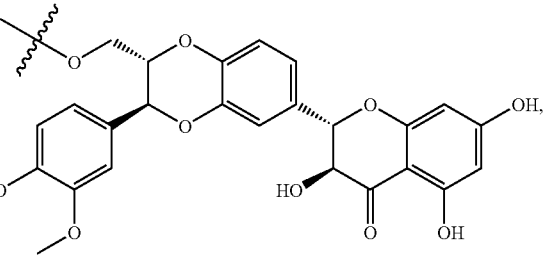

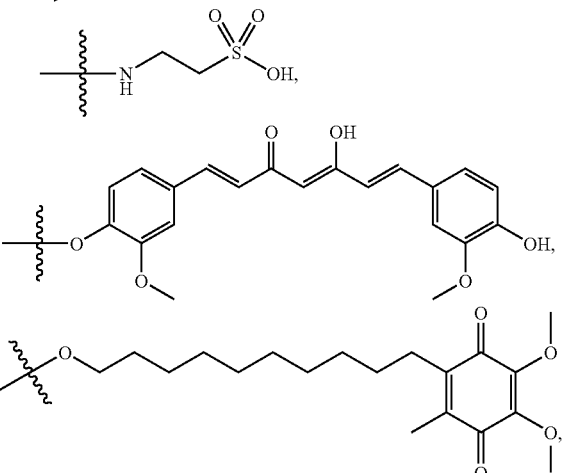

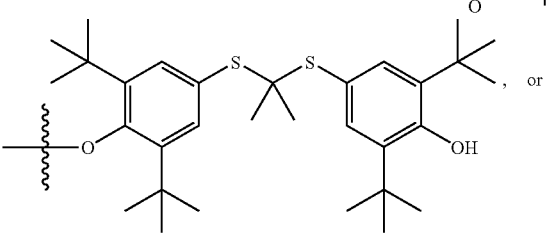

$R_7$ is $(C_1-C_6)$alkoxy, $(C_1-C_6)$alkyl, $(C_1-C_6)$alkylthio, hydroxy, $-NZ_9Z_{10}$, or $-O$-phenyl, wherein the phenyl is optionally substituted with 1, 2, 3, 4, or 5 groups that are independently $(C_1-C_6)$alkoxy, $(C_1-C_6)$alkoxycarbonyl, $(C_1-C_6)$alkyl, $(C_1-C_6)$alkylcarbonyl, $(C_1-C_6)$alkylcarbonyloxy, carboxy, cyano, formyl, halo$(C_1-C_6)$alkoxy, halo$(C_1-C_6)$alkyl, halogen, hydroxy, or hydroxy$(C_1-C_6)$alkyl;

$R_8$ is hydrogen or $(C_1-C_6)$alkyl;

$R_9$ is hydrogen, $(C_1-C_6)$alkyl, or $(C_1-C_6)$alkylcarbonyl;

$R_{10}$ is $(C_1-C_6)$alkoxy, $(C_1-C_6)$alkylthio, hydroxy, or $-NZ_9Z_{10}$;

$X_1$ and $X_2$ are independently O or S;

L is $(C_1-C_6)$alkylene; and $Z_9$ and $Z_{10}$ are independently hydrogen, $(C_1-C_6)$alkyl, or $(C_1-C_6)$alkylcarbonyl.

Representative conjugates of Formula (VIII) include, but are not limited to, the compounds shown below.

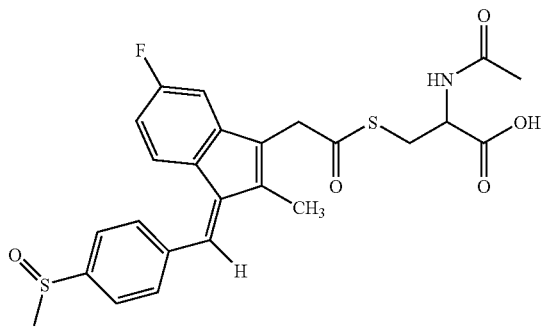

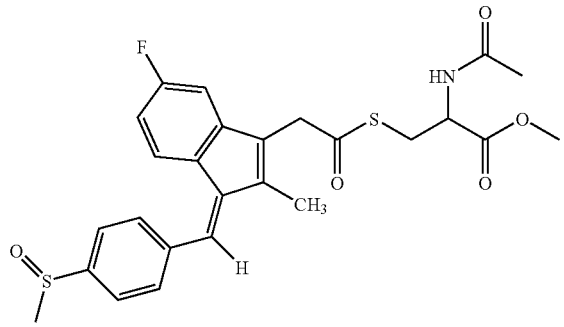

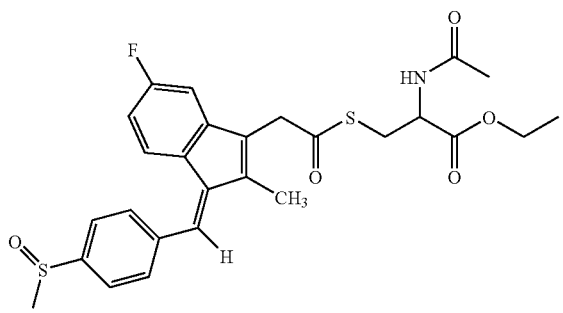

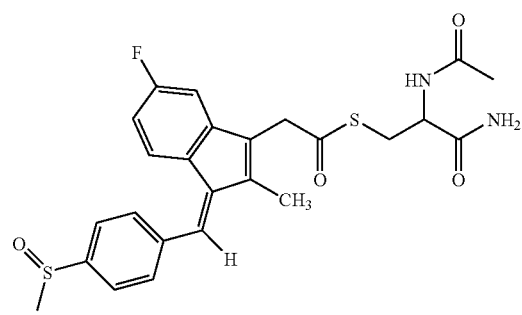

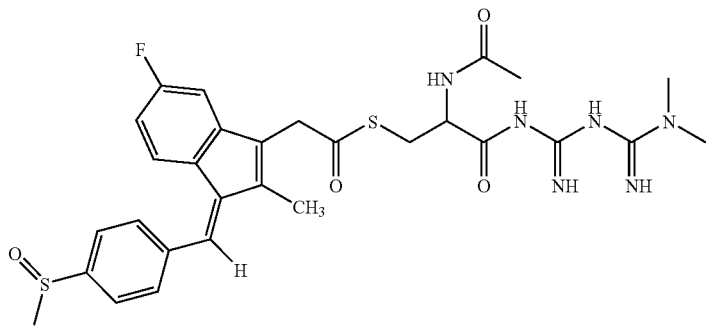

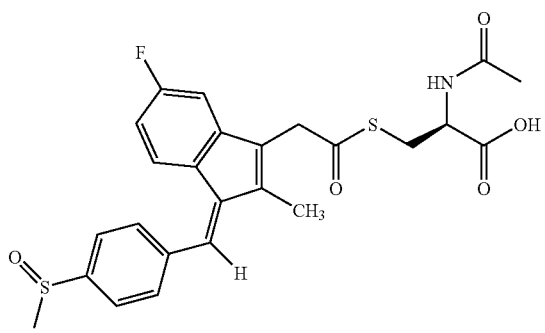

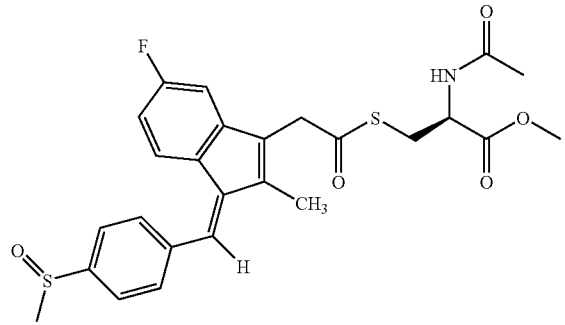

-continued
165
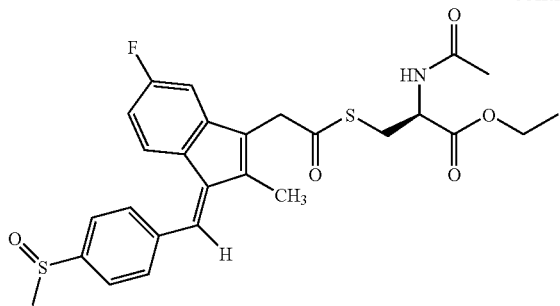
166
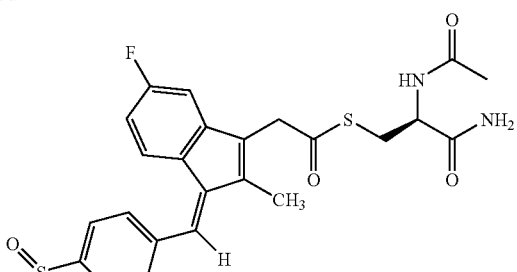
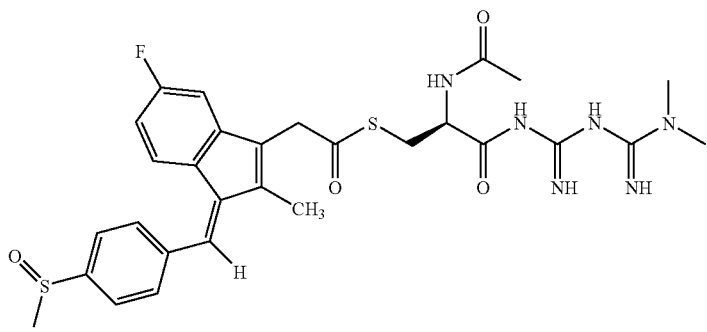
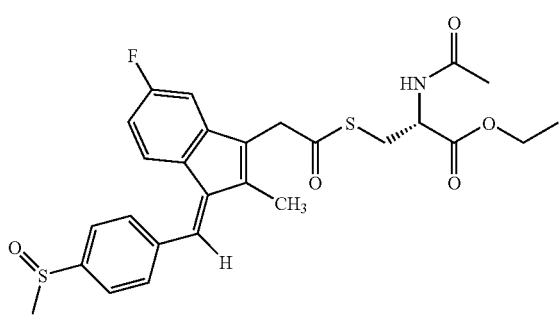
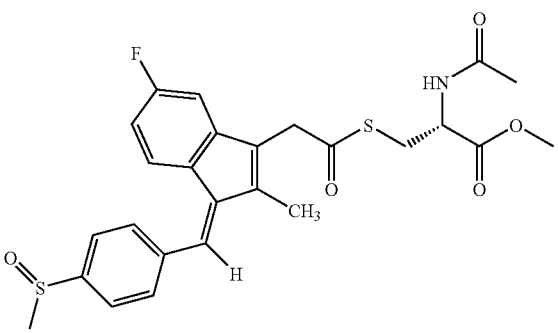
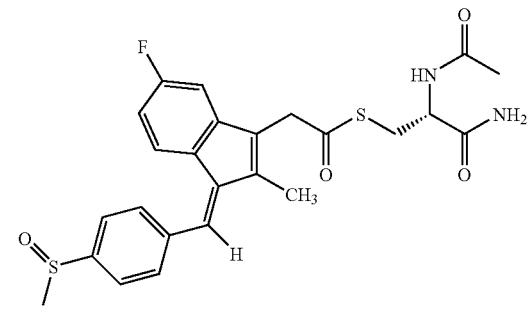
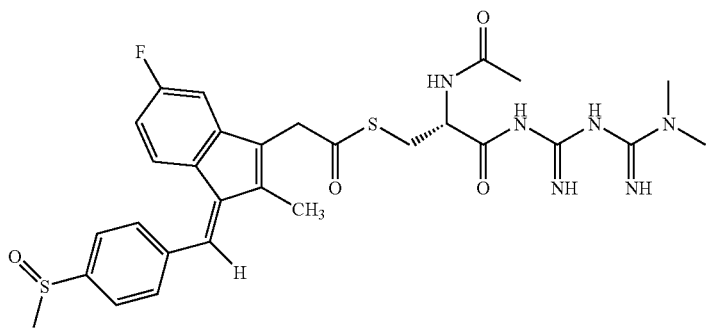

-continued
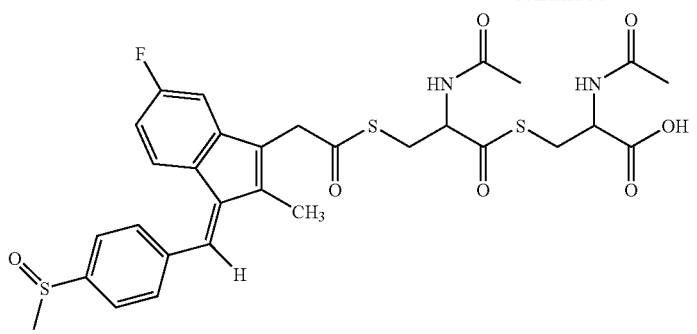
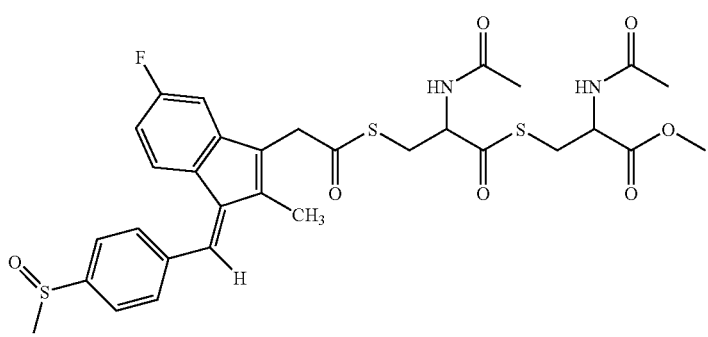
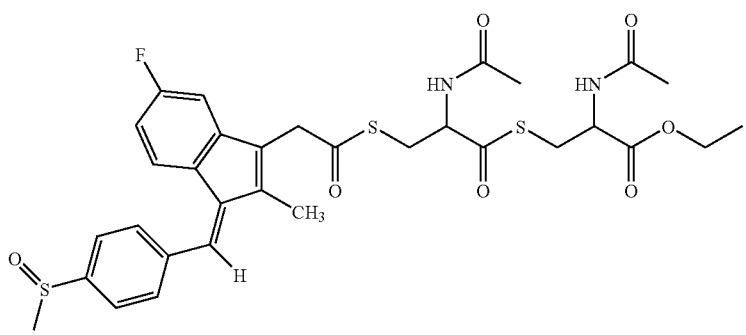
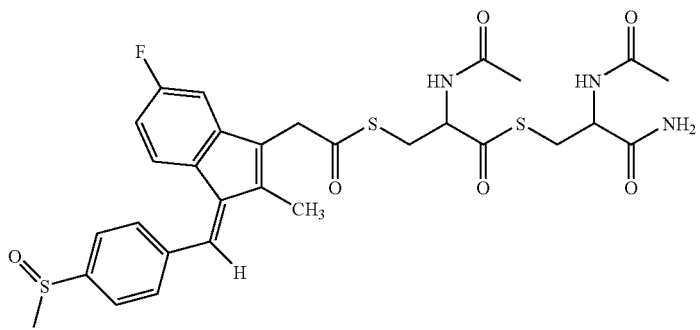
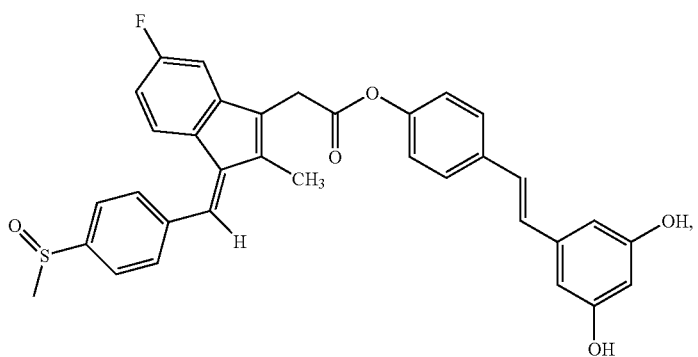

-continued
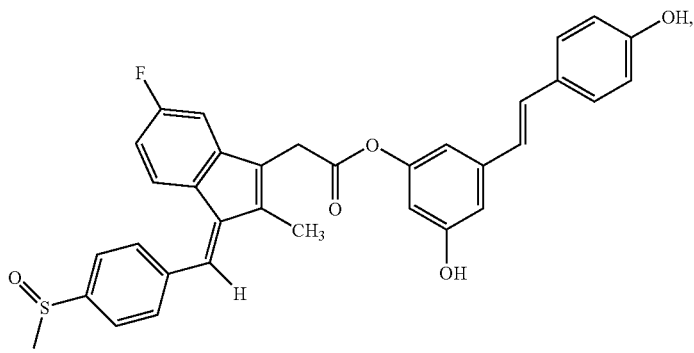
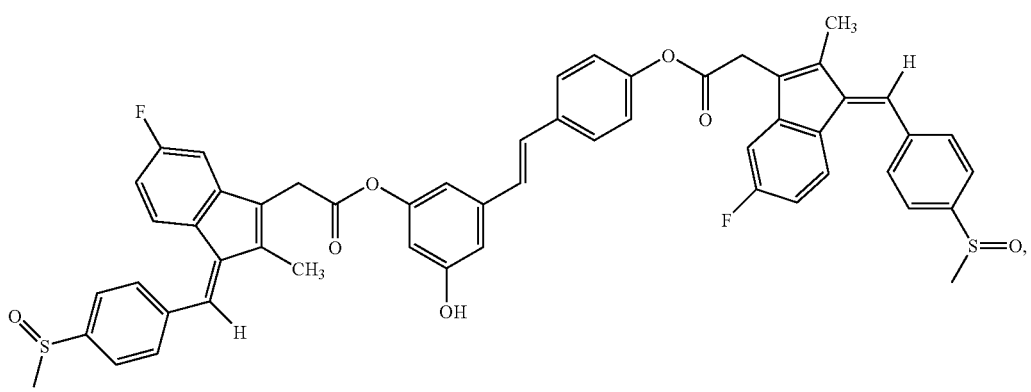
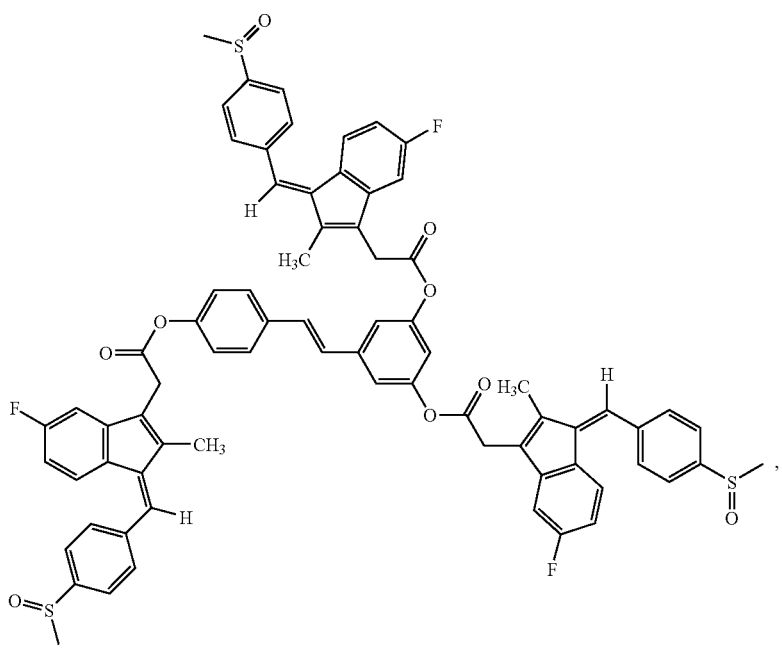
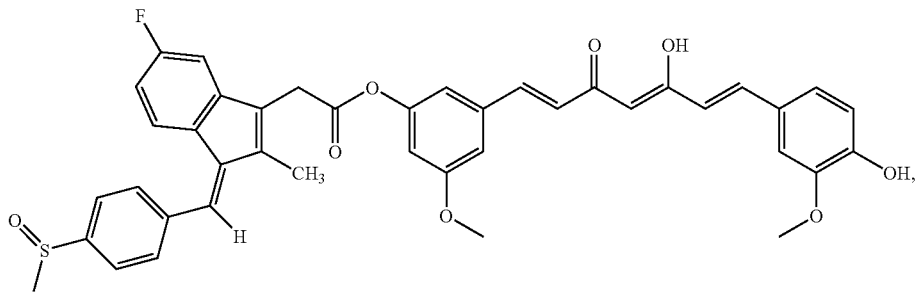

-continued
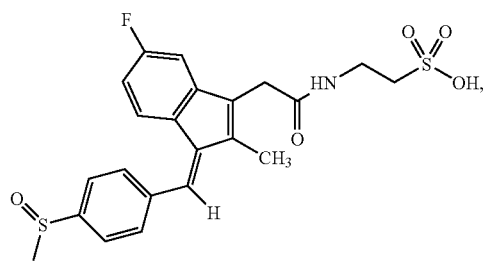 171
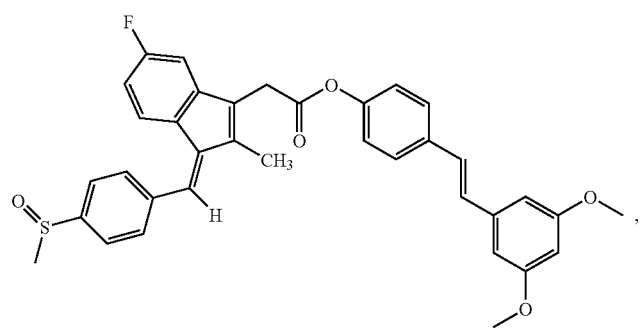 172
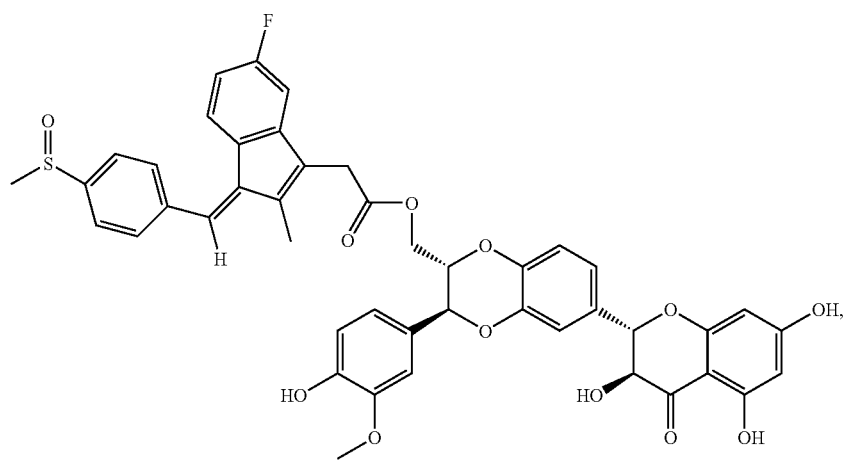
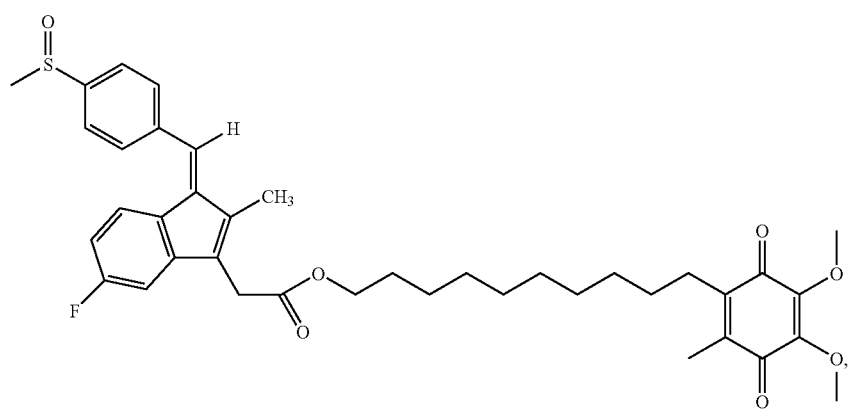
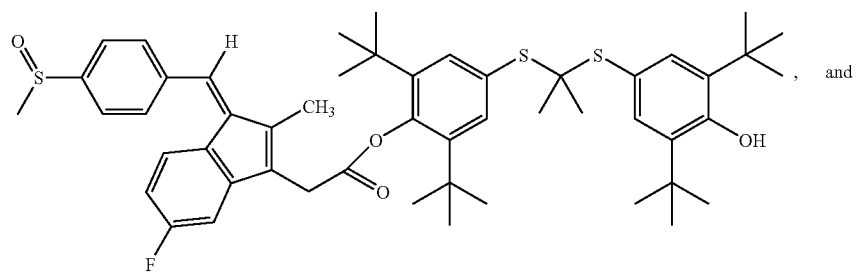 and

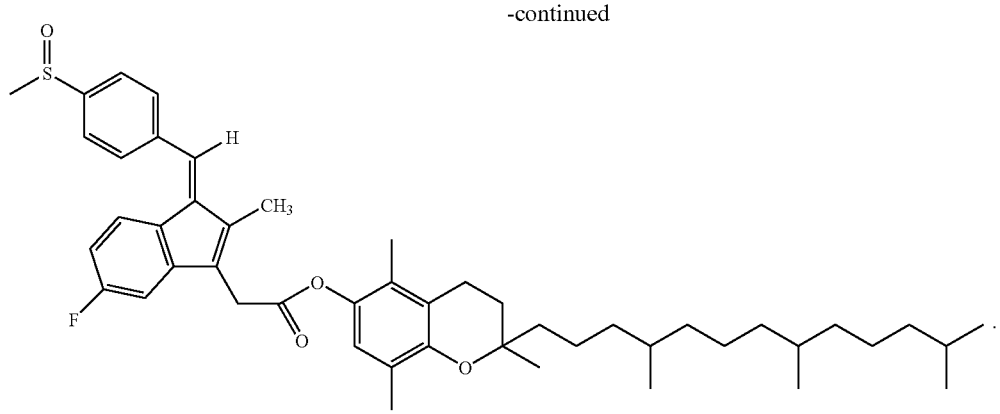
In another aspect, the present invention provides pharmaceutical compositions comprised of a compound of Formula (VIII), as shown above, and at least one pharmaceutically acceptable carrier.
In another aspect, the present invention provides conjugates of Formula (IX)
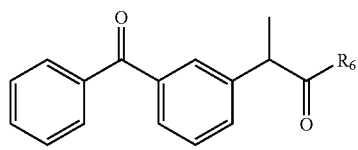
(IX)
wherein $R_6$ is
formula (i)
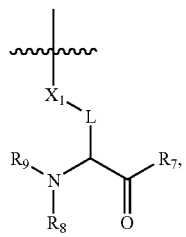
formula (ii)
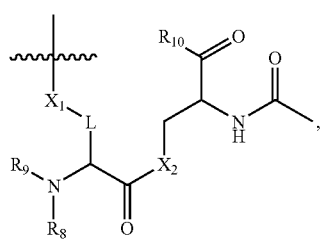
formula (iii)
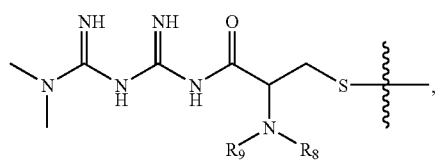
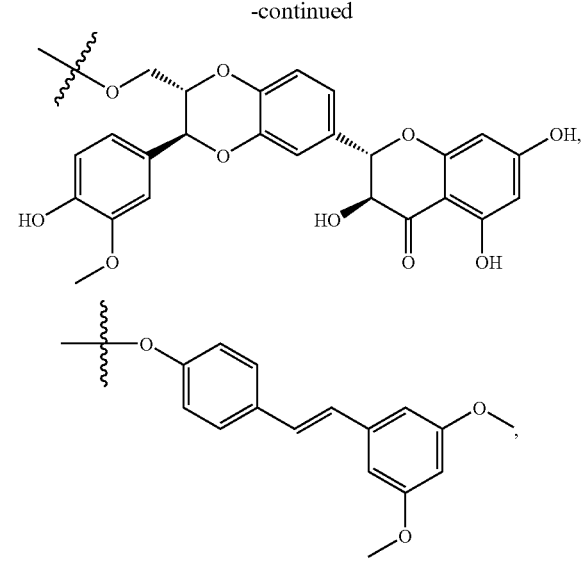
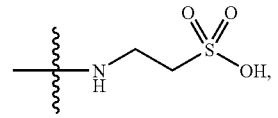

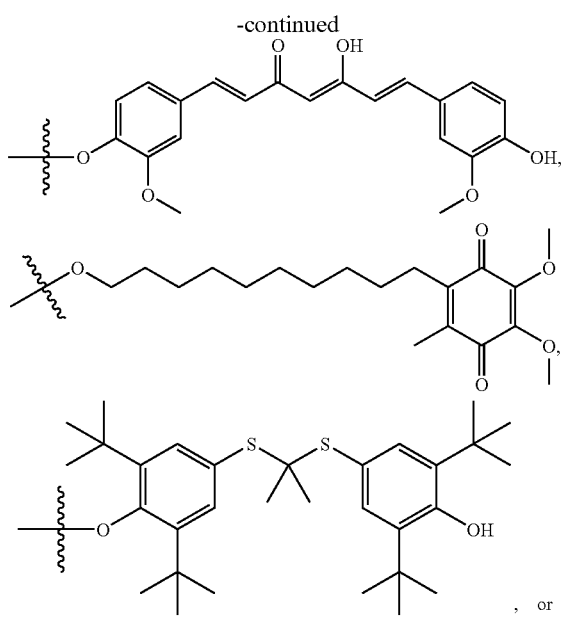, or

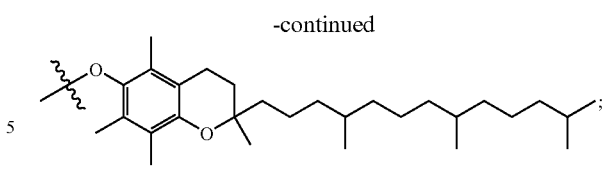;

$R_7$ is $(C_1$-$C_6)$alkoxy, $(C_1$-$C_6)$alkyl, $(C_1$-$C_6)$alkylthio, hydroxy, —$NZ_9Z_{10}$, or —O-phenyl, wherein the phenyl is optionally substituted with 1, 2, 3, 4, or 5 groups that are independently $(C_1$-$C_6)$alkoxy, $(C_1$-$C_6)$alkoxycarbonyl, $(C_1$-$C_6)$alkyl, $(C_1$-$C_6)$alkylcarbonyl, $(C_1$-$C_6)$alkylcarbonyloxy, carboxy, cyano, formyl, halo$(C_1$-$C_6)$alkoxy, halo$(C_1$-$C_6)$alkyl, halogen, hydroxy, or hydroxy$(C_1$-$C_6)$alkyl;

$R_8$ is hydrogen or $(C_1$-$C_6)$alkyl;

$R_9$ is hydrogen, $(C_1$-$C_6)$alkyl, or $(C_1$-$C_6)$alkylcarbonyl;

$R_{10}$ is $(C_1$-$C_6)$alkoxy, $(C_1$-$C_6)$alkylthio, hydroxy, or —$NZ_9Z_{10}$;

$X_1$ and $X_2$ are independently O or S;

L is $(C_1$-$C_6)$alkylene; and $Z_9$ and $Z_{10}$ are independently hydrogen, $(C_1$-$C_6)$alkyl, or $(C_1$-$C_6)$alkylcarbonyl.

Representative conjugates of Formula (IX) include, but are not limited to, the compounds shown below.

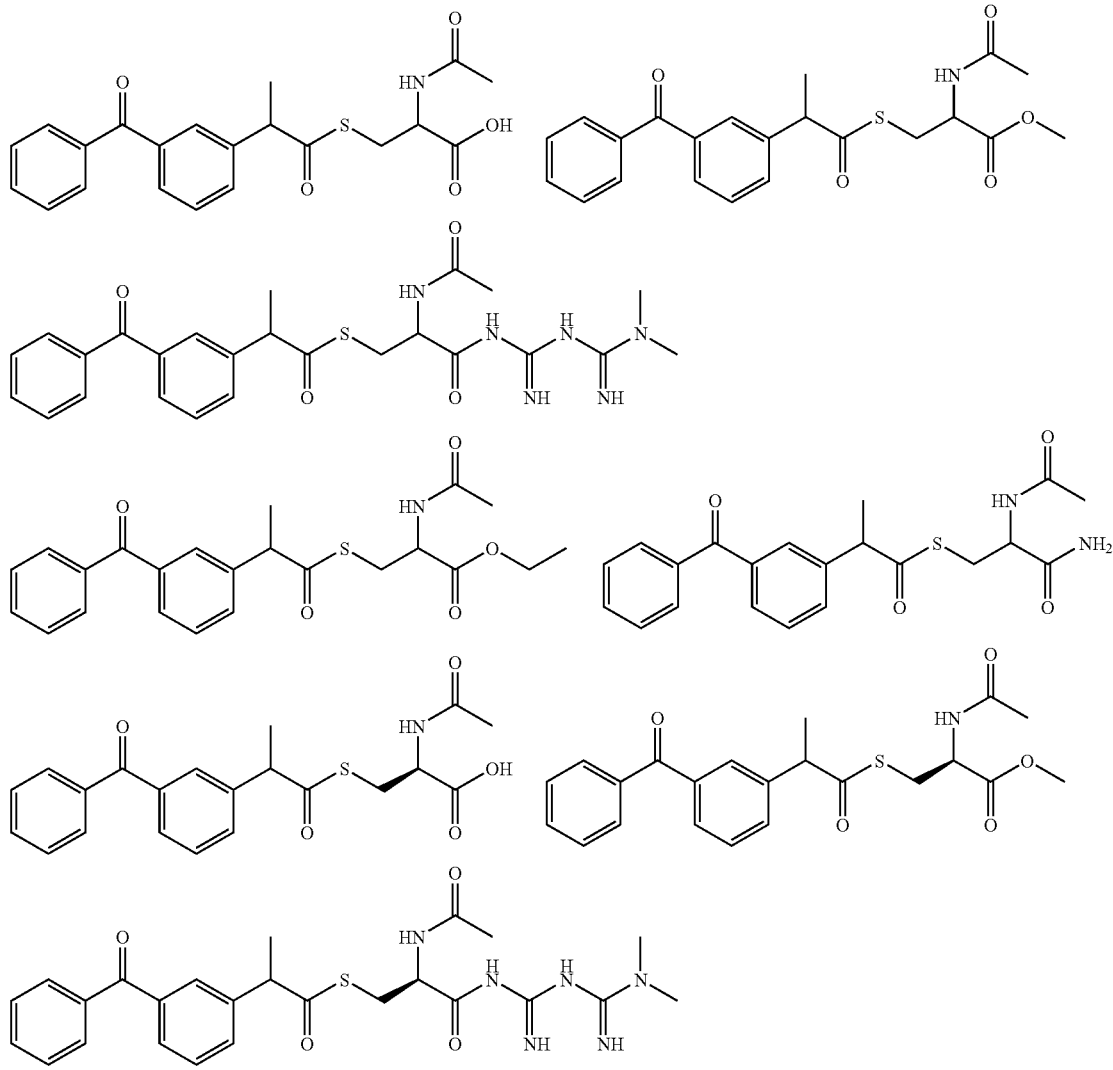

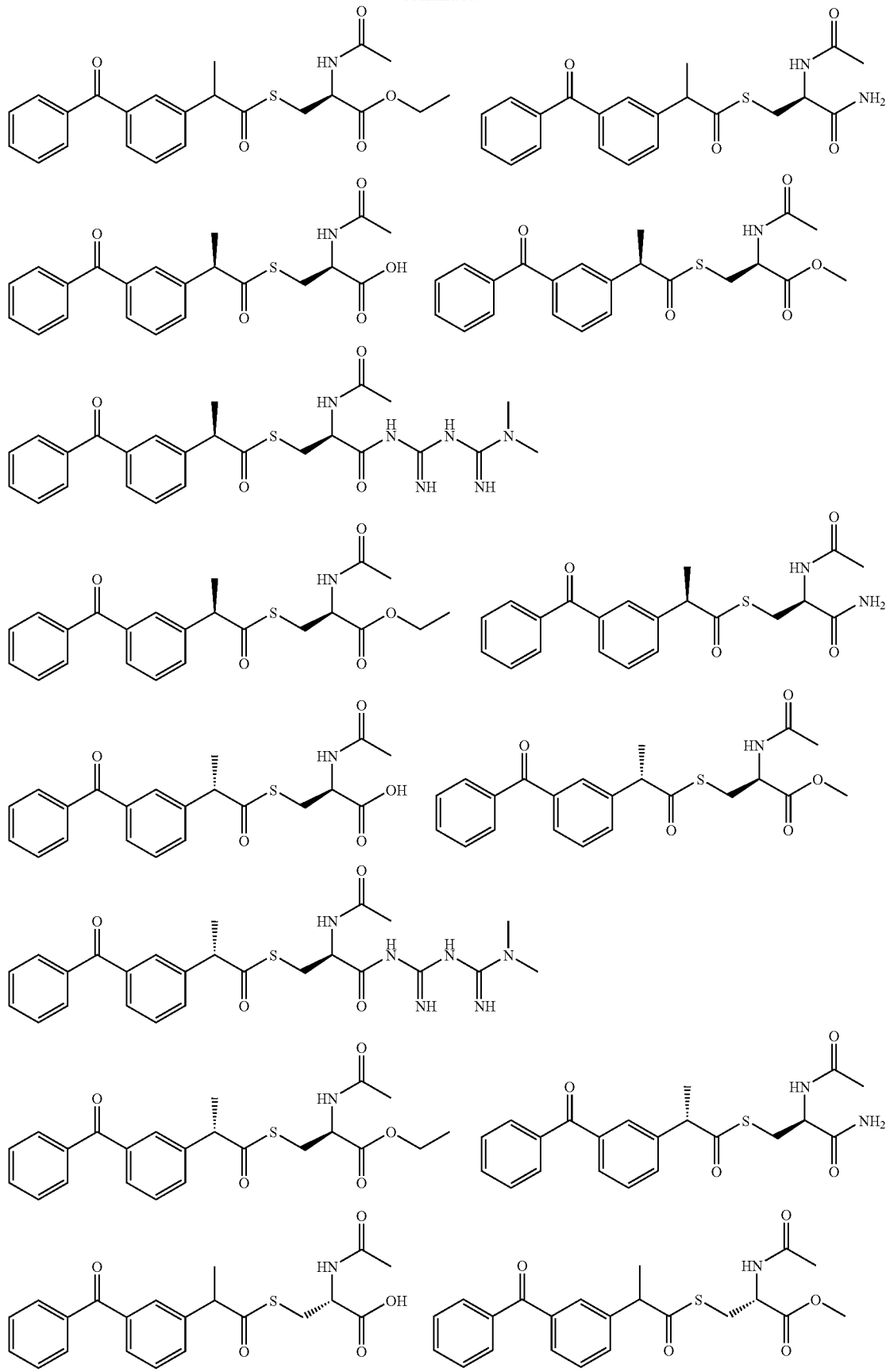

-continued
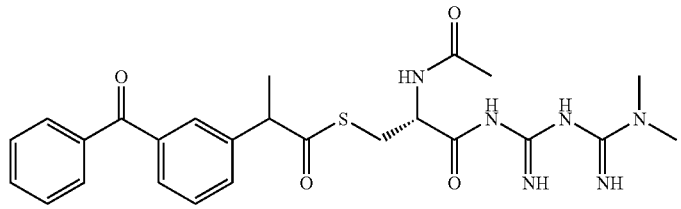
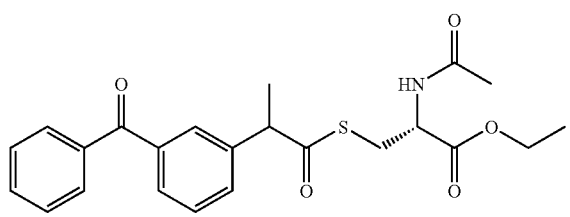
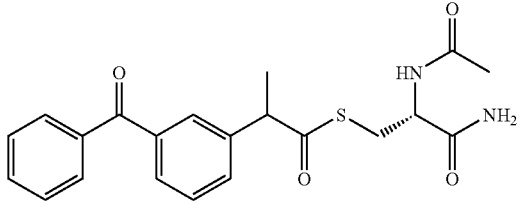
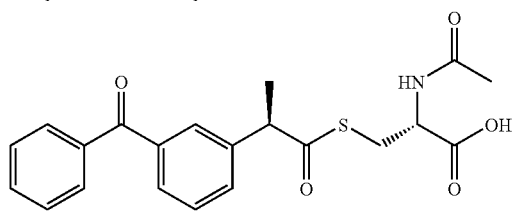
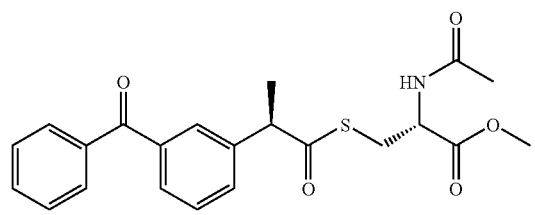
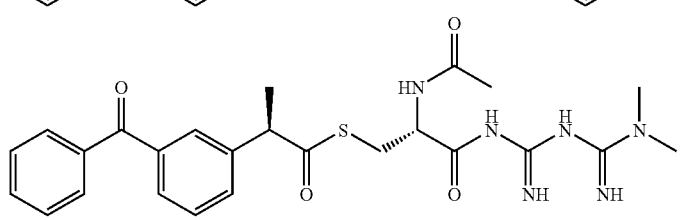
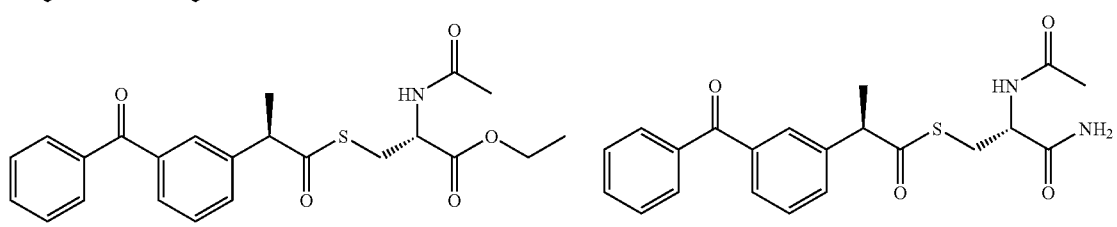
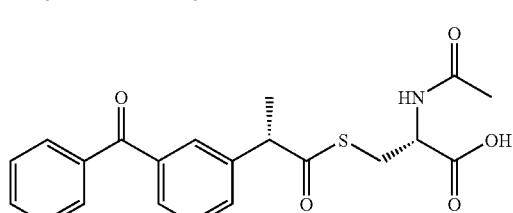
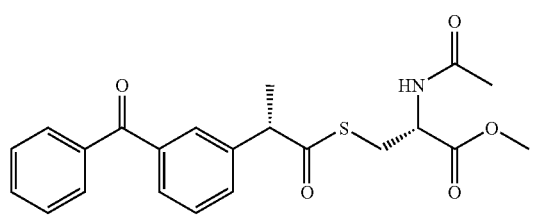
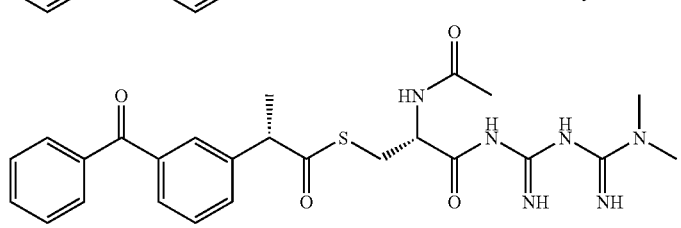
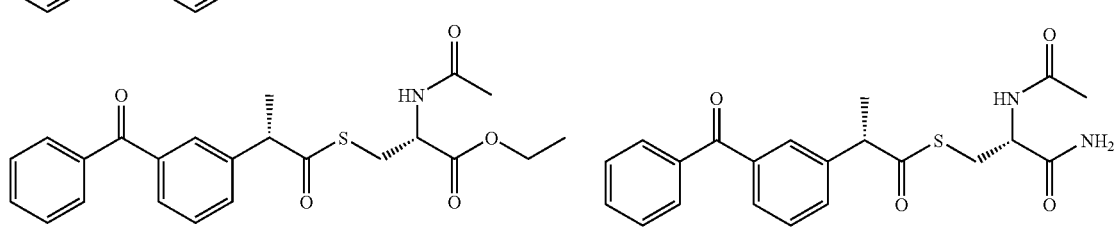

-continued
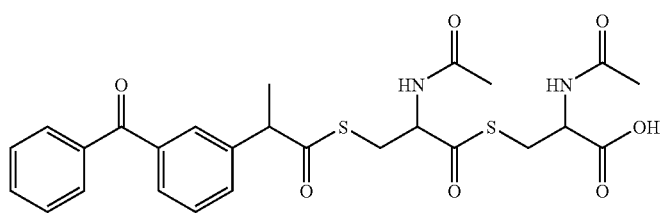
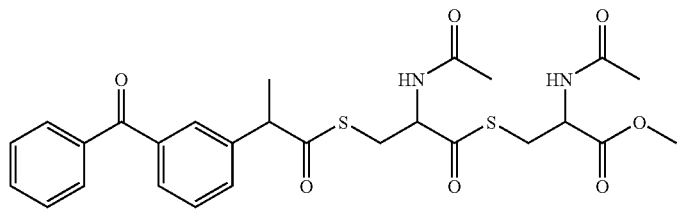
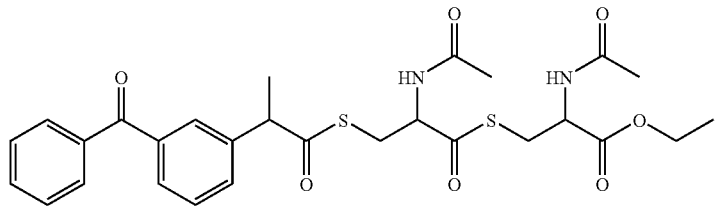
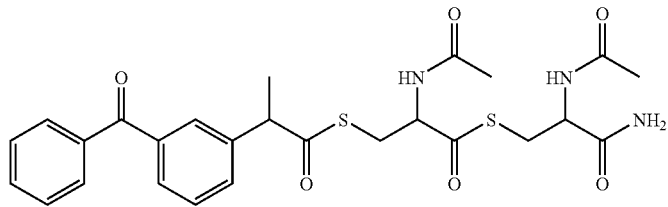
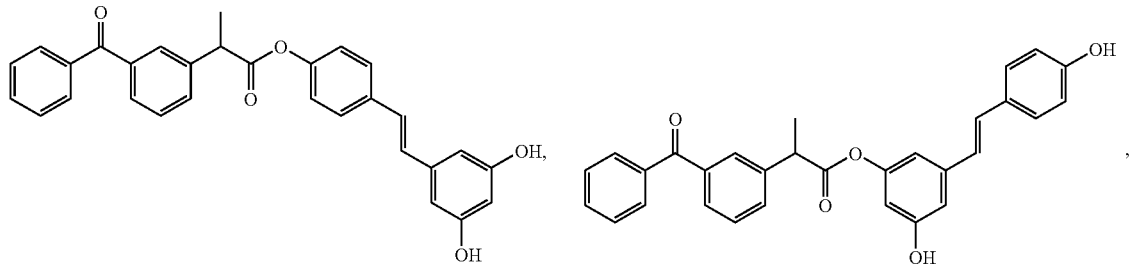
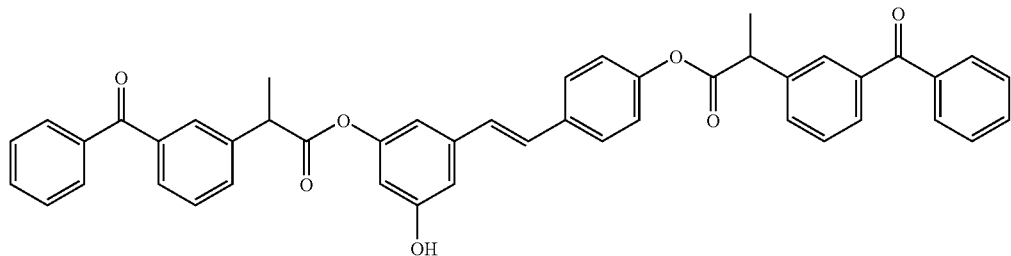

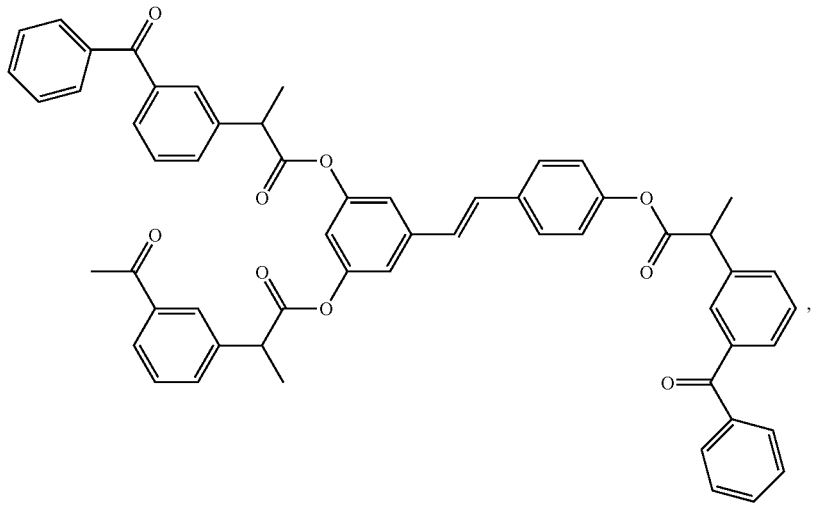
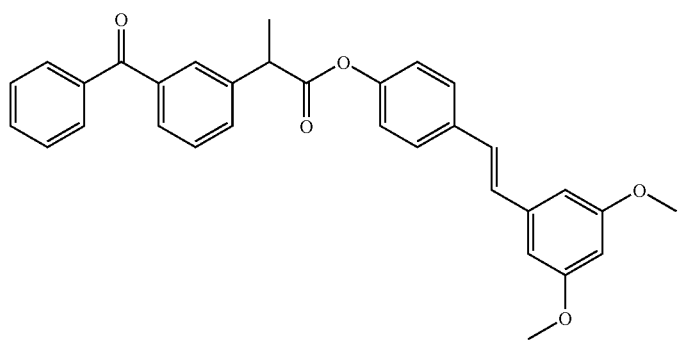
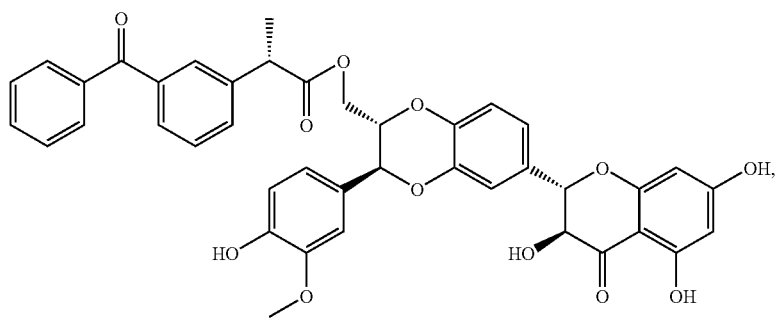
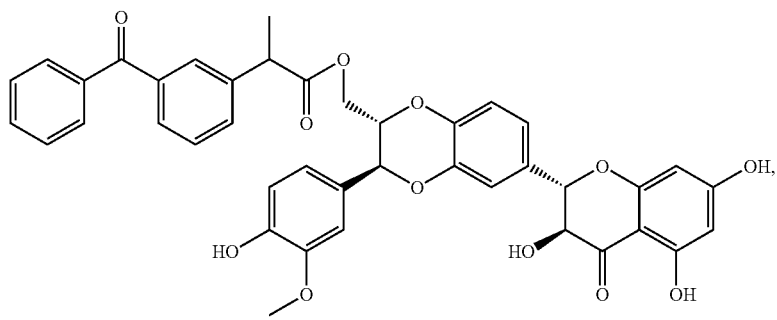

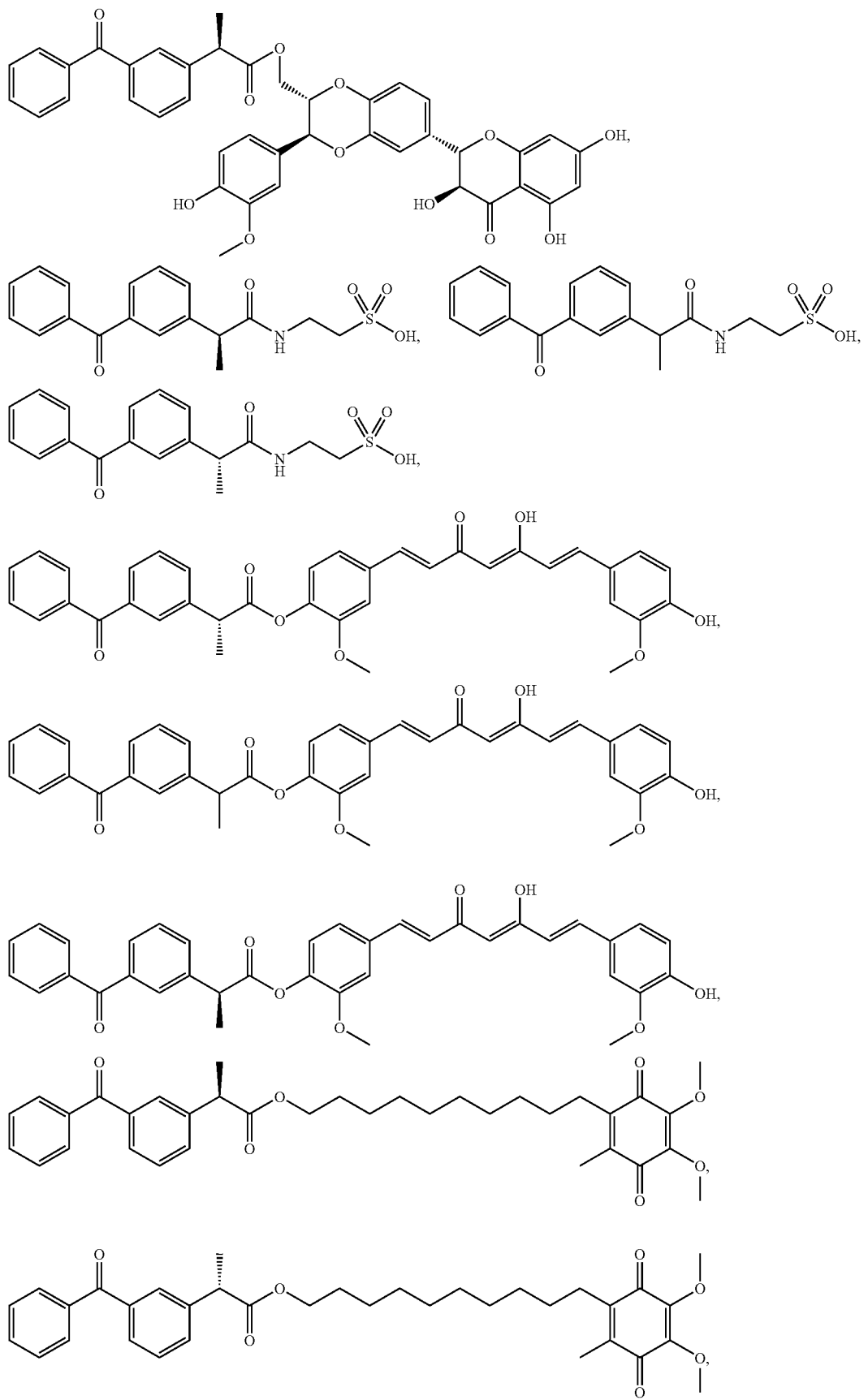

-continued
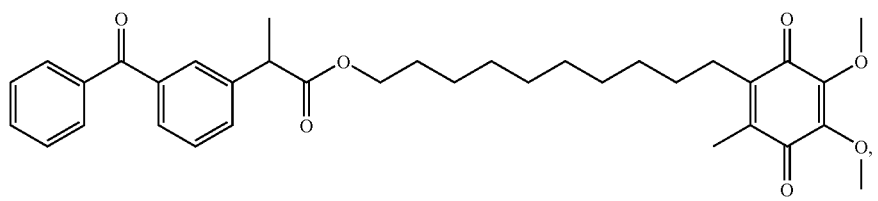
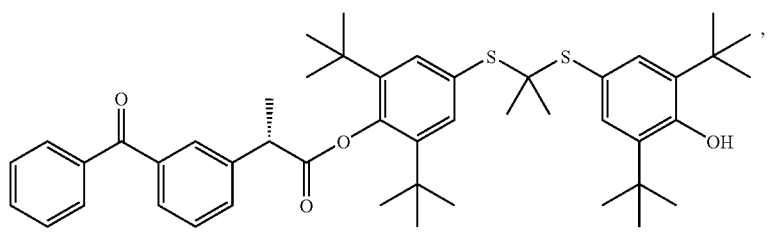
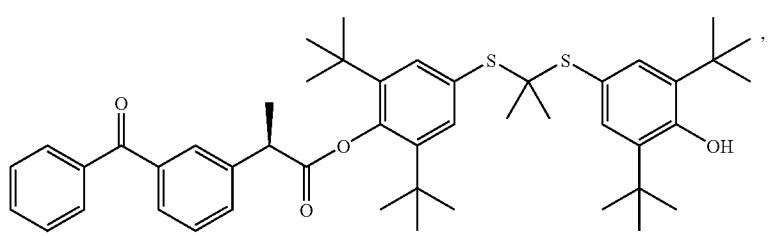
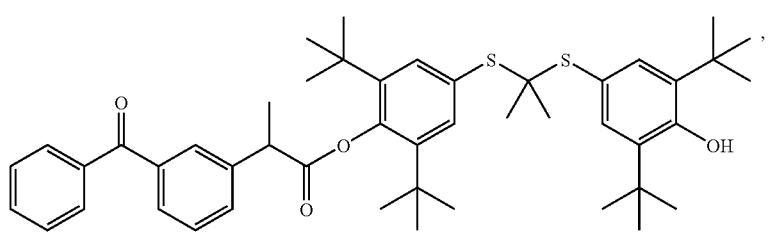
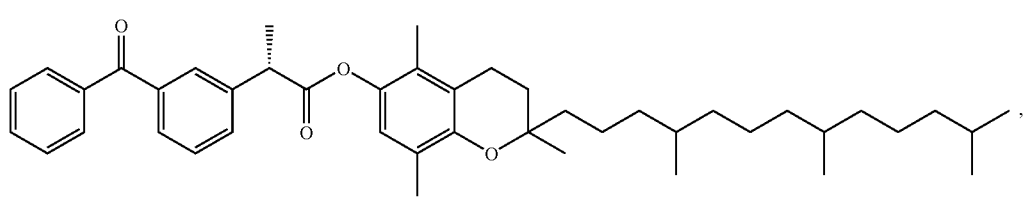
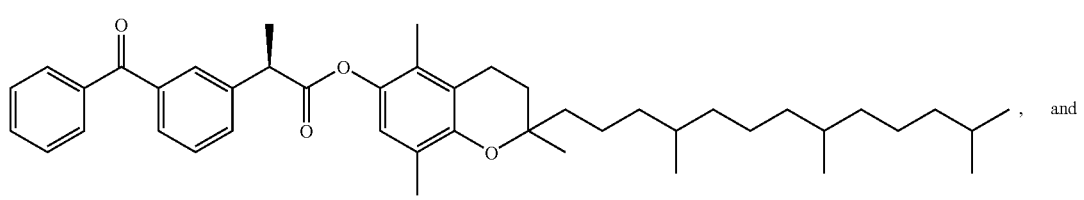, and
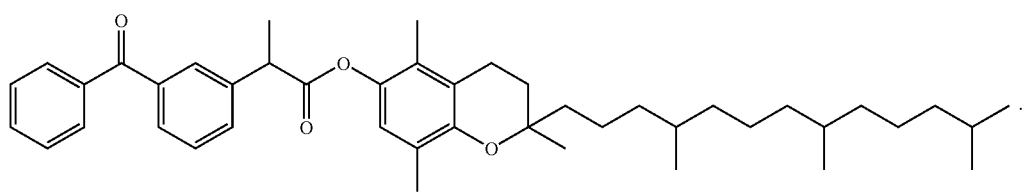.

In another aspect, the present invention provides pharmaceutical compositions comprised of a compound of Formula (IX), as shown above, and at least one pharmaceutically acceptable carrier.

In another aspect, the present invention provides conjugates of Formula (X)

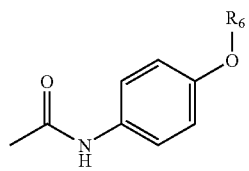
(X)

wherein $R_6$ is

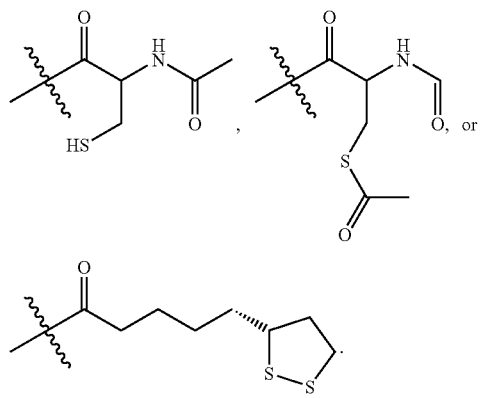

Representative conjugates of Formula (X) include, but are not limited to, the compounds shown below.

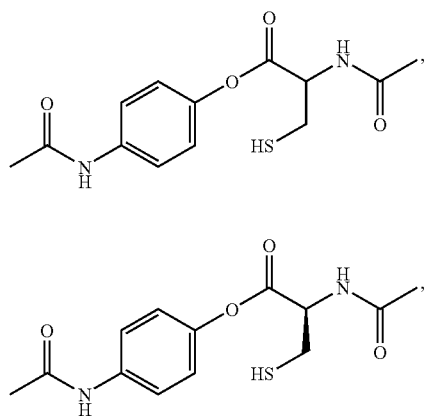

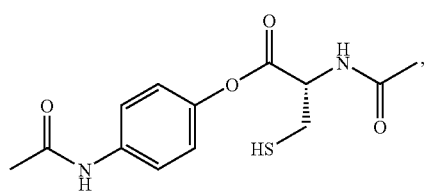

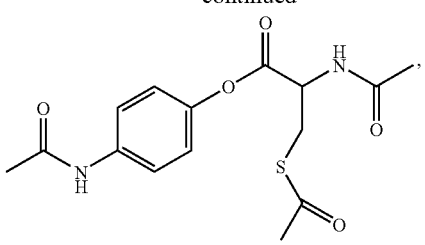

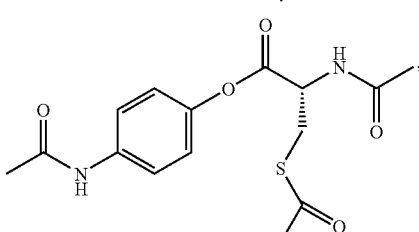

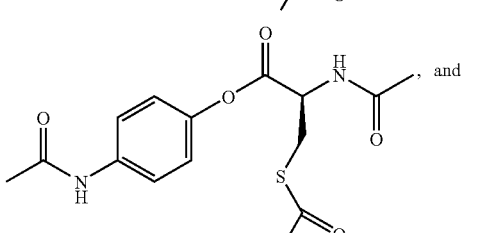

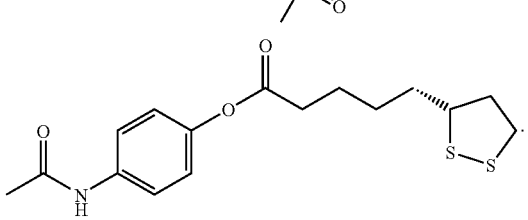

In another aspect, the present invention provides pharmaceutical compositions comprised of a compound of Formula (X), as shown above, and at least one pharmaceutically acceptable carrier.

In another aspect, the present invention provides conjugates of Formula (XI)

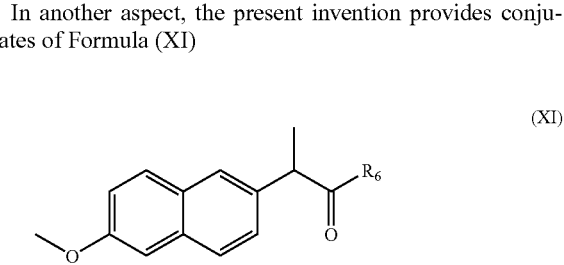
(XI)

wherein $R_6$ is

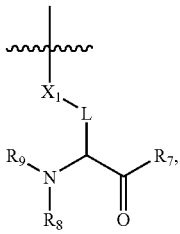
formula (i)

formula (ii)

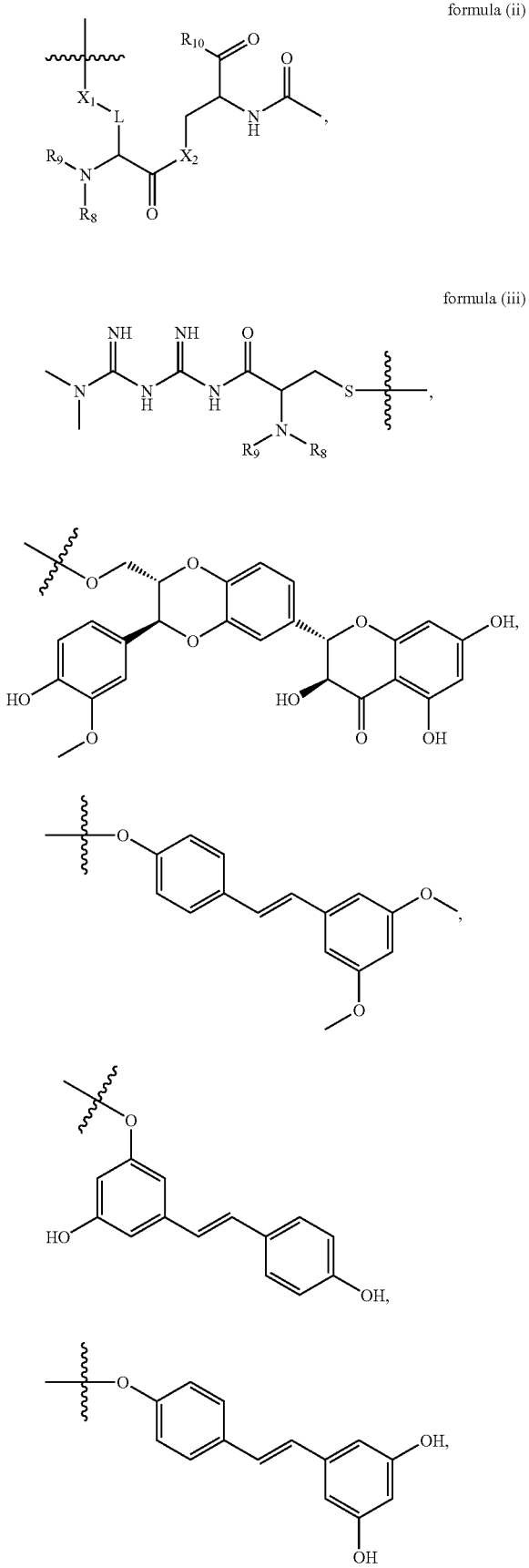

formula (iii)

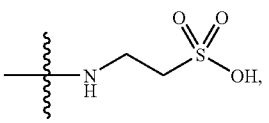

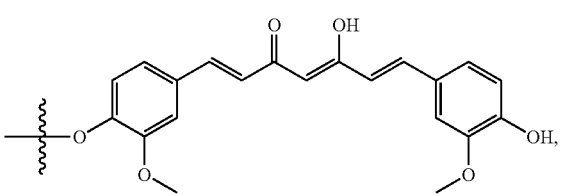

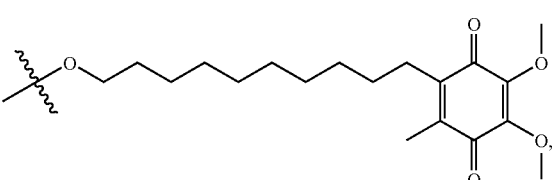

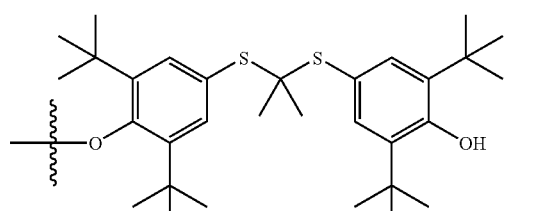

, or

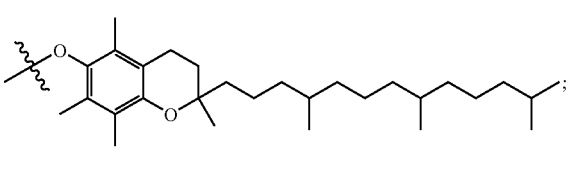

;

R$_2$ is (C$_1$-C$_6$)alkoxy, (C$_1$-C$_6$)alkyl, (C$_1$-C$_6$)alkylthio, hydroxy, —NZ$_9$Z$_{10}$, or —O-phenyl, wherein the phenyl is optionally substituted with 1, 2, 3, 4, or 5 groups that are independently (C$_1$-C$_6$)alkoxy, (C$_1$-C$_6$)alkoxycarbonyl, (C$_1$-C$_6$)alkyl, (C$_1$-C$_6$)alkylcarbonyl, (C$_1$-C$_6$)alkylcarbonyloxy, carboxy, cyano, formyl, halo(C$_1$-C$_6$)alkoxy, halo(C$_1$-C$_6$)alkyl, halogen, hydroxy, or hydroxy(C$_1$-C$_6$)alkyl;

R$_8$ is hydrogen or (C$_1$-C$_6$)alkyl;

R$_9$ is hydrogen, (C$_1$-C$_6$)alkyl, or (C$_1$-C$_6$)alkylcarbonyl;

R$_{10}$ is (C$_1$-C$_6$)alkoxy, (C$_1$-C$_6$)alkylthio, hydroxy, or —NZ$_9$Z$_{10}$;

X$_1$ and X$_2$ are independently O or S;

L is (C$_1$-C$_6$)alkylene; and

Z$_9$ and Z$_{10}$ are independently hydrogen, (C$_1$-C$_6$)alkyl, or (C$_1$-C$_6$)alkylcarbonyl.

Representative conjugates of Formula (XI) include, but are not limited to, the compounds shown below.

193 194
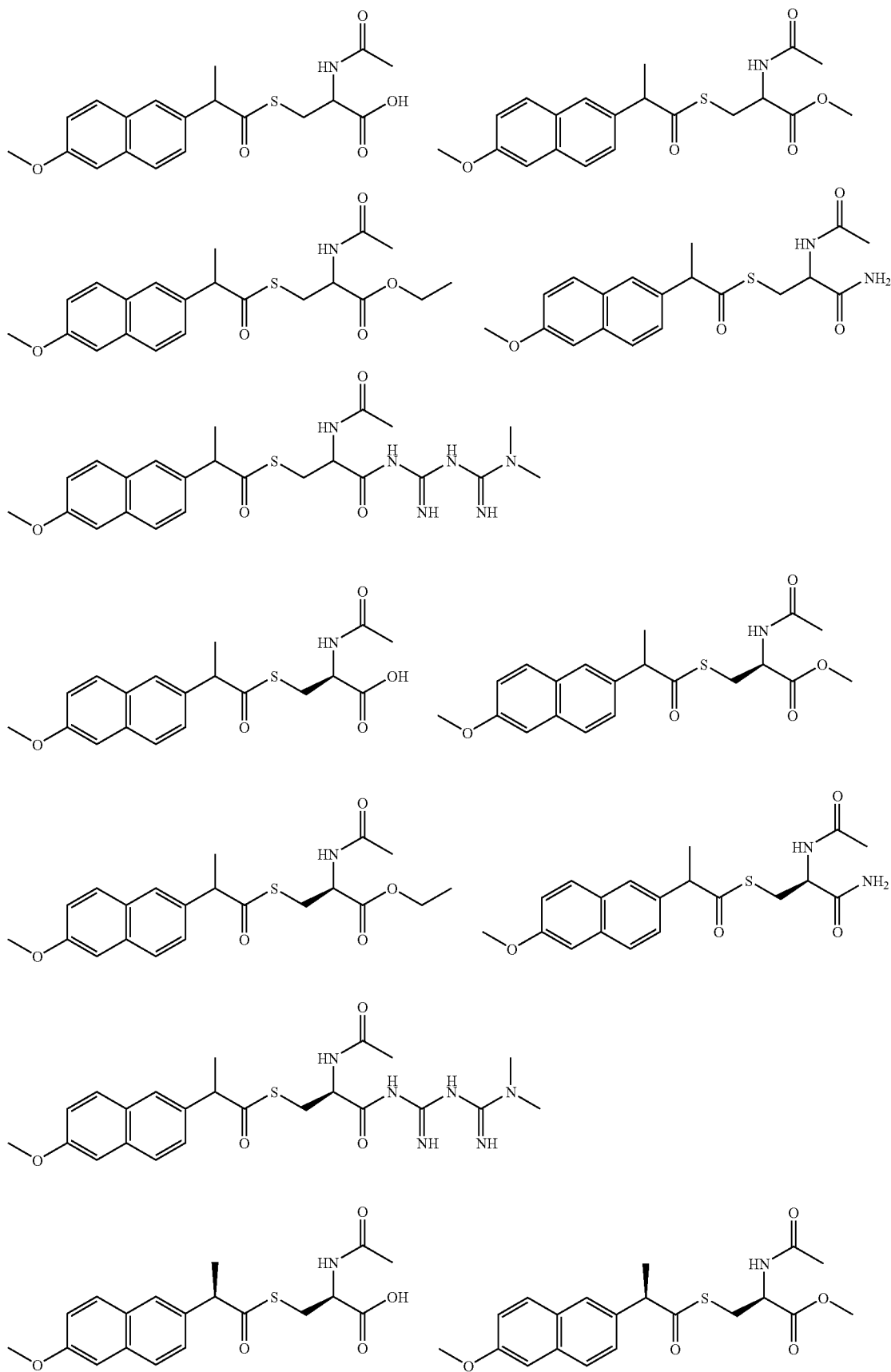

195 196
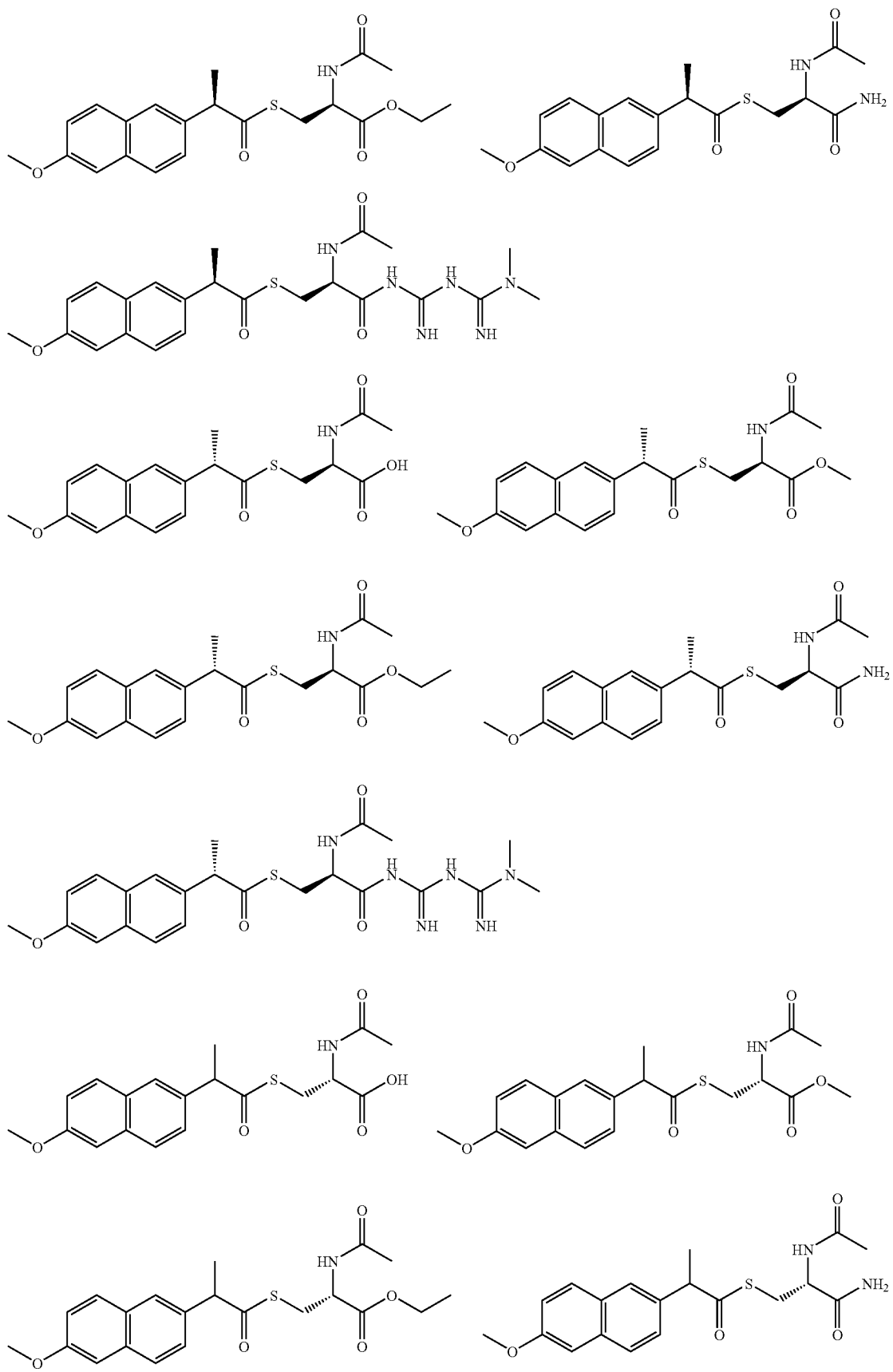

197 198
-continued
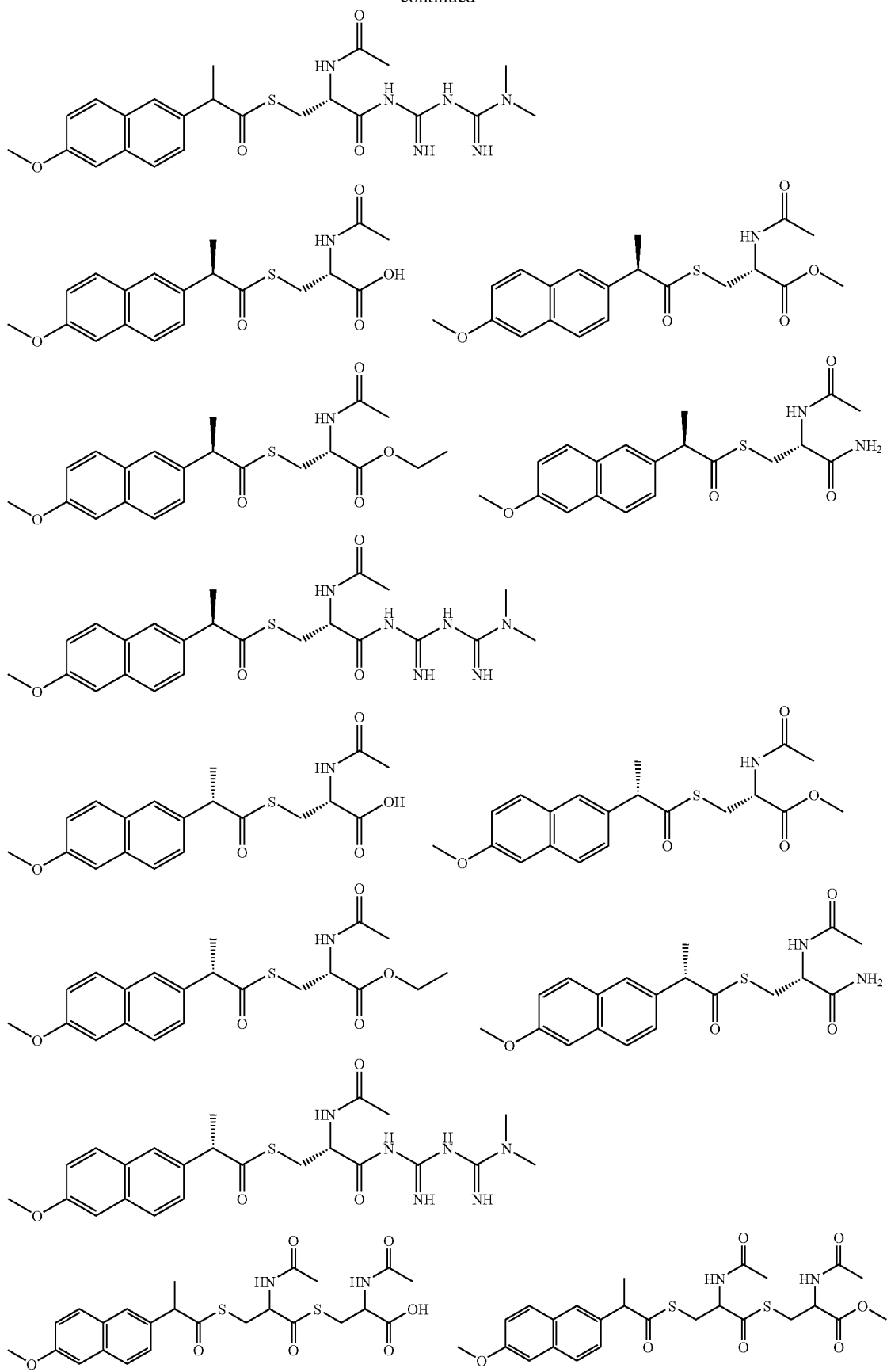

-continued
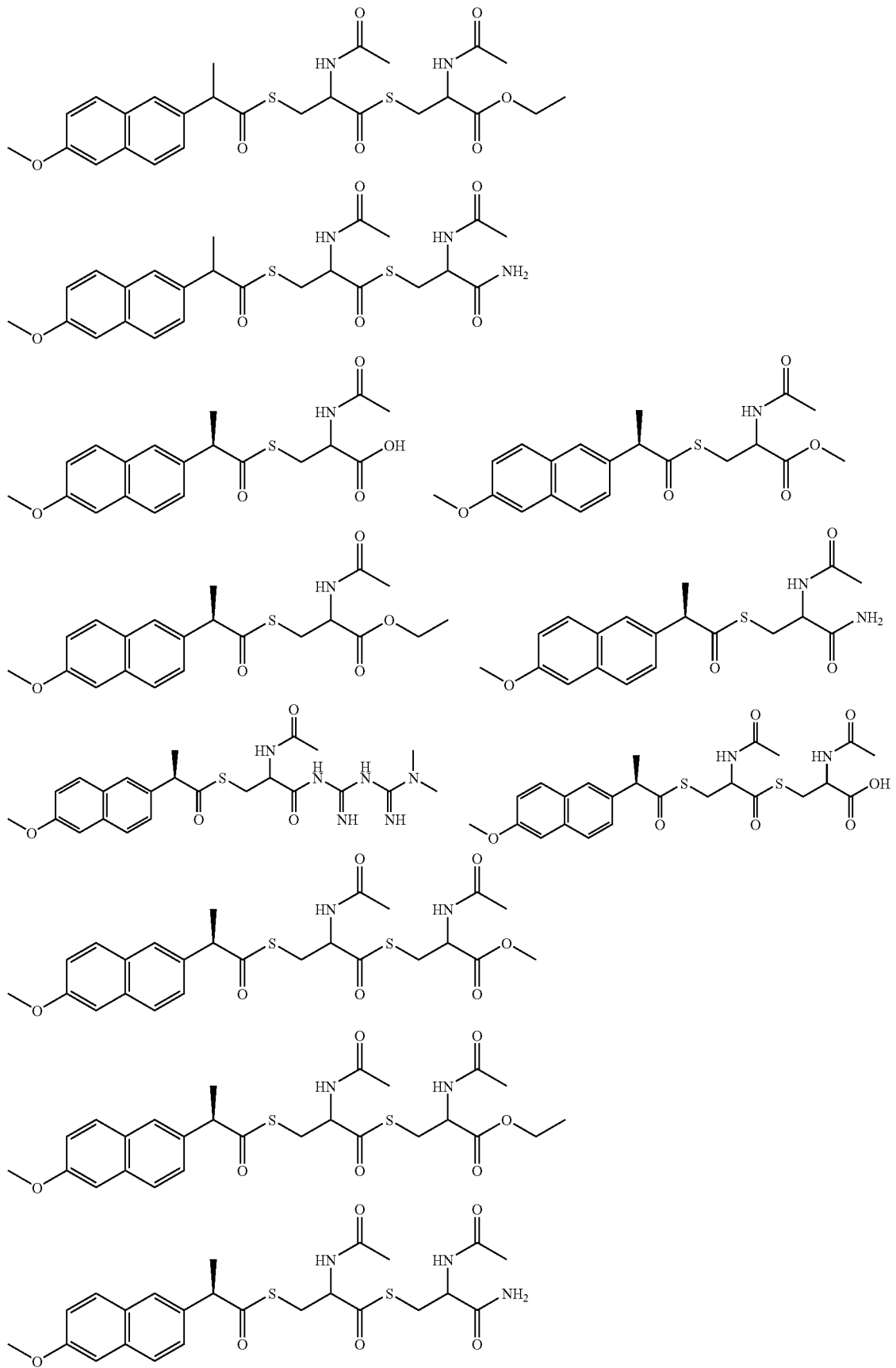

201 202
-continued
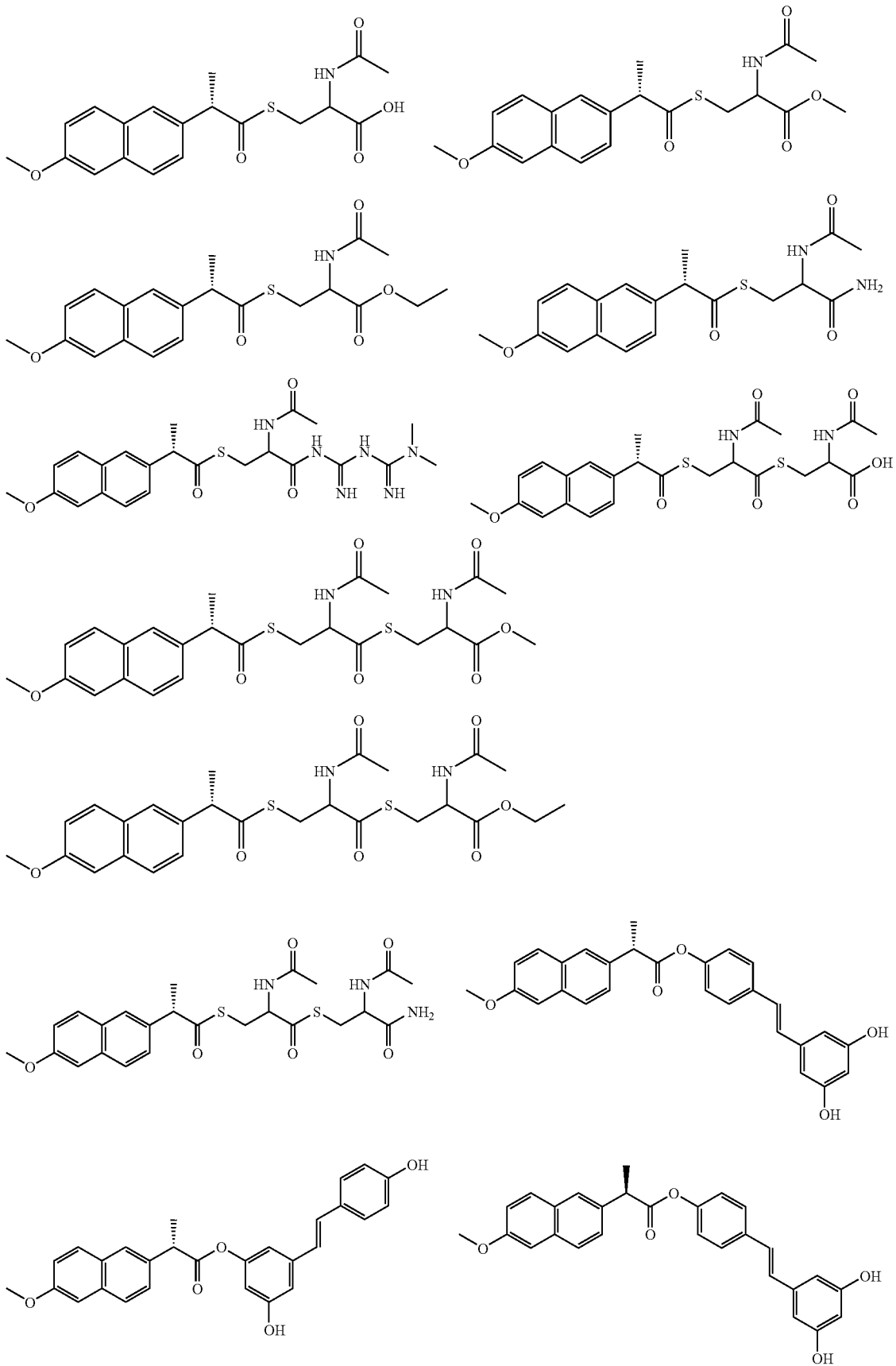

-continued
203
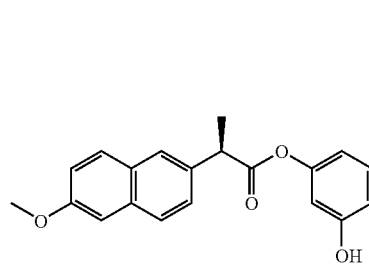
204
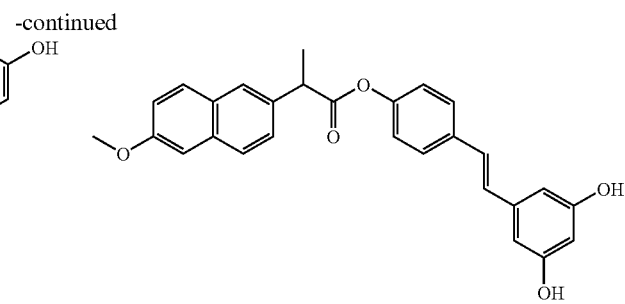
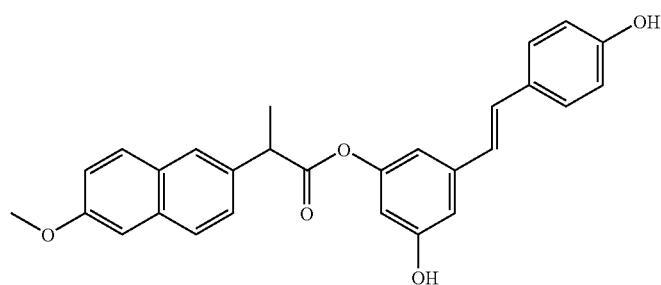
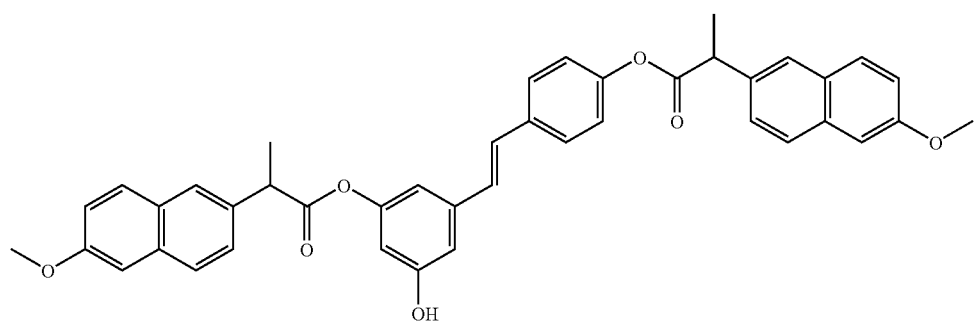
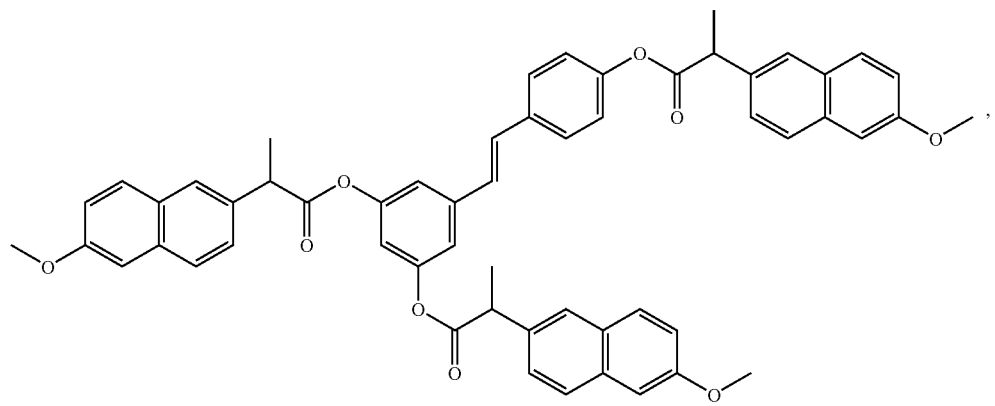
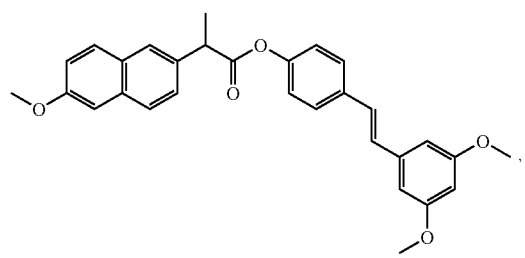
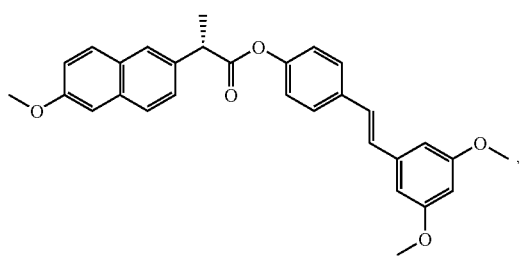

205 206
-continued
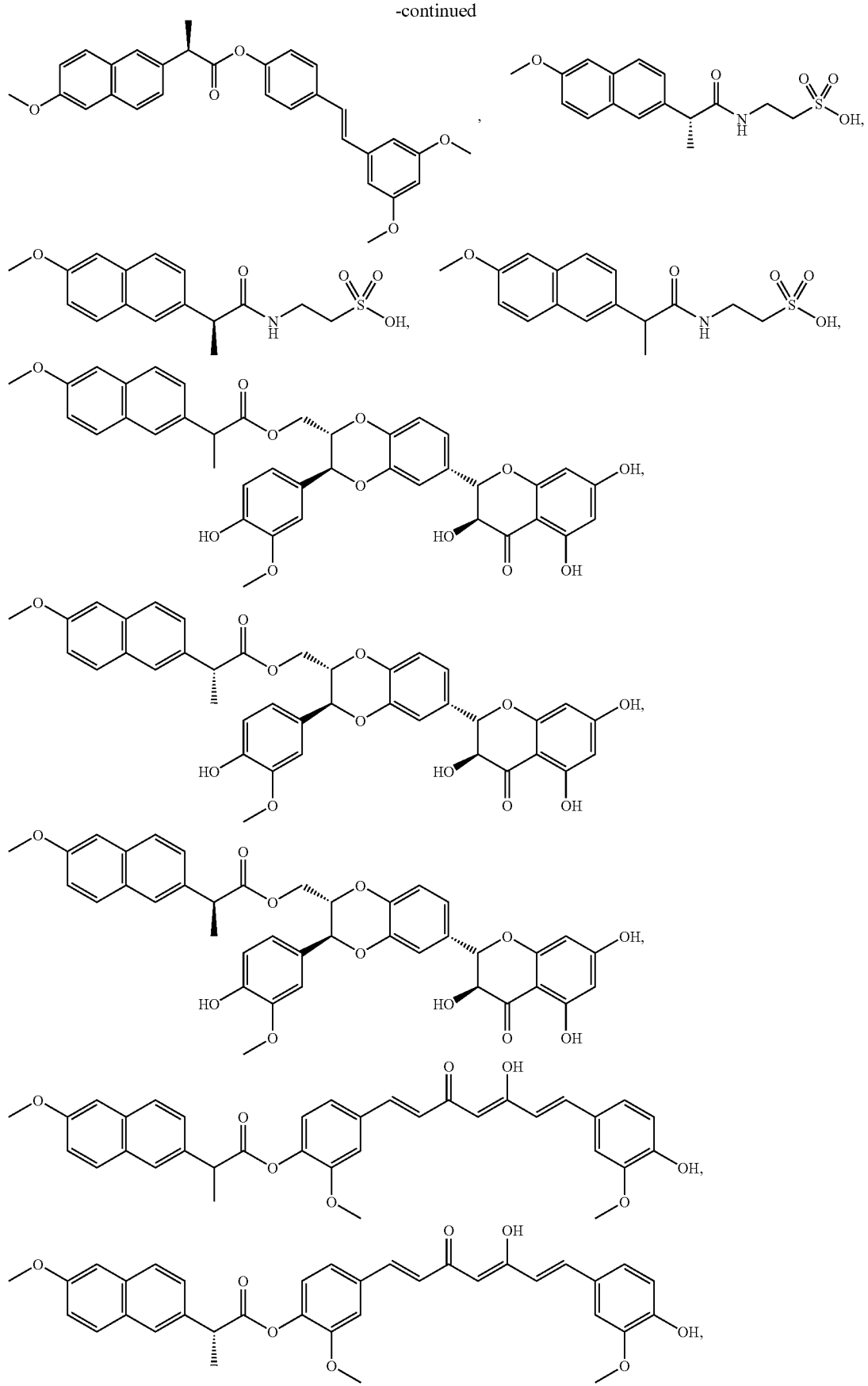

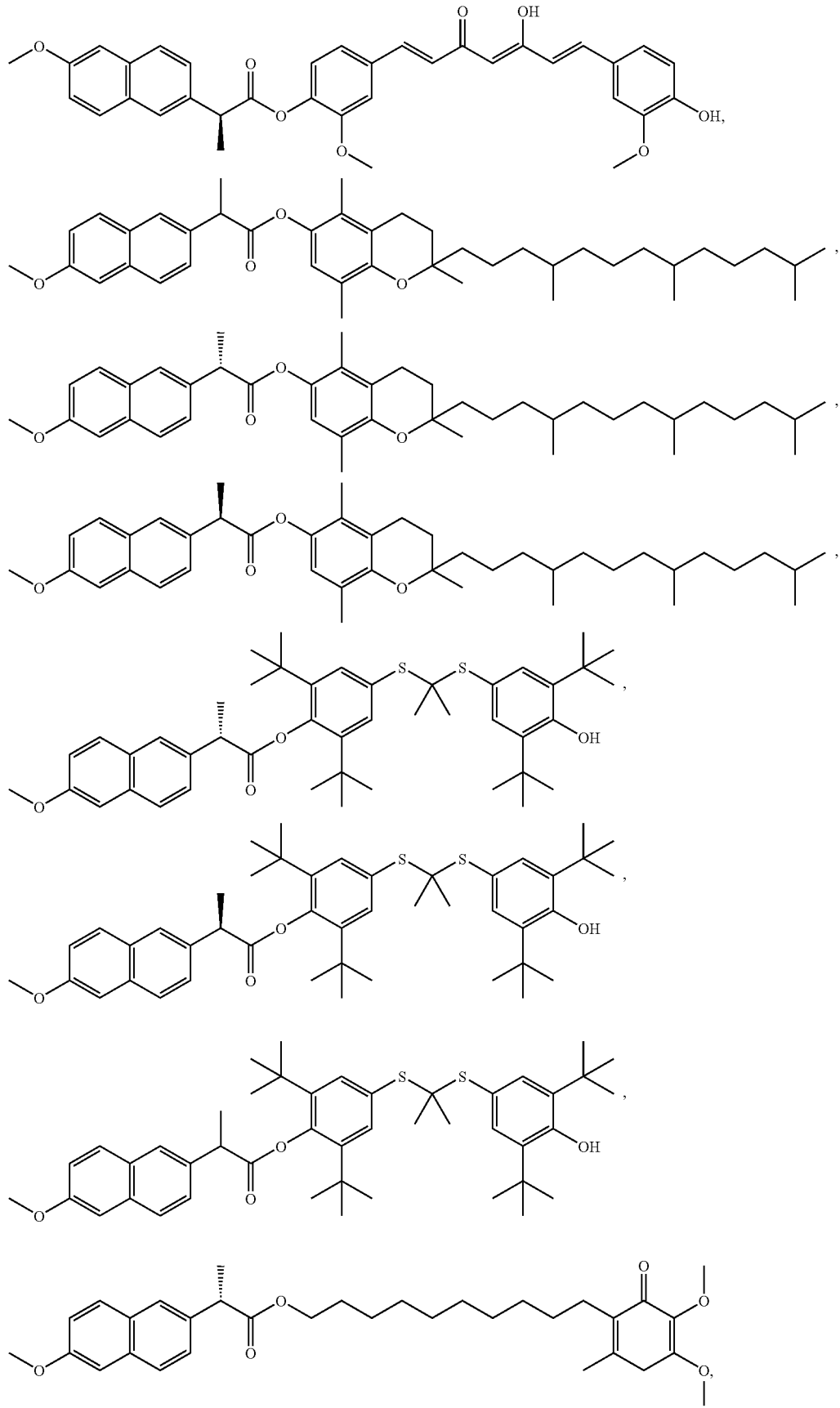

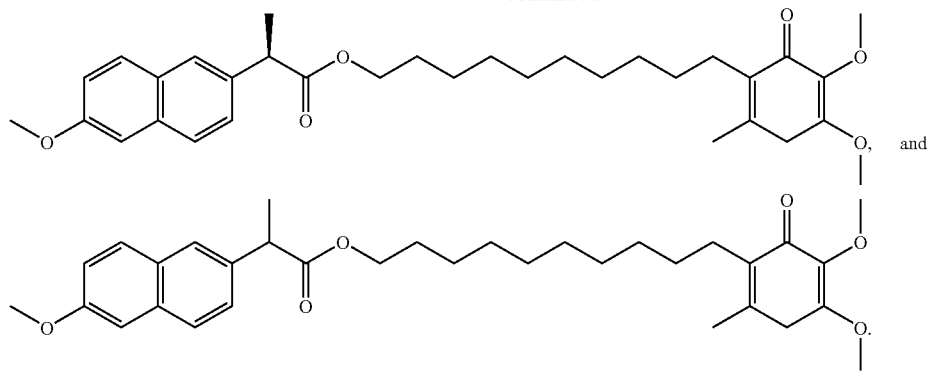
In another aspect, the present invention provides pharmaceutical compositions comprised of a compound of Formula (XI), as shown above, and at least one pharmaceutically acceptable carrier.
The present invention also provides conjugates of Formula (XII)
A-L-B      (XII),
wherein
A is
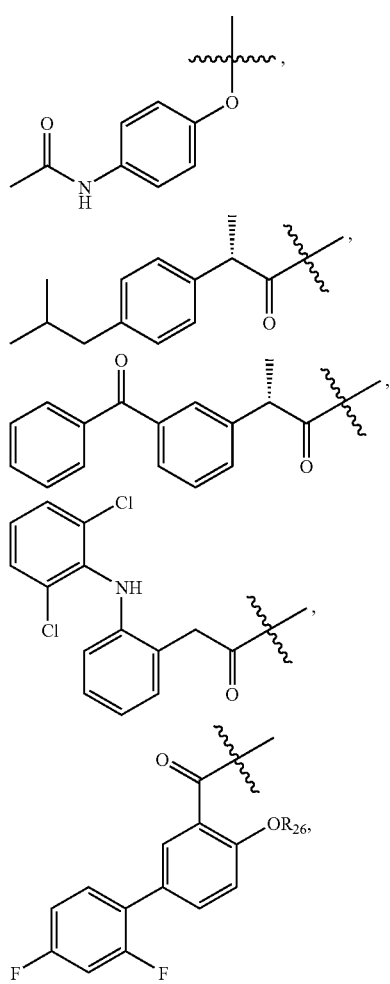
-continued
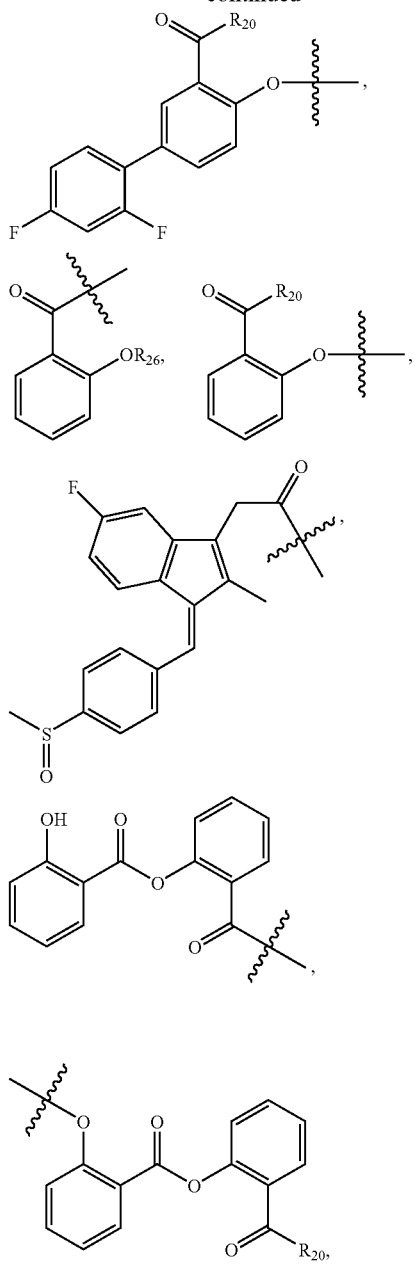

-continued

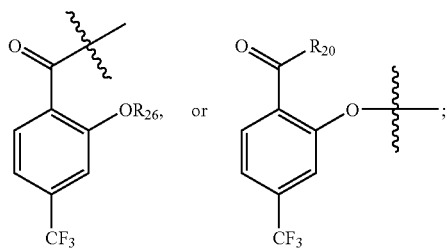

$R_{20}$ is $(C_1-C_4)$alkoxy, hydroxy, or $NZ_{20}Z_{21}$;
$Z_{20}$ and $Z_{21}$ are independently hydrogen or $(C_1-C_4)$alkyl;
L is selected from

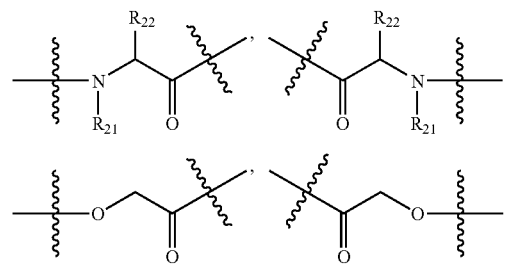

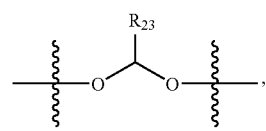

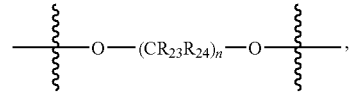

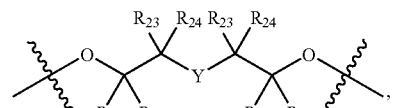

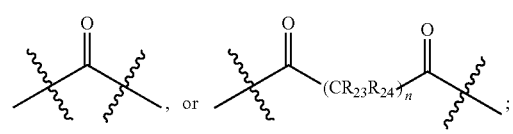

n is 2, 3, or 4;
Y is O, S, S—S, NH, NCH$_3$;
$R_{21}$ is hydrogen or $(C_1-C_4)$alkyl;
$R_{22}$ is hydrogen, CH$_3$, CH(CH$_3$)$_2$, CH$_2$CH(CH$_3$)$_2$, CH(CH$_3$)CH$_2$CH$_3$; CH$_2$OH, CH(OH)CH$_3$, CH$_2$SH, CH$_2$COOH, CH$_2$CH$_2$COOH, CH$_2$C(=O)NH$_2$, CH$_2$CH$_2$CH$_2$NHC(=NH)NH$_2$, CH$_2$CH$_2$CH$_2$CH$_2$NH$_2$, CH$_2$CH$_2$SCH$_3$, CH$_2$CH$_2$C(=O)NH$_2$,

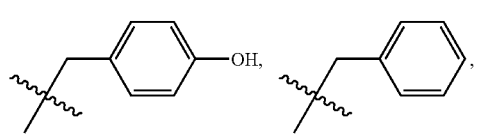

-continued

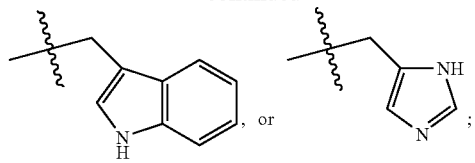

$R_{23}$ and $R_{24}$ are independently hydrogen or $(C_1-C_6)$alkyl;
B is

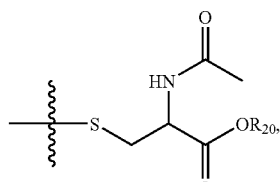

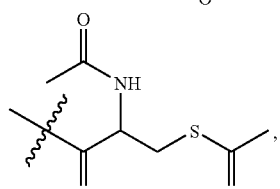

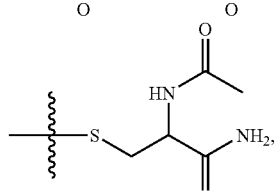

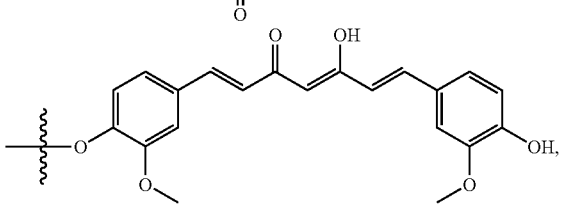

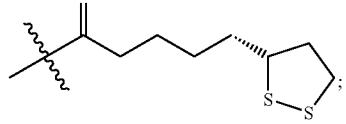

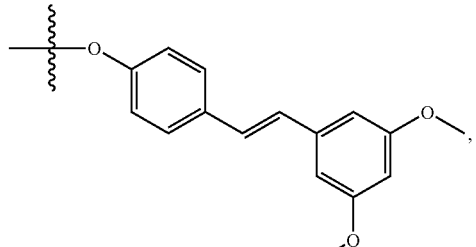

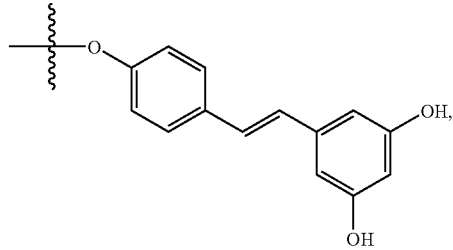

213
-continued
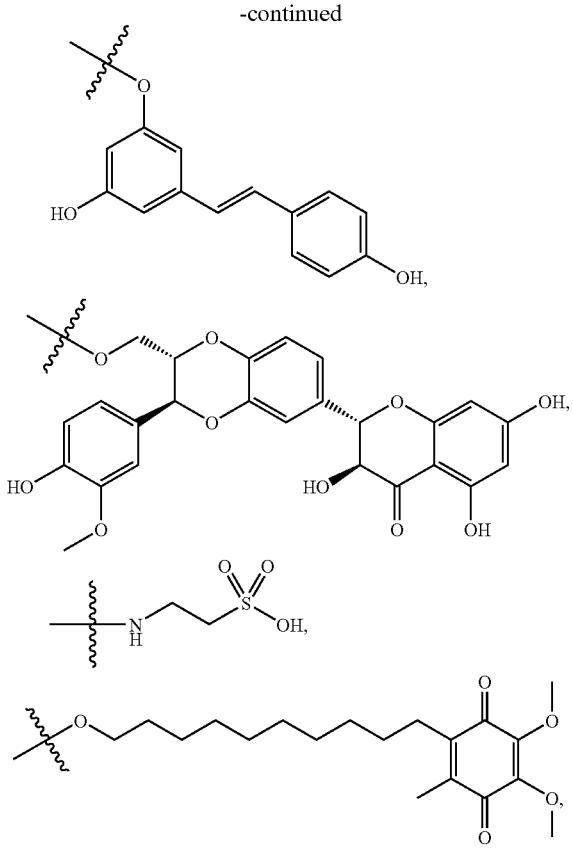
214
-continued
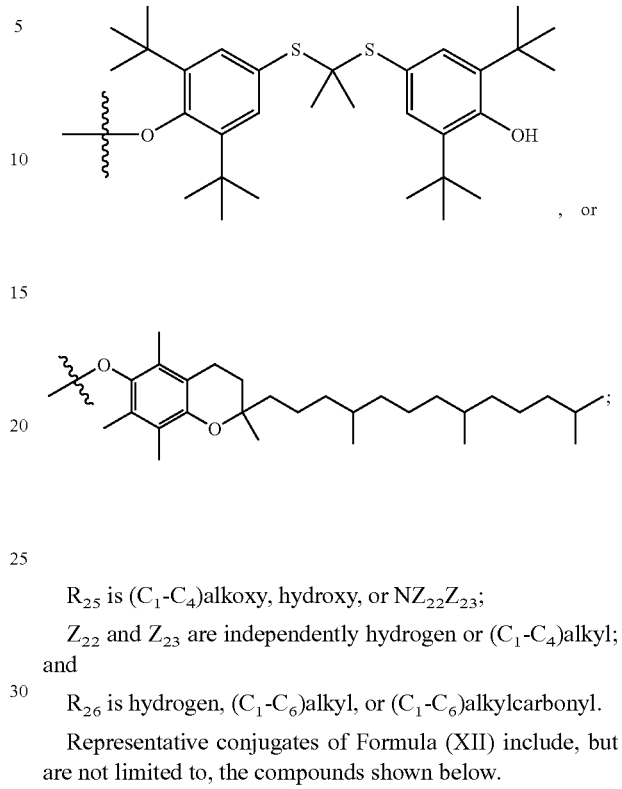
$R_{25}$ is $(C_1-C_4)$alkoxy, hydroxy, or $NZ_{22}Z_{23}$;
$Z_{22}$ and $Z_{23}$ are independently hydrogen or $(C_1-C_4)$alkyl; and
$R_{26}$ is hydrogen, $(C_1-C_6)$alkyl, or $(C_1-C_6)$alkylcarbonyl.
Representative conjugates of Formula (XII) include, but are not limited to, the compounds shown below.
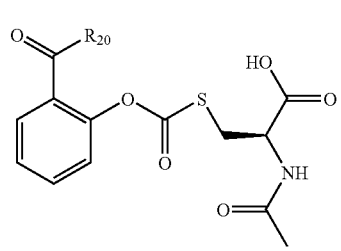
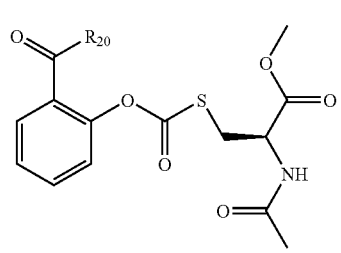
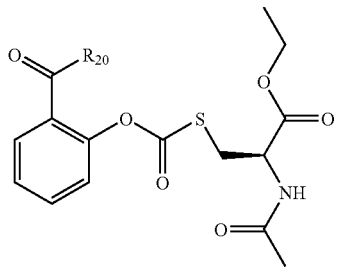
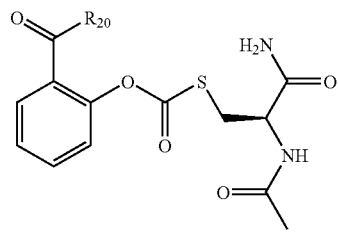
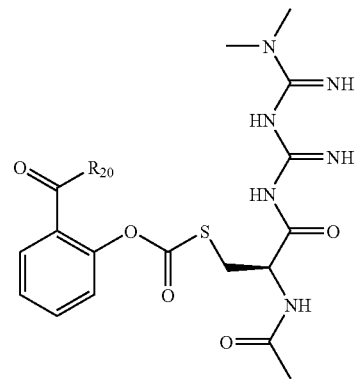
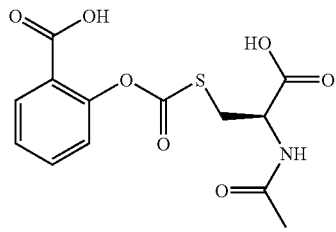

215
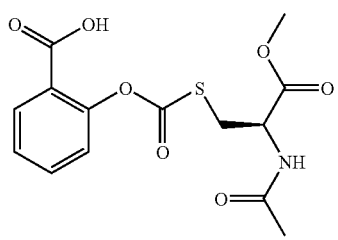
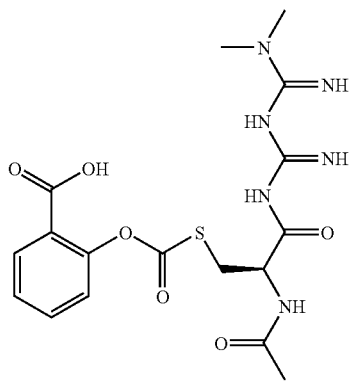
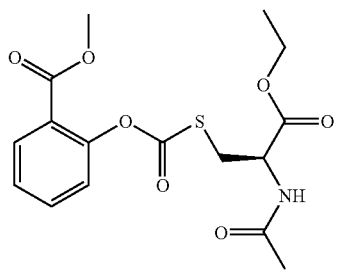
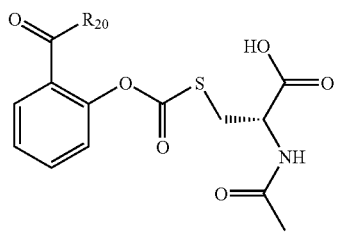
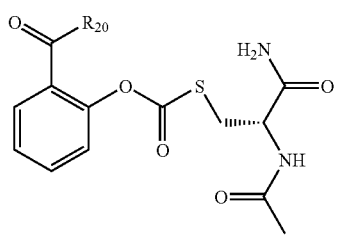
-continued
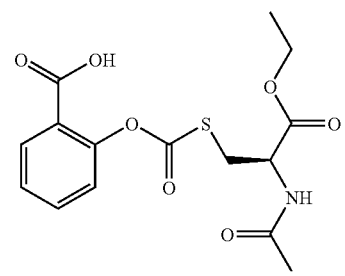
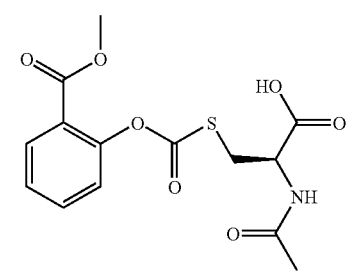
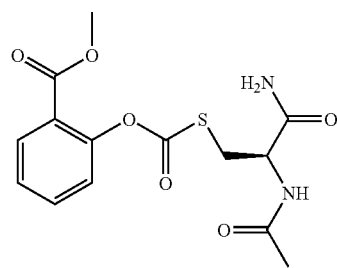
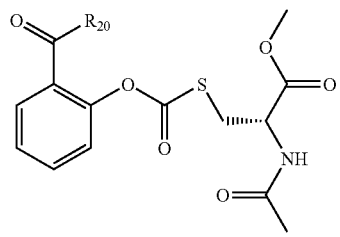
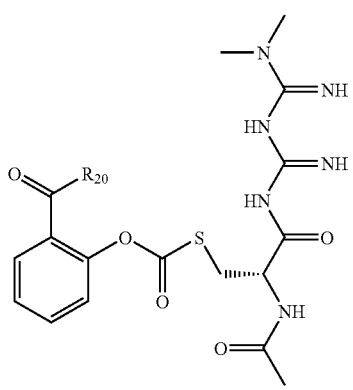
216
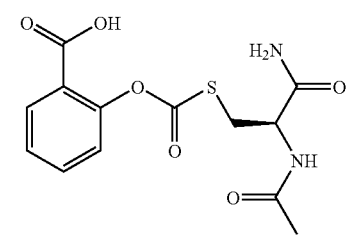
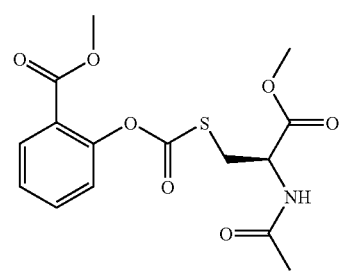
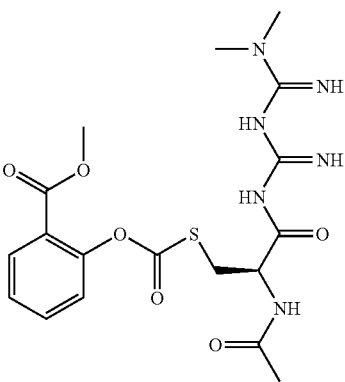
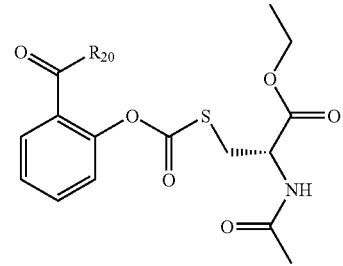
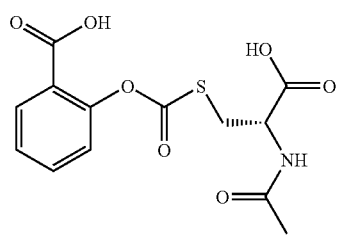

217
-continued
218
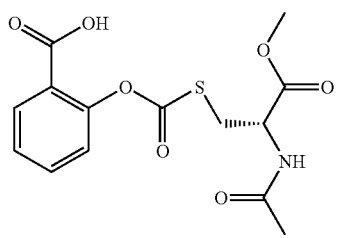
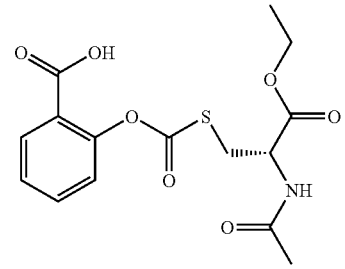
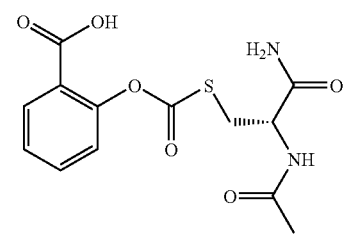
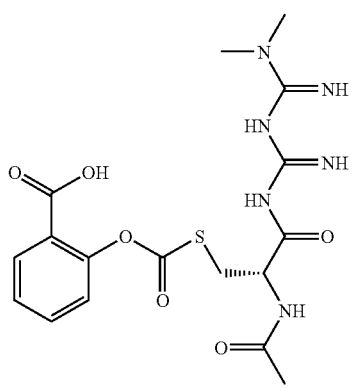
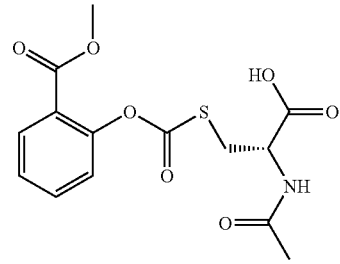
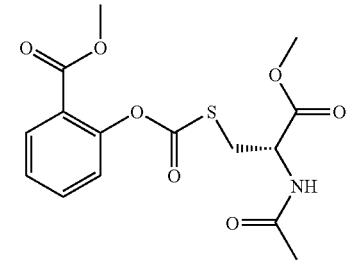
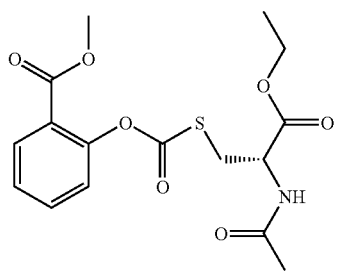
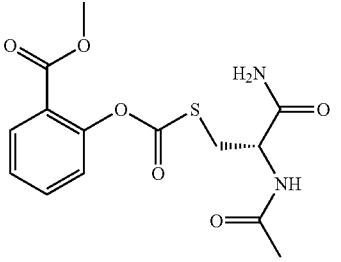
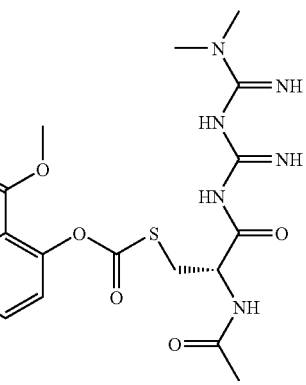
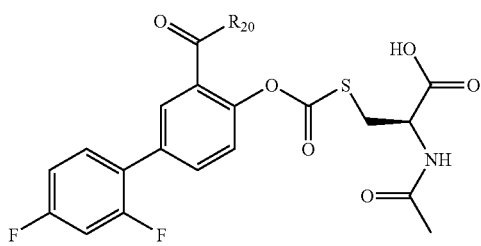
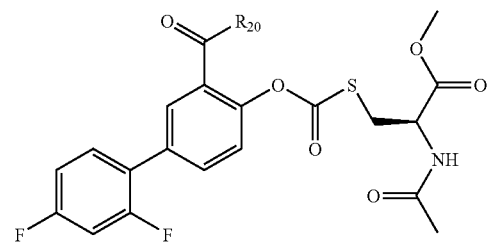
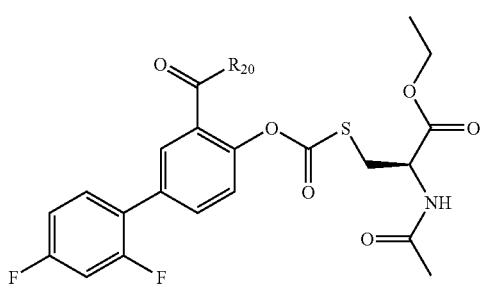
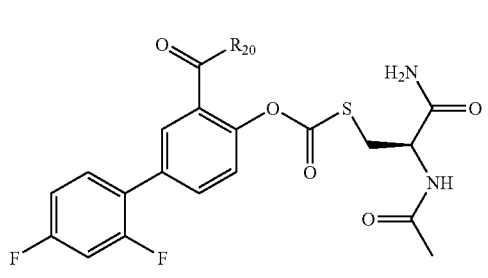

219 220
-continued
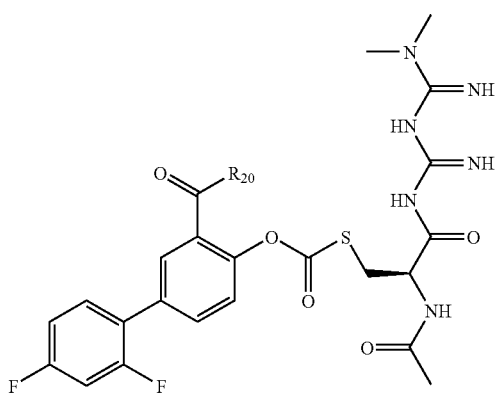
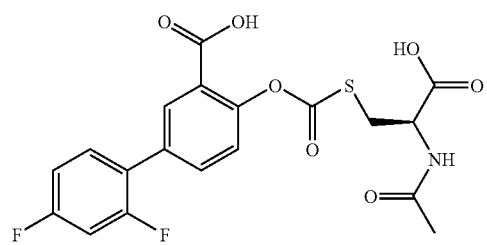
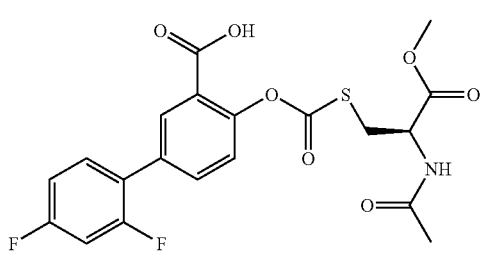
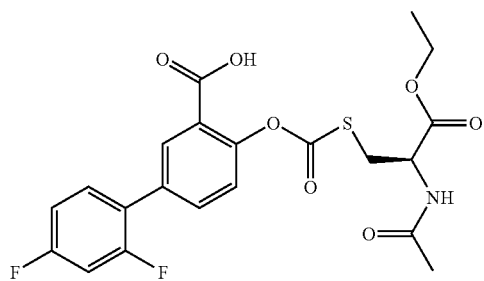
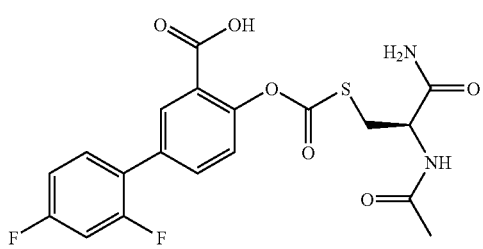
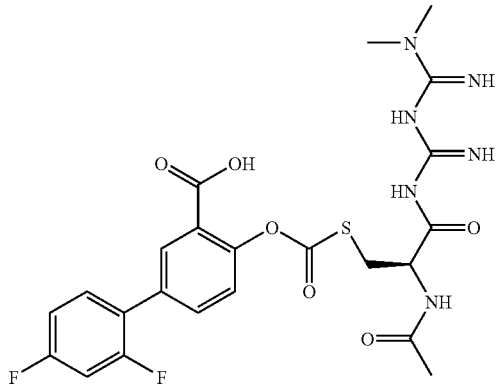
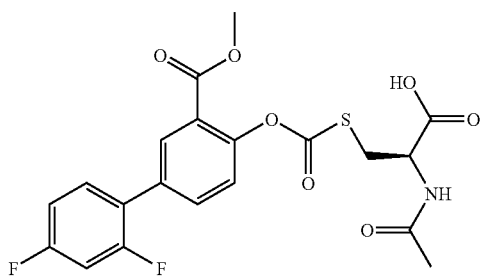
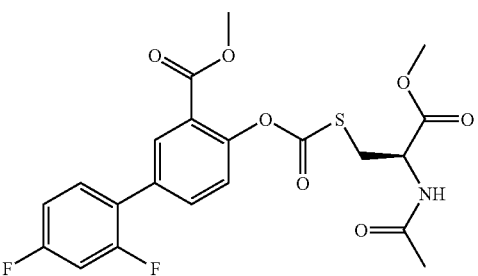
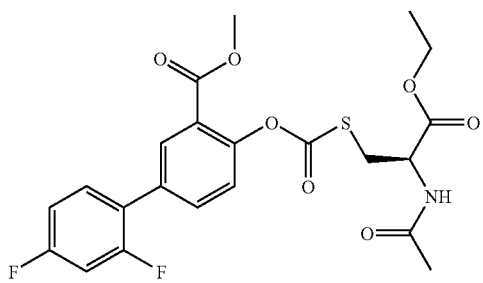
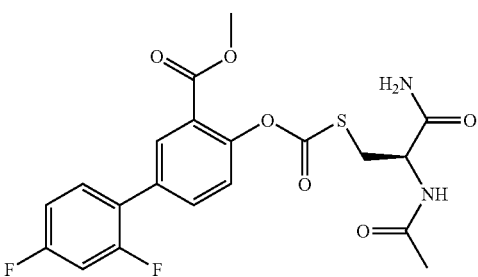

-continued
| 221 | 222 |
|---|---|
| 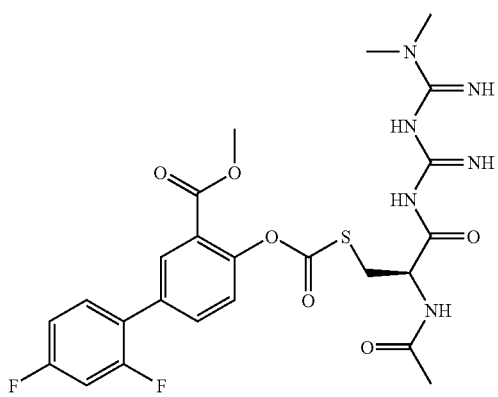 | 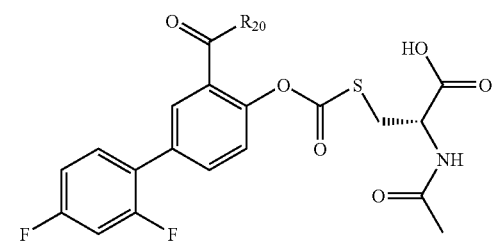 |
| 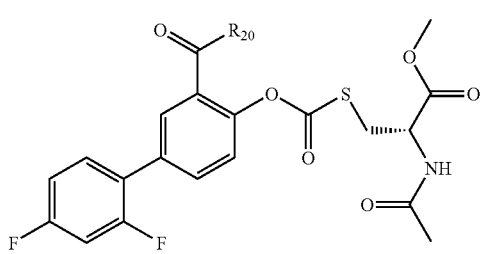 | 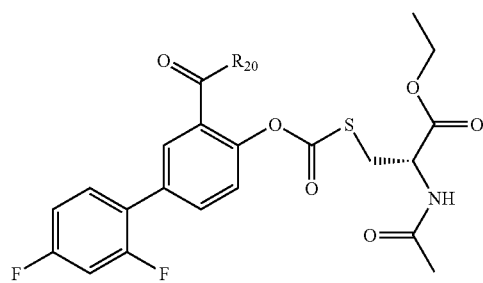 |
| 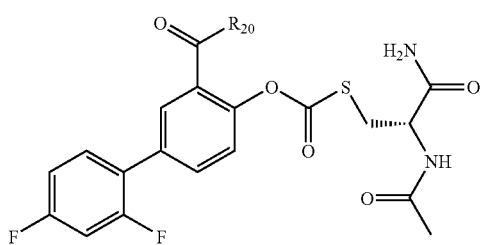 | 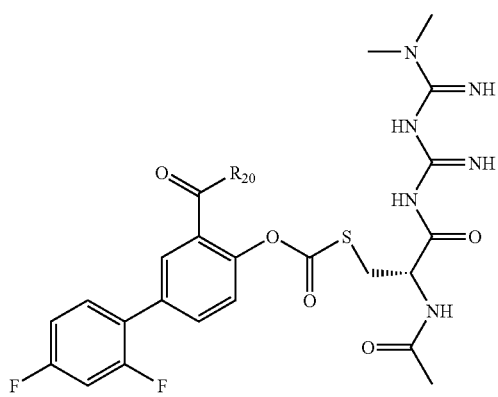 |
| 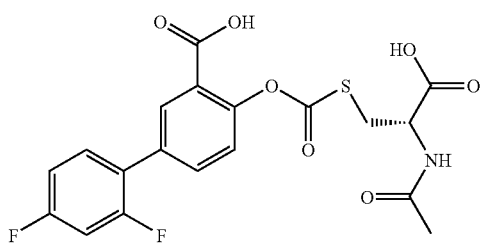 | 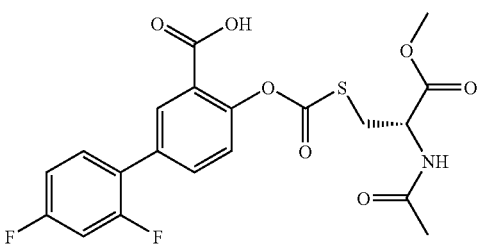 |
| 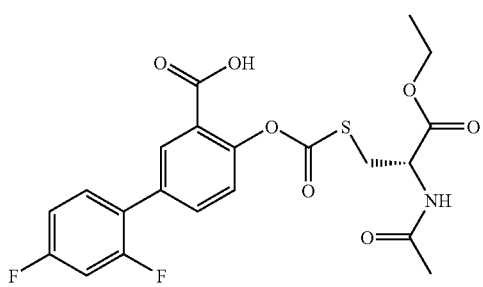 | 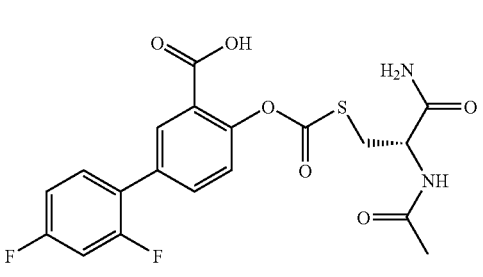 |

223
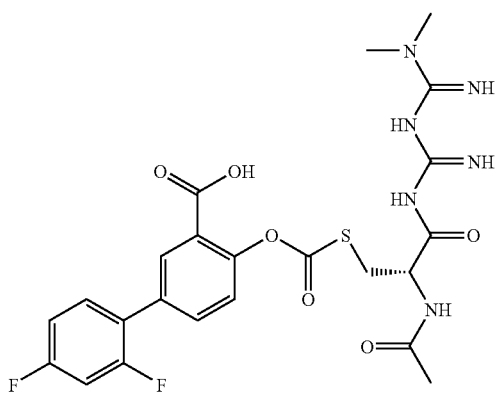
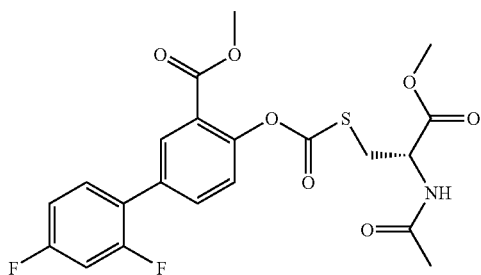
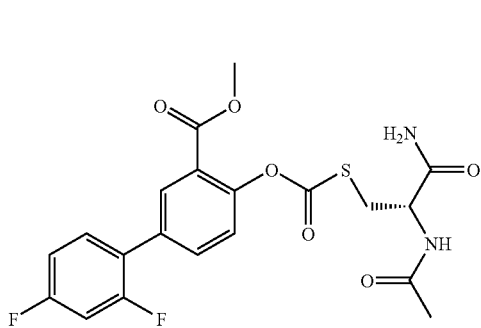
224
-continued
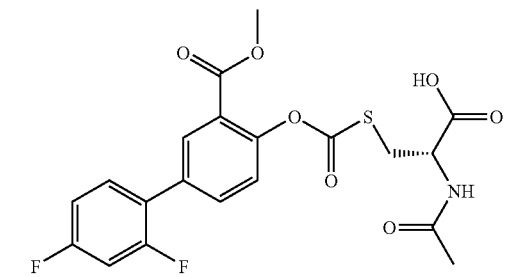
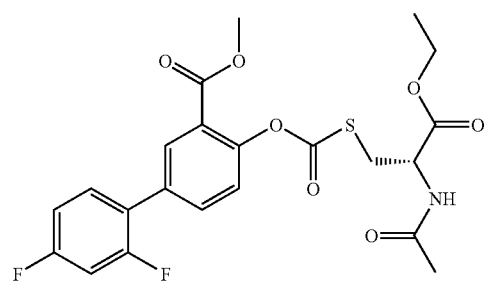
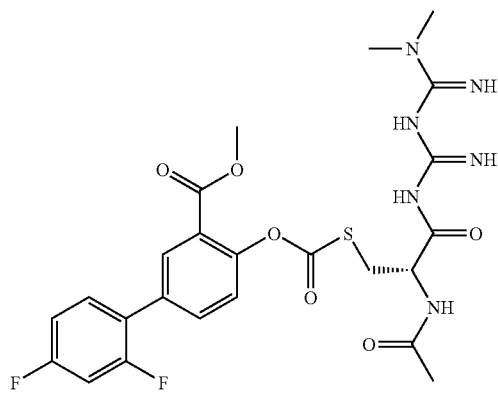
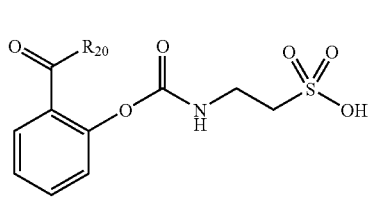
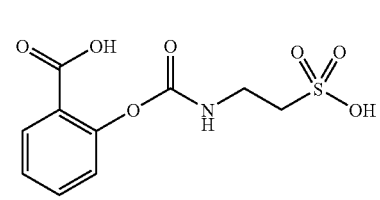
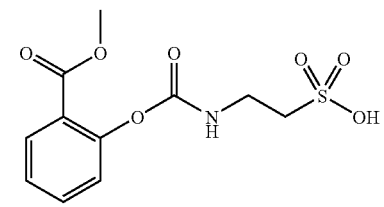
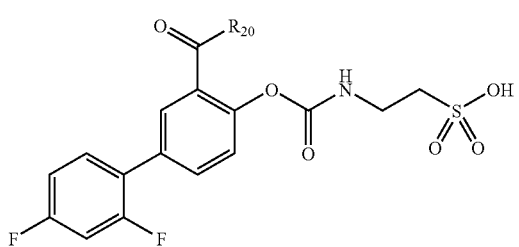
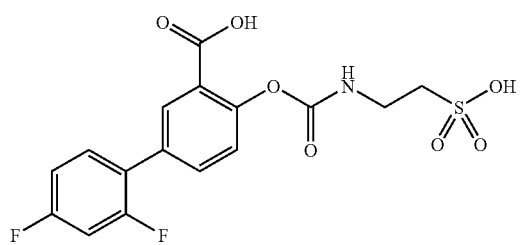

225 226
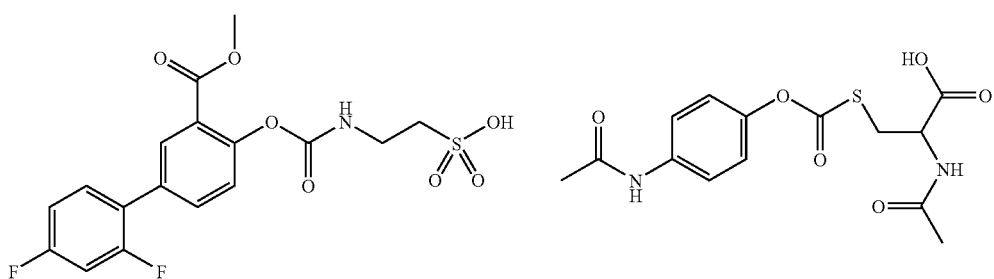
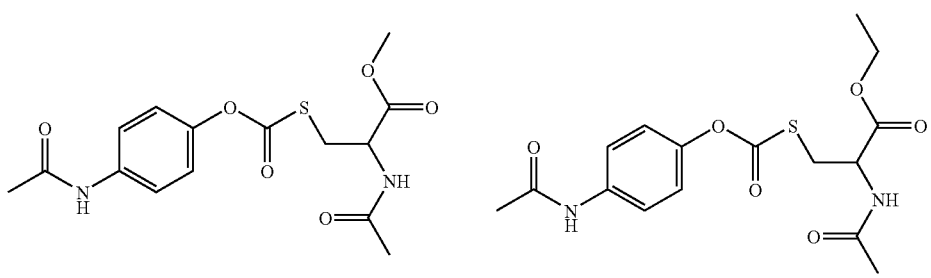
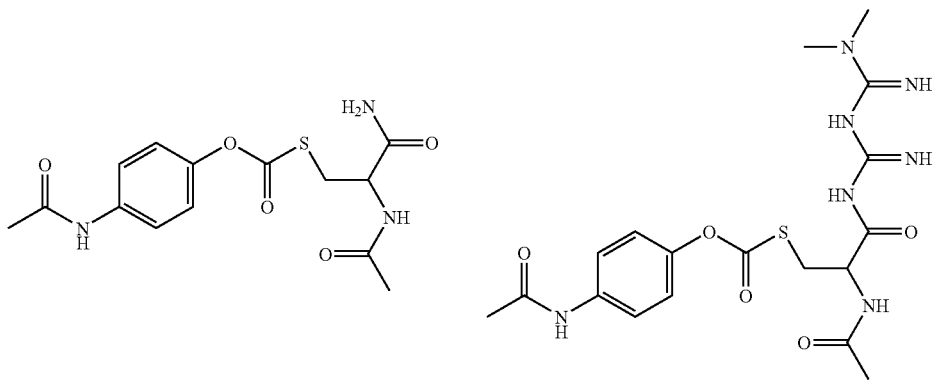
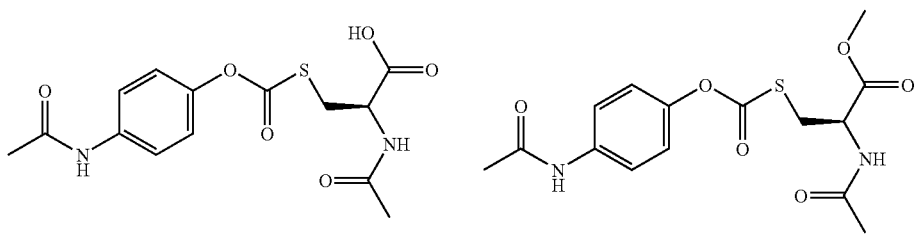
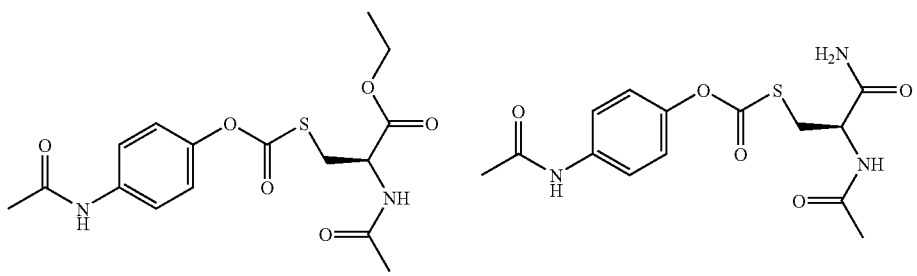

-continued
227
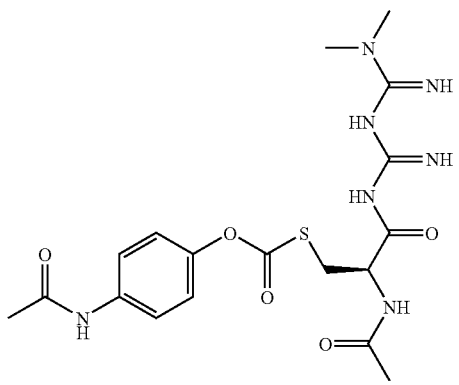
228
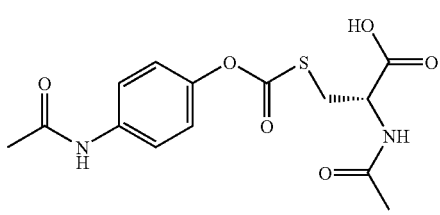
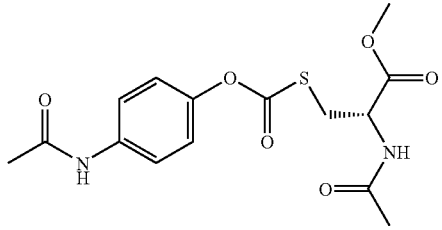
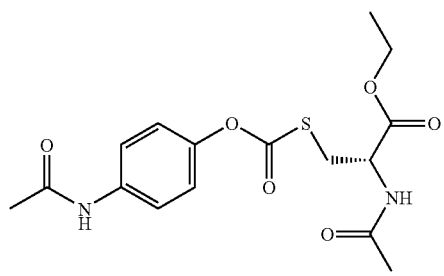
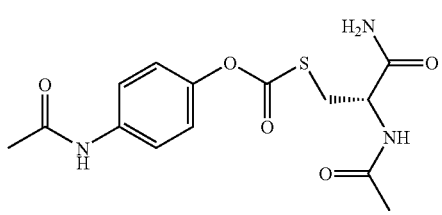
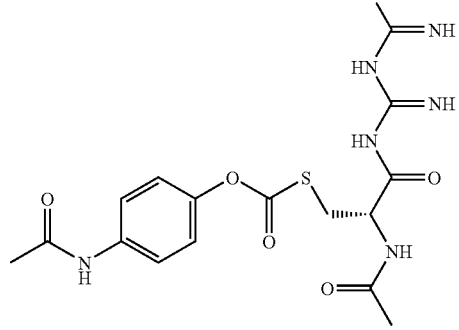
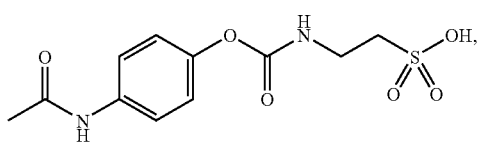
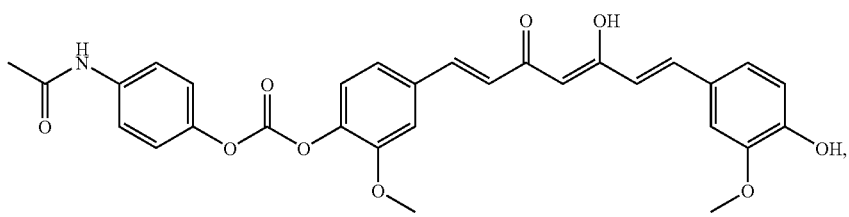
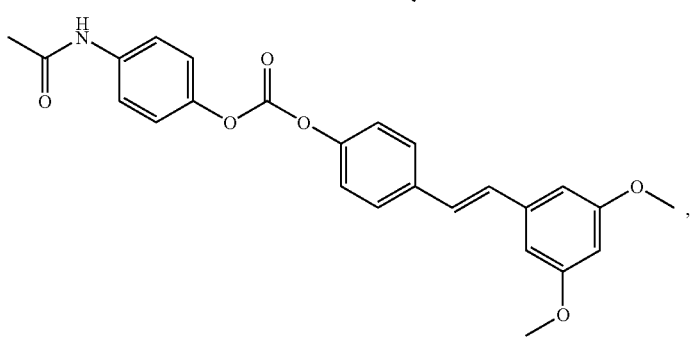

-continued
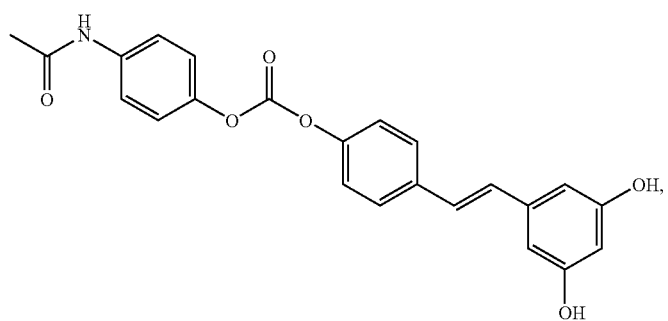
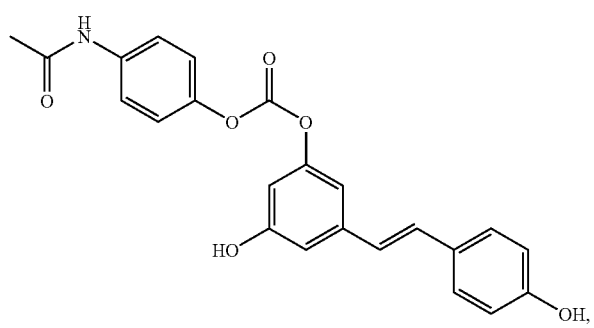
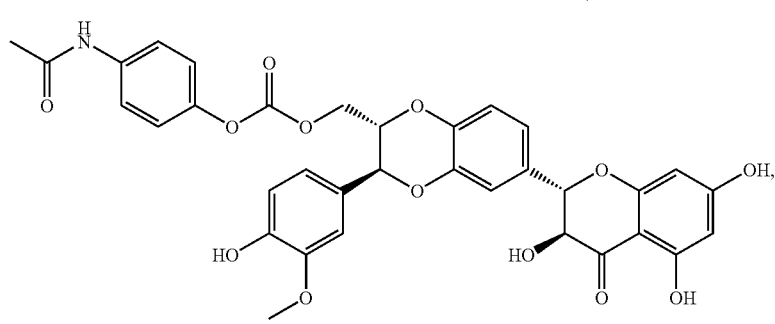
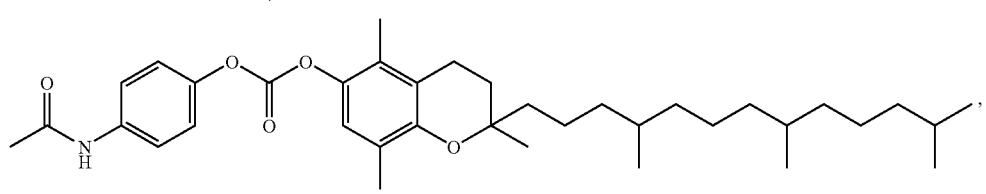
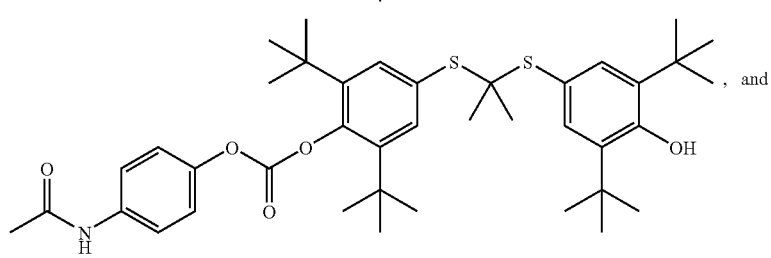
, and
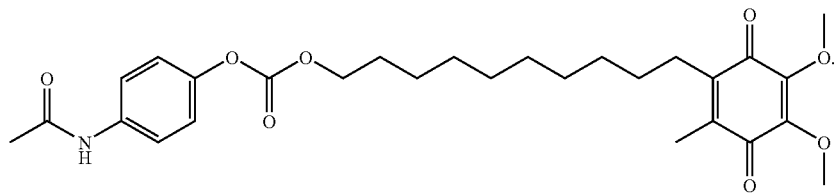

In another aspect, the present invention provides pharmaceutical compositions comprised of a compound of Formula (XII), as shown above, and at least one pharmaceutically acceptable carrier.

The present invention provides compounds of Formula (XIII):

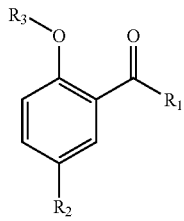
(XIII)

or a pharmaceutically acceptable salt thereof, wherein $R_1$ is $OR_6$ or $NR_4R_5$;

$R_2$ is H or 2,4-difluorophenyl;

$R_3$ is

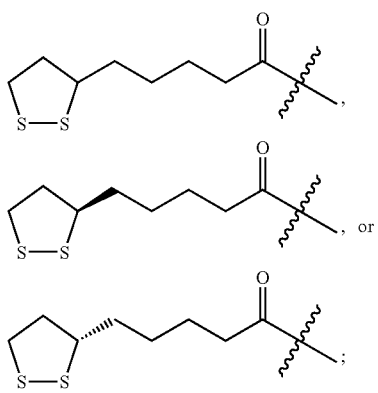

$R_4$ and $R_5$ are independently H, $(C_1-C_6)$alkyl, $(C_3-C_8)$cycloalkyl, or $(C_3-C_8)$cycloalkyl$(C_1-C_6)$alkyl, wherein the $(C_1-C_6)$alkyl, $(C_3-C_8)$cycloalkyl, and $(C_3-C_8)$cycloalkyl$(C_1-C_6)$alkyl are optionally substituted with 1, 2, 3, or 4 substituents that are independently $(C_1-C_6)$alkoxy, $(C_1-C_6)$alkoxy$(C_1-C_6)$alkyl, $(C_1-C_6)$alkoxycarbonyl, $(C_1-C_6)$alkylthio, halogen, hydroxy, hydroxycarbonyl, $NZ_1Z_2$, or phenyl, wherein the phenyl is optionally substituted with 1, 2, 3, 4, or 5 halogens; or $R_4$ and $R_5$ together with the nitrogen atom to which they are attached form azetidine, pyrrolidine, piperidine, piperazine, N-methylpiperazine, morpholine, or azepane;

$R_6$ is H, $(C_1-C_6)$alkyl, $(C_3-C_8)$cycloalkyl, or $(C_3-C_8)$cycloalkyl$(C_1-C_6)$alkyl, wherein the $(C_1-C_6)$alkyl, $(C_3-C_8)$cycloalkyl, and $(C_3-C_8)$cycloalkyl$(C_1-C_6)$alkyl are optionally substituted with 1, 2, 3, or 4 substituents that are independently $(C_1-C_6)$alkoxy, $(C_1-C_6)$alkoxy$(C_1-C_6)$alkyl, $(C_1-C_6)$alkoxycarbonyl, $(C_1-C_6)$alkylthio, halogen, hydroxy, hydroxycarbonyl, $NZ_1Z_2$, or phenyl, wherein the phenyl is optionally substituted with 1, 2, 3, 4, or 5 halogens; and $Z_1$ and $Z_2$ are independently H or $(C_1-C_6)$alkyl.

Representative compounds of Formula (XIII) include, but are not limited to, the compounds shown below:

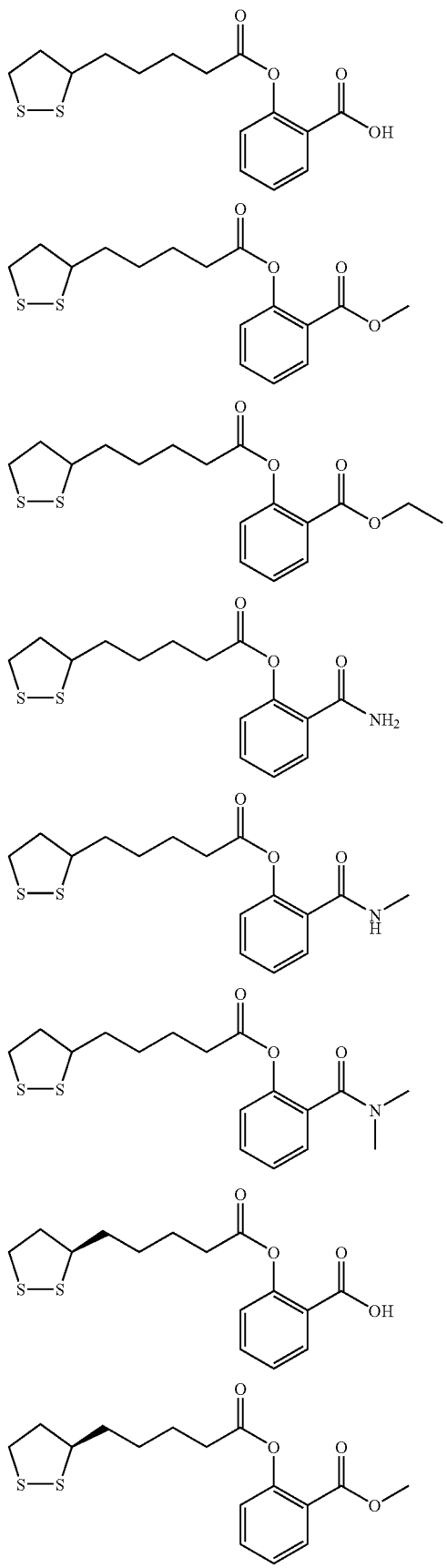

233
-continued
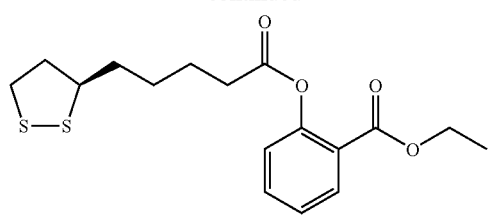
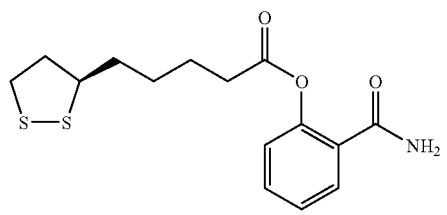
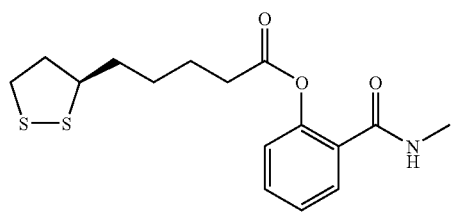
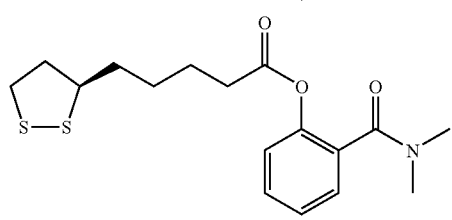
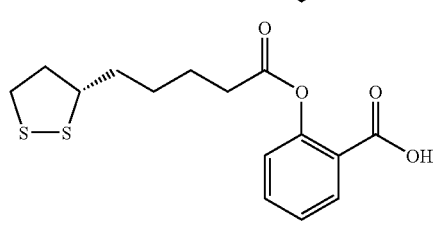
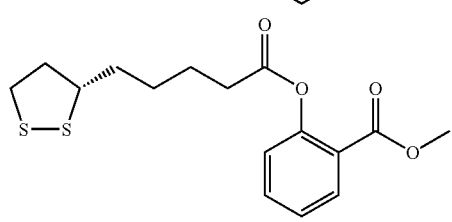
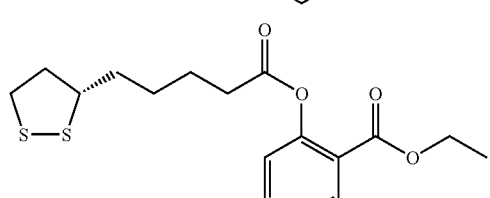
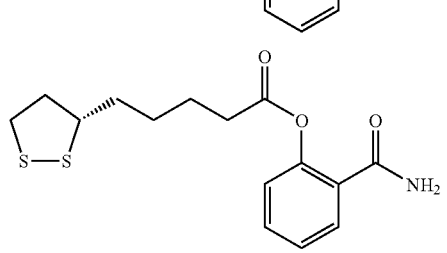
234
-continued
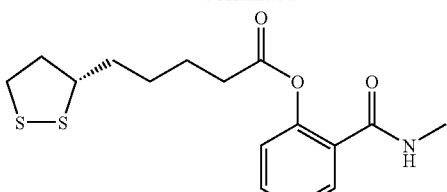
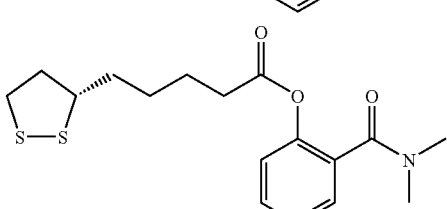
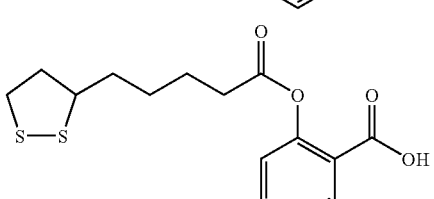
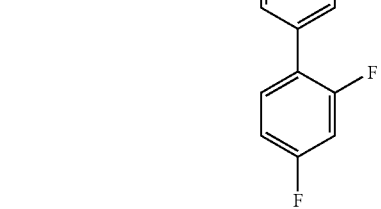
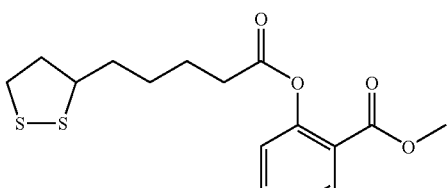
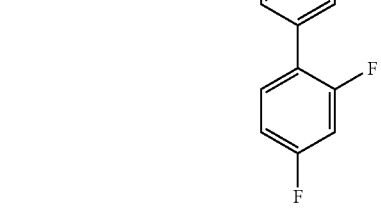
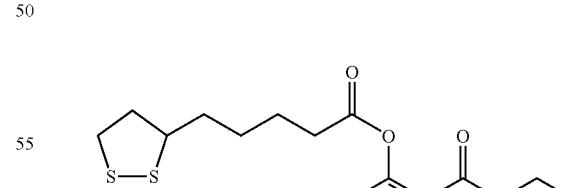
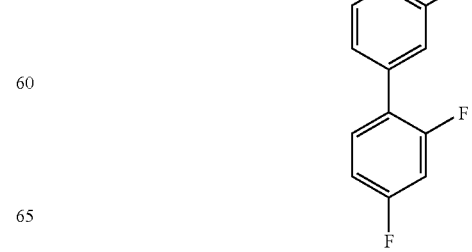

235
-continued
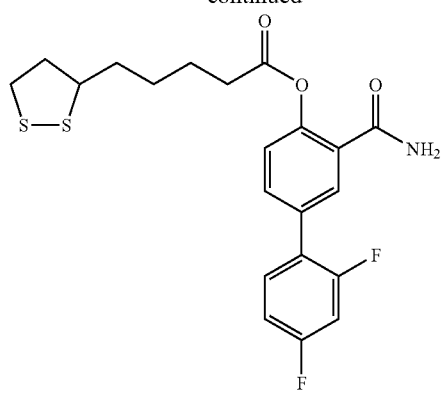
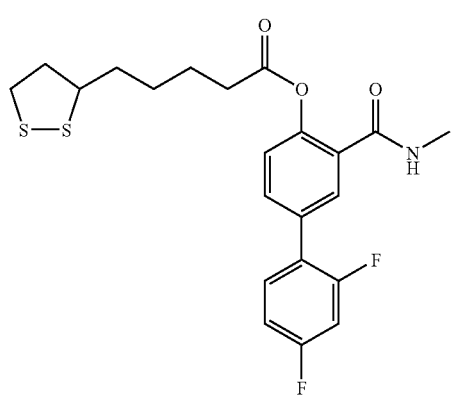
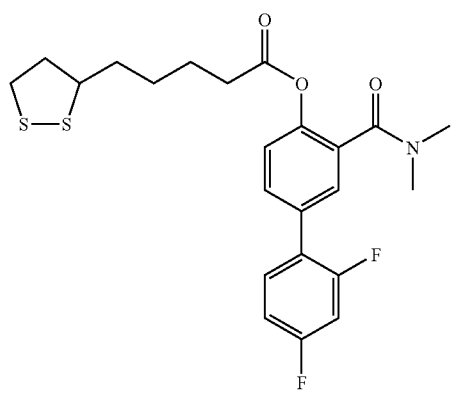
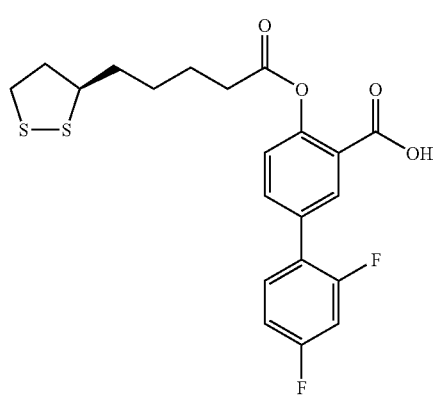
236
-continued
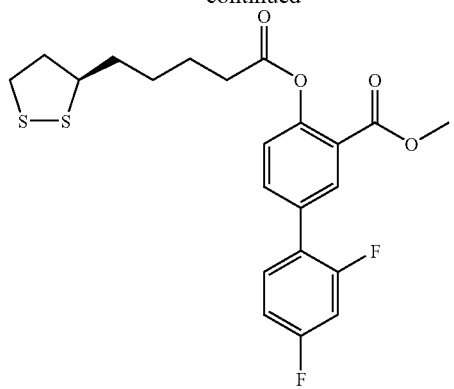
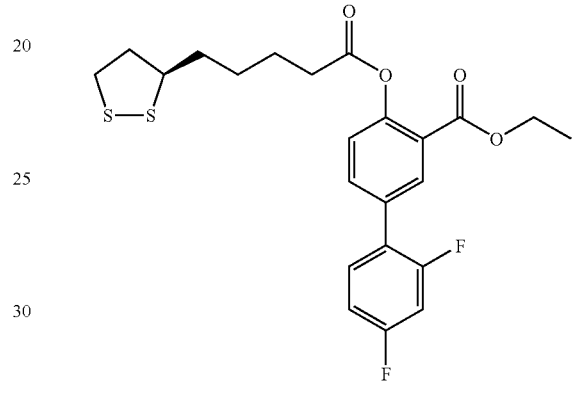
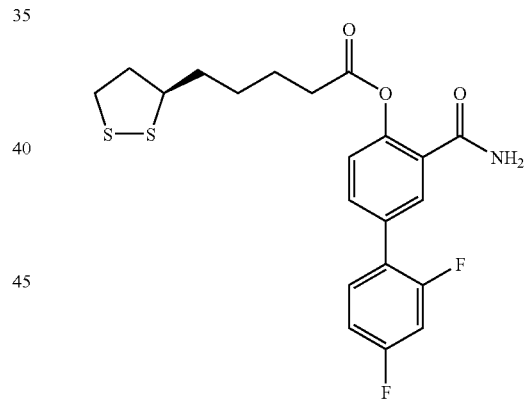
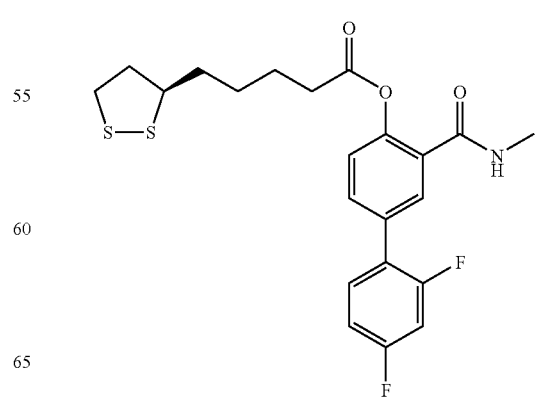

237
-continued
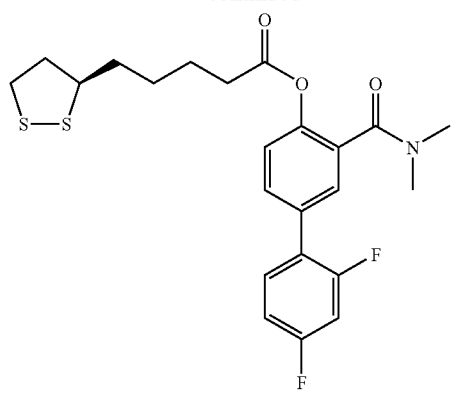
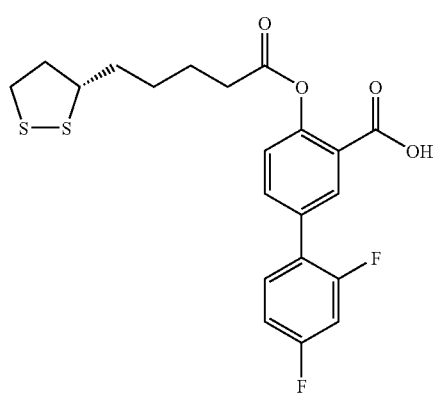
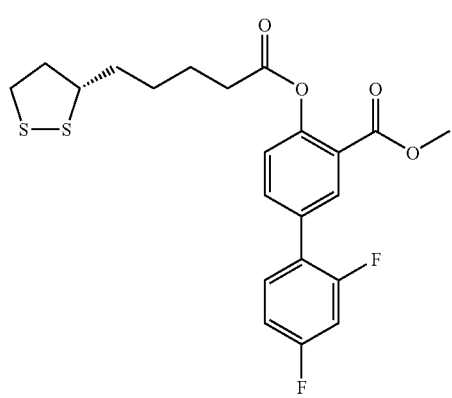
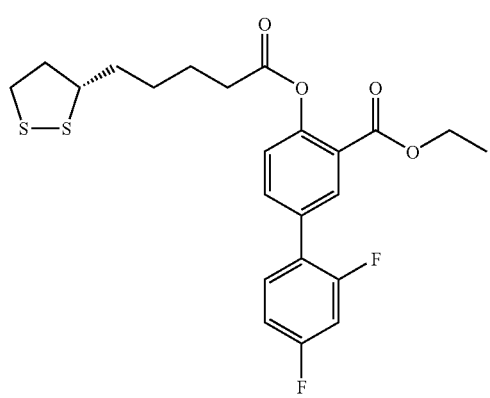
238
-continued
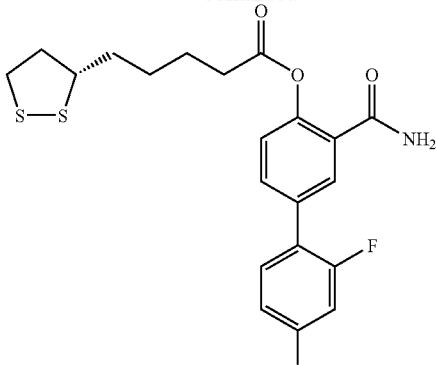
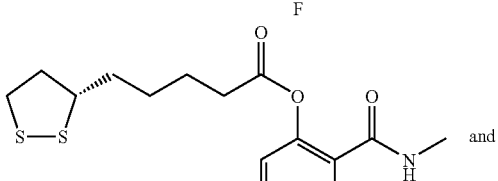
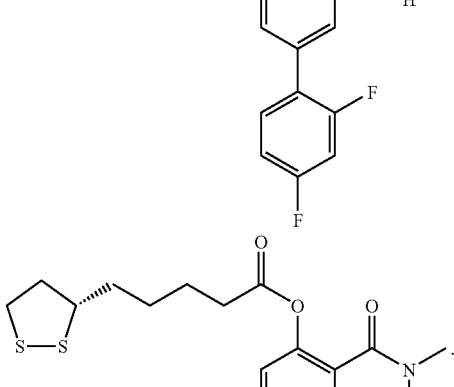
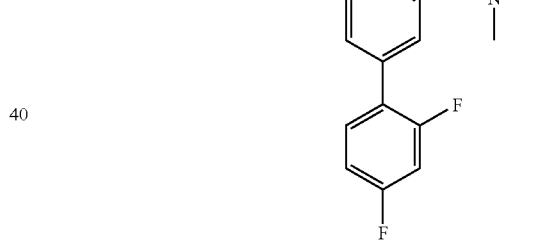 and
In another aspect, the present invention provides pharmaceutical compositions comprised of a compound of Formula (XIII), as shown above, and at least one pharmaceutically acceptable carrier.
In another aspect, the present invention provides compounds of Formula (XIV)
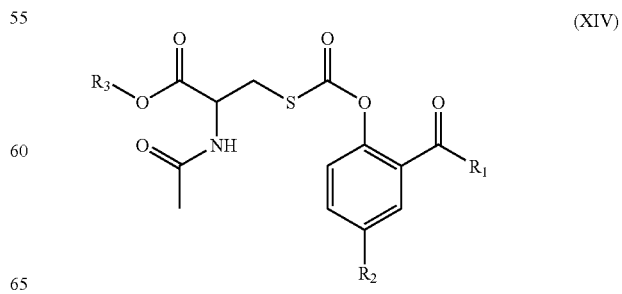
(XIV)

or a pharmaceutically acceptable salt thereof, wherein $R_1$ is $OR_6$ or $NR_4R_5$;

$R_2$ is H or 2,4-difluorophenyl;

$R_3$ is H or $(C_1-C_6)$alkyl;

$R_4$ and $R_5$ are independently H, $(C_1-C_6)$alkyl, $(C_3-C_8)$cycloalkyl, or $(C_3-C_8)$cycloalkyl$(C_1-C_6)$alkyl, wherein the $(C_1-C_6)$alkyl, $(C_3-C_8)$cycloalkyl, and $(C_3-C_8)$cycloalkyl$(C_1-C_6)$alkyl are optionally substituted with 1, 2, 3, or 4 substituents that are independently $(C_1-C_6)$alkoxy, $(C_1-C_6)$alkoxy$(C_1-C_6)$alkyl, $(C_1-C_6)$alkoxycarbonyl, $(C_1-C_6)$alkylthio, halogen, hydroxy, hydroxycarbonyl, $NZ_1Z_2$, or phenyl, wherein the phenyl is optionally substituted with 1, 2, 3, 4, or 5 halogens; or $R_4$ and $R_5$ together with the nitrogen atom to which they are attached form azetidine, pyrrolidine, piperidine, piperazine, N-methylpiperazine, morpholine, or azepane;

$R_6$ is H, $(C_1-C_6)$alkyl, $(C_3-C_8)$cycloalkyl, or $(C_3-C_8)$cycloalkyl$(C_1-C_6)$alkyl, wherein the $(C_1-C_6)$alkyl, $(C_3-C_8)$cycloalkyl, and $(C_3-C_8)$cycloalkyl$(C_1-C_6)$alkyl are optionally substituted with 1, 2, 3, or 4 substituents that are independently $(C_1-C_6)$alkoxy, $(C_1-C_6)$alkoxy$(C_1-C_6)$alkyl, $(C_1-C_6)$alkoxycarbonyl, $(C_1-C_6)$alkylthio, halogen, hydroxy, hydroxycarbonyl, $NZ_1Z_2$, or phenyl, wherein the phenyl is optionally substituted with 1, 2, 3, 4, or 5 halogens; and $Z_1$ and $Z_2$ are independently H or $(C_1-C_6)$alkyl.

Representative compounds of Formula (XIV) include, but are not limited to, the compounds shown below:

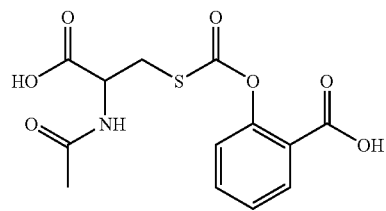

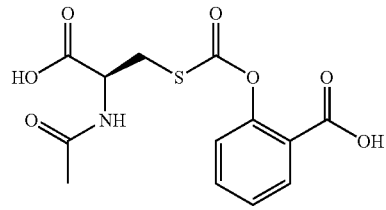

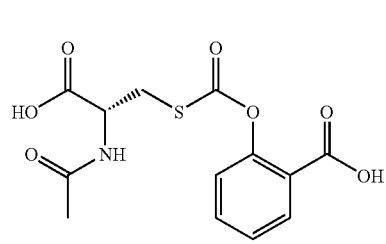

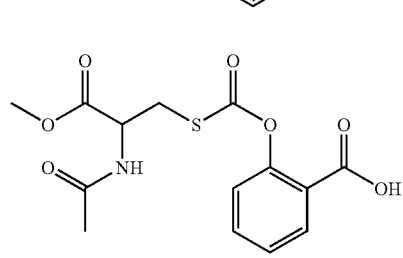

-continued

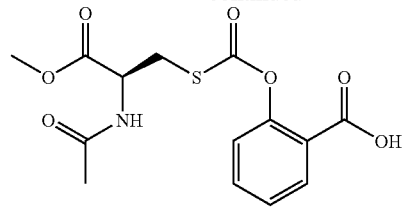

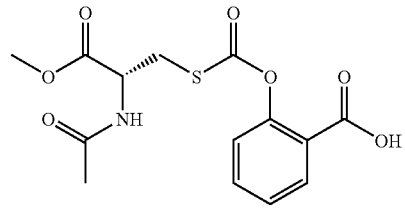

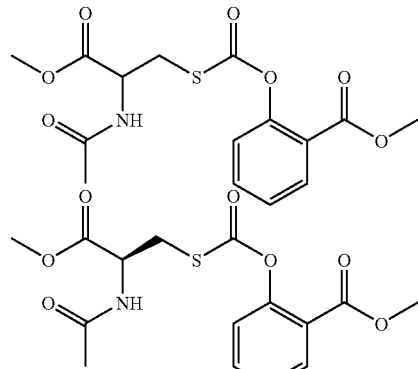

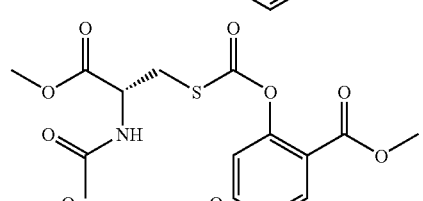

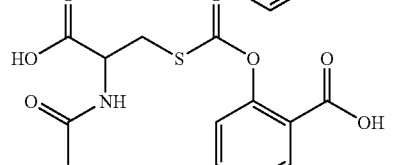

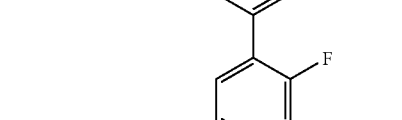

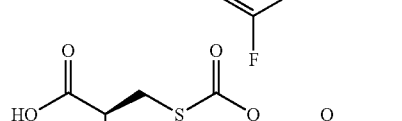

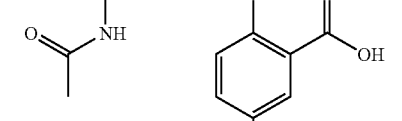

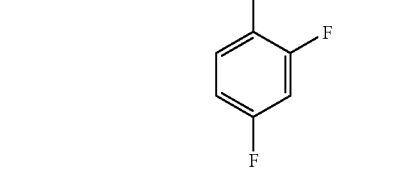

241
-continued
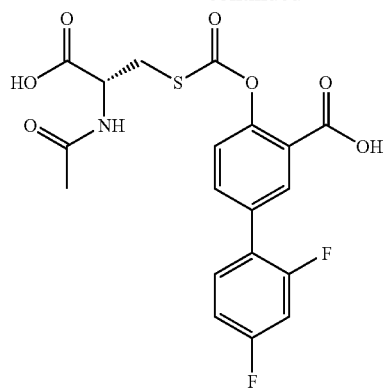
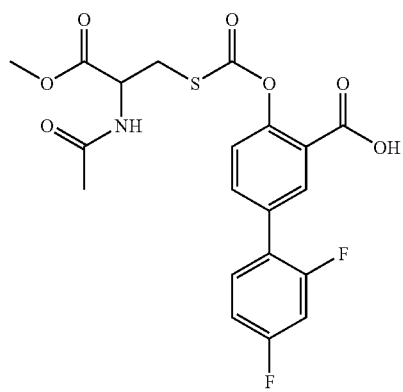
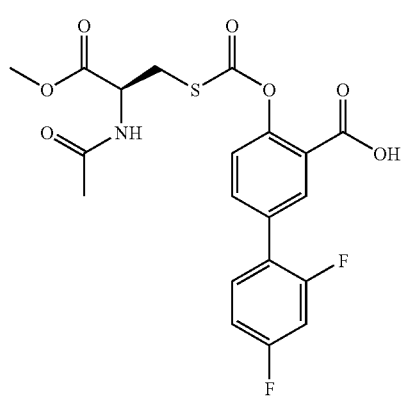
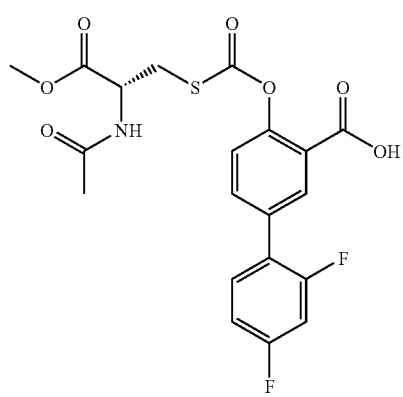
242
-continued
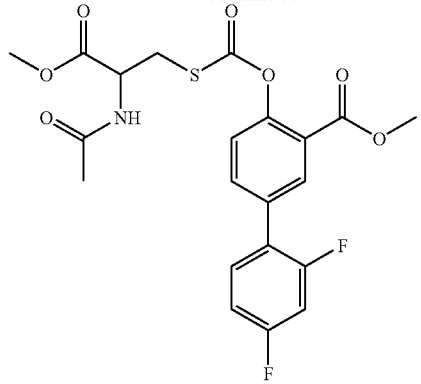
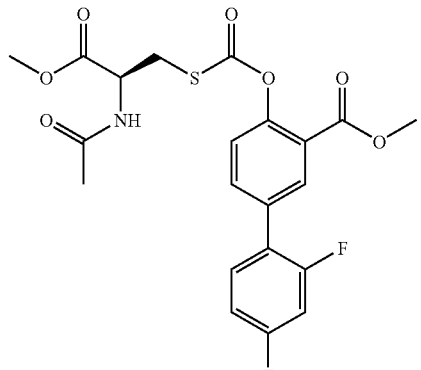
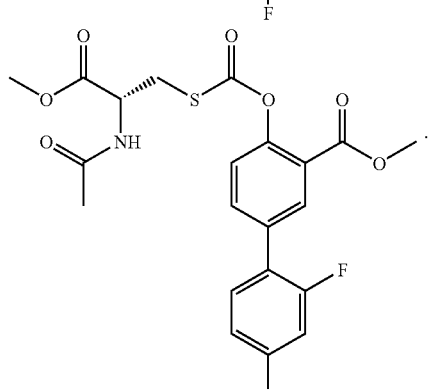
and
In another aspect, the present invention provides pharmaceutical compositions comprised of a compound of Formula (XIV), as shown above, and at least one pharmaceutically acceptable carrier.
In another aspect, the present invention provides compounds of Formula (XV)
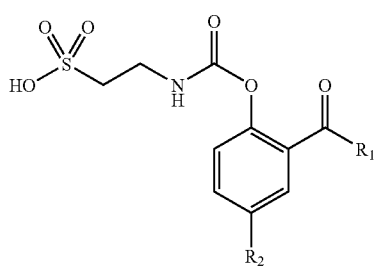
(XV)

or a pharmaceutically acceptable salt thereof, wherein $R_1$ is $OR_3$ or $NR_4R_5$;

$R_2$ is H or 2,4-difluorophenyl;

$R_3$ is H, $(C_1-C_6)$alkyl, $(C_3-C_8)$cycloalkyl, or $(C_3-C_8)$cycloalkyl$(C_1-C_6)$alkyl, wherein the $(C_1-C_6)$alkyl, $(C_3-C_8)$cycloalkyl, and $(C_3-C_8)$cycloalkyl$(C_1-C_6)$alkyl are optionally substituted with 1, 2, 3, or 4 substituents that are independently $(C_1-C_6)$alkoxy, $(C_1-C_6)$alkoxy$(C_1-C_6)$alkyl, $(C_1-C_6)$alkoxycarbonyl, $(C_1-C_6)$alkylthio, halogen, hydroxy, hydroxycarbonyl, $NZ_1Z_2$, or phenyl, wherein the phenyl is optionally substituted with 1, 2, 3, 4, or 5 halogens;

$R_4$ and $R_5$ are independently H, $(C_1-C_6)$alkyl, $(C_3-C_8)$cycloalkyl, or $(C_3-C_8)$cycloalkyl$(C_1-C_6)$alkyl, wherein the $(C_1-C_6)$alkyl, $(C_3-C_8)$cycloalkyl, and $(C_3-C_8)$cycloalkyl$(C_1-C_6)$alkyl are optionally substituted with 1, 2, 3, or 4 substituents that are independently $(C_1-C_6)$alkoxy, $(C_1-C_6)$alkoxy$(C_1-C_6)$alkyl, $(C_1-C_6)$alkoxycarbonyl, $(C_1-C_6)$alkylthio, halogen, hydroxy, hydroxycarbonyl, $NZ_1Z_2$, or phenyl, wherein the phenyl is optionally substituted with 1, 2, 3, 4, or 5 halogens; or $R_4$ and $R_5$ together with the nitrogen atom to which they are attached form azetidine, pyrrolidine, piperidine, piperazine, N-methylpiperazine, morpholine, or azepane; and $Z_1$ and $Z_2$ are independently H or $(C_1-C_6)$alkyl.

Representative compounds of Formula (XV) include, but are not limited to, the compounds shown below:

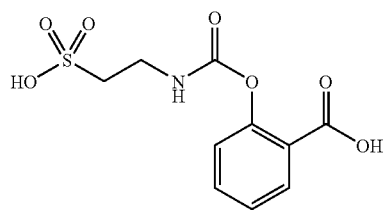

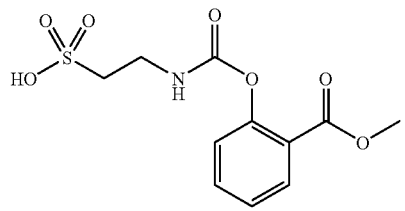

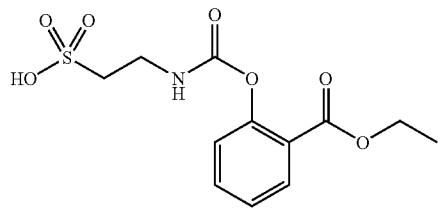

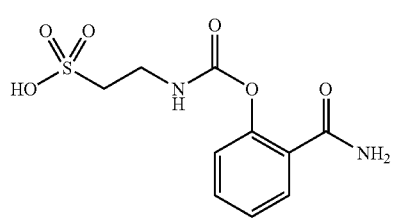

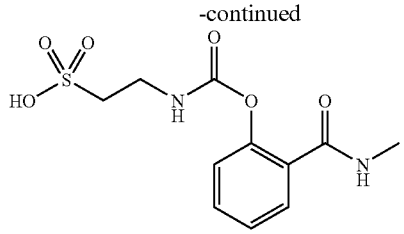

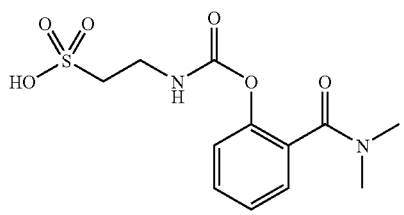

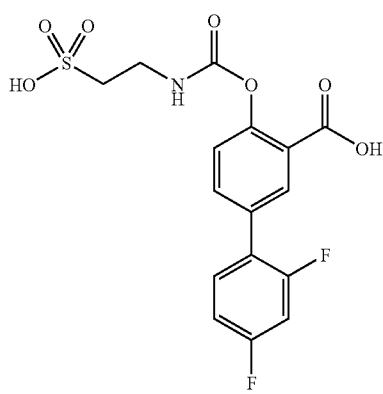

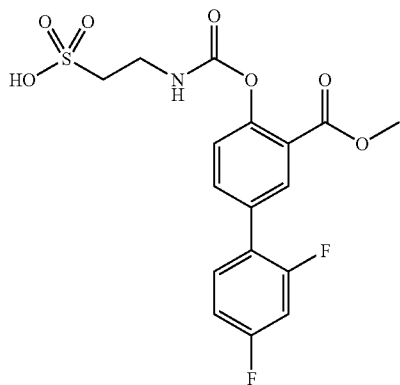

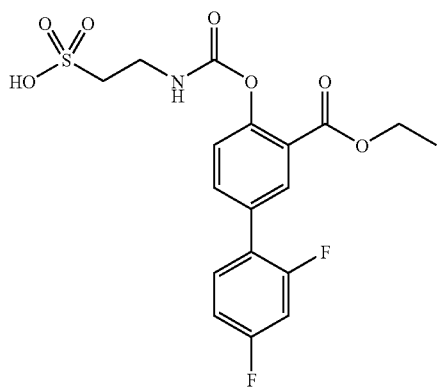

-continued

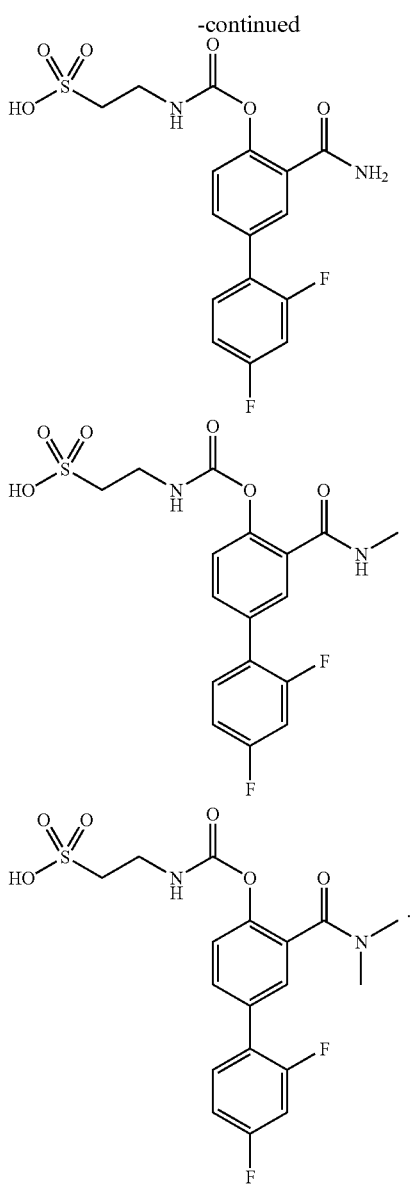

and

In another aspect, the present invention provides pharmaceutical compositions comprised of a compound of Formula (XV), as shown above, and at least one pharmaceutically acceptable carrier.

In another aspect, the present invention provides a compound of Formula (XVI)

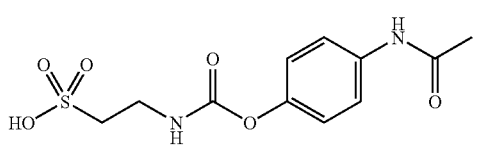
(XVI)

or a pharmaceutically acceptable salt thereof.

In another aspect, the present invention provides pharmaceutical compositions comprised of a compound of Formula (XVI), as shown above, and at least one pharmaceutically acceptable carrier.

In another aspect, the present invention provides compounds of Formula (XVII)

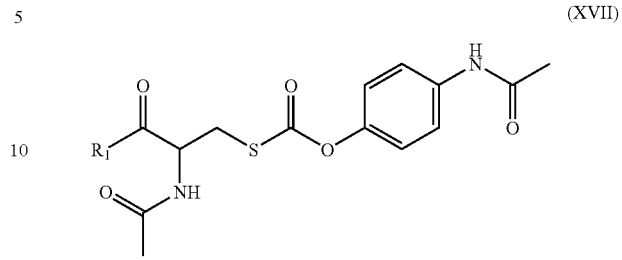
(XVII)

or a pharmaceutically acceptable salt thereof, wherein
$R_1$ is $OR_2$ or $NR_4R_5$;
$R_2$ is H, $(C_1\text{-}C_6)$alkyl, $(C_3\text{-}C_8)$cycloalkyl, or $(C_3\text{-}C_8)$cycloalkyl$(C_1\text{-}C_6)$alkyl, wherein the $(C_1\text{-}C_6)$alkyl, $(C_3\text{-}C_8)$cycloalkyl, and $(C_3\text{-}C_8)$cycloalkyl$(C_1\text{-}C_6)$alkyl are optionally substituted with 1, 2, 3, or 4 substituents that are independently $(C_1\text{-}C_6)$alkoxy, $(C_1\text{-}C_6)$alkoxy$(C_1\text{-}C_6)$alkyl, $(C_1\text{-}C_6)$alkoxycarbonyl, $(C_1\text{-}C_6)$alkylthio, halogen, hydroxy, hydroxycarbonyl, $NZ_1Z_2$, or phenyl, wherein the phenyl is optionally substituted with 1, 2, 3, 4, or 5 halogens;
$R_4$ and $R_5$ are independently H, $(C_1\text{-}C_6)$alkyl, $(C_3\text{-}C_8)$cycloalkyl, or $(C_3\text{-}C_8)$cycloalkyl$(C_1\text{-}C_6)$alkyl, wherein the $(C_1\text{-}C_6)$alkyl, $(C_3\text{-}C_8)$cycloalkyl, and $(C_3\text{-}C_8)$cycloalkyl$(C_1\text{-}C_6)$alkyl are optionally substituted with 1, 2, 3, or 4 substituents that are independently $(C_1\text{-}C_6)$alkoxy, $(C_1\text{-}C_6)$alkoxy$(C_1\text{-}C_6)$alkyl, $(C_1\text{-}C_6)$alkoxycarbonyl, $(C_1\text{-}C_6)$alkylthio, halogen, hydroxy, hydroxycarbonyl, $NZ_1Z_2$, or phenyl, wherein the phenyl is optionally substituted with 1, 2, 3, 4, or 5 halogens; or $R_4$ and $R_5$ together with the nitrogen atom to which they are attached form azetidine, pyrrolidine, piperidine, piperazine, N-methylpiperazine, morpholine, or azepane; and
$Z_1$ and $Z_2$ are independently H or $(C_1\text{-}C_6)$alkyl.

Representative compounds of Formula (XVII) include, but are not limited to, the compounds shown below:

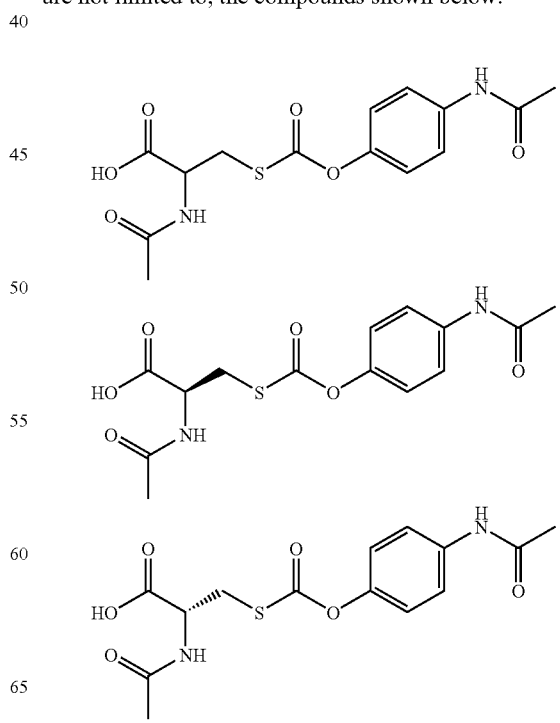

247
-continued
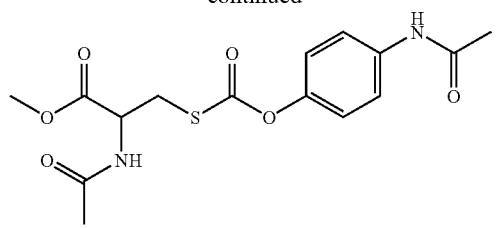
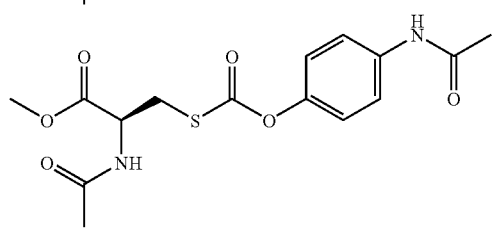
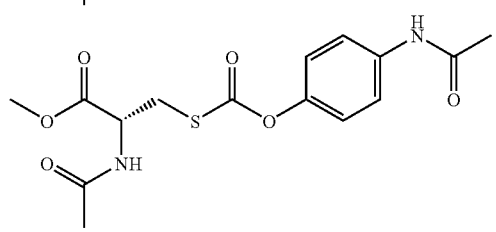
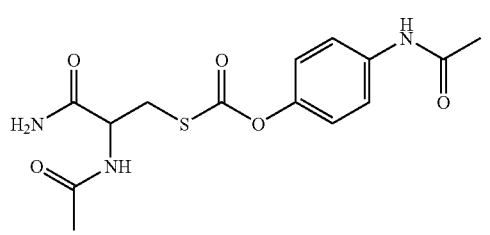
248
-continued
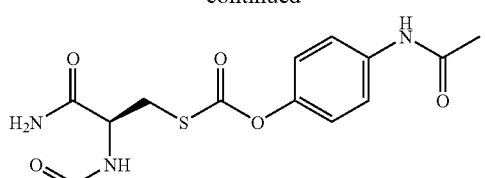
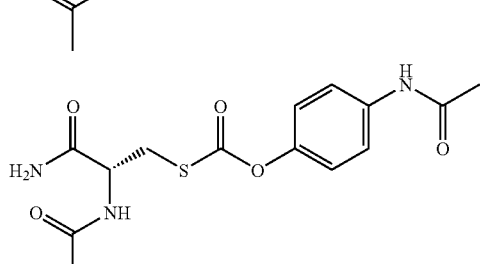
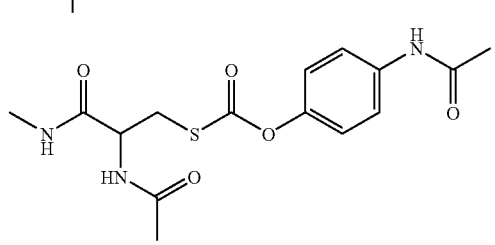
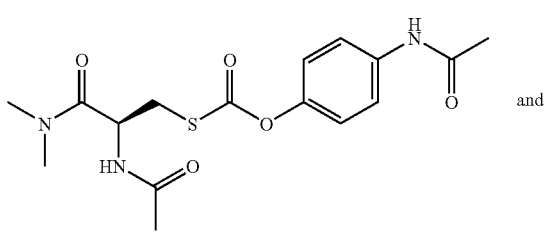
and -continued

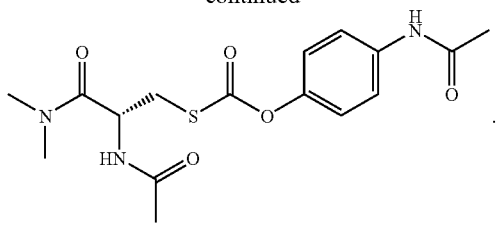

In another aspect, the present invention provides pharmaceutical compositions comprised of a compound of Formula (XVII), as shown above, and at least one pharmaceutically acceptable carrier.

In another aspect, the present invention provides compounds of Formula (XVIII)

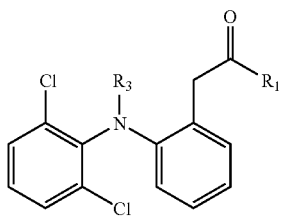

(XVIII)

or a pharmaceutically acceptable salt thereof, wherein
$R_1$ is $OR_2$ or $NR_4R_5$;
$R_2$ is H, $(C_1-C_6)$alkyl, $(C_3-C_8)$cycloalkyl, or $(C_3-C_8)$cycloalkyl$(C_1-C_6)$alkyl, wherein the $(C_1-C_6)$alkyl, $(C_3-C_8)$cycloalkyl, and $(C_3-C_8)$cycloalkyl$(C_1-C_6)$alkyl are optionally substituted with 1, 2, 3, or 4 substituents that are independently $(C_1-C_6)$alkoxy, $(C_1-C_6)$alkoxy$(C_1-C_6)$alkyl, $(C_1-C_6)$alkoxycarbonyl, $(C_1-C_6)$alkylthio, halogen, hydroxy, hydroxycarbonyl, $NZ_1Z_2$, or phenyl, wherein the phenyl is optionally substituted with 1, 2, 3, 4, or 5 halogens;
$R_3$ is

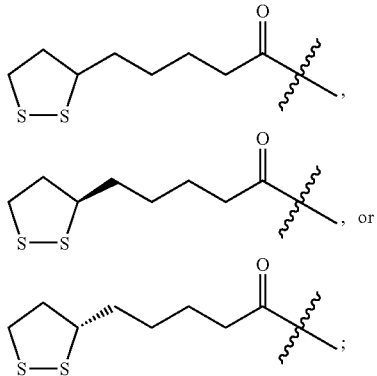

$R_4$ and $R_5$ are independently H, $(C_1-C_6)$alkyl, $(C_3-C_8)$cycloalkyl, or $(C_3-C_8)$cycloalkyl$(C_1-C_6)$alkyl, wherein the $(C_1-C_6)$alkyl, $(C_3-C_8)$cycloalkyl, and $(C_3-C_8)$cycloalkyl$(C_1-C_6)$alkyl are optionally substituted with 1, 2, 3, or 4 substituents that are independently $(C_1-C_6)$alkoxy, $(C_1-C_6)$alkoxy$(C_1-C_6)$alkyl, $(C_1-C_6)$alkoxycarbonyl, $(C_1-C_6)$alkylthio, halogen, hydroxy, hydroxycarbonyl, $NZ_1Z_2$, or phenyl, wherein the phenyl is optionally substituted with 1, 2, 3, 4, or 5 halogens; or $R_4$ and $R_5$ together with the nitrogen atom to which they are attached form azetidine, pyrrolidine, piperidine, piperazine, N-methylpiperazine, morpholine, or azepane; and
$Z_1$ and $Z_2$ are independently H or $(C_1-C_6)$alkyl.

Representative compounds of Formula (XVIII) include, but are not limited to, the compounds shown below:

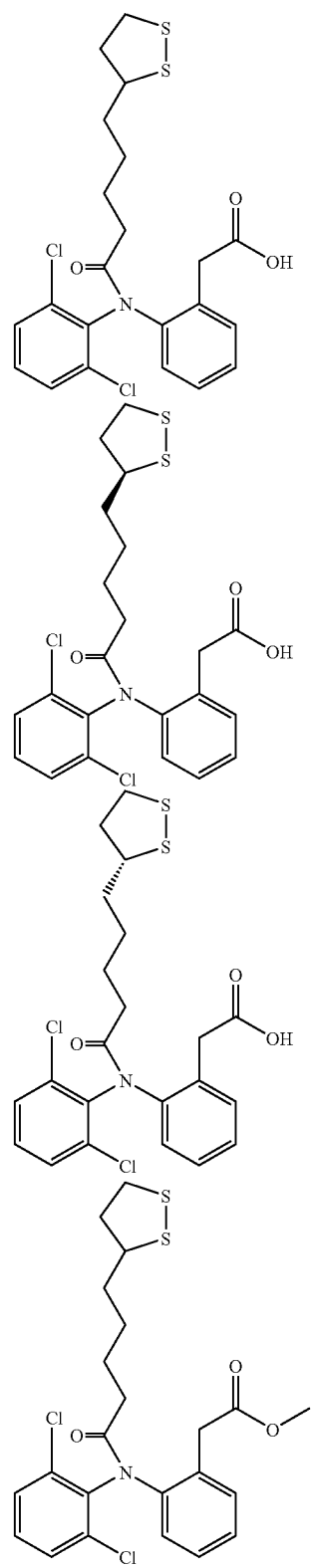

251
-continued
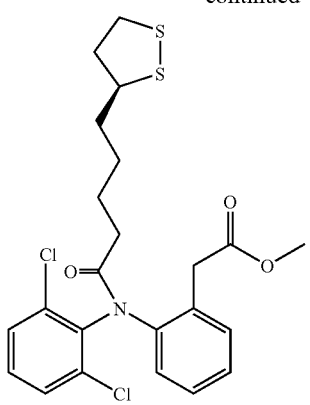
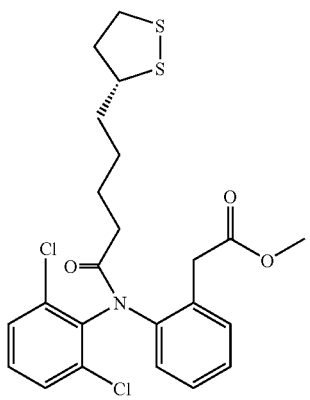
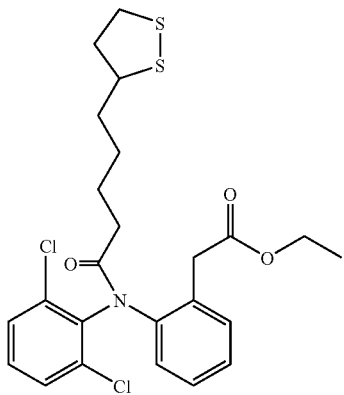
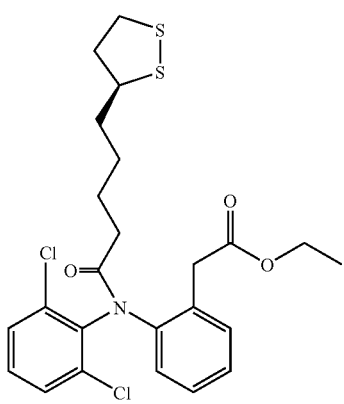
252
-continued
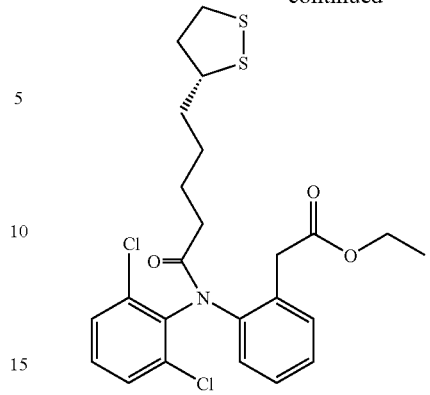
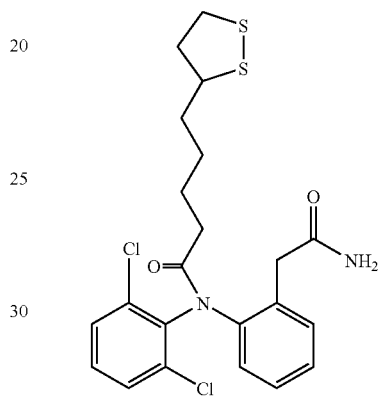
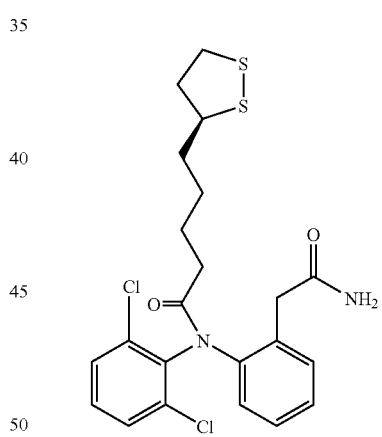
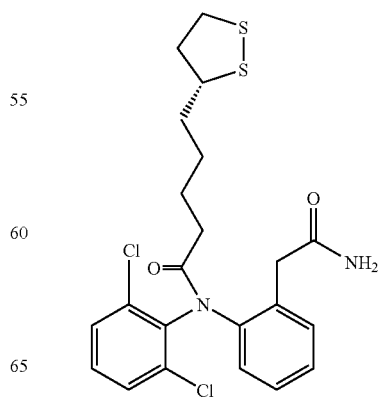

-continued

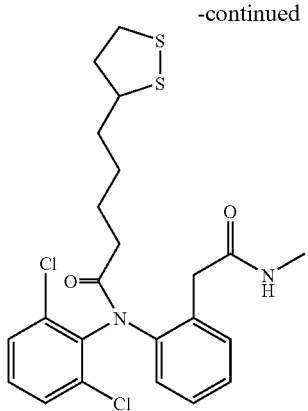

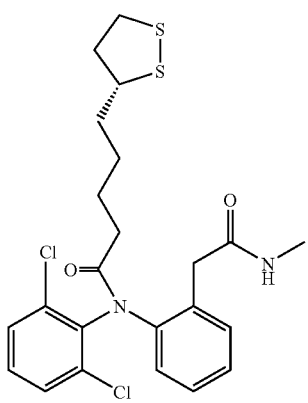

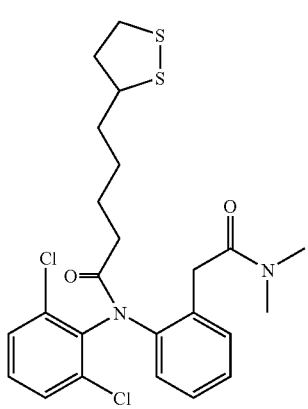

-continued

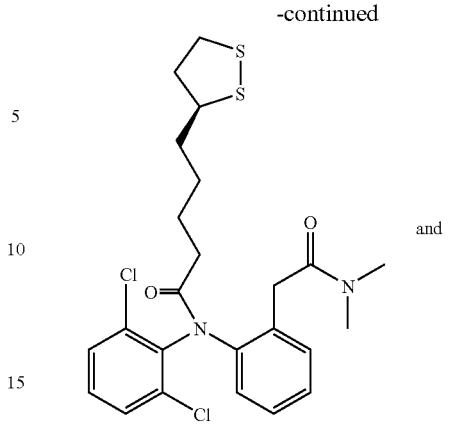
and

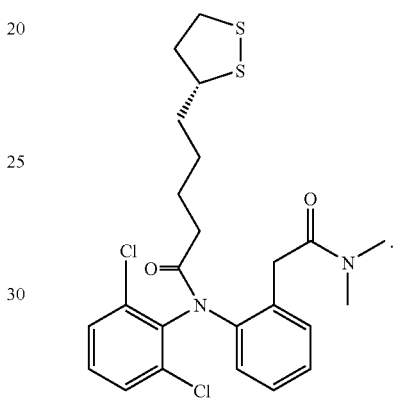

In another aspect, the present invention provides pharmaceutical compositions comprised of a compound of Formula (XVIII), as shown above, and at least one pharmaceutically acceptable carrier.

In another aspect, the present invention provides compounds of Formula (XIX)

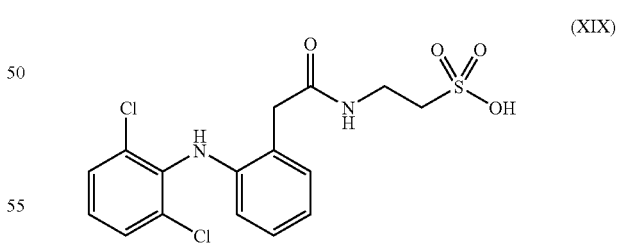

(XIX)

or a pharmaceutically acceptable salt thereof.

In another aspect, the present invention provides pharmaceutical compositions comprised of a compound of Formula (XIX), as shown above, and at least one pharmaceutically acceptable carrier.

In another aspect, the present invention provides compounds of Formula (XX)

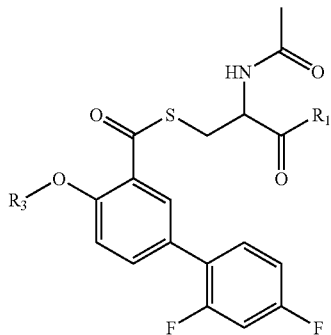

(XX)

or a pharmaceutically acceptable salt thereof, wherein
R₁ is OR₂, NR₄R₅, or

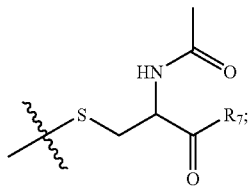

R₂ is (C₁-C₆)alkyl, (C₃-C₈)cycloalkyl, or (C₃-C₈)cycloalkyl(C₁-C₆)alkyl, wherein (C₁-C₆)alkyl, (C₃-C₈)cycloalkyl, and (C₃-C₈)cycloalkyl(C₁-C₆)alkyl are optionally substituted with 1, 2, 3, or 4 substituents that are independently (C₁-C₆)alkoxy, (C₁-C₆)alkoxy(C₁-C₆)alkyl, (C₁-C₆)alkoxycarbonyl, (C₁-C₆)alkylthio, halogen, hydroxy, hydroxycarbonyl, NZ₁Z₂, or phenyl, wherein the phenyl is optionally substituted with 1, 2, 3, 4, or 5 halogens;

Z₁ and Z₂ are independently H or (C₁-C₆)alkyl;

R₃ is H or C(O)R₆;

R₄ and R₅ are independently H, (C₁-C₆)alkyl, (C₃-C₈)cycloalkyl, or (C₃-C₈)cycloalkyl(C₁-C₆)alkyl, wherein the (C₁-C₆)alkyl, (C₃-C₈)cycloalkyl, and (C₃-C₈)cycloalkyl(C₁-C₆)alkyl are optionally substituted with 1, 2, 3, or 4 substituents that are independently (C₁-C₆)alkoxy, (C₁-C₆)alkoxy(C₁-C₆)alkyl, (C₁-C₆)alkoxycarbonyl, (C₁-C₆)alkylthio, halogen, hydroxy, hydroxycarbonyl, NZ₁Z₂, or phenyl, wherein the phenyl is optionally substituted with 1, 2, 3, 4, or 5 halogens; or R₄ and R₅ together with the nitrogen atom to which they are attached form azetidine, pyrrolidine, piperidine, piperazine, N-methylpiperazine, morpholine, or azepane;

R₆ is H, (C₁-C₆)alkyl, (C₃-C₈)cycloalkyl, or (C₃-C₈)cycloalkyl(C₁-C₆)alkyl, wherein the (C₁-C₆)alkyl, (C₃-C₈)cycloalkyl, and (C₃-C₈)cycloalkyl(C₁-C₆)alkyl are optionally substituted with 1, 2, 3, or 4 substituents that are independently (C₁-C₆)alkoxy, (C₁-C₆)alkoxy(C₁-C₆)alkyl, (C₁-C₆)alkoxycarbonyl, (C₁-C₆)alkylthio, halogen, hydroxy, hydroxycarbonyl, NZ₃Z₄, or phenyl, wherein the phenyl is optionally substituted with 1, 2, 3, 4, or 5 halogens;

Z₃ and Z₄ are independently H or (C₁-C₆)alkyl; and

R₇ is OR₂ or NR₄R₅;

provided that the compound is not

N-acetyl-S-[(2',4'-difluoro-4-hydroxy[1,1'-biphenyl]-3-yl)carbonyl]-L-cysteine methyl ester;

N-acetyl-S-[(2',4'-difluoro-4-hydroxy[1,1'-biphenyl]-3-yl)carbonyl]-L-cysteine ethyl ester;

N-acetyl-S-[(2',4'-difluoro-4-acetyloxy[1,1'-biphenyl]-3-yl)carbonyl]-L-cysteine methyl ester; and N-acetyl-S-[(2',4'-difluoro-4-acetyloxy[1,1'-biphenyl]-3-yl)carbonyl]-L-cysteine ethyl ester.

Representative compounds of Formula (XX) include, but are not limited to, the compounds shown below:

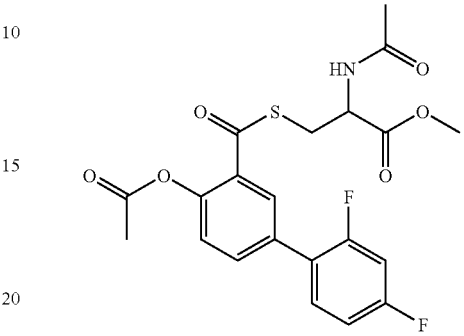

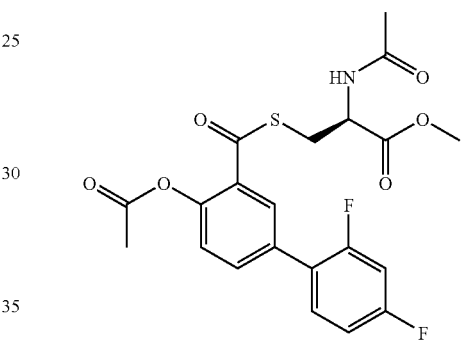

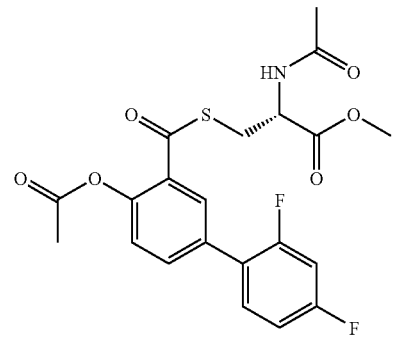

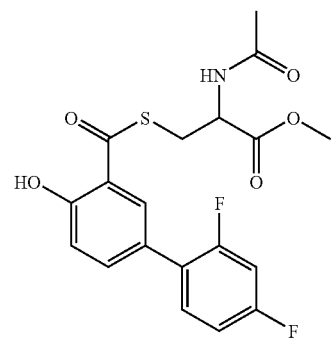

257
-continued
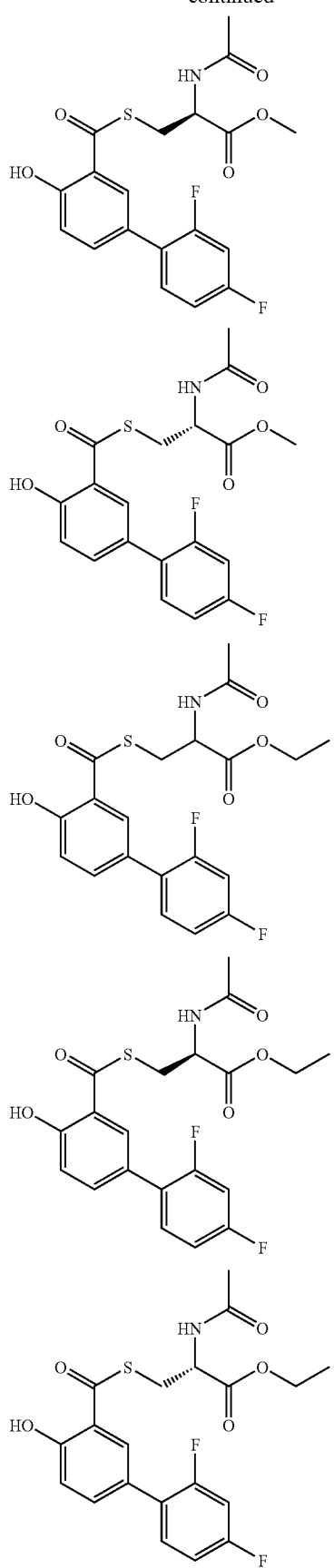
258
-continued
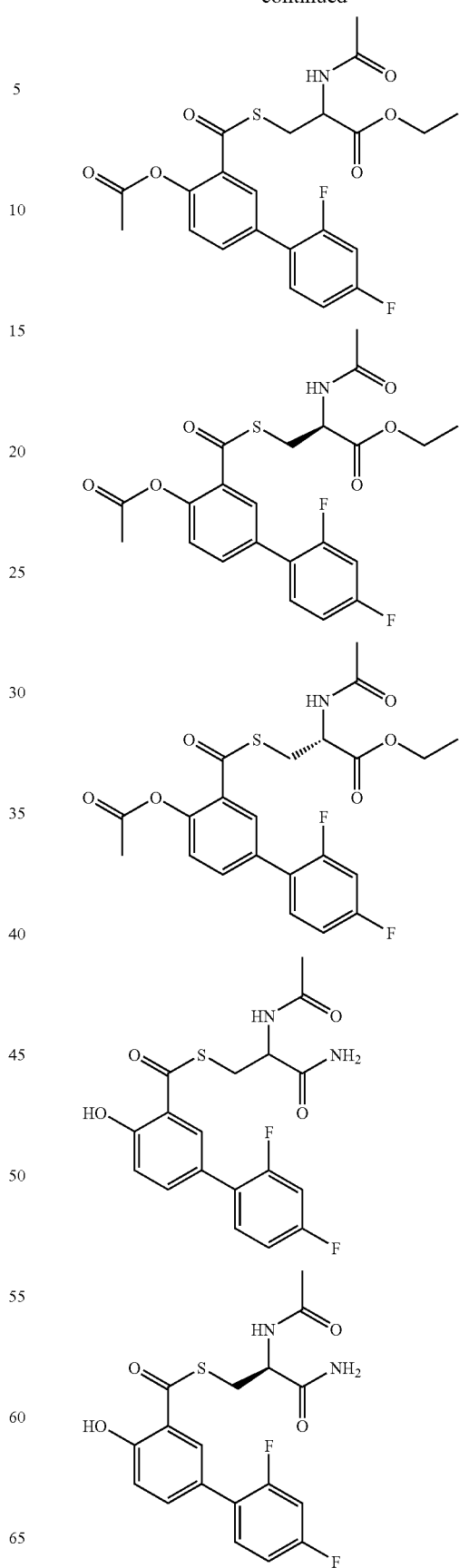

259
-continued
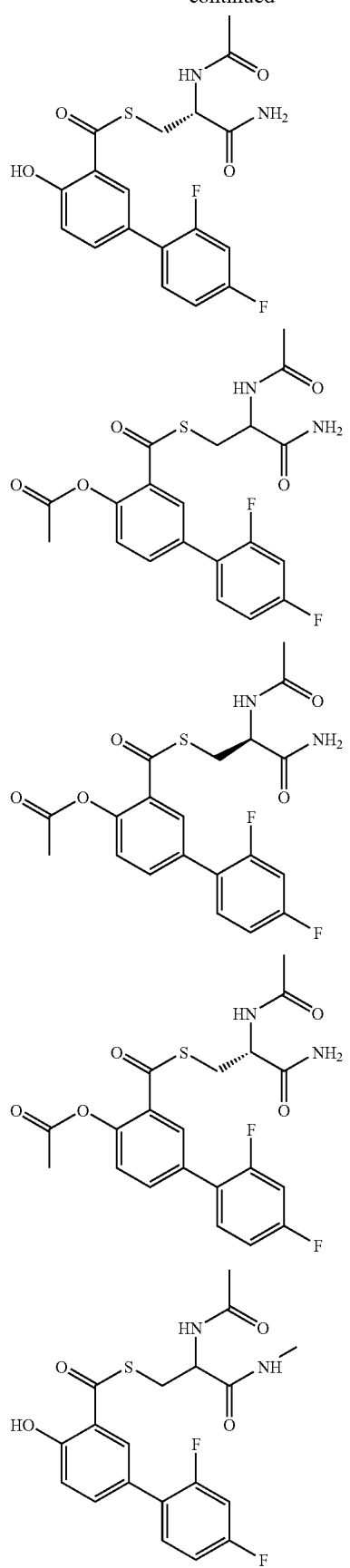
260
-continued
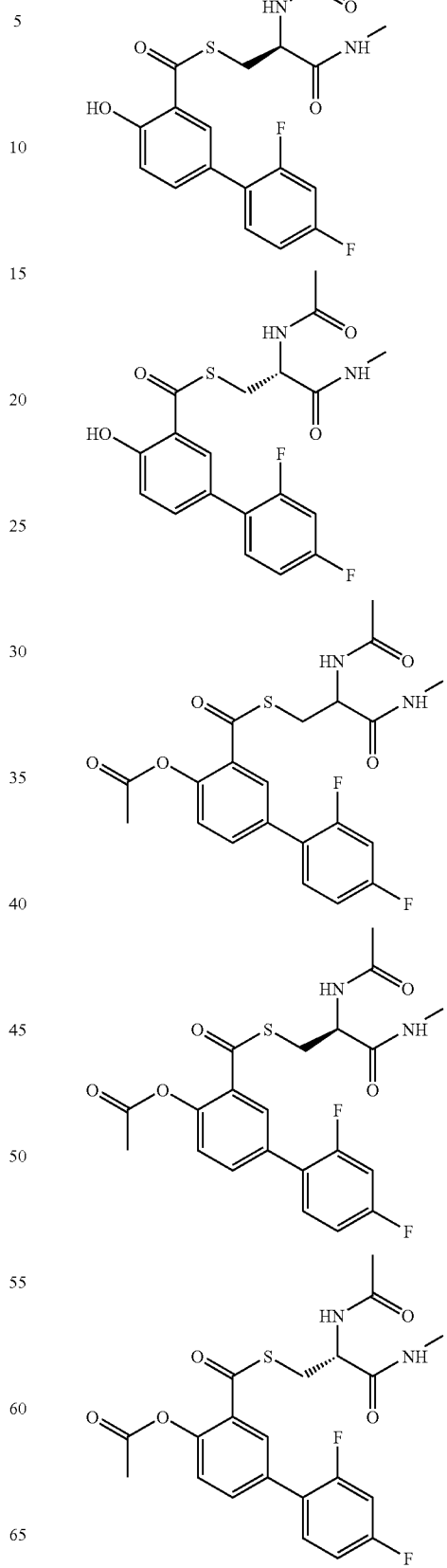

261
-continued
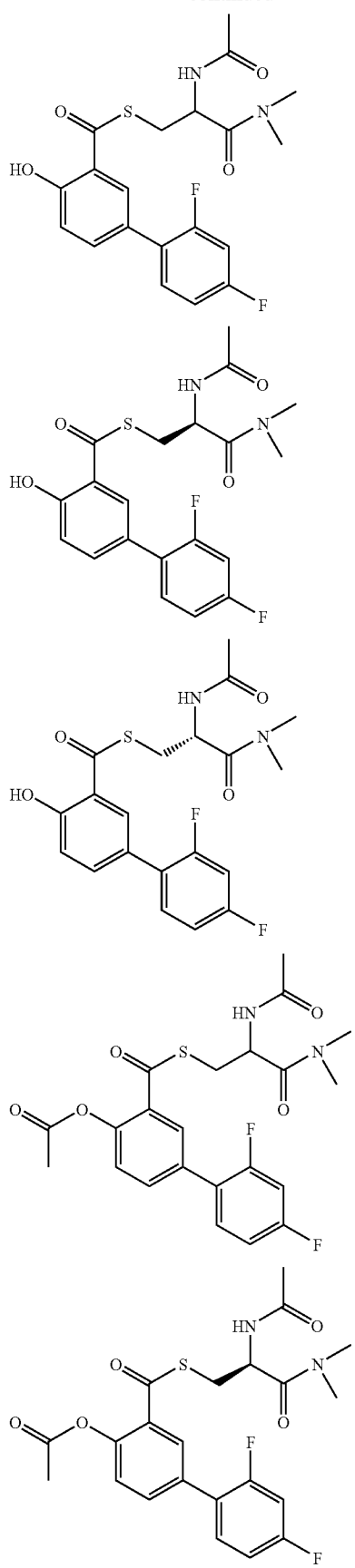
262
-continued
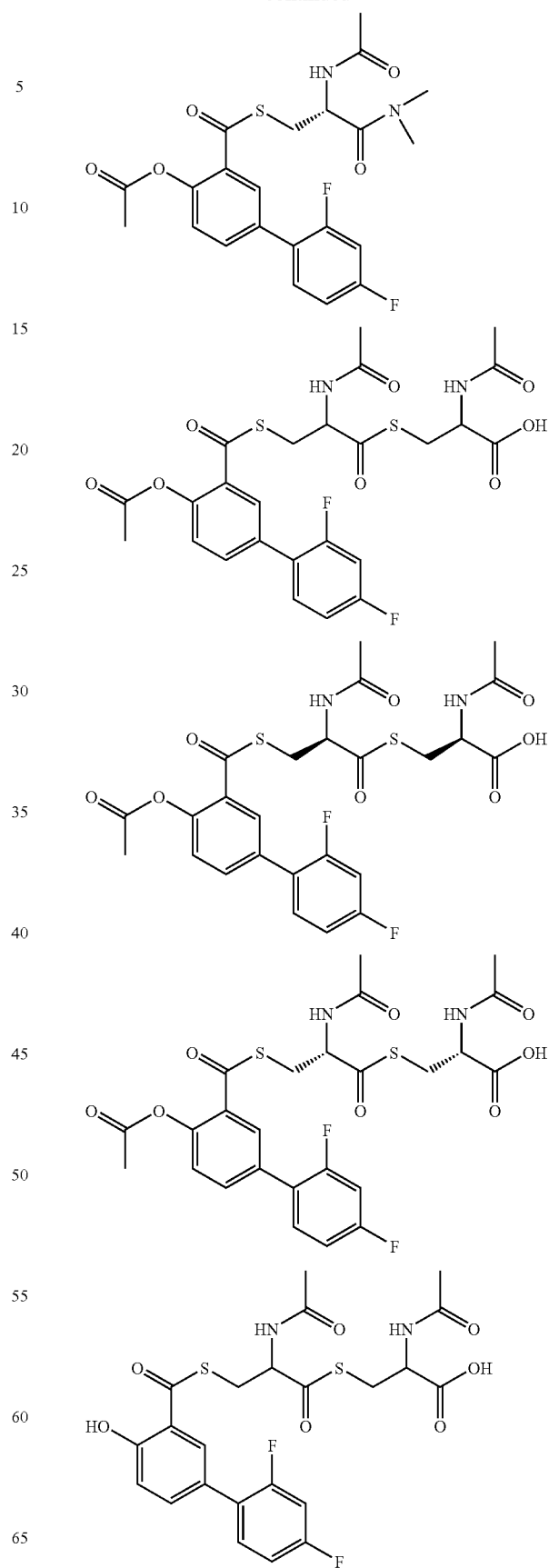

263
-continued
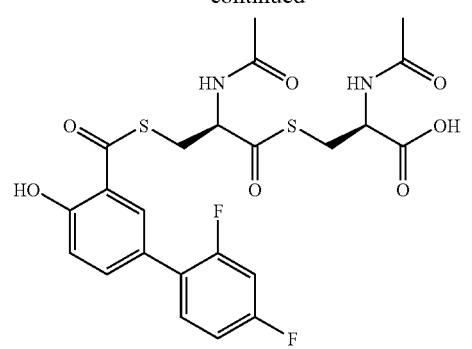
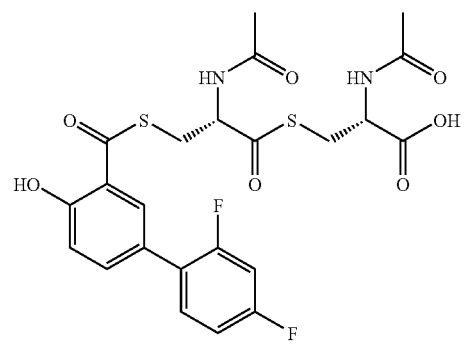
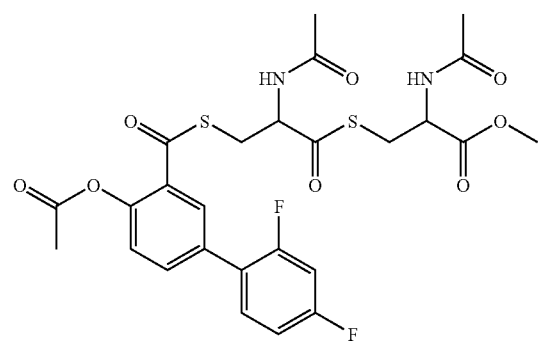
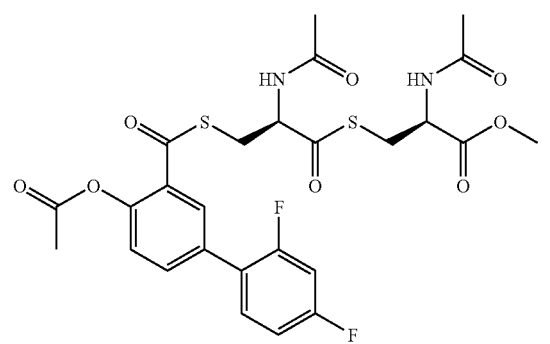
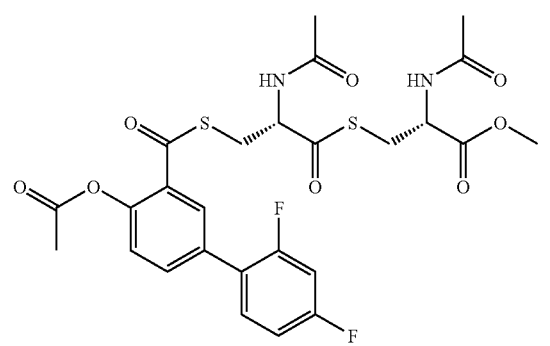
264
-continued
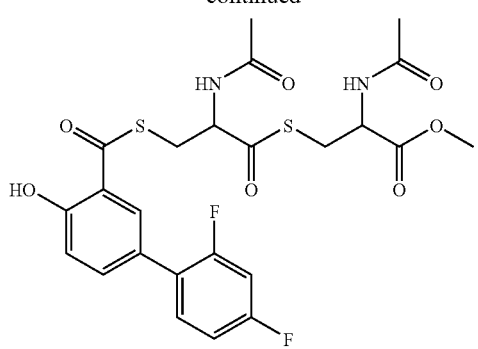
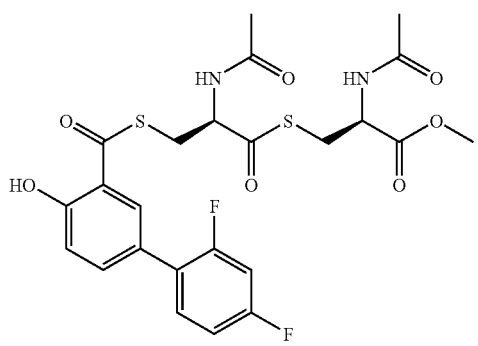
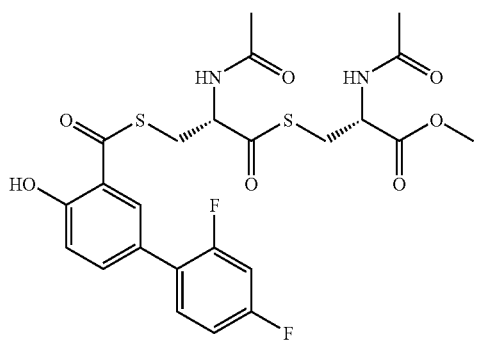
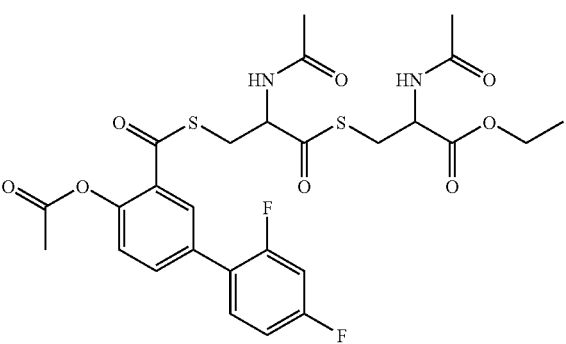
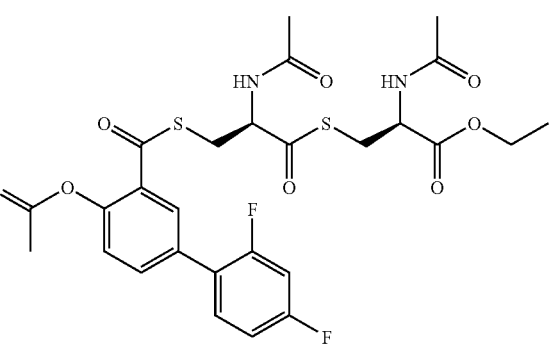

265
-continued
266
-continued
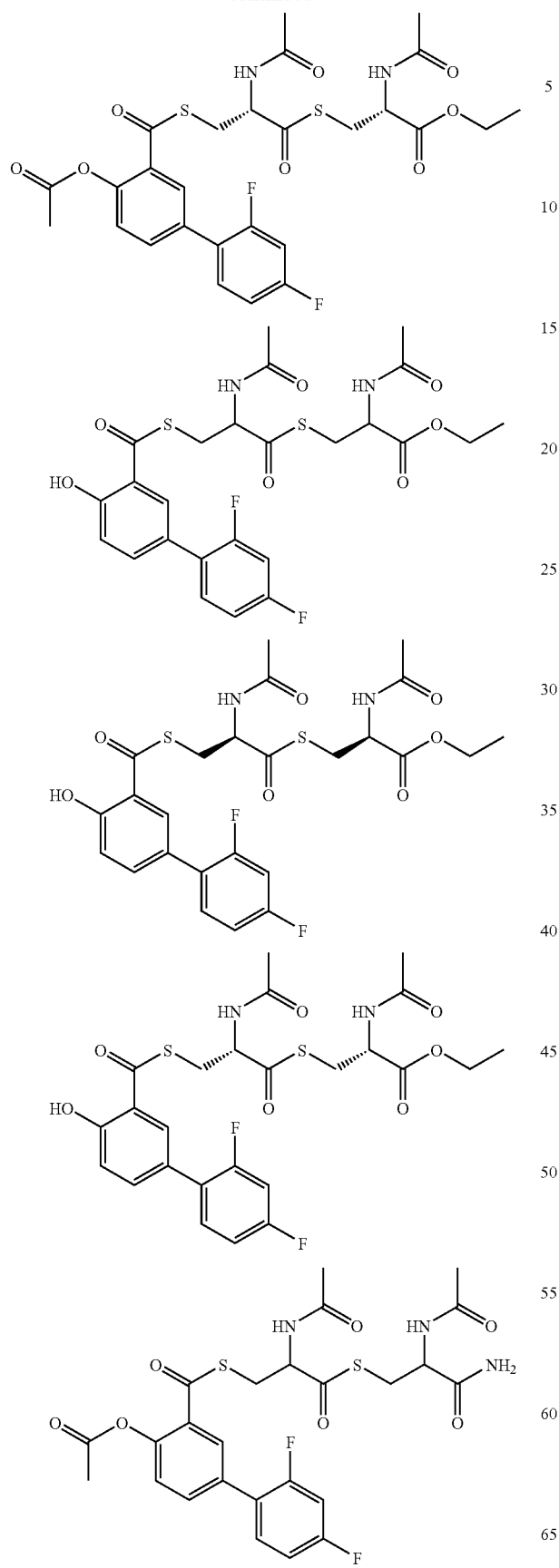
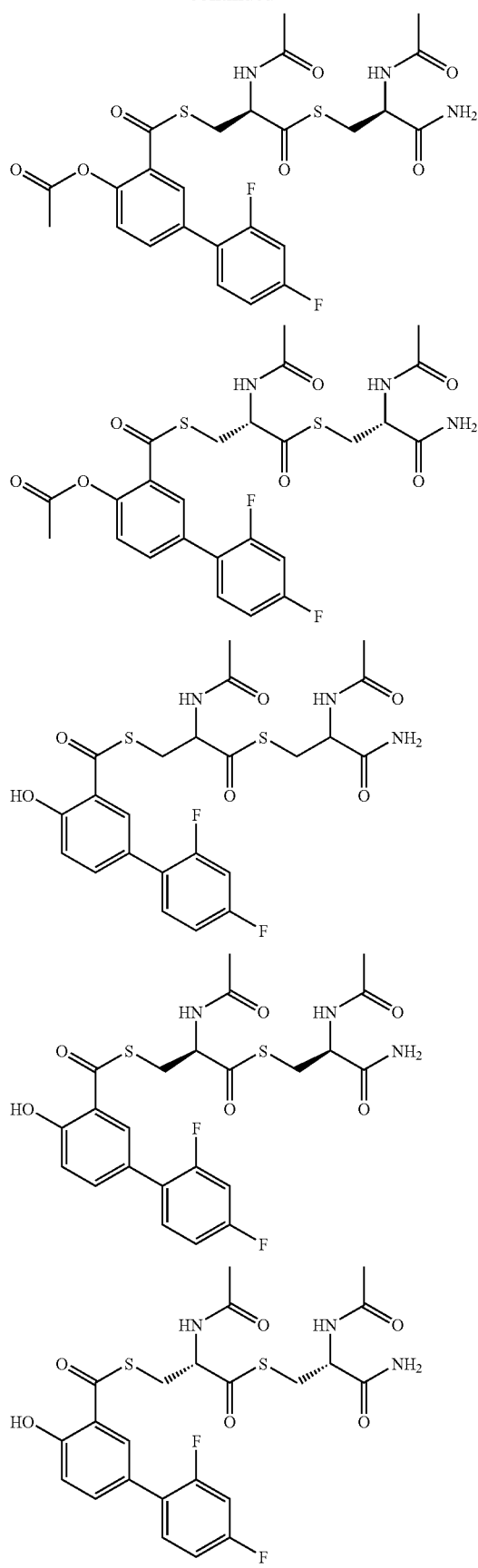

267
-continued
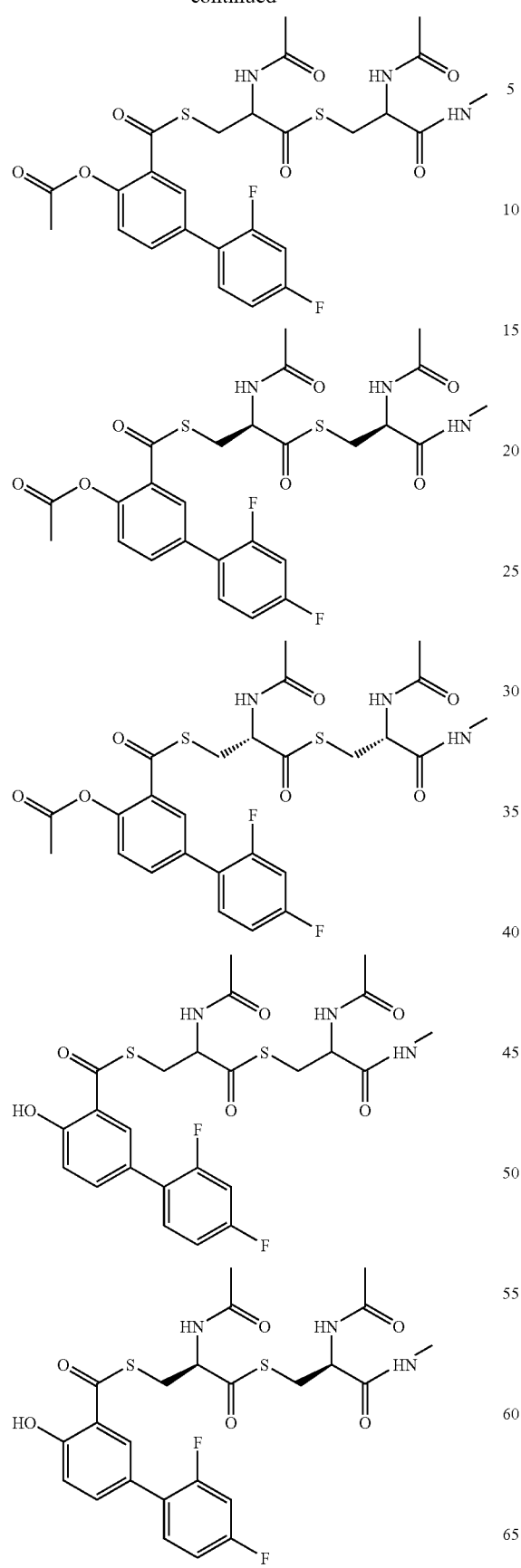
268
-continued
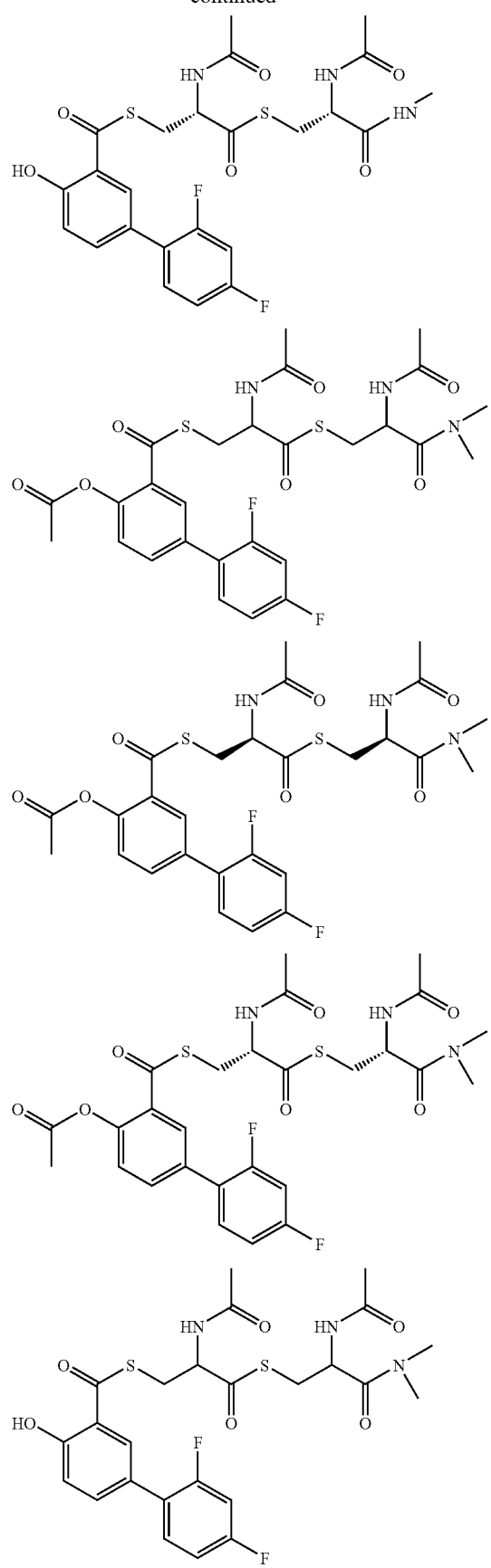

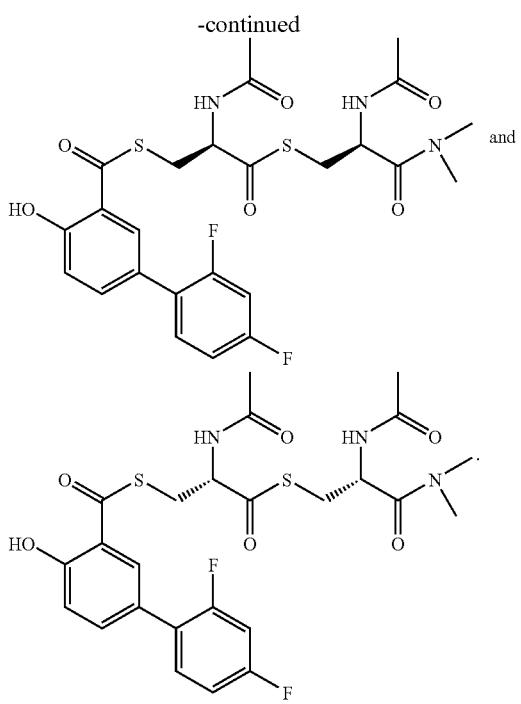

In another aspect, the present invention provides pharmaceutical compositions comprised of a compound of Formula (XX), as shown above, and at least one pharmaceutically acceptable carrier.

In another aspect, the present invention provides compounds of Formula (XXI)

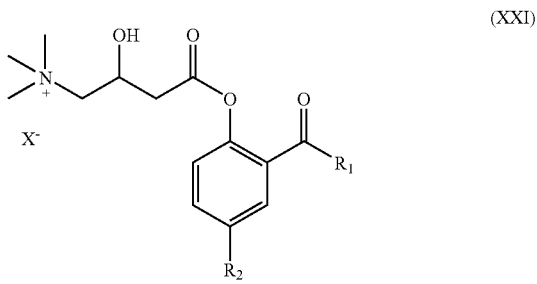

(XXI)

wherein
X is absent, halogen, $HSO_4$, $HPO_4$, $CH_3CO_2$, or $CF_3CO_2$;
$R_1$ is $OR_3$ or $NR_4R_5$;
$R_2$ is H or 2,4-difluorophenyl;
$R_3$ is H, ($C_1$-$C_6$)alkyl, ($C_3$-$C_8$)cycloalkyl, or ($C_3$-$C_8$)cycloalkyl($C_1$-$C_6$)alkyl, wherein the ($C_1$-$C_6$)alkyl, ($C_3$-$C_8$)cycloalkyl, and ($C_3$-$C_8$)cycloalkyl($C_1$-$C_6$)alkyl are optionally substituted with 1, 2, 3, or 4 substituents that are independently ($C_1$-$C_6$)alkoxy, ($C_1$-$C_6$)alkoxy($C_1$-$C_6$)alkyl, ($C_1$-$C_6$)alkoxycarbonyl, ($C_1$-$C_6$)alkylthio, halogen, hydroxy, hydroxycarbonyl, $NZ_1Z_2$, or phenyl, wherein the phenyl is optionally substituted with 1, 2, 3, 4, or 5 halogens;
$R_4$ and $R_5$ are independently H, ($C_1$-$C_6$)alkyl, ($C_3$-$C_8$)cycloalkyl, or ($C_3$-$C_8$)cycloalkyl($C_1$-$C_6$)alkyl, wherein the ($C_1$-$C_6$)alkyl, ($C_3$-$C_8$)cycloalkyl, and ($C_3$-$C_8$)cycloalkyl($C_1$-$C_6$) alkyl are optionally substituted with 1, 2, 3, or 4 substituents that are independently ($C_1$-$C_6$)alkoxy, ($C_1$-$C_6$)alkoxy($C_1$-$C_6$) alkyl, ($C_1$-$C_6$)alkoxycarbonyl, ($C_1$-$C_6$)alkylthio, halogen, hydroxy, hydroxycarbonyl, $NZ_1Z_2$, or phenyl, wherein the phenyl is optionally substituted with 1, 2, 3, 4, or 5 halogens; or $R_4$ and $R_5$ together with the nitrogen atom to which they are attached form azetidine, pyrrolidine, piperidine, piperazine, N-methylpiperazine, morpholine, or azepane; and
$Z_1$ and $Z_2$ are independently H or ($C_1$-$C_6$)alkyl.

Representative compounds of Formula (XXI) include, but are not limited to, the compounds shown below, wherein X is absent, Cl, Br, I, $HSO_4$, or $CH_3CO_2$:

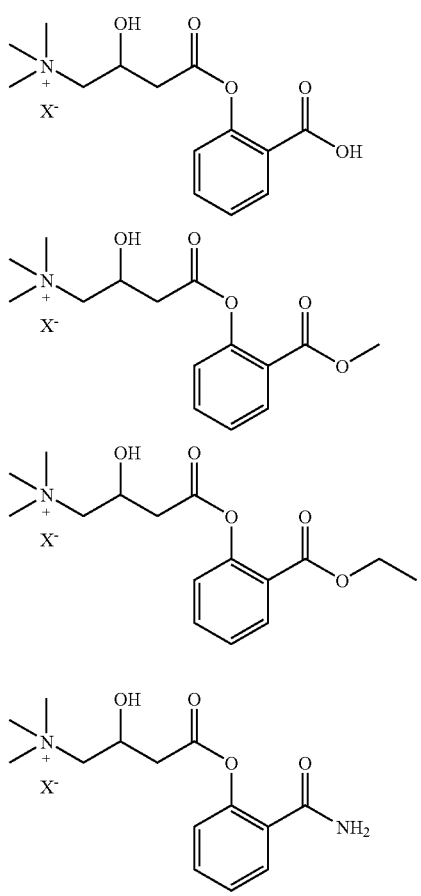

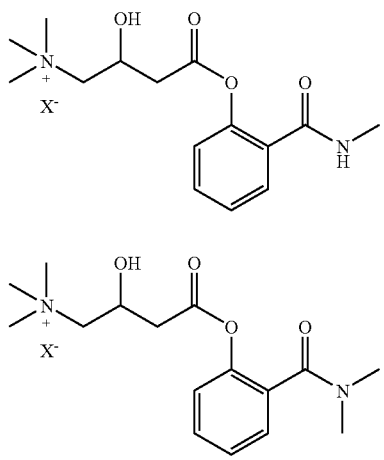

-continued
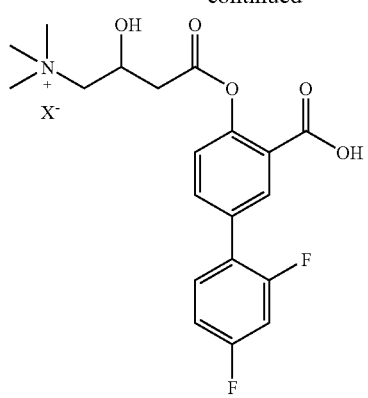
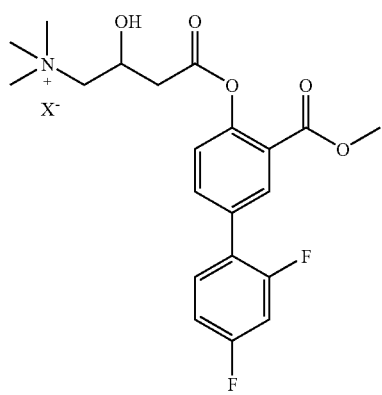
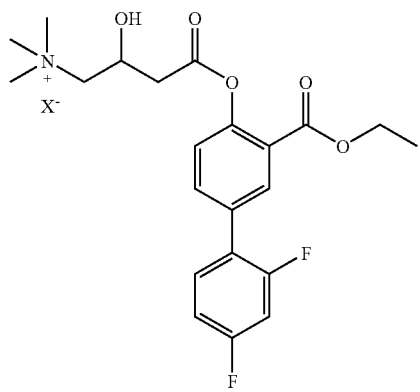
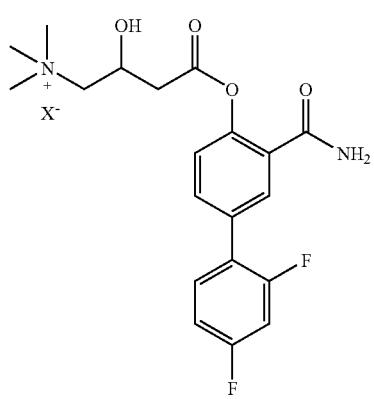
-continued
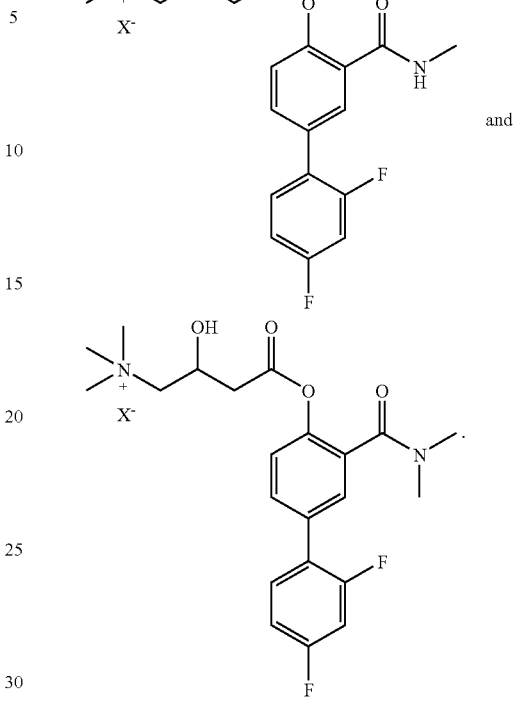
In another aspect, the present invention provides pharmaceutical compositions comprised of a compound of Formula (XXI), as shown above, and at least one pharmaceutically acceptable carrier.
In another aspect, the present invention provides conjugates of Formula (XXII)
(XXII)
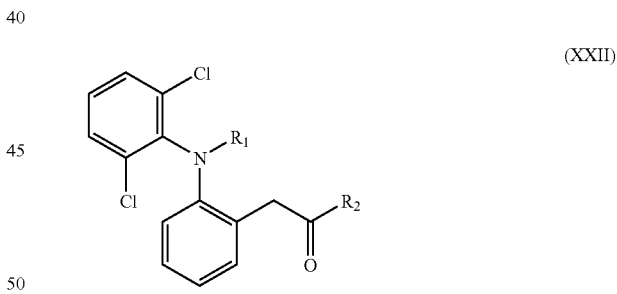
wherein $R_1$ is
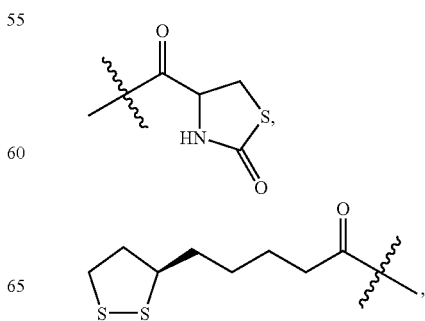

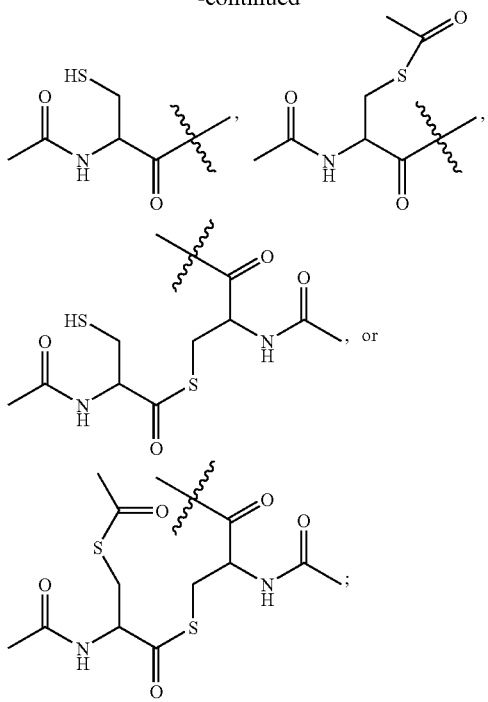
$R_2$ is $(C_1\text{-}C_4)$alkoxy, hydroxy, or $NZ_1Z_2$; and
$Z_1$ and $Z_2$ are independently hydrogen or $(C_1\text{-}C_4)$alkyl;
Representative conjugates of Formula (XXII) include, but are not limited to, the compounds shown below.
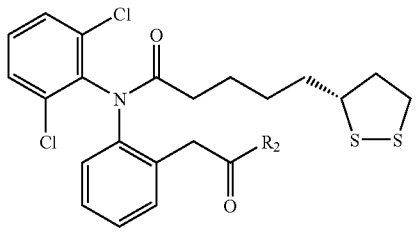
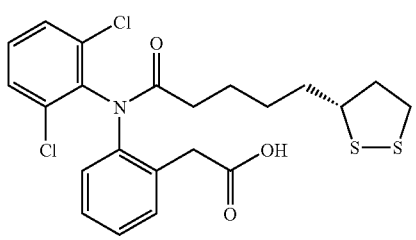
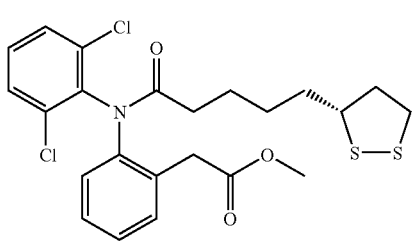
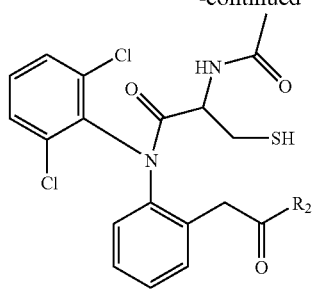
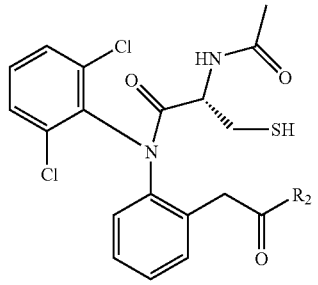
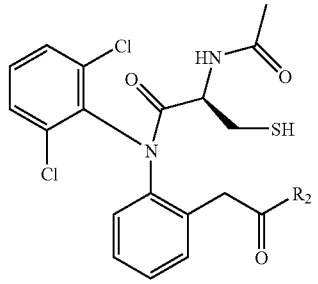
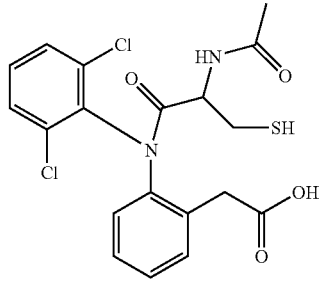
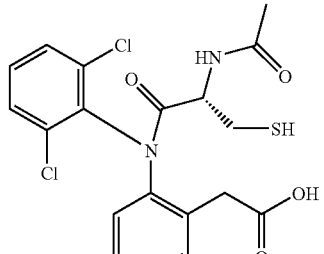
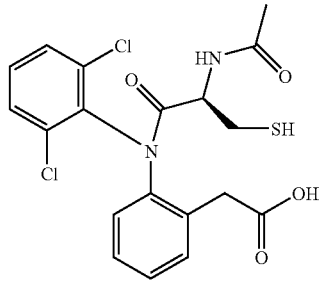

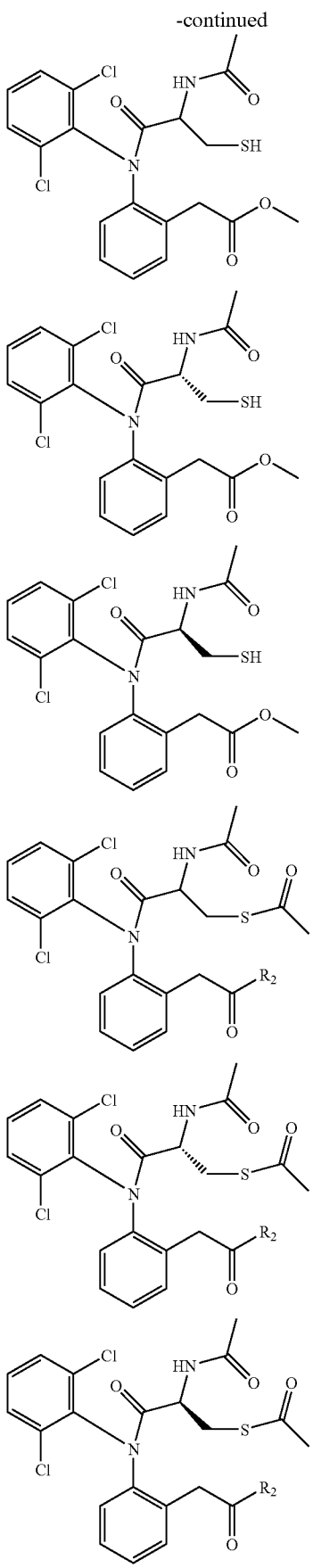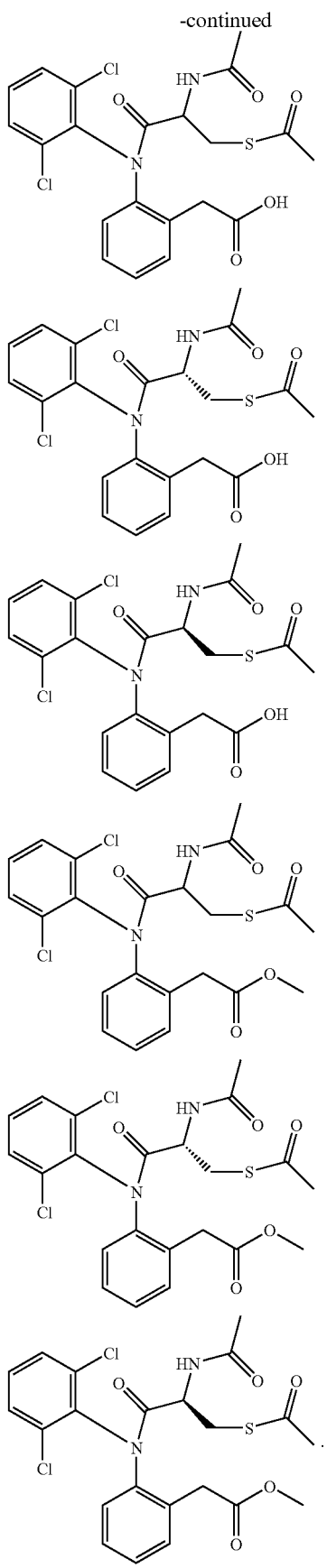

In another aspect, the present invention provides pharmaceutical compositions comprised of a compound of Formula (XXII), as shown above, and at least one pharmaceutically acceptable carrier.

For each of the compounds of Formulae (I-XXII) set forth herein, the invention provides in separate aspects methods for treating atherosclerosis, neuropathy, nephropathy, retinopathy, inflammatory disorders, Chronic Obstructive Pulmonary Disease, cardiovascular diseases, metabolic disorders, type I diabetes mellitus, type II diabetes mellitus, Latent Autoimmune Diabetes of Adulthood, metabolic syndrome, dyslipidemia, hyperglycemia, or insulin resistance in a mammal or human patient comprising administering to the mammal or human patient in need of such treatment a therapeutically effective amount of a compound of Formulae (I-XXII), as shown above, or a pharmaceutical composition comprised of a compound of Formulae (I-XXII) and at least one pharmaceutically acceptable carrier.

For each of the compounds of Formulae (I-XXII) set forth herein, the invention provides in separate aspects methods for treating type II diabetes mellitus, metabolic syndrome, dyslipidemia, or insulin resistance in a mammal or human patient comprising administering to the mammal or human patient in need of such treatment a therapeutically effective amount of a compound of Formulae (I-XXII), as shown above, or a pharmaceutical composition comprised of a compound of Formulae (I-XXII) and at least one pharmaceutically acceptable carrier.

For each of the compounds of Formulae (I-XXII) set forth herein, the invention provides in separate aspects provides methods for reducing free fatty acids, triglycerides, advanced glycated end products, ROS, lipid peroxidation, tissue and plasma TNFa and IL6 levels, or for delaying or preventing cardiovascular complications associated with atherosclerosis in a mammal or human patient comprising administering to the mammal or human patient in need of such treatment a therapeutically effective amount of a compound of Formulae (I-XXII), as shown above, or a pharmaceutical composition comprised of a compound of Formulae (I-XXII) and at least one pharmaceutically acceptable carrier.

For each of the compounds of Formulae (I-XXII) set forth herein, the invention provides in separate aspects provides provides methods for protecting pancreatic beta-cells, preventing their impairment or failure and subsequent lower insulin secretion, in a mammal or human patient comprising administering to the mammal or human patient in need of such treatment a therapeutically effective amount of a compound of Formulae (I-XXII), as shown above, or a pharmaceutical composition comprised of a compound of Formulae (I-XXII) and at least one pharmaceutically acceptable carrier.

For each of the compounds of Formulae (I-XXII) set forth herein, the invention provides in separate aspects provides provides uses for compounds of Formulae (I-XXII), or pharmaceutical compositions comprised of a compound of Formulae (I-XXII) and at least one pharmaceutically acceptable carrier, for preparing, or for the manufacture of, a medicament for treating atherosclerosis, neuropathy, nephropathy, retinopathy, inflammatory disorders, COPD, cardiovascular diseases, metabolic disorders, type I diabetes mellitus, type II diabetes mellitus, LADA, metabolic syndrome, dyslipidemia, hyperglycemia, or insulin resistance in a mammal or human patient. The present invention also provides uses for compounds of Formulae (I-XXII), or pharmaceutical compositions comprised of a compound of Formulae (I-XXII) and at least one pharmaceutically acceptable carrier, for preparing, or for the manufacture of, a medicament for reducing free fatty acids, triglycerides, advanced glycated end products, ROS, lipid peroxidation, tissue and plasma TNFa and IL6 levels, or for delaying or preventing cardiovascular complications associated with atherosclerosis in a mammal or human patient. The present invention also provides uses for compounds of Formulae (I-XXII), or pharmaceutical compositions comprised of a compound of Formulae (I-XXII) and at least one pharmaceutically acceptable carrier, for preparing, or for the manufacture of, a medicament for protecting pancreatic b-cells, preventing their impairment or failure and subsequent lower insulin secretion, in a mammal or human patient.

In another aspect, the present invention provides methods for treating adipocyte dysfunction related diseases, carbohydrate metabolism related diseases, vascular diseases, neurodegenerative diseases, cancers, arthritis, osteoarthritis, spondylitis, bone resorption diseases, sepsis, septic shock, chronic pulmonary inflammatory disease, fever, periodontal diseases, ulcerative colitis, pyresis, Alzheimer's disease, Parkinson's diseases, cystic fibrosis, dysfunctions of the immune system, stroke, multiple sclerosis, migraine, pain, inflammatory eye conditions including uveitis, glaucoma and conjunctivitis, degenerative bone or joint conditions including osteoarthritis, rheumatoid arthritis, rheumatoid spondylitis, gouty arthritis ankylosing spondylitis, psoriatic arthritis and other arthritic conditions, as well as inflamed joints, chronic inflammatory skin conditions, including allergic lesions, lichen planus, pityriasis rosea, eczema, psoriasis, and dermatitis, diseases and disorders of the gastrointestinal tract, including inflammatory bowel disease, Crohn's disease, atrophic gastritis, gastritis varialoforme, ulcerative colitis, coeliac disease, regional ileitis, peptic ulceration, particularly irritable bowel syndrome, reflux oesophagitis, and damage to the gastrointestinal tract resulting from infections, for example, by *Helicobacter pylori*, inflammatory lung disorders such as asthma, bronchitis, particularly chronic obstructive pulmonary disease, farmer's lung, acute respiratory distress syndrome; bacteraemia, endotoxaemia (septic shock), aphthous ulcers, gingivitis, pyresis, particularly pain, including inflammatory pain, neuropathic pain, acute pain or pain of a central origin; meningitis and pancreatitis, and other conditions associated with inflammation, central nervous system inflammatory conditions and diseases, including ischaemia-reperfusion injury associated with ischemic stroke; vascular diseases, such as atheromatous and nonatheromatous, ischemic heart disease, and Raynaud's Disease and Phenomenon in a mammal or patient comprising administering to the mammal or patient in need of such treatment a therapeutically effective amount of a conjugate of Formulae (I-XXII), or a pharmaceutically acceptable salt thereof In certain embodiments, the present invention provides uses for conjugates of Formula (I-XXII) for preparing, or for the manufacture of, a medicament for treating the diseases/disorders listed above.

In another aspect, the present invention provides methods for treating adipocyte dysfunction related diseases, carbohydrate metabolism related diseases, vascular diseases, neurodegenerative diseases, cancers, arthritis, osteoarthritis, spondylitis, bone resorption diseases, sepsis, septic shock, chronic pulmonary inflammatory disease, fever, periodontal diseases, ulcerative colitis, pyresis, Alzheimer's disease, Parkinson's diseases, cystic fibrosis, dysfunctions of the immune system, stroke, multiple sclerosis, migraine, pain, inflammatory eye conditions including uveitis, glaucoma and conjunctivitis, degenerative bone or joint conditions including osteoarthritis, rheumatoid arthritis, rheumatoid spondylitis, gouty arthritis ankylosing spondylitis, psoriatic arthritis and other arthritic conditions, as well as inflamed joints, chronic inflammatory skin conditions, including allergic lesions, lichen planus, pityriasis rosea, eczema, psoriasis, and dermatitis, diseases and disorders of the gastrointestinal tract, including inflammatory bowel disease, Crohn's disease, atrophic gastritis, gastritis varialoforme, ulcerative colitis, coeliac disease, regional ileitis, peptic ulceration, particularly irritable bowel syndrome, reflux oesophagitis, and damage to the gastrointestinal tract resulting from infections, for example, by *Helicobacter pylori* inflammatory lung disorders such as asthma, bronchitis, particularly chronic obstructive pulmonary disease, farmer's lung, acute respiratory distress syndrome; bacteraemia, endotoxaemia (septic shock), aphthous ulcers, gingivitis, pyresis, particularly pain, including inflammatory pain, neuropathic pain, acute pain or pain of a central origin; meningitis and pancreatitis, and other conditions associated with inflammation, central nervous system inflammatory conditions and diseases, including ischaemia-reperfusion injury associated with ischemic stroke; vascular diseases, such as atheromatous and nonatheromatous, ischemic heart disease, and Raynaud's Disease and Phenomenon in in a patient comprising administering to the patient in need of such treatment a therapeutically effective amount of a pharmaceutical composition comprising at least one pharmaceutically acceptable carrier and a conjugate of Formula (I-XXII), or a pharmaceutically acceptable salt thereof In certain embodiments, the present invention provides uses for pharmaceutical compositions for preparing, or for the manufacture of, a medicament for treating the diseases/disorders listed above, wherein the pharmaceutical composition comprises at least one pharmaceutically acceptable carrier and a m conjugate of Formula (I-XXII), or a pharmaceutically acceptable salt thereof

DEFINITIONS

As used throughout this specification and the appended claims, the following terms have the following meanings:

The term "$(C_1-C_6)$alkoxy" as used herein, means a $(C_1-C_6)$ alkyl group, as defined herein, appended to the parent molecular moiety through an oxygen atom. Representative examples of $(C_1-C_6)$alkoxy include, but are not limited to, methoxy, ethoxy, propoxy, 2-propoxy, butoxy, tert-butoxy, pentyloxy, and hexyloxy.

The term "$(C_1-C_6)$alkoxycarbonyl" as used herein, means a $(C_1-C_6)$alkoxy group, as defined herein, appended to the parent molecular moiety through a carbonyl group, as defined herein. Representative examples of $(C_1-C_6)$alkoxycarbonyl include, but are not limited to, methoxycarbonyl, ethoxycarbonyl, and tert-butoxycarbonyl.

The term "$(C_1-C_6)$alkoxysulfonyl" as used herein, means a $(C_1-C_6)$alkoxy group, as defined herein, appended appended to the parent molecular moiety through a sulfonyl group, as defined herein. Representative examples of $(C_1-C_6)$alkoxysulfonyl include, but are not limited to, methoxysulfonyl, ethoxysulfonyl and propoxysulfonyl.

The term "$(C_1-C_6)$alkyl" as used herein, means a straight or branched chain hydrocarbon containing from 1 to 6 carbon atoms. Representative examples of $(C_1-C_6)$alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, and hexyl.

The term "$(C_1-C_6)$alkylcarbonyl" as used herein, means a $(C_1-C_6)$alkyl group, as defined herein, appended to the parent molecular moiety through a carbonyl group, as defined herein. Representative examples of $(C_1-C_6)$alkylcarbonyl include, but are not limited to, acetyl, 1-oxopropyl, 2,2-dimethyl-1-oxopropyl, 1-oxobutyl, and 1-oxopentyl.

The term "$(C_1-C_6)$alkylcarbonyloxy" as used herein, means a $(C_1-C_6)$alkylcarbonyl group, as defined herein, appended to the parent molecular moiety through an oxygen atom. Representative examples of $(C_1-C_6)$alkylcarbonyloxy include, but are not limited to, acetyloxy, ethylcarbonyloxy, and tert-butylcarbonyloxy.

The term "$(C_1-C_6)$alkylene" means a divalent group derived from a straight or branched chain hydrocarbon of from 1 to 6 carbon atoms. Representative examples of $(C_1-C_6)$alkylene include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, —CH$_2$CH(CH$_3$)CH$_2$—, and —CH$_2$CH$_2$CH$_2$CH$_2$CH$_2$—.

The term "$(C_1-C_6)$alkylsulfonyl" as used herein, means an $(C_1-C_6)$alkyl group, as defined herein, appended to the parent molecular moiety through a sulfonyl group, as defined herein. Representative examples of $(C_1-C_6)$alkylsulfonyl include, but are not limited to, methylsulfonyl and ethylsulfonyl.

The term "$(C_1-C_6)$alkylthio" as used herein, means a $(C_1-C_6)$alkyl group, as defined herein, appended to the parent molecular moiety through a sulfur atom. Representative examples of $(C_1-C_6)$alkylthio include, but are not limited, methylthio, ethylthio, tert-butylthio, and hexylthio.

The term "carbonyl" as used herein, means a —C(O)— group.

The term "carboxy" as used herein, means a —CO$_2$H group.

The term "cyano" as used herein, means a —CN group.

The term "formyl" as used herein, means a —C(O)H group.

The term "halo" or "halogen" as used herein, means —Cl, —Br, —I or —F.

The term "halo$(C_1-C_6)$alkoxy" as used herein, means at least one halogen, as defined herein, appended to the parent molecular moiety through a $(C_1-C_6)$alkoxy group, as defined herein. Representative examples of halo$(C_1-C_6)$alkoxy include, but are not limited to, chloromethoxy, 2-fluoroethoxy, trifluoromethoxy, and pentafluoroethoxy.

The term "halo$(C_1-C_6)$alkyl" as used herein, means at least one halogen, as defined herein, appended to the parent molecular moiety through a $(C_1-C_6)$alkyl group, as defined herein. Representative examples of halo$(C_1-C_6)$alkyl include, but are not limited to, chloromethyl, 2-fluoroethyl, trifluoromethyl, pentafluoroethyl, and 2-chloro-3-fluoropentyl.

The term "HTB" as used herein means 2-hydroxy-4-(trifluoromethyl)benzoic acid, a metabolite of triflusal. Conjugates comprised of HTB and one or more antioxidants are specifically contemplated by the present invention.

The term "hydroxy" as used herein, means an —OH group.

The term "hydroxy$(C_1-C_6)$alkyl" as used herein, means at least one hydroxy group, as defined herein, is appended to the parent molecular moiety through a $(C_1-C_6)$alkyl group, as defined herein. Representative examples of hydroxy$(C_1-C_6)$ alkyl include, but are not limited to, hydroxymethyl, 2-hydroxyethyl, 3-hydroxypropyl, and 2,3-dihydroxypentyl.

The term "mercapto" as used herein, means a —SH group.

The term "nitro" as used herein, means a —NO$_2$ group.

The term "sulfonyl" as used herein, means a —SO$_2$— group.

Compounds of the present invention include α-amino acids, or derivatives thereof such as esters or amides, that can exist as stereoisomers, wherein the asymmetric or chiral center is present at the α-carbon. The chiral center is designated (L) or (D) based on the Fischer projections of (L) or (D) aldose. Ernest L. Eliel and Samuel H. Wilen, *Stereochemistry of Organic Compounds*, John Wiley & Sons, Inc., New York, page 112, 1994. Further, compounds of the present invention may contain a stereocenter that is not an α-carbon of an α-amino acid (or derivative thereof). This center is designated (R) or (S), depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13-30. Individual stereoisomers of compounds of the present invention may be prepared synthetically from commercially available starting materials which contain asymmetric or chiral centers or by preparation of racemic mixtures followed by resolution, a technique well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) direct separation of the mixture of optical enantiomers on chiral chromatographic columns, or (3) formation of a diastereomeric salt followed by selective recrystallization of one of the diastereomeric salts.

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The term "pharmaceutically acceptable carrier" as used herein means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The present invention provides pharmaceutical compositions which comprise compounds of the present invention formulated together with one or more non-toxic pharmaceutically acceptable carriers. The pharmaceutical compositions can be formulated for oral administration in solid or liquid form, for parenteral injection or for rectal administration.

The pharmaceutical compositions of this invention can be administered to humans (patients) and other mammals orally, rectally, parenterally, intracisternally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous, intraarticular injection and infusion.

Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the present invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

The active compounds can also be in micro-encapsulated form, if appropriate, with one or more pharmaceutically acceptable carriers as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of such composition that they release the active ingredient(s) only, or preferentially, in a certain part of the intestinal tract in a delayed manner. Examples of embedding compositions which can be used include polymeric substances and waxes.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, free fatty acids such as oleic acid are used in the preparation of injectables.

Solid dosage forms for oral administration include capsules, tablets, pills, powders, and granules. In such solid dosage forms, the active compound is mixed with at least one inert pharmaceutically acceptable carrier such as sodium citrate or calcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions which can be used include polymeric substances and waxes.

Compositions for rectal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and free fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

The phrase "therapeutically effective amount" of the compound of the present invention means a sufficient amount of the compound to treat metabolic disorders, at a reasonable benefit/risk ratio applicable to any medical treatment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Actual dosage levels of active ingredients in the pharmaceutical compositions of this invention can be varied so as to obtain an amount of the active compound(s) which is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated.

The total daily dose of the compounds of this invention administered to a mammal, and particularly a human, from about 0.03 to about 20 mg/kg/day. For purposes of oral administration, more preferable doses can be in the range of from about 0.1 to about 10 mg/kg/day. If desired, the effective daily dose can be divided into multiple doses for purposes of administration, e.g. two to four separate doses per day.

The term "pharmaceutically acceptable salt," as used herein, means a positively-charged inorganic or organic cation that is generally considered suitable for human consumption. Examples of pharmaceutically acceptable cations are alkali metals (lithium, sodium and potassium), magnesium, calcium, ferrous, ferric, ammonium, alkylammonium, dialkylammonium, trialkylammonium, tetraalkylammonium, diethanolammmonium, and choline. Cations may be interchanged by methods known in the art, such as ion exchange. Where compounds of the present invention are prepared in the carboxylic acid form, addition of a base (such as a hydroxide or a free amine such as an alpha amino acid) will yield the appropriate salt form, (L) lysine is a preferred free amine for preparing salts of the present invention.

The present invention contemplates pharmaceutically active metabolites formed by in vivo biotransformation of conjugates of Formula (I). The term pharmaceutically active metabolite, as used herein, means a compound formed by the in vivo biotransformation of conjugates of Formula (I). The present invention contemplates conjugates of Formula (I) and metabolites thereof. A thorough discussion of biotransformation is provided in (Goodman and Gilman's, The Pharmacological Basis of Therapeutics, seventh edition).

All patents, patent applications, and literature references cited in the specification are herein incorporated by reference in their entirety for any purpose.

The following Schemes and Examples are provided for the purposes of illustration and are not intended to limit the scope of the present invention. The invention is not limited in scope by the exemplified embodiments, which are intended as illustrations of individual aspects of the invention. Various modifications of the invention in addition to those shown and described herein will become apparent to those skilled in the art from the foregoing description and accompanying drawings. Such modifications are intended to fall within the scope of the appended claims.

Preparation of Compounds of the Invention

Scheme 1

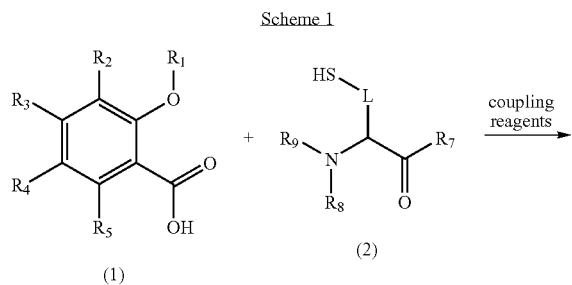

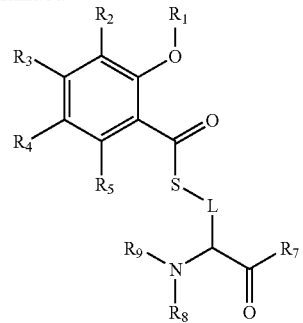

Formula (I)

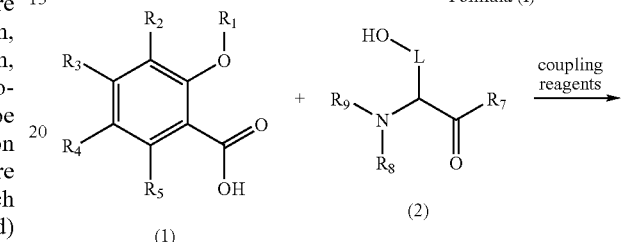

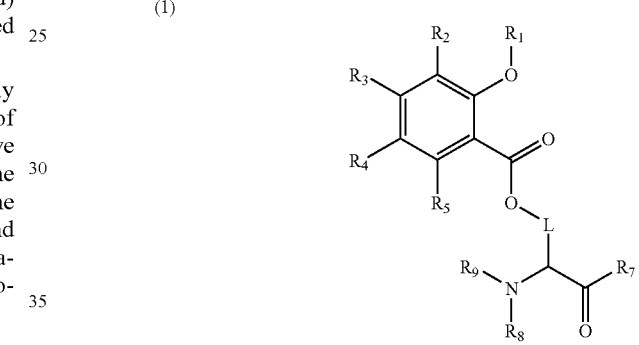

Formula (I)

Conjugates of Formula (I), wherein $R_1$, $R_2$, $R_3$, $R_4$, $R_5$, $R_7$, $R_8$, $R_9$, and L are as defined in the Summary section herein, are prepared as described EP 0 080 229, BE 900328, or Scheme 1. Acids of formula (1) are treated with an alcohol or mercaptan of formula (2) in an appropriate solvent optionally with heating and optionally with one or more coupling reagents to provide conjugates of Formula (I). Coupling reagents useful for preparing compounds of the present invention include, but are not limited to, dimethylaminopyridine (DMAP), 1,3-di-tert-butylcarbodiimide, 1,1'-carbonyldiimidazole (CDI), 1,1'-thiocarbonyldiimidazole, 1,1'-carbonylbis(2-methylimidazole), 1-(3-dimethylaminopropyl)-3-ethylcarbodiimide hydrochloride (EDCI), benzotriazol-1-yloxy-tris-pyrrolidino-phosphoniumhexafluorophosphate (PyBOP), bromo-tris-pyrrolidino-phosphonium hexafluorophosphate (PyBrop), O-(-7-azabenzotriazol-1-yl)-N,N,N',N',-tetramethyluronium hexafluorophosphate, N-[(dimethylamino)(3H-[1,2,3]triazolo[4,5-b]pyridin-3-yloxy) methylene]-N-methylmethanaminium, benzotriazol-1-yloxytris(dimethylamino)phosphonium hexafluorophosphate (BOP), Bis(2-oxo-3-oxazolidinyl) phosphinic chloride (BOPCl), 1,3-dicyclohexylcarbodiimide (DCC), 1-Hydroxy-7-azabenzotriazole (HOAT), 1-hydroxybenzotriazole hydrate (HOBT), 3-hydroxy-1,2,3-benzotriazin-4(3H)-one (HOOBT), O-(7-azabenzotriazol-1-yl)-N,N,N',N'-tetramethyluronium hexafluorophosphate (HATU), O-benzotriazol-1-yl-N,N,N',N'-tetramethyluronium hexafluorophosphate (HBTU), and O-benzotriazol-1-yl-N,N',N'-tetramethyluronium tetrafluoroborate (TBTU).

Scheme 2

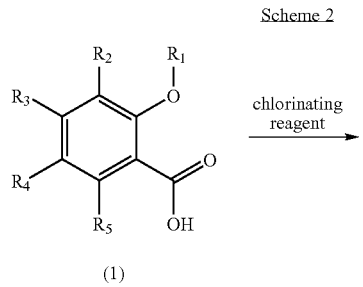

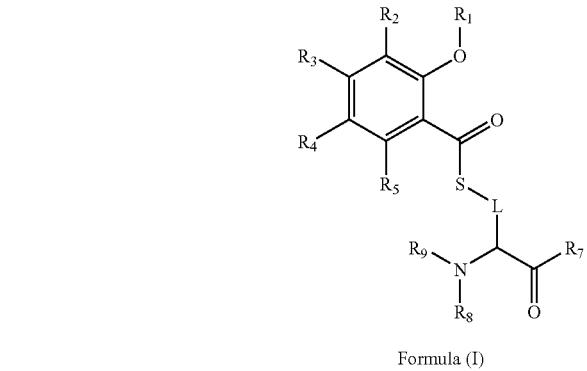

-continued

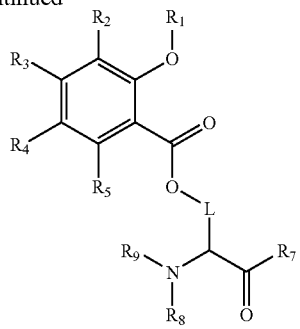

Formula (I)

Alternatively, conjugates of Formula (I), wherein $R_1$, $R_2$, $R_3$, $R_4$, $R_5$, $R_7$, $R_8$, $R_9$, and L are as defined in Formula (I) of the Summary section herein, are prepared as described in Scheme 2. Acids of formula (1) are treated with a chlorinating reagent such as thionyl chloride (or $PCl_3$) in an appropriate solvent to provide acid chlorides of formula (3). Conjugates of Formula (3) are treated with a base such as triethylamine (or diisopropylethylamine) and an alcohol or thiol of formula (2) in an appropriate solvent, optionally with heating, to provide conjugates of Formula (I).

Scheme 3

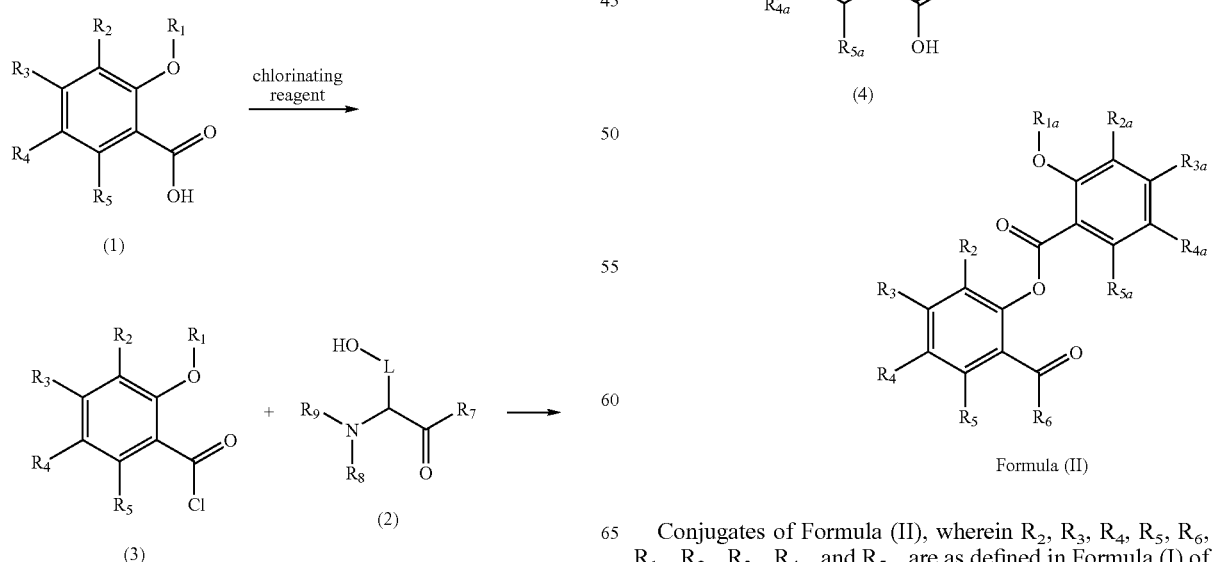

Conjugates of Formula (II), wherein $R_2$, $R_3$, $R_4$, $R_5$, $R_6$, $R_{1a}$, $R_{2a}$, $R_{3a}$, $R_{4a}$, and $R_{5a}$, are as defined in Formula (I) of the Summary section herein, are prepared as described in Scheme 3. Conjugates of Formula (I) are treated with a benzoic acid of formula (4) in the presence of one or more coupling reagents, as disclosed in Scheme 1, in an appropriate solvent to provide conjugates of Formula (II). Alternatively, a conjugate of Formula (4) can be treated with a chlorinating agent (see Scheme 2) and a base including, but not limited to triethylamine or diisopropylethylamine, to provide the corresponding acid chloride. The acid chloride is treated with a conjugate of Formula (I) in an appropriate solvent, optionally with heating, to provide conjugates of Formula (II).

vide the corresponding acid chloride. The acid chloride is treated with a conjugate of Formula (II) in an appropriate solvent, optionally with heating, to provide conjugates of Formula (III).

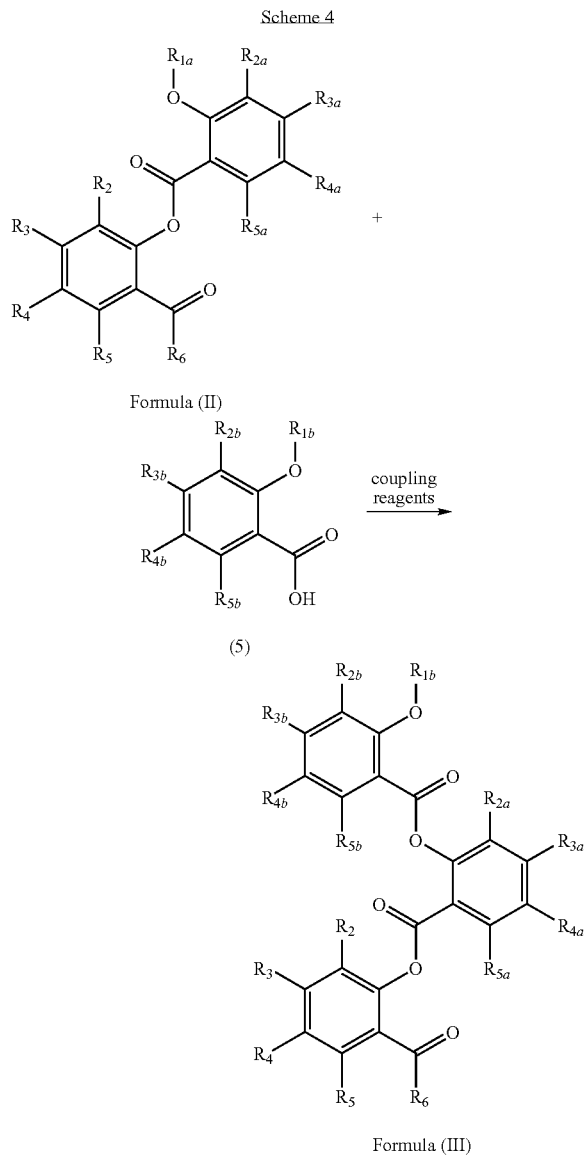

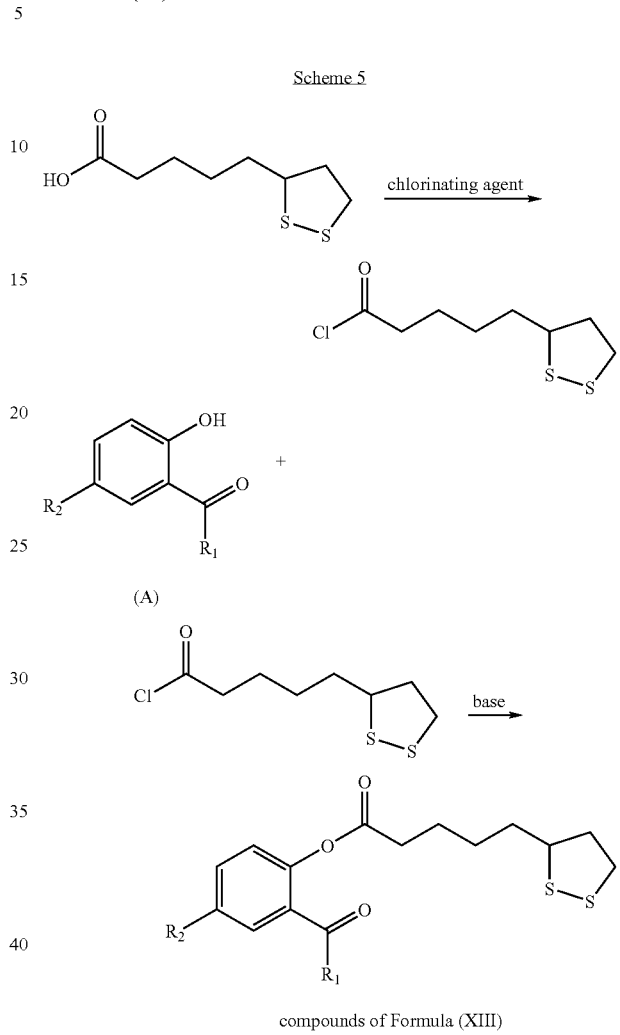

Compounds of Formula (XIII), wherein $R_2$ is H or 2,4-difluorophenyl and $R_1$ is as defined herein, are prepared as described in Scheme 5. Lipoic acid is treated with a chlorinating agent (such as thionyl chloride or $POCl_3$ or $PCl_3$) to provide the corresponding acid chloride. Phenols of formula (A) are treated with the acid chloride of lipoic acid in the presence of base, such as triethylamine or diisopropylethylamine, to provide compounds of Formula (XIII).

Conjugates of Formula (III), wherein $R_2$, $R_3$, $R_4$, $R_5$, $R_6$, $R_{2a}$, $R_{3a}$, $R_{4a}$, $R_{5a}$, $R_{1b}$, $R_{2b}$, $R_{3b}$, $R_{4b}$, and $R_{5b}$ are as defined in Formula (I) of the Summary section herein, are prepared as described in Scheme 4. Conjugates of Formula (II) are treated with a benzoic acid of formula (5) in the presence of one or more coupling reagents, as disclosed in Scheme 1, in an appropriate solvent to provide conjugates of Formula (III). Alternatively, a conjugate of Formula (5) can be treated with a chlorinating agent (see Scheme 2) and a base including, but not limited to triethylamine or diisopropylethylamine, to pro-

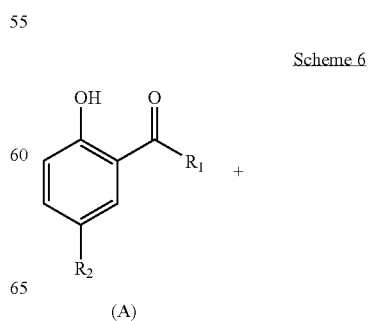

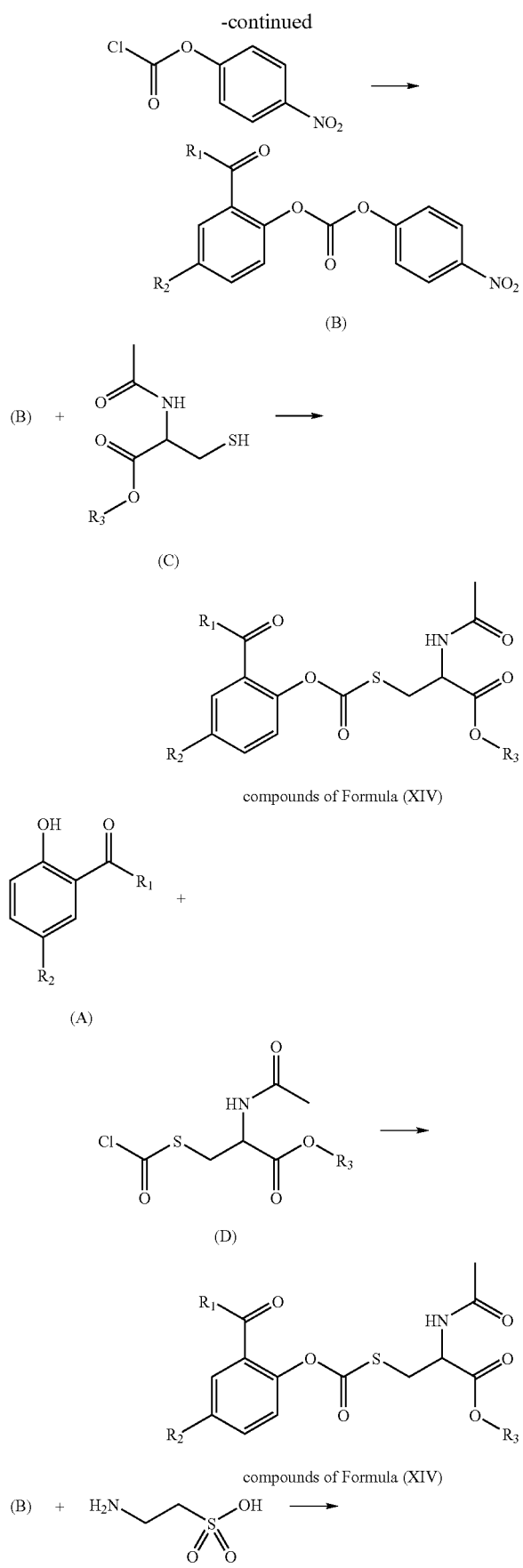

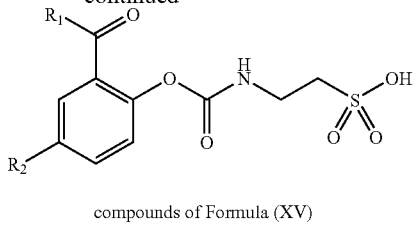

compounds of Formula (XV)

Compounds of Formula (XIV) and (XV), wherein $R_2$ is H or 2,4-difluorophenyl and $R_1$ and $R_3$ are as defined herein, are prepared as described in Scheme 6. Compounds of Formula (II) are prepared by treating phenols of formula (A) with 4-nitrophenyl carbonochloridate to provide carbonates of formula (B). Carbonates of formula (B) are treated with derivatives of N-acetylcysteine (compounds of formula (C)) to provide compounds of Formula (XIV). *Bioorganic Med. Chem.,* 13 (19) pg 5592 (2005). Alternatively, acyl chlorides of formula (D), prepared using similar methodology as disclosed in *Bull. Chem. Soc. Japan,* 37 (2) pgs 242-244, (1964), are treated with phenols of formula (A) to provide compounds of Formula (XIV). Compounds of Formula (XV) are prepared by treating taurine with carbonates of formula (B).

Scheme 7

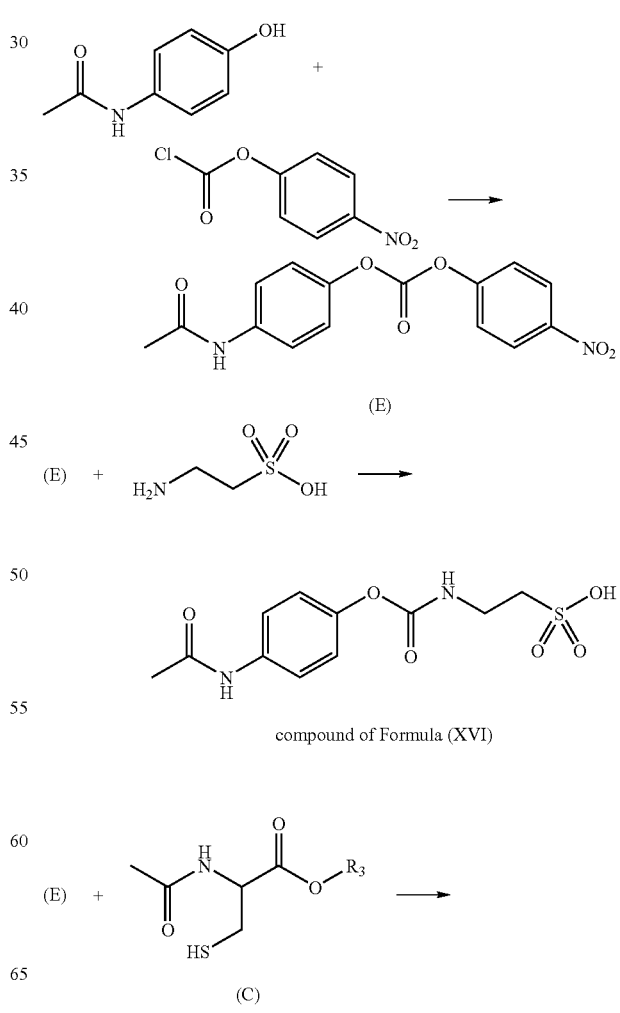

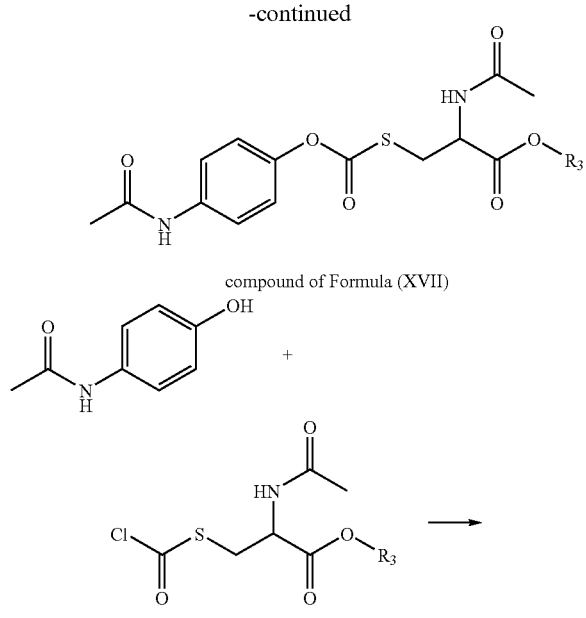

compound of Formula (XVII)

(D)

compound of Formula (XVII)

The compound of Formula (XVI) and compounds Formula (XVII) are prepared as described in Scheme 7. The compound of Formula (XVI) are prepared by treating 4-nitrophenyl carbonochloridate with acetaminophen (paracetamol) to provide the compound of formula (E). The compound of formula (E) is treated with taurine to provide the compound of Formula (XVI). *Bioorganic Med. Chem.*, 13 (19) pg 5592 (2005).

Compounds of Formula (XVII), wherein $R_3$ is as defined herein, are prepared by treating 4-nitrophenyl carbonochloridate (compound of formula (E)) with a compound of formula (C) to provide compounds of Formula (XVII). Alternatively, acyl chlorides of formula (D), prepared in a similar manner as disclosed in *Bull. Chem. Soc. Japan*, 37 (2) pgs 242-244, (1964), are treated with acetaminophen to provide compounds of Formula (XVII).

Scheme 8

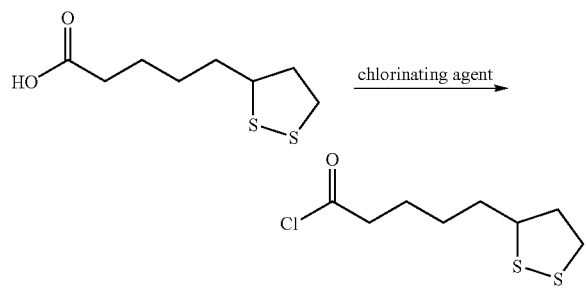

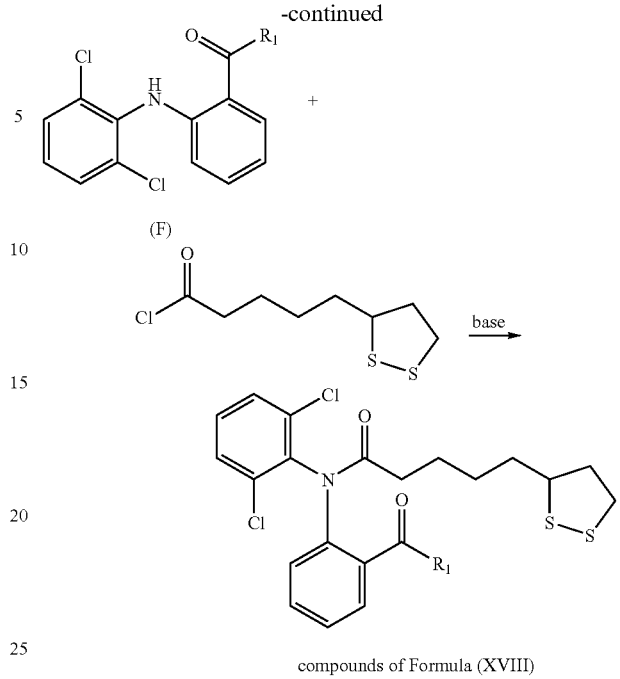

(F)

compounds of Formula (XVIII)

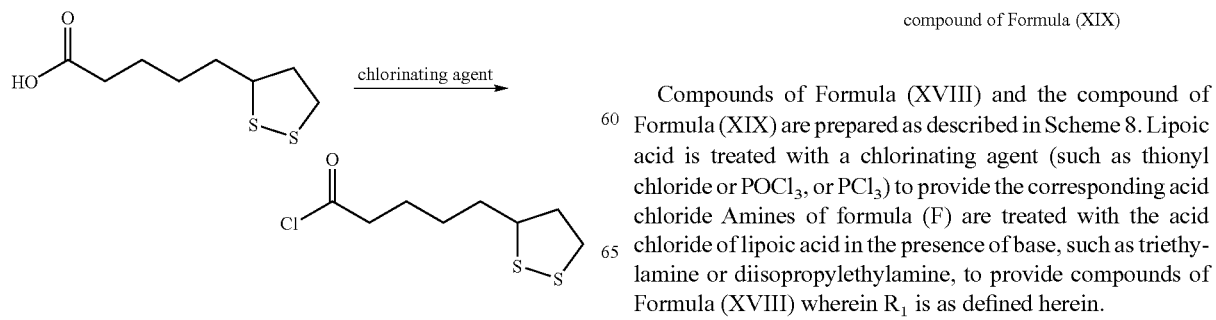

compound of Formula (XIX)

Compounds of Formula (XVIII) and the compound of Formula (XIX) are prepared as described in Scheme 8. Lipoic acid is treated with a chlorinating agent (such as thionyl chloride or $POCl_3$, or $PCl_3$) to provide the corresponding acid chloride Amines of formula (F) are treated with the acid chloride of lipoic acid in the presence of base, such as triethylamine or diisopropylethylamine, to provide compounds of Formula (XVIII) wherein $R_1$ is as defined herein.

The compound of Formula (XIX) is prepared by treating 2-(2,6-dichlorophenylamino)benzoic acid with taurine in the presence of coupling reagents. Coupling reagents useful for preparing the compound of Formula (XIX) include, but are not limited to, dimethylaminopyridine (DMAP), 1,3-di-tert-butylcarbodiimide, 1,1'-carbonyldiimidazole (CDI), 1,1'-thiocarbonyldiimidazole, 1,1'-carbonylbis(2-methylimidazole), 1-(3-dimethylaminopropyl)-3-ethylcarbodiimide hydrochloride (EDCI), benzotriazol-1-yl-oxy-tris-pyrrolidino-phosphoniumhexafluorophosphate (PyBOP), bromo-tris-pyrrolidino-phosphonium hexafluorophosphate (Py-Brop), O-(-7-azabenzotriazol-1-yl)-N,N,N',N'-tetramethyluronium hexafluorophosphate, N-[(dimethylamino)(3H-[1,2,3]triazolo[4,5-b]pyridin-3-yloxy)methylene]-N-methylmethanaminium, benzotriazol-1-yloxytris(dimethylamino)phosphonium hexafluorophosphate (BOP), Bis(2-oxo-3-oxazolidinyl)phosphinic chloride (BOPCl), 1,3-dicyclohexylcarbodiimide (DCC), 1-Hydroxy-7-azabenzotriazole (HOAT), 1-hydroxybenzotriazole hydrate (HOBT), 3-hydroxy-1,2,3-benzotriazin-4(3H)-one (HOOBT), O-(7-azabenzotriazol-1-yl)-N,N,N',N'-tetramethyluronium hexafluorophosphate (HATU), O-benzotriazol-1-yl-N,N,N',N'-tetramethyluronium hexafluorophosphate (HBTU), and O-benzotriazol-1-yl-N,N,N',N'-tetramethyluronium tetrafluoroborate (TBTU). Alternatively, the compound of Formula (XIX) is prepared by treating 2-(2, 6-dichlorophenylamino)benzoyl chloride with taurine.

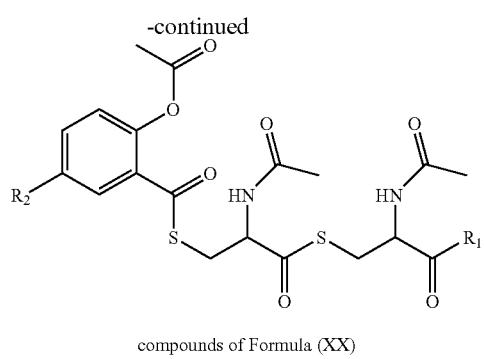

compounds of Formula (XX)

Compounds of Formula (XX), wherein $R_2$ is H or 2,4-difluorophenyl and $R_1$ is as defined herein, are prepared as described in Scheme 9. Acids of formula (G) are treated with a chlorinating reagent such as thionyl chloride (or $PCl_3$) in an appropriate solvent to provide acid chlorides of formula (H). Acid chlorides of formula (H) are treated with compounds of formula (J) and a base such as triethylamine (or diisopropylethylamine) to provide compounds of Formula (XX). Alternatively, the compounds of Formula (XX) are prepared using similar methodology as that described in European patent application no. 88112028.1 (publication no. EP 0 301 474 A2).

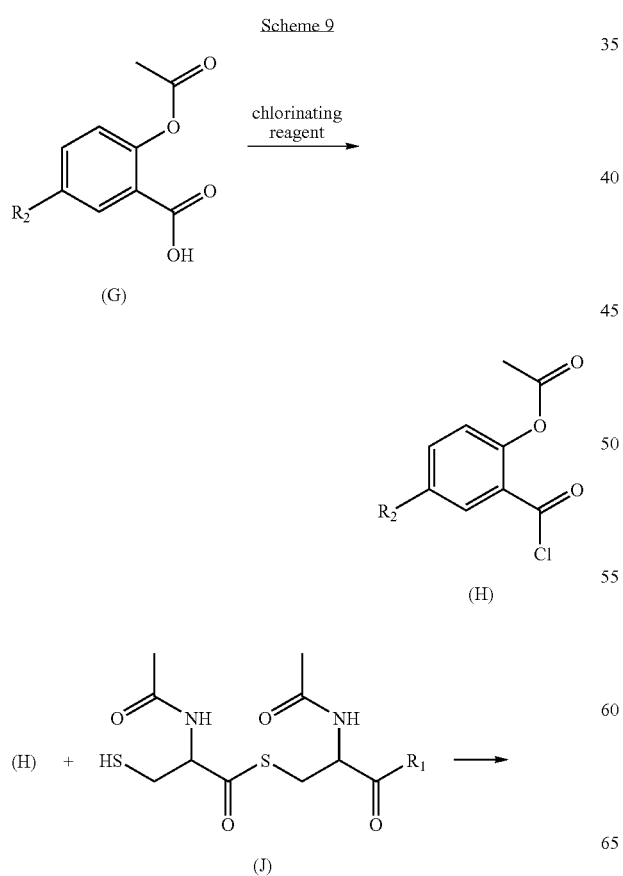

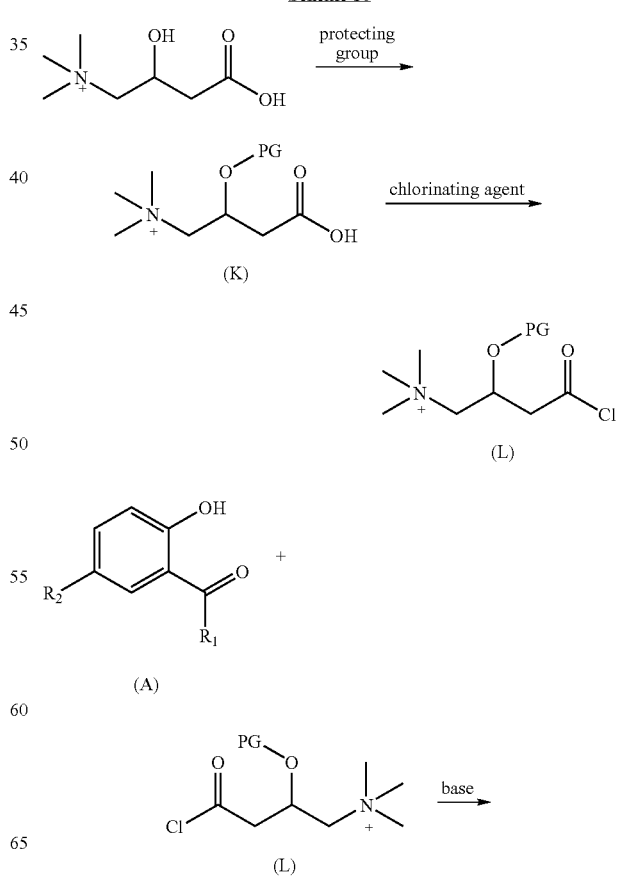

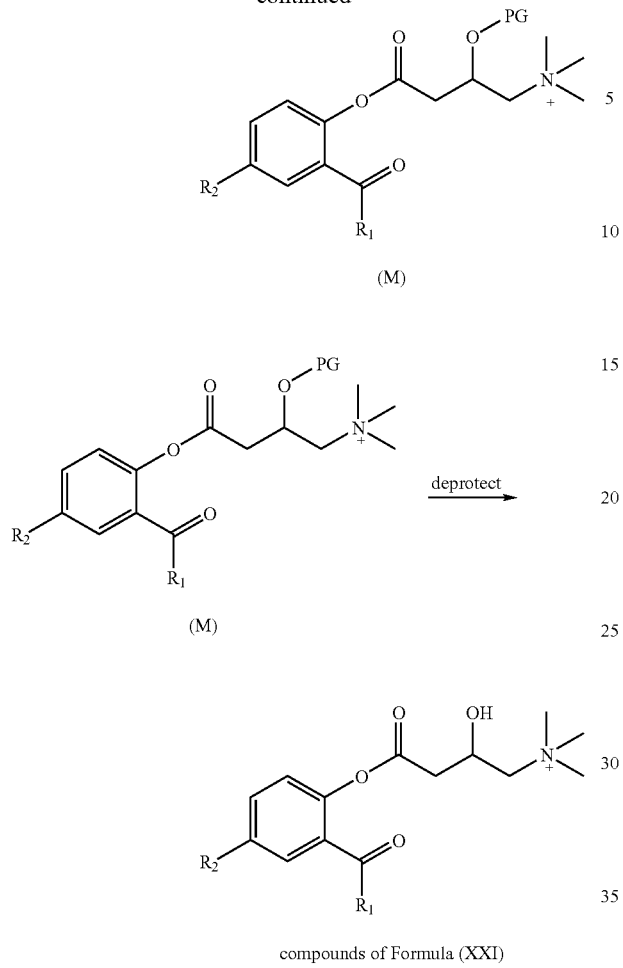

compounds of Formula (XXI)

Compounds of Formula (XXI), wherein $R_2$ is H or 2,4-difluorophenyl and $R_1$ is as defined herein, are prepared as described in Scheme 10. (3-Carboxy-2-hydroxypropyl)trimethyl ammonium is treated with a reagent such as methoxymethyl chloride, (chloromethyl)(methyl)sulfane, tert-butyldimethylsilyl chloride, tert-butyldiphenylsilyl chloride, or benzyl bromide in the presence of a base such as triethylamine, diisopropylethylamine, imidazole, or sodium hydride to provide a compound of formula (K), wherein PG is a hydroxy protecting group. The compound of formula (K) is treated with a chlorinating agent (such as thionyl chloride or $POCl_3$ or $PCl_3$) to provide the corresponding acid chloride of formula (L). Phenols of formula (A) are treated with an acid chloride of formula (L) in the presence of base, such as triethylamine or diisopropylethylamine, to provide compounds of formula (M). The hydroxy protecting group is removed from compounds of formula (M) to provide compounds of Formula (XXI). In particular, the methoxymethyl, methylthiomethyl, tert-butyldimethylsilyl, tert-butyldiphenylsilyl, or benzyl protecting groups are removed by treating compounds of formula (M) with: $Ph_3^+BF_4^-$ in $CH_2Cl_2$; $HgCl_2$ in $CH_3CN$; $Bu_4N^+F^-$ in THF; $Bu_3N^+F^-$ in THF; and $BF_3 \cdot Et_2O$ NaI in $CH_3CN$, respectively.

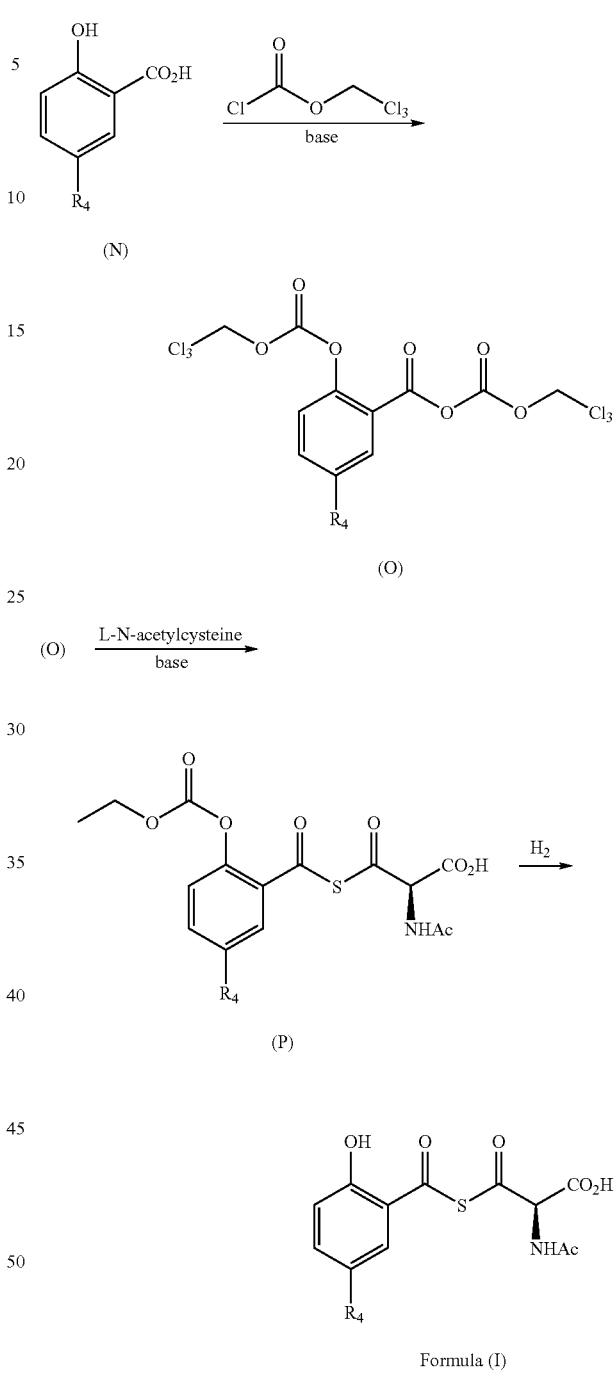

Compounds of Formula (I), wherein $R_4$ is H or 2,4-difluorophenyl, are prepared as described in Scheme 11. A compound of formula (N) is treated with 2,2,2-trichloroethylchlorocarbonate and a base such as triethylamine in acetone at $-3°$ C. to provide the anhydride of formula (O). Compounds of formula (O) are treated with L-N-acetylcysteine and triethylamine dropwise in acetone at $0°$ C. to provide compounds of formula (P). Compounds of formula (P) in glacial acetic acid are treated with Zn (powder) and hydrogen gas to provide compounds of Formula (I).

Example 1

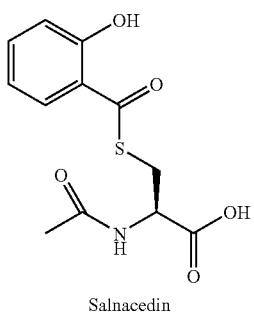 [SMILES: CC(=O)N[C@@H](CSC(=O)c1ccccc1O)C(=O)O]

Salnacedin (R)-2-acetamido-3-(2-hydroxybenzoylthio)propanoic acid

The title compound is prepared using the procedures described in EP 0 080 229.

Example 2

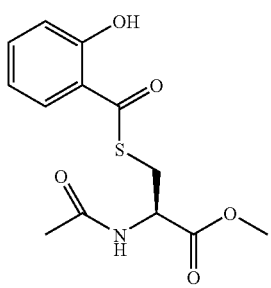 [SMILES: COC(=O)[C@H](CSC(=O)c1ccccc1O)NC(C)=O]

(R)-methyl 2-acetamido-3-(2-hydroxybenzoylthio)propanoate

The title compound is prepared using similar procedures as described in EP 0 080 229.

Example 3

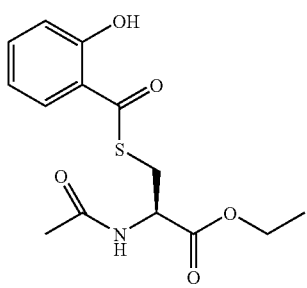 [SMILES: CCOC(=O)[C@H](CSC(=O)c1ccccc1O)NC(C)=O]

(R)-ethyl 2-acetamido-3-(2-hydroxybenzoylthio)propanoate

The title compound is prepared using similar procedures as described in EP 0 080 22929.

Example 4

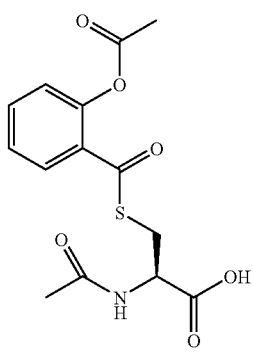 [SMILES: CC(=O)N[C@@H](CSC(=O)c1ccccc1OC(C)=O)C(=O)O]

(R)-2-acetamido-3-(2-acetoxybenzoylthio)propanoic acid

The title compound is prepared using similar procedures as described in EP 0 080 229.

Example 5

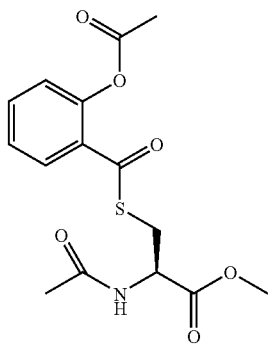 [SMILES: COC(=O)[C@H](CSC(=O)c1ccccc1OC(C)=O)NC(C)=O]

(R)-methyl 2-acetamido-3-(2-acetoxybenzoylthio)propanoate

The title compound is prepared using similar procedures as described in EP 0 080 229.

Example 6

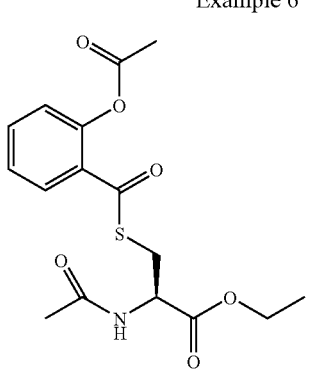

(R)-ethyl 2-acetamido-3-(2-acetoxybenzoylthio)propanoate

The title compound is prepared using similar procedures as described in EP 0 080 229.

Example 7

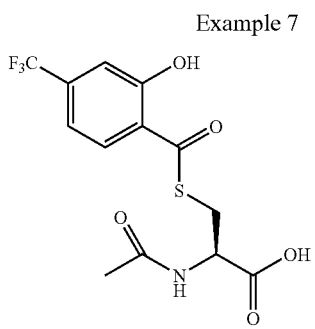

(R)-2-acetamido-3-(2-hydroxy-4-(trifluoromethyl)benzoylthio)propanoic acid

The title compound is prepared using similar procedures as described in EP 0 080 229.

Example 8

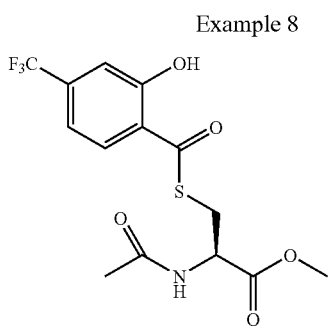

(R)-methyl 2-acetamido-3-(2-hydroxy-4-(trifluoromethyl)benzoylthio)propanoate

The title compound is prepared using similar procedures as described in EP 0 080 229.

Example 9

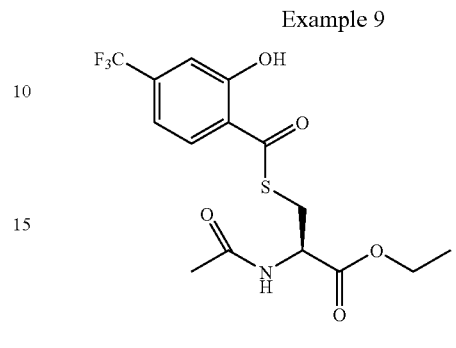

(R)-ethyl 2-acetamido-3-(2-hydroxy-4-(trifluoromethyl)benzoylthio)propanoate

The title compound is prepared using similar procedures as described in EP 0 080 229.

Example 10

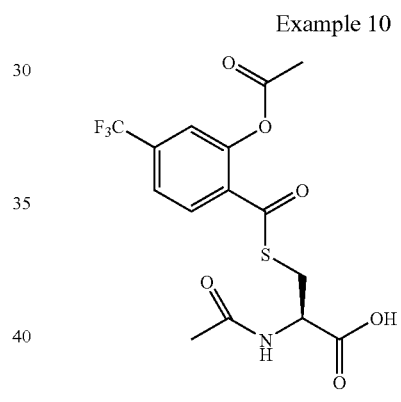

(R)-2-acetamido-3-(2-acetoxy-4-(trifluoromethyl)benzoylthio)propanoic acid

The title compound is prepared using similar procedures as described in EP 0 080 229.

Example 11

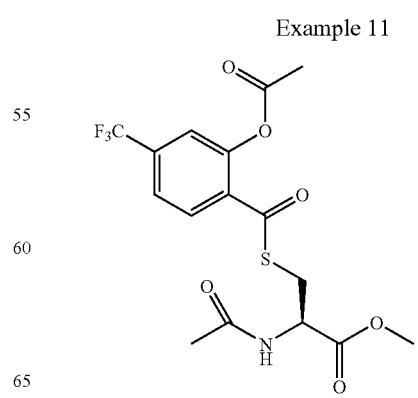

(R)-methyl 2-acetamido-3-(2-acetoxy-4-(trifluoromethyl)benzoylthio)propanoate

The title compound is prepared using similar procedures as described in EP 0 080 229.

Example 12

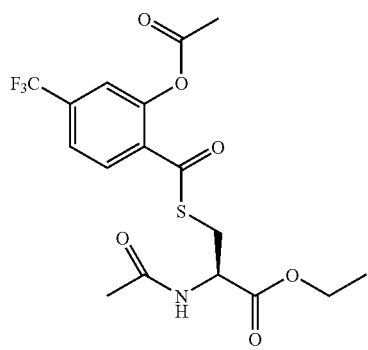 [SMILES: CCOC(=O)[C@H](CSC(=O)c1ccc(C(F)(F)F)cc1OC(C)=O)NC(C)=O]

(R)-ethyl 2-acetamido-3-(2-acetoxy-4-(trifluoromethyl)benzoylthio)propanoate

The title compound is prepared using similar procedures as described in EP 0 080 229.

Example 13

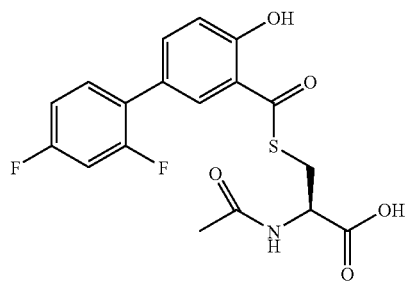 [SMILES: CC(=O)N[C@@H](CSC(=O)c1cc(-c2ccc(F)cc2F)ccc1O)C(=O)O]

(R)-2-acetamido-3-(2',4'-difluoro-4-hydroxybiphenylcarbonylthio)propanoic acid

The title compound is prepared using the procedures described in BE 900328. The title compound was also commercially available. However, alternatively the compound was synthesized as follows.

Example 13a

To a solution of 2',4'-difluoro-4-hydroxy-1,1'-diphenyl-3-carboxylic acid (Diflunisal, 82.5 g, 0.329 mol) dissolved in acetone (450 mL) and cooled to −10° C. (refrigerant mixture: ice-EtOH) was added Et$_3$N (101 mL, 0.725 mol) slowly (addition: 25 min, internal temperature: from −8° C. to 9° C.). To the resulting solution was added 2,2,2-trichloroethyl chloroformate (100 mL, 0.725 mol) slowly (addition: 60 min, internal temperature was maintained below 0° C.: from −10° C. to 0° C.). The mixture was stirred for 1 h at 0° C. (a white precipitate of triethylamine hydrochloride was gradually formed). At the end of the reaction, the mixture was filtered under vacuum, the precipitate (triethylamine hydrochloride) was washed with acetone (4×180 mL) and the filtrate was evaporated under vacuum at 30° C. The oily residue was taken with Et$_2$O (150 mL) and the suspension was evaporated again under vacuum. The operation was repeated three times to remove excess of chlorocarbonate. The residue was dissolved in acetone (180 mL), and added to a refrigerated solution of N-acetyl-L-cysteine (N-Ac-Cys, 53.81 g, 0.329 mol) and Et$_3$N (46 mL, 0.329 mol) in acetone (140 mL) slowly (addition: 55 min, internal temperature was maintained below 15° C.: from 0° C. to 15° C.). The reaction mixture was stirred at 15° C. for 4 h. The mixture was cooled to −12° C. (internal temperature), and Et$_3$N (115 mL, 0.824 mol) was added. The mixture was stirred for 15 h at −12° C. (internal temperature), and at the end of the reaction, the mixture was filtered under vacuum and the precipitate was washed with acetone (3×150 mL). The oily precipitate was suspended in CH$_2$Cl$_2$ (400 mL), cooled to 0° C. and an aqueous HCl solution (15% v:v) was added with vigorous stirring until the pH was lowered to 3. Ethanol (80 mL) was added, and the aqueous phase was extracted with CH$_2$Cl$_2$ (2×400 mL). The combined organic layers were washed with a 10% HCl aqueous solution (1×500 mL) and with water (2×600 mL), were dried over anhydrous Na$_2$SO$_4$, filtered and concentrated. The residue was purified by trituration with Et$_2$O (100 mL), affording 44.13 g of the title compound (HPLC purity: 88.26%) To increase purity, the solid was suspended in Et$_2$O (100 mL) and stirred at room temperature for 20 min. The solid was filtered under vacuum and was washed with Et$_2$O (3×100 mL), to afford 31.33 g of the title compound GMC-3b (Rf=0.3 CH$_2$Cl$_2$/MeOH/AcOH 95:5:1), white solid, 24% yield, 96.22% HPLC purity); Purity was determined by NMR analysis and mass spectrometry to conform to the following parameters: 1H-NMR (CD$_3$OD, 250 MHz, δ): 8.00 (m, 1H, ArH); 7.66 (dm, J=8.2 Hz, 1H, ArH); 7.50 (m, 1H, ArH); 7.06 (m, 3H, ArH); 4.74 (m, 1H, CH); 3.77 (dd, J=4.7 and 13.7 Hz, 1H, CH); 3.40 (m, 1H, CH); 1.98 (s, 3H, CH$_3$); MS-EI+m/z: 396.00 (M+1); LC-MS: M+1: 396.00; purity: 96.52% (HPLC method: SunFire C18 3.5 um, 2.1×100 mm, flow: 0.3 mL/min, gradient: A:B 3 min 10:90+ from 10:90 to 95:5 in 17 min+10 min 95:5; A: CH$_3$CN:MeOH 1:1; B: NH$_4$OAc buffer 5 mM pH 7).

Example 13b

Synthesis of (2R)-2-(Acetylamino)-3-{[(2',4'-difluoro-4-hydroxy-1,1'-biphenyl-3-yl)carbonyl]thio}propanoic acid L-Lysine Salt

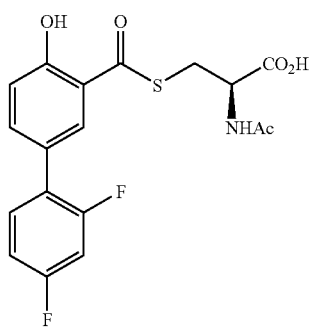

-continued

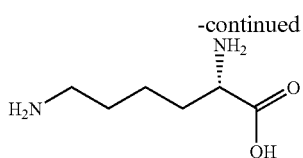

Starting material (GMC-3b, 18.33 g, 46.37 mmol, Example 13a) was dissolved in acetone (300 mL) and L-Lysine (L-Lys, 6.44 g, 44.05 mmol) dissolved in H$_2$O (60 mL) was added. Acetone (100 mL) was added and the mixture was stirred at room temperature for 1 h. The resulting solid was filtered under vacuum, washed with acetone (3×100 mL), Et$_2$O (2×80 mL), and hexanes (2×80 mL). The solid was dried at room temperature to give 22.01 g of title salt GMC-3b·L-Lys as a white solid. (92% yield, 99.59% HPLC purity). $^1$H-NMR (D$_2$O, 250 MHz) δ 7.77 (m, 1H, ArH); 7.50 (d, J=8.5 Hz, 1H, ArH); 7.23 (m, 1H, ArH); 6.90 (m, 3H, ArH); 4.47 (m, 1H, CH); 3.73-3.59 (m, 2H, CH); 3.25 (m, 1H, CH); 2.97 (t, J=7.4 Hz, 2H, CH$_2$); 1.94 (s, 3H, CH$_3$);); 1.84 (m, 2H, CH$_2$); 1.67 (m, 2H, CH$_2$); 1.44 (m, 2H, CH$_2$); MS-EL m/z: 396.00 (M+1-L-Lys); LC-MS: M+11-L-Lys: 396.00; purity: 99.59% (HPLC method: SunFire C18 3.5 um, 2.1×100 mm, flow: 0.3 mL/min, gradient: A:B 3 min 10:90+ from 10:90 to 95:5 in 17 min+10 min 95:5; A: CH$_3$CN:MeOH 1:1; B: NH$_4$OAc buffer 5 mM pH 7).

Example 14

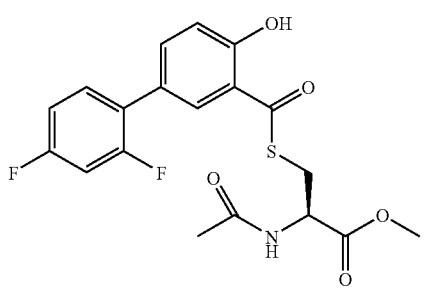 [SMILES: COC(=O)[C@H](CSC(=O)c1cc(-c2ccc(F)cc2F)ccc1O)NC(C)=O]

(R)-methyl 2-acetamido-3-(2',4'-difluoro-4-hydroxy-biphenylcarbonylthio)propanoate The title compound is prepared using similar procedures as described in BE 900328.

Example 15

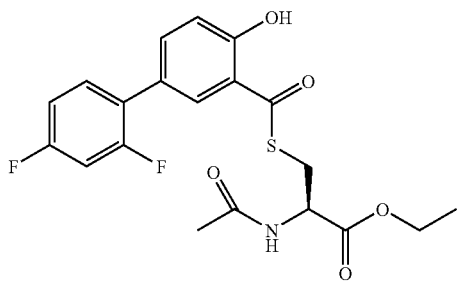 [SMILES: CCOC(=O)[C@H](CSC(=O)c1cc(-c2ccc(F)cc2F)ccc1O)NC(C)=O]

(R)-ethyl 2-acetamido-3-(2',4'-difluoro-4-hydroxybi-phenylcarbonylthio)propanoate The title compound is prepared using similar procedures as described in BE 900328.

Example 16

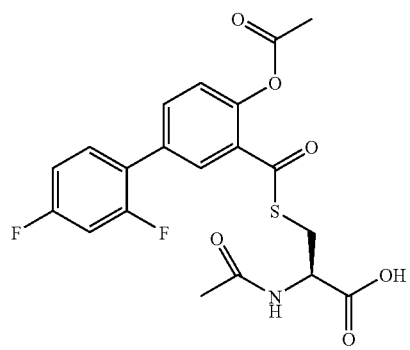 [SMILES: CC(=O)N[C@@H](CSC(=O)c1cc(-c2ccc(F)cc2F)ccc1OC(C)=O)C(=O)O]

(R)-2-acetamido-3-(4-acetoxy-2',4'-difluorobiphe-nylcarbonylthio)propanoic acid

The title compound is prepared using similar procedures as described in BE 900328.

Example 17

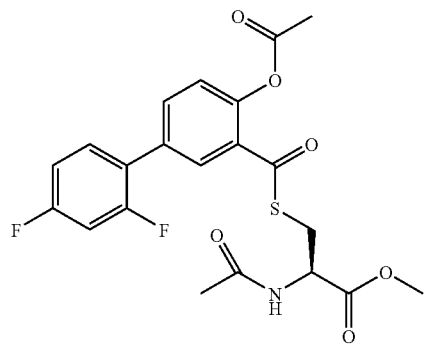 [SMILES: COC(=O)[C@H](CSC(=O)c1cc(-c2ccc(F)cc2F)ccc1OC(C)=O)NC(C)=O]

(R)-methyl 2-acetamido-3-(4-acetoxy-2',4'-difluoro-biphenylcarbonylthio)propanoate The title compound is prepared using similar procedures as described in BE 900328.

Example 18

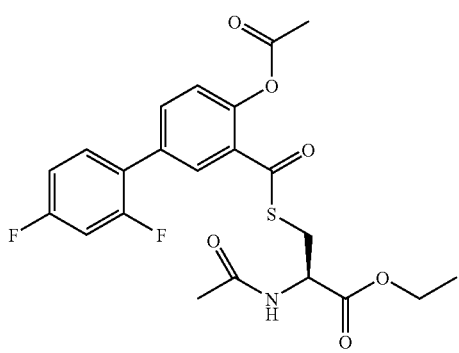 [SMILES: CCOC(=O)[C@H](CSC(=O)c1cc(-c2ccc(F)cc2F)ccc1OC(C)=O)NC(C)=O]

(R)-ethyl 2-acetamido-3-(4-acetoxy-2',4'-difluorobi-phenylcarbonylthio)propanoate The title compound is prepared using similar procedures as described in BE 900328.

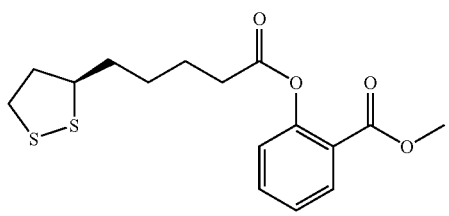 [SMILES: COC(=O)c1ccccc1OC(=O)CCCC[C@@H]1CCSS1]

Example 19

Methyl 2-(5-((R)-1,2-dithiolan-3-yl)pentanoyloxy)benzoate

Lipoyl chloride (commercially available, 300 mg) was added slowly to a solution of Methyl 2-hydroxybenzoate (commercially available, 260 mg) and triethylamine (300 mg) in dichloromethane. The reaction was stirred at room temperature for 12 h. The reaction was then concentrated and the residue purified by column chromatography to obtain the desired compound (160 mg) as a pale yellow solid. $^1$H-NMR (DMSO) δ: 1.29 (m, 2H); 1.55 (m, 4H); 1.80 (m, 4H); 2.23 (m, 2H); 2.58 (m, 3H); 3.80 (s, 3H); 7.18 (m, 2H); 7.44 (m, 1H); 7.94 (m, 1H).

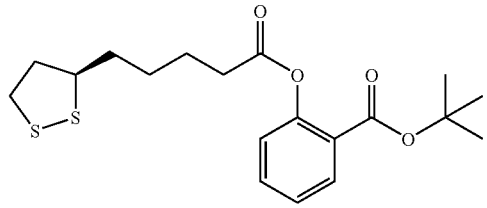 [SMILES: CC(C)(C)OC(=O)c1ccccc1OC(=O)CCCC[C@@H]1CCSS1]

Example 20 tert-Butyl 2-(5-((R)-1,2-dithiolan-3-yl)pentanoyloxy)benzoate

The title compound was prepared in a similar manner as that described in Example 19 except using tert-butyl 2-hydroxybenzoate instead of methyl 2-hydroxybenzoate. $^1$H-NMR (DMSO) δ: 1.29 (m, 2H); 1.40 (s, 9H); 1.55 (m, 4H); 1.80 (m, 4H); 2.23 (m, 2H); 2.58 (m, 3H); 7.18 (m, 2H); 7.44 (m, 1H); 7.94 (m, 1H).

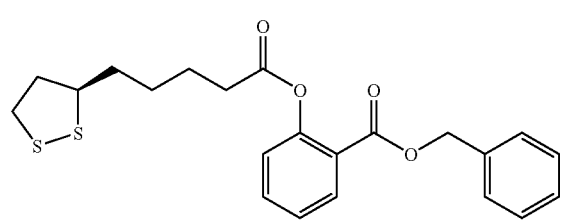 [SMILES: O=C(CCCC[C@@H]1CCSS1)Oc1ccccc1C(=O)OCc1ccccc1]

Example 21

Benzyl 2-(5-((R)-1,2-dithiolan-3-yl)pentanoyloxy)benzoate

The title compound was prepared in a similar manner as that described in Example 19 except using benzyl 2-hydroxybenzoate instead of methyl 2-hydroxybenzoate. $^1$H-NMR (DMSO) δ: 1.29 (m, 2H); 1.55 (m, 4H); 1.80 (m, 4H); 2.23 (m, 2H); 2.58 (m, 3H); 5.51 (m, 2H); 7.18 (m, 7H); 7.44 (m, 1H); 7.94 (m, 1H).

Experimental Methods for FIGS. 1-27

The experiments described herein illustrate beneficial embodiments of the invention comprising distinct antioxidat-antiinflammatory agent conjugates. The advantageous and beneficial properties of alternative conjugates as provided by this invention can be demonstrated using substantially the same experiments and assays.

Animals.

Male cd-1 mice weighing 25-30 g were purchased from Charles River Laboratories Spain. The animals were housed in animal quarters at 22° C. with a 12-h light/12-h dark cycle and fed ad libitum. 5-weeks old Male mice C57BL/Ks bearing the db/db mutation (The Jackson Laboratories) were purchased from Charles River Laboratories Spain (Sant Cugat del Vallés, Spain).

Chemicals.

The chemicals N-Acetyl-cysteine and Sodium Salicylate were purchase from Sigma (Sigma Aldrich, St. Louis, Mo., USA) and PBS was purchase from Invitrogen. The compounds of diflunisal, dexibuprofen, and salnacedin (GMC-1.3a), and their lysine salts were purchase from Galchimia, S. L. (Galchimia S. L., A Coruña, Spain). All the compounds were dissolved in PBS, with lysine salt when indicated, and the pH of the compounds without lysine was adjusted with NaOH 6N until pH 7.

In Vitro β-Cell Protection Model

INS-1E β-cells were cultivated in the presence of a high glucose concentration (11 mM) and a high palmitate concentration (0.4 mM bound to BSA 0.5%) in order to promote glucotoxicity and lipotoxicity. The combination of both stressors promote the apoptosis of the β-cells. INS-1E cells were seeded at a density of 80.000 cells/$cm_2$ in 96 wells plates 4 days before the beginning of the treatment. At 60-80% of confluence, cells were fasted with RPMI 5 mM of glucose+ FBS 10%. 8 h later, antioxidants and anti-inflammatory agents, alone or in combination were added overnight at the indicated concentrations. The day after, fasting medium was changed by the stressing medium (glucose 25 mM+palmitate 0.4 mM bound to BSA 0.5%). Medium, and tested agents when present, were changed every 24 h. 48 h after the addition of the stressing medium, apoptosis was measured with Apo-One Homogeneous Caspase 3/7 Assay (Promega) which determine the activity of caspase 3 and 7. Cells were frozen at −80° C. for 2 hours, defrost at room temperature and incubated in the presence of 100 µl of caspase reactive for 20 hours. Resulting fluorescence was read at 485/530 (excitation/emission wave lenght). The background apoptosis, in absence of stressing condition, was determined with INS1E cells cultured in the presence of fasting medium (RPMI 5 mM glucose+FBS 10%). Staurosporine 0.2% in the presence of 0.5% BSA was used as a positive control of apoptosis.

In Vivo Beta Cell Protection Model

Beta-cell destruction was induced in cd-1 mice after 3 hours of fasting by a single intraperitoneal injection of a freshly prepared solution of alloxan 200 mg/kg (Sigma-Aldrich, San Luis, Mo.) that was dissolved in NaCl 0.9%. Single intraperitoneal drug administration was 1 hour before the alloxan administration. Animals received the different drugs dissolved in PBS pH 7.4, and the animals that not received any drug were injected with the vehicle, in this case PBS pH 7.4. At the end of the treatment, at day 4, animals were killed and the plasma collected and kept at −20° C. until used.

Microsomal Cleavage Assays

In vitro cleavage experiments were performed substantiallas described in Singh et al., 1996, In vitro metabolism of a potent HIV-protease inhibitor (141W94) using rat, monkey and human liver S9, Rapid Commun. Mass Spectrom. 10: 1019-1026. Briefly, conjugate compounds of the invention were incubated at a final concentration of 1 microM for 1 hour in the presence of human or rat liver microsome S9 (obtained from Xenotech). At the end of incubation at each of the time points reported, an equal volume of an organic mixture (acetonitrile/methanol, 50/50, v/v) was added to the incubation mixture followed by centrifugation. At this time blank microsomal extract was spiked with metabolites to create calibration standards for each metabolite at the following concentrations: 0 (blank), 0.05, 0.1, 0.5 and 1 microM. All samples were analyzed by HPLC-MS/MS and the peak areas corresponding to the expected metabolites (generally, antioxidant and anti-inflammatory cleaysasge products) were determined by HPLC-MS/MS. The amount of each metabolite present in the 60 minute incubation samples was determined from the corresponding calibration curve.

Chronic Treatment in db/db Mice.

5-weeks old Male mice C57BL/Ks bearing the db/db mutation (The Jackson Laboratories) were purchased from Charles River Laboratories Spain (Sant Cugat del Vallés, Spain). The animals were housed in animal quarters at 22° C. with a 12-h light/12-h dark cycle and fed ad libitum. The animals were treated with the indicated drugs for a month. The administration route was a single intraperitoneal injection. The glycemia levels were determined in blood from the Tail Vein, using a rapid glucose analyzer (Accu-Chek Aviva; Roche) 3 times per week, as body weight measure too. The food and water intake were measured twice a week. At the end of the treatment, the mice were sacrificed, in feeding state, with $CO_2$ euthanasia, and the blood was extracted from the Inferior Cave Vein, using heparin as an anticoagulant, and maintained at 4° C. until the preparation of plasma.

Intraperitoneal Insulin Tolerance Test.

At the third week of treatment, an Insulin Tolerance Test was done to the mice in feeding state. The animals received an ip injection of Insulin 2 UI/kg (Humulin®). The glycemia levels were determined at the indicated time in blood from the Tail Vein, after the Insulin injection using a rapid glucose analyzer.

Intraperitoneal Glucose Tolerance Test.

At the fourth week of treatment, a Glucose Tolerance Test was done to the mice after an overnight fasting. The animals received an ip injection of Glucose 0.5 g/kg (Glucosmon 50®). The glycemia levels were determined in blood at the indicated time from the Tail Vein after the Glucose injection using a rapid glucose analyzer.

Determination of Biochemical Parameters.

The circulating glucose concentration was determined by a rapid glucose analyzer (Accu-Chek Aviva; Roche). Plasma triglycerides and non esterified fatty acids were determined with standard colorimetric methods (Biosystems, Barcelona, Spain, and Wako Chemicals, Neuss, Germany, respectively). Plasma insulin concentration was determined by enzyme-linked immunosorbent assay method (CrystalChem, Downers Grove, Ill.). Total pancreas insulin content has been determined after extraction of insulin with a mixture Ethanol (70%)/HCl (0.15 N) from pancreas homogenates.

Preparation of Pancreas Sections and Immunohistochemical Analyses.

The pancreas was removed from each mouse and fixed overnight in a solution of 4% formalin. Fixed tissues were processed routinely for paraffin embedding, and 6-µm sections were prepared and mounted on slides treated with xilane. For detection of insulin, the avidin-biotin complex (ABC) method was performed using Vectastain ABC Kit (Vector Laboratories). Deparaffinized and dehydrated sections were microwaved in citrate buffer (pH 6.0) for antigen retrieval, then were incubated in Tris 100 mM pH 7.4 containing 3% BSA, and 0.01% Triton, to permeabilize and block nonspecific staining, for 30 min, and after that, were incubated with the guinea pig polyclonal anti-insulin antibody (Dako), diluted 1/500 in blocking solution for 2 hours. Negative controls were incubated with blocking solution without the primary antibody. The sections were then incubated with biotinylated antiguinea pig IgG (Vector Laboratories), diluted 1:100 in PBS containing donkey serum 10%, for 45 min. The sections were then incubated with ABC reagent for 45 min, and positive reactions were visualized by incubation with the peroxidase substrate solution containing 3,3'-diaminobenzidine tetrahydrochloride (DAB) (Vector Laboratories). The sections were mounted using Fluoromount G (Electron Microscopy Sciences). Sections were then examined using a Nikon E-600 upright microscope, and microscopic pictures were obtained with a digital camera Olympus DP 72 using Olympus-SIS Cell F software. This program and Fiji Software were used to measure pancreas sections and islets areas.

Statistical Analysis.

Statistical comparisons between groups were established by two-way ANOVA using Prism 4 (GraphPad, San Diego, Calif.). A p value of less than 0.05 was considered to be statistically significant. Statisticaly significant differences are indicated as follow: *, P<0.05; , P<0.01; *, P<0.001.

Biological Data

Exemplary expérimental results showing the efficacy of certain embodiments of the combinations of the invention are set forth in the drawings. Stability studies were performed on thioester conjugates of N-acetylcysteine and salicylate, diflunisal or dexibuprofen, at neutral (pH 7), acidic, or basic (9) pH in phosphate-buffered saline (PBS). The free acid as well as the lysine salt of salicylate-NAC was tested at room température (RT); under basic conditions only the lysine salt showed any (sparing) détectable conjugate after a 3 hour incubation. In contrast, the lysine salt was stable after 3 hours under acidic conditions, while the free acid in the absence of lysine lost stability during a 3-day timecourse. Diflunisal-NAC conjugates were tested for 3 or 24 hours under the same neutral, acidic and basic conditions, at room température or 4° C., and in PBS or mixture of water and méthanol. Under thèse conditions, the free acid was stable over 3 and 24 hours in the water/méthanol mixture at neutral pH and room température, as was the lysine salt in PBS at neutral pH and room température after 3 hours (but not after 24 hours). However, the lysine salt did not show comparable stability in the water/méthanol mixture. Dexibuprofen-NAC conjugates were stable as lysine salts under neutral pH conditions at room température or 4° C.; the free acid was stable for 3- and 24-hour incubation as the free acid in in water/méthanol. These results are shown in FIG. 1.

Figure 3:
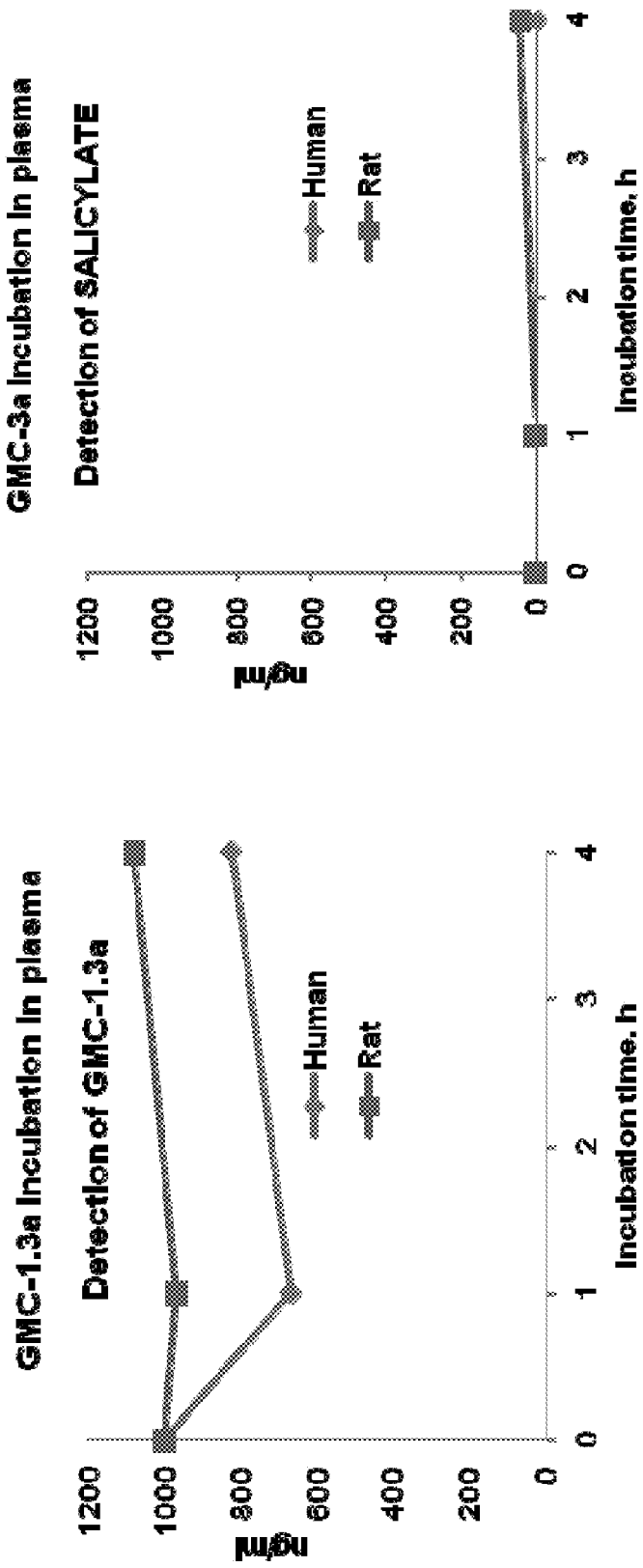
Figure 4:
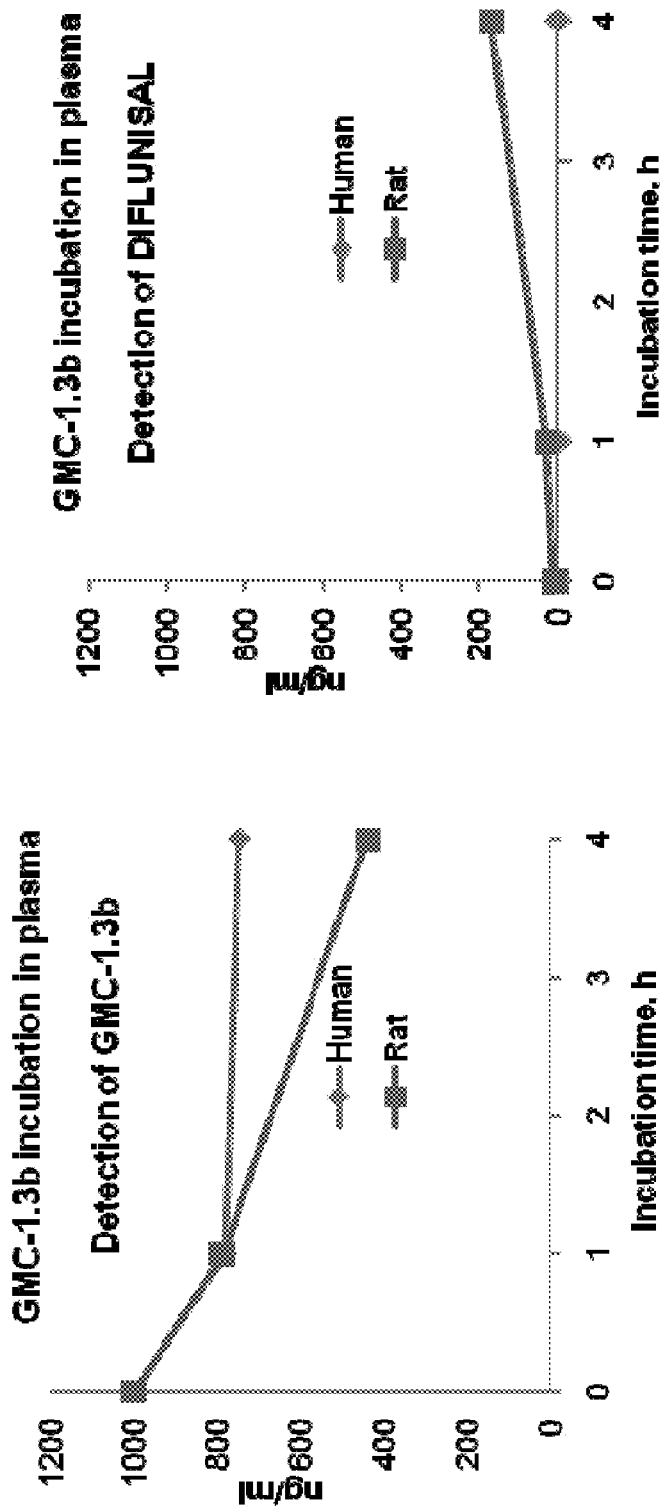

The capacity for conjugates of the invention to be cleaved was tested in vitro using rat or human liver microsomes. As shown in FIG. 2, salicylate-NAC and diflunisal-NAC thioester conjugates were incubated for 1 hour in the présence of microsomes and the amout of free salicylate or diflunisal assayed. Rat microsomes were found to be more potent in cleaving thèse conjugates, and a higher percentage of diflunisal that salicyalte was released by both rat and human liver microsomes. Similar experiments were performed in plasma from rat or human for salicylate-NAC or diflunisal-NAC conjugates; thèse results are shown in FIGS. 3 and 4, respectively.

Figure 5:
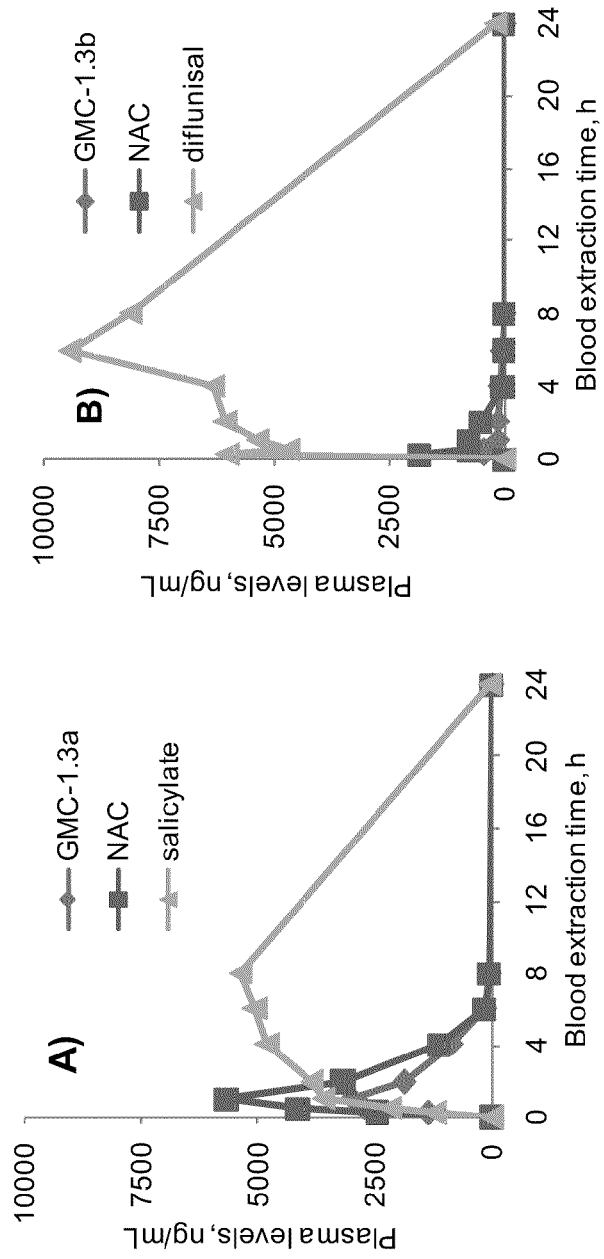
FIG. 5 is a graphical illustration of the cleavage efficiency for salicylic acid-(L) N-acetyl cysteine (GMC-3a), diflunisal-(L) N-acetyl cysteine (GMC-3b) in vivo in rats.

Cleavage of conjugates of the invention in vivo was assayed by oral adminstration of salicylate-NAC or diflunisal-NAC conjugates to rats. As shown in FIG. 5, both the conjugate and the NAC components were quickly cleared from the systemic circulation (within 8 hours), while both salicylate and diflunisal persisted between 8 and 24 hours after administration.

Figure 6:
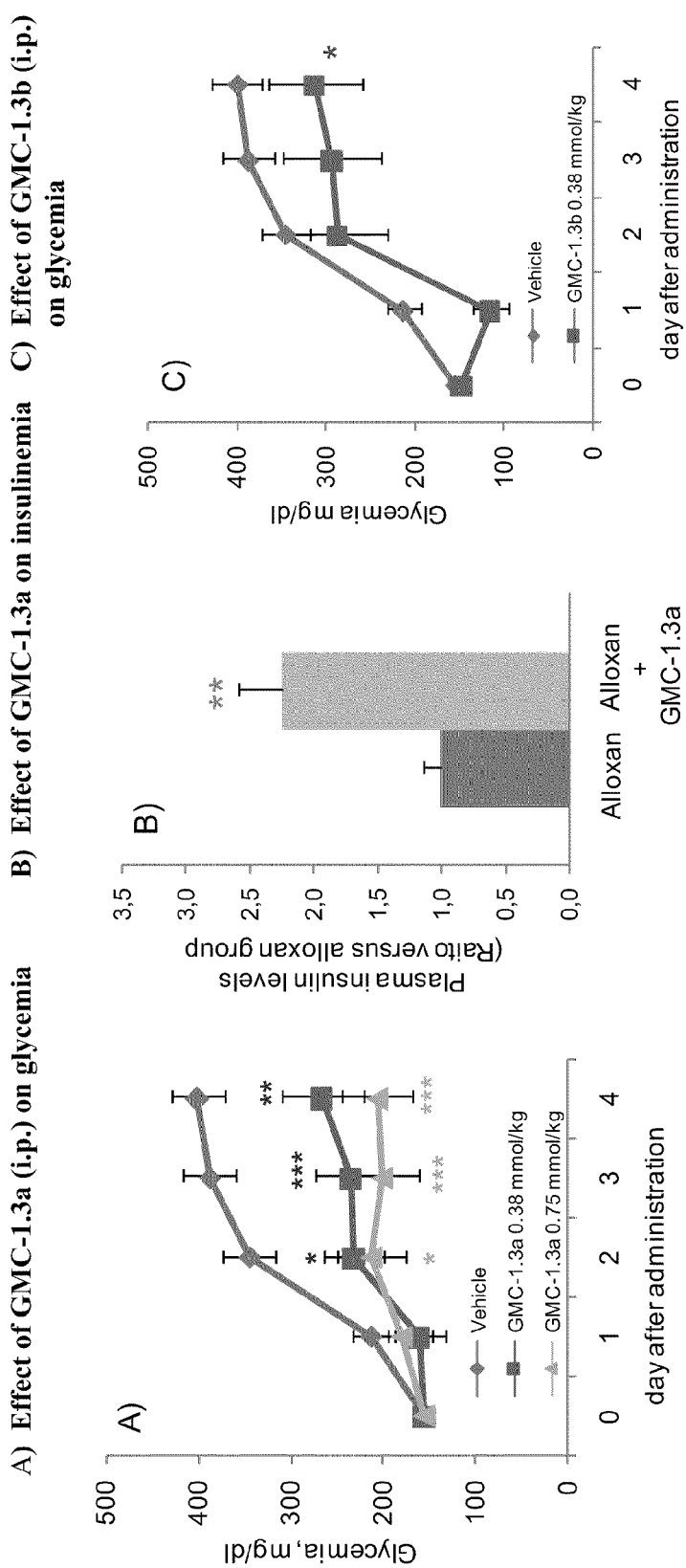
FIG. 6 is a graphical illustration of the effects of salicylic acid-(L) N-acetyl cysteine (GMC-1.3a) and diflunisal-(L) N-acetyl cysteine (GMC-1.3b), as lysine salts, at protecting beta-cells in vivo in the alloxan model. The alloxan model is a well known model of β-cell dysfunction that mimicks the biochemical events involved in type 2 diabetes, including inflammation and oxidative stress. The results in FIG. 6 indicate that both conjugates reduce the effect of alloxan on β-cells. Further, the preservation of insulin levels in alloxan rats treated with GMC-3a, as shown in FIG. 6, indicates a beta cell protection mechanism of action.

The effects of salicylate-NAC or diflunisal-NAC conjugates on glycemia or insulemia in vivo was assayed using alloxan-treated cd-1 mice. The alloxan model is a well-known model of β-cell dysfunction that mimicks the biochemical events involved in type 2 diabetes, including inflammation and oxidative stress. Conjugates were administered as lysine salts i.p. over a 4-day timecourse, and both conjugates showed statistically-significant reductions in glycemia, as shown in FIG. 6. In addition, salicylate-NAC conjugate showed an increase in plasma insulin levels in alloxan-treated mice, indicating that the conjugate protected thèse mice from the beta-cell toxicity of alloxan.

Figure 7:
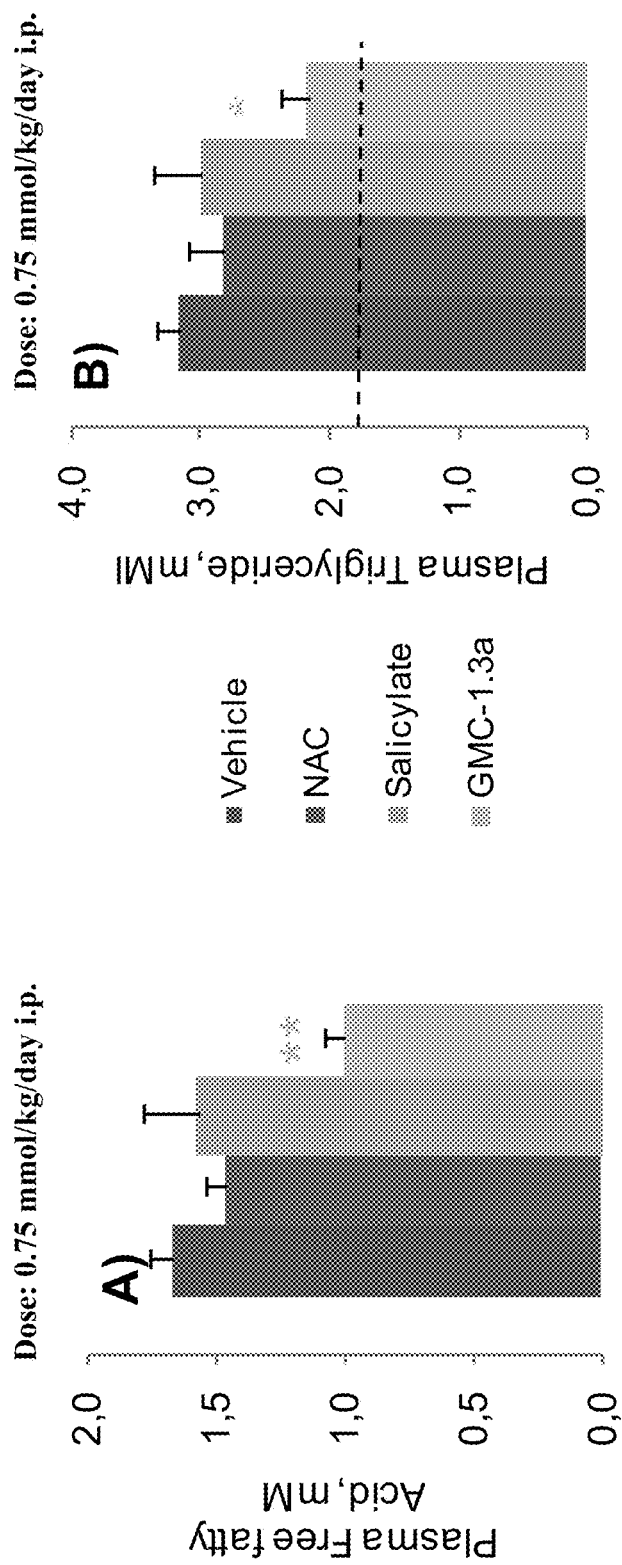
FIG. 7 is a graphical illustration of the comparative effects of the conjugate salicylic acid-(L) N-acetyl cysteine (GMC-1.3a) as the lysine salt, salicylate, and NAC, on free fatty acid and triglyceride levels in db/db mice (ip administration).

The conjugates were also tested in mouse diabètes model, specifically db/db mice. As shown in FIG. 7, free fatty acid and plasma triglycéride levels were significantly improved in mice administered salicylate-NAC conjugate (0.75 mmol/kg/day as the lysine salt), compared with separate administration of either component of the conjugate.

Figure 8:
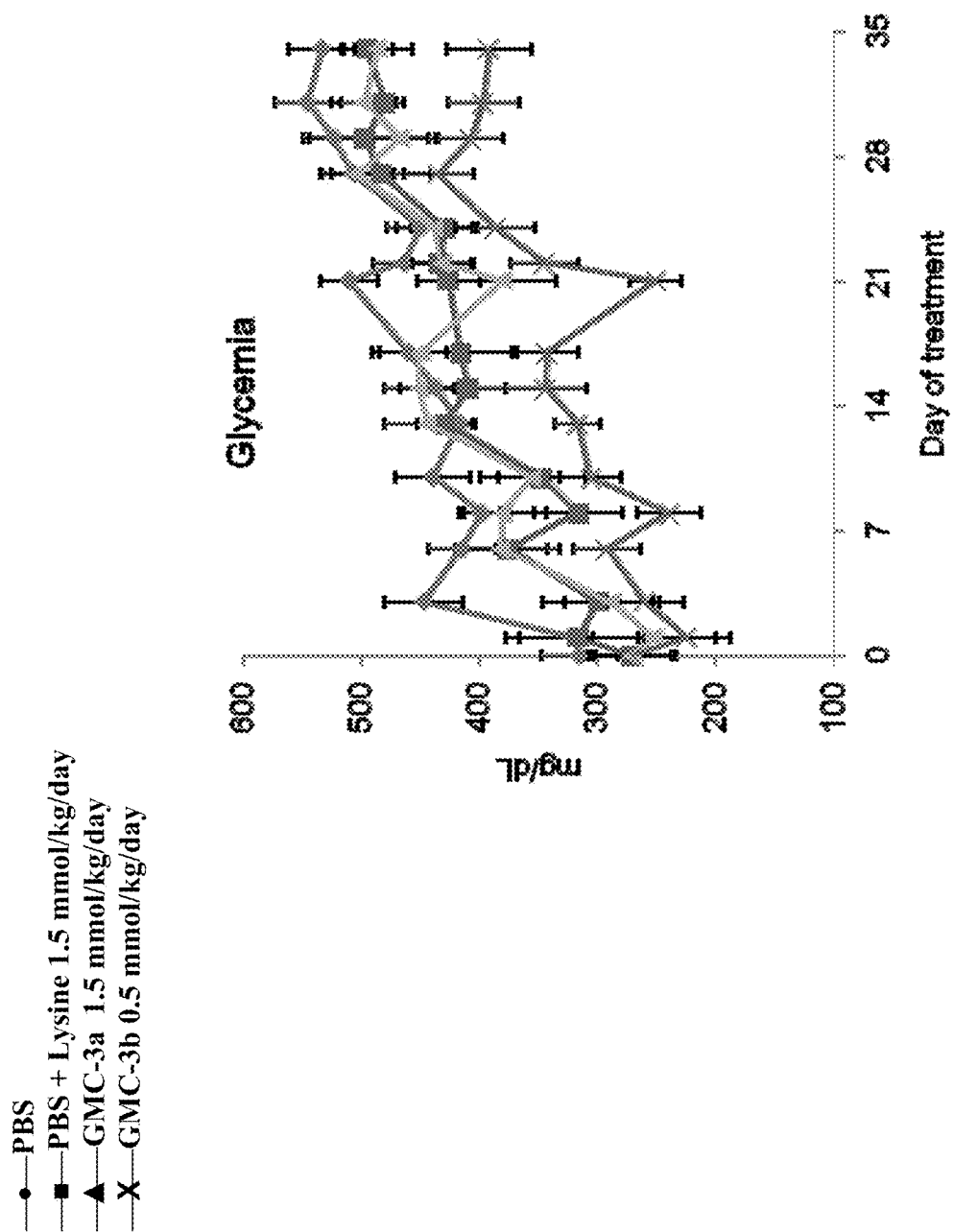
FIGS. 8-10 is a graphical illustration of the acute and chronic effects of the conjugate diflunisal-(L) N-acetyl cysteine (GMC-1.3b), as the lysine salt, on hyperglycemia in db/db mice subsequent (oral administration).

Mice (db/db) used as a mouse model for human diabetes were tested using a protocol set forth in FIG. 14. The effects of oral administration of salicylate-NAC or diflunisal-NAC conjugates to db/db mice on glycemia is shown in FIG. 8, wherein lysine (1.5 mmol/kg/day), salicylate-NAC (1.5 mmol/kg/day, as the lysine salt) or diflunisal-NAC (0.5 mmol/ kg/day, as the lysine salt) was administered to mice over 35-day course of treatment. Although glucose concentrations increased over the course of the experiment, mice treated with the diflusinal-NAC conjugate showed lower glycemia levels.

Figure 9:
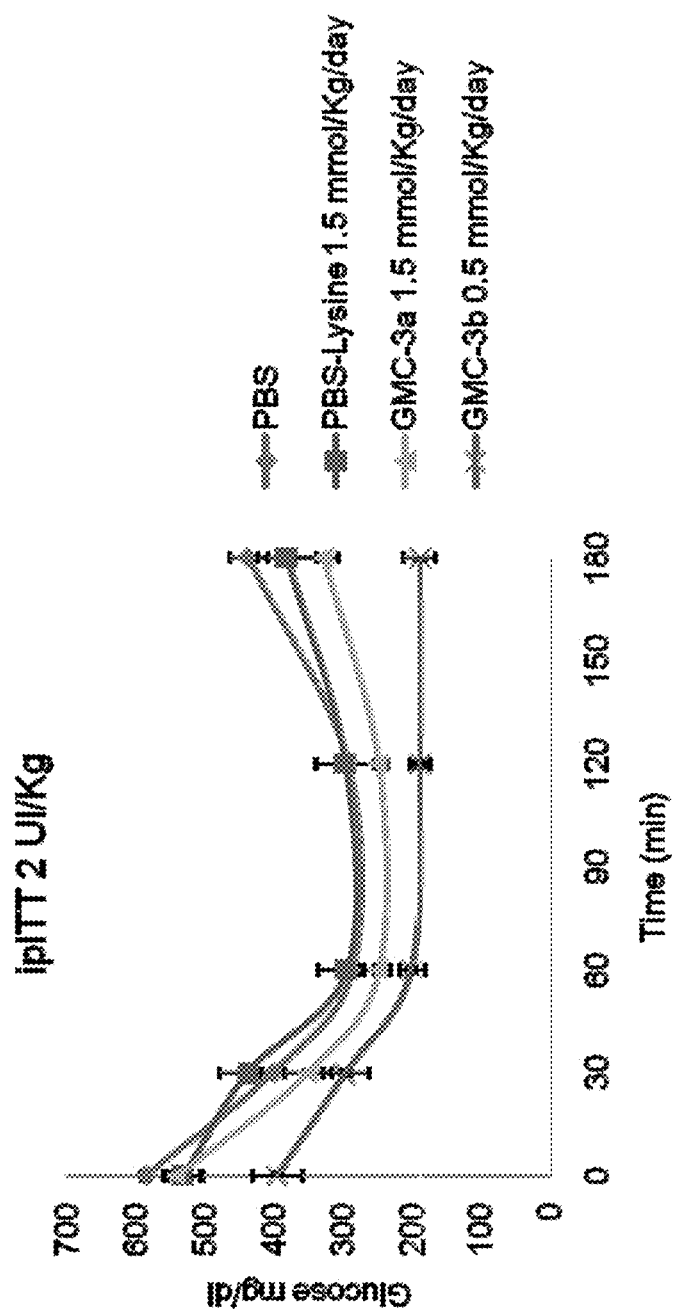
Figure 10:
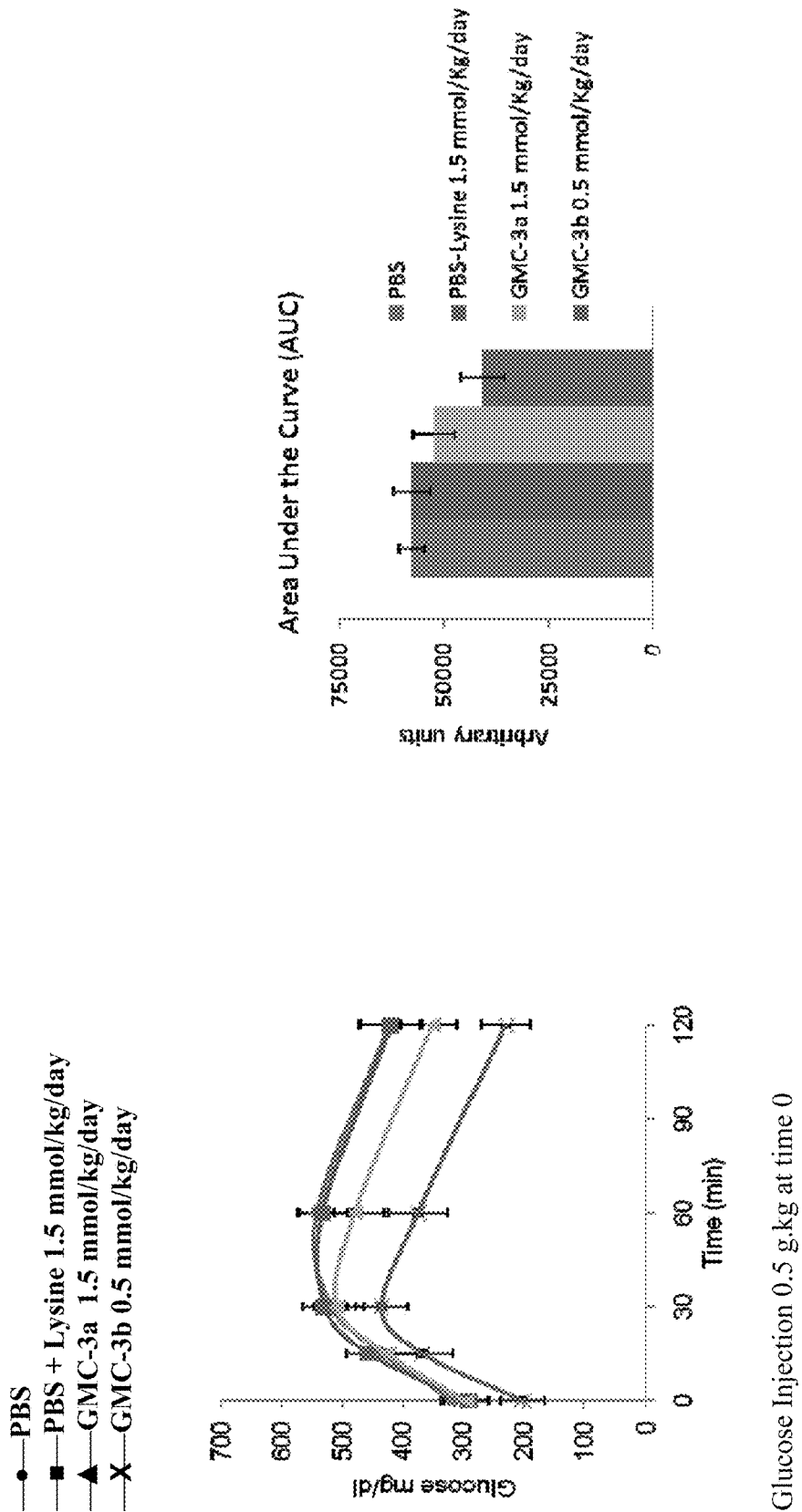

Intraperitoneal insulin tolérance tests were performed on db/db mice in the feeding state by injecting mice i.p with 2 IU/kg human insulin (Humulin®). Tail vein blood was assayed for glucose concentration in mice treated with lysine (1.5 mmol/kg/day), salicylate-NAC (1.5 mmol/kg/day, as the lysine salt) or diflunisal-NAC (0.5 mmol/kg/day, as the lysine salt). The diflunisal-NAC conjugate showed the greatest sustained insulin sensitivity over the 3-hour time course of thèse experiments, as shown in FIG. 9.

Intraperitoneal glucose tolerance tests were also performed onb db/db mice after an overnight fast. The animals received an ip injection of Glucose 0.5 g/kg (Glucosmon 50®) and glycemia levels were determined from tail vein blood. Lysine (1.5 mmol/kg/day), salicylate-NAC (1.5 mmol/kg/day, as the lysine salt) or diflunisal-NAC (0.5 mmol/kg/day, as the lysine salt) were administered and showed reductions in plasma glucose over the 120 minute experimental timecourse, with the diflunisal-NAC conjugate having the greatest effect.

Figure 11:
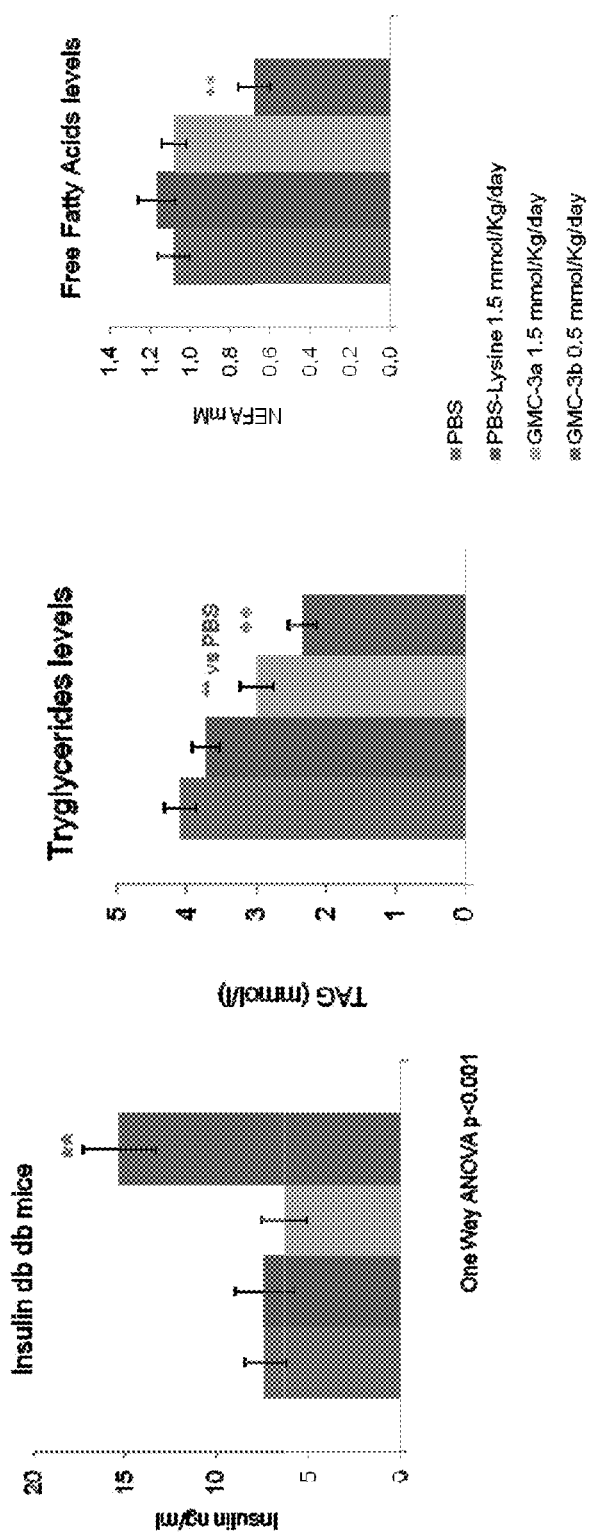
FIG. 11 is a graphical illustration of the effect of the conjugates salicylate-(L) N-acetyl cysteine (GMC-3a) and diflunisal-(L) N-acetyl cysteine (GMC-3b), as the lysine salt, on plasma insulin levels, free fatty acid levels, and triglyceride levels in db/db mice (chronic oral administration).
Figure 12:
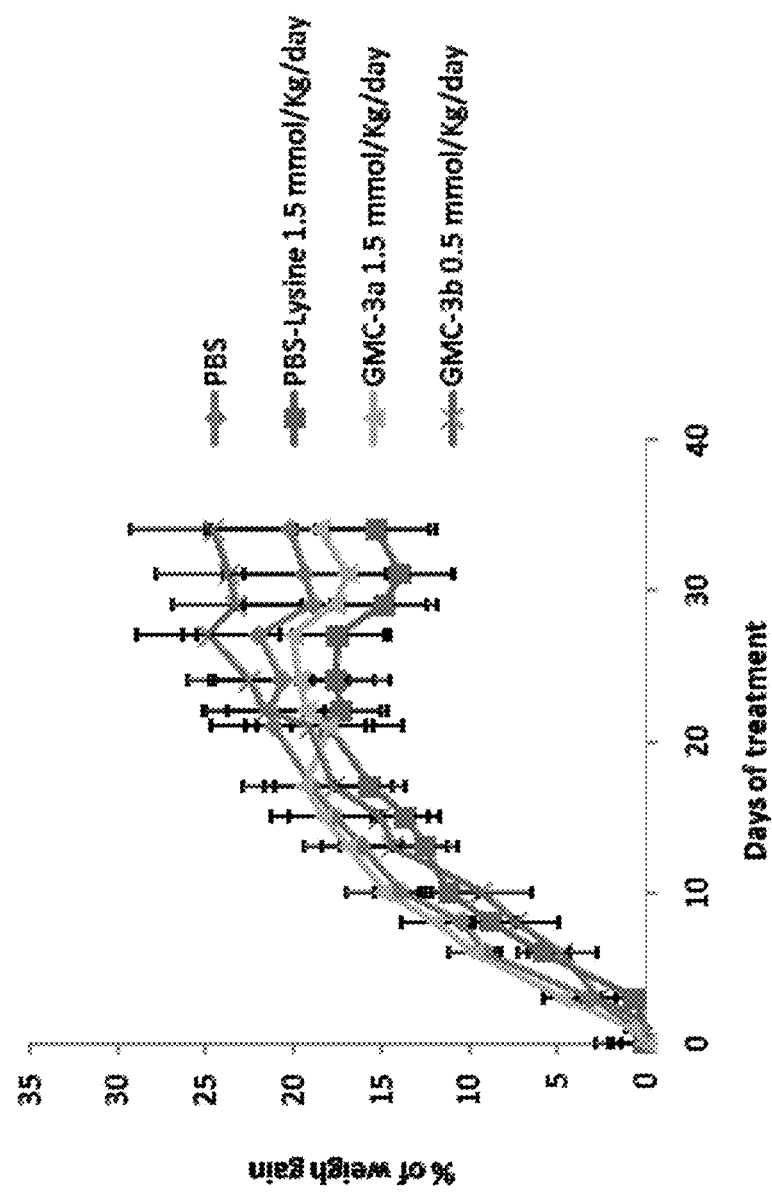
FIG. 12 is a graphical illustration of the effects of the conjugates salicylic acid-(L) N-acetyl cysteine (GMC-3a) and diflunisal-(L) N-acetyl cysteine (GMC-3b) on body weight gain in db/db mice (chronic oral administration).
Figure 13:
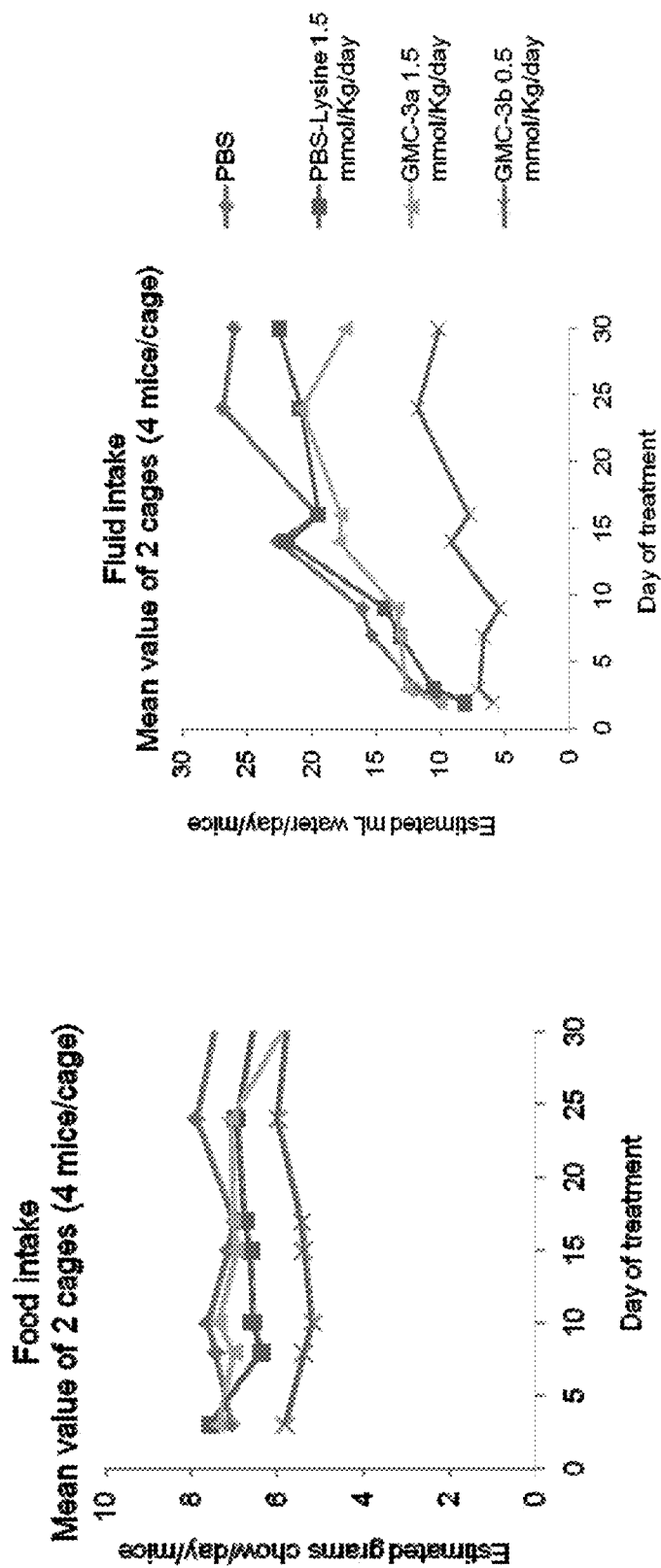
FIG. 13 is a graphical illustration of the effects of the conjugates salicylic acid-(L) N-acetyl cysteine (GMC-3a) and diflunisal-(L) N-acetyl cysteine (GMC-3b) on fluid and food intake in db/db mice (chronic oral administration).

Chronic oral administration of conjugates of the invention was shown to have beneficial effects on insulin, triglycéride and free fatty acid levels in db/db mice. Statistically-significant increase in plasma insulin, and decreases in free fatty acid and triglycerides were detected after administation of diflunisal-NAC (0.5 mmol/kg/day, as the lysine salt), and significant réductions in triglycerides was detected in db/db mice administered salicylate-NAC (1.5 mmol/kg/day, as the lysine salt). These results are shown in FIG. 11. Weight m gain in db/db mice was also assayed after chronic oral administration of lysine (1.5 mmol/kg/day), salicylate-NAC (1.5 mmol/kg/day, as the lysine salt) or diflunisal-NAC (0.5 mmol/ kg/day, as the lysine salt). These results are shown in FIG. 12, wherein mice administered the diflunisal-NAC conjugate showed the greatest effect on weight gain. Mice administered the diflunisal-NAC conjugate also showed reduced consumption of food and water, as shown in FIG. 13.

Figure 16:
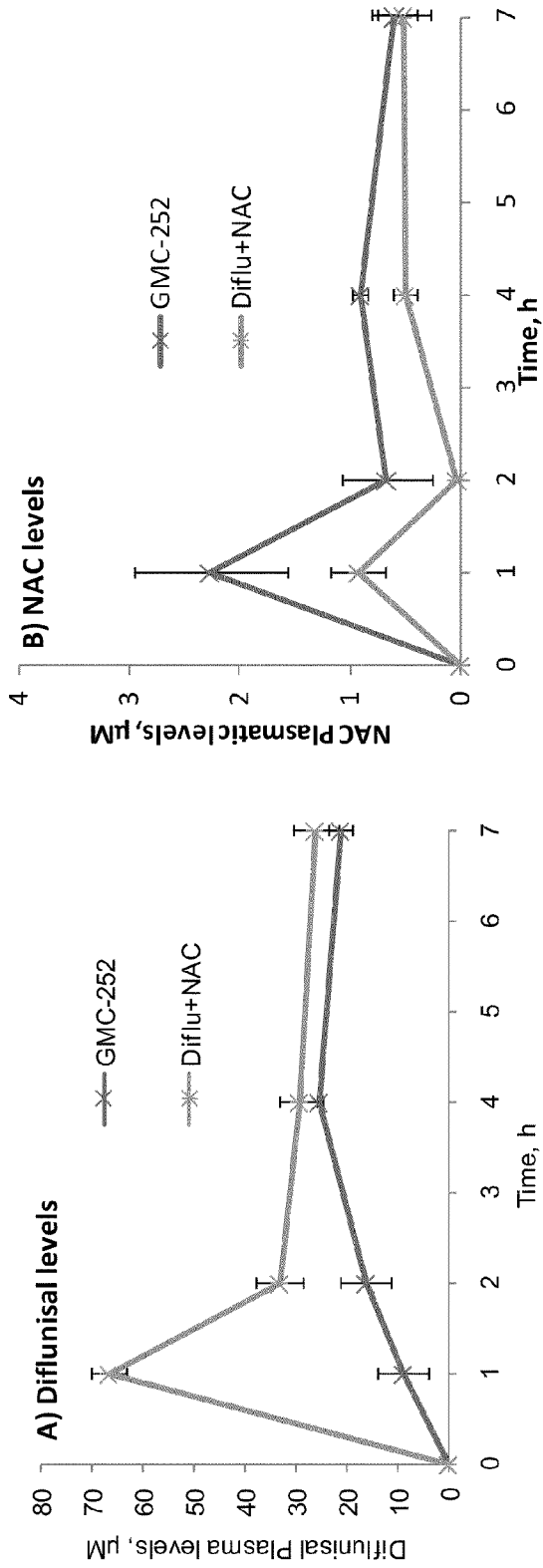
FIG. 16 is a graphical illustration comparing diflunisal and NAC plasma levels in mice following oral administration (20 mg/kg) of the conjugate diflunisal-NAC and the combination of diflunisal+NAC.

A comparison of diflunisal and NAC levels in blood after oral administration was performed in rats by administration of the diflunisal-NAC conjugate (GMC-252) or the individual components separately (i.e., not chemically conjugated). Conjugate (20 mg/kg) or the equivalent amount of difliunisal and NAC were administered and blood assayed over a 7-hour timecourse. In contrast with the blood plasma profiles of diflunical and NAC administered separately, the conjugate showed a more gradual increase in plasma concentrations (albeit the final concentrations were the same whether administered as a conjugate or as separate components, as shown in FIG. 16.

Figure 17:
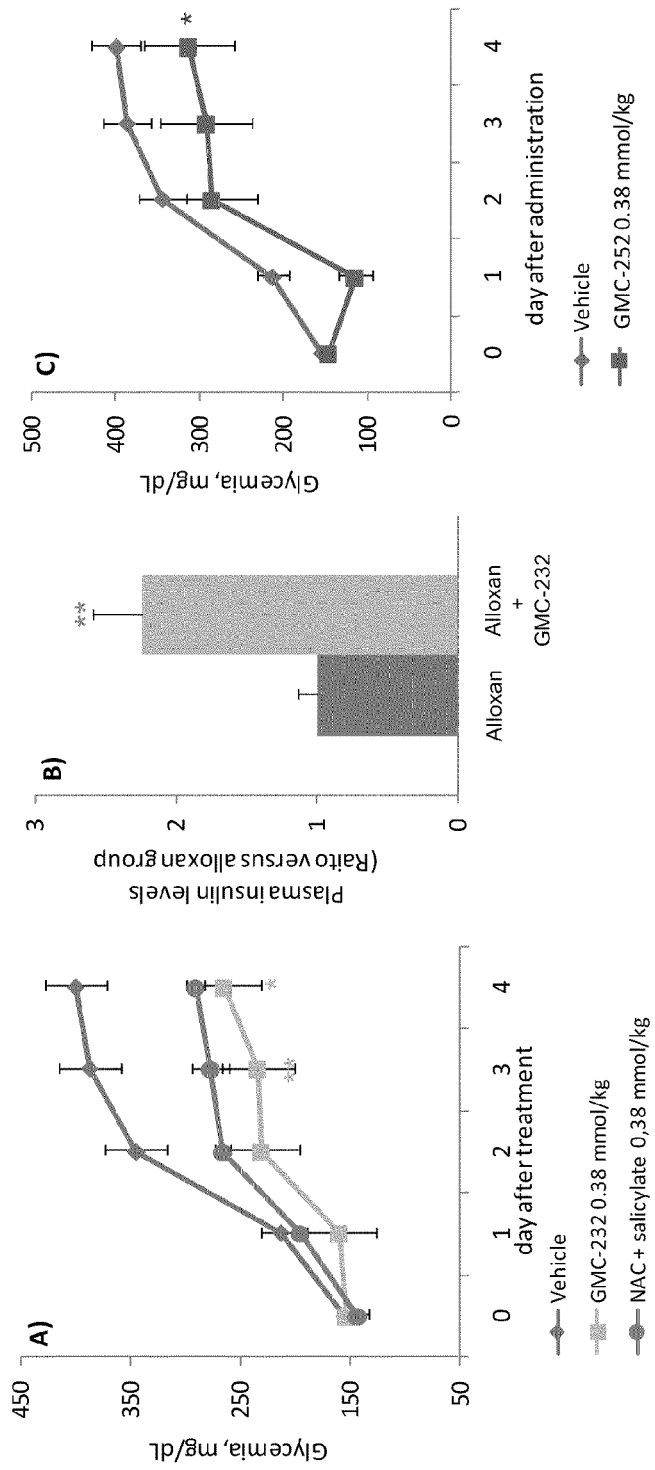
FIG. 17 is a graphical illustration comparing the beta-cell protective effects of the conjugate salicylate-NAC to the combination of salicylate+NAC in cd-1 male mice.
Figure 18:
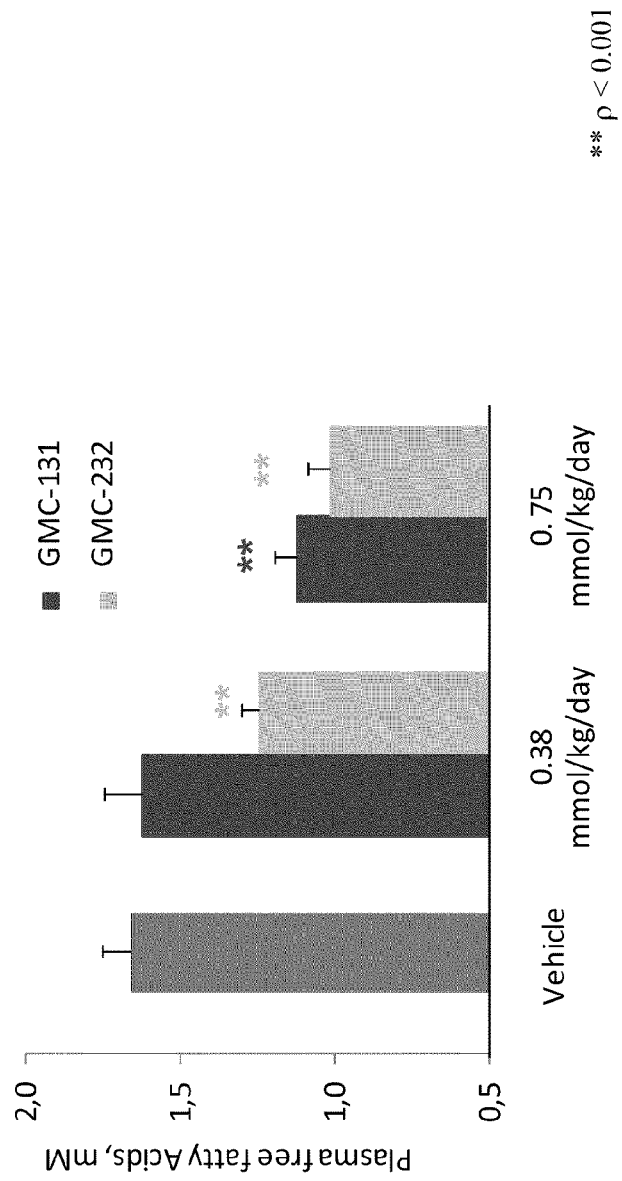
FIG. 18 is a graphical illustration comparing the effects of the conjugate salicylate-NAC to the combination of salicylate+NAC at reducing Free Fatty Acids in db/db mice.

Pancreatic beta-cell protection of conjugates of the invention was assayed using alloxan-treated cd-1 mice. In thèse experiments, salicylate-NAC (0.38 mmol/kg) or an equivalent amount of the combination of salicylate+NAC was administered to male cd-1 mice and glycemia assayed over a 4-day timecourse. As shown in FIG. 17, both the conjugate and the combination reduced glycemia, although only the conjugate showed a statistically-significant reduction. Similar results are shown for diflunisal-NAC conjugate administration (0.38 mmol/kg). In addition, the conjugate showed statistically-significant potection of pancreatic beta-cell function (as assessed by plasma insulin levels) in mice treated with alloxan. Similar experiments were performed comparing the effects of salicylate-NAC (0.38 mmol/kg/day or 0.75 mmol/kg/day) or an equivalent amount of the combination of salicylate+NAC on free fatty acid levels in db/db mice, wherein statistically-significant reductions were found at 0.75 mmol/kg/day for both the conjugate and the combination, but free fatty acid levels were lowered significantly only by the conjugate when administered at 0.38 mmol/kg/day. These results are shown in FIG. 18.

Figure 19:
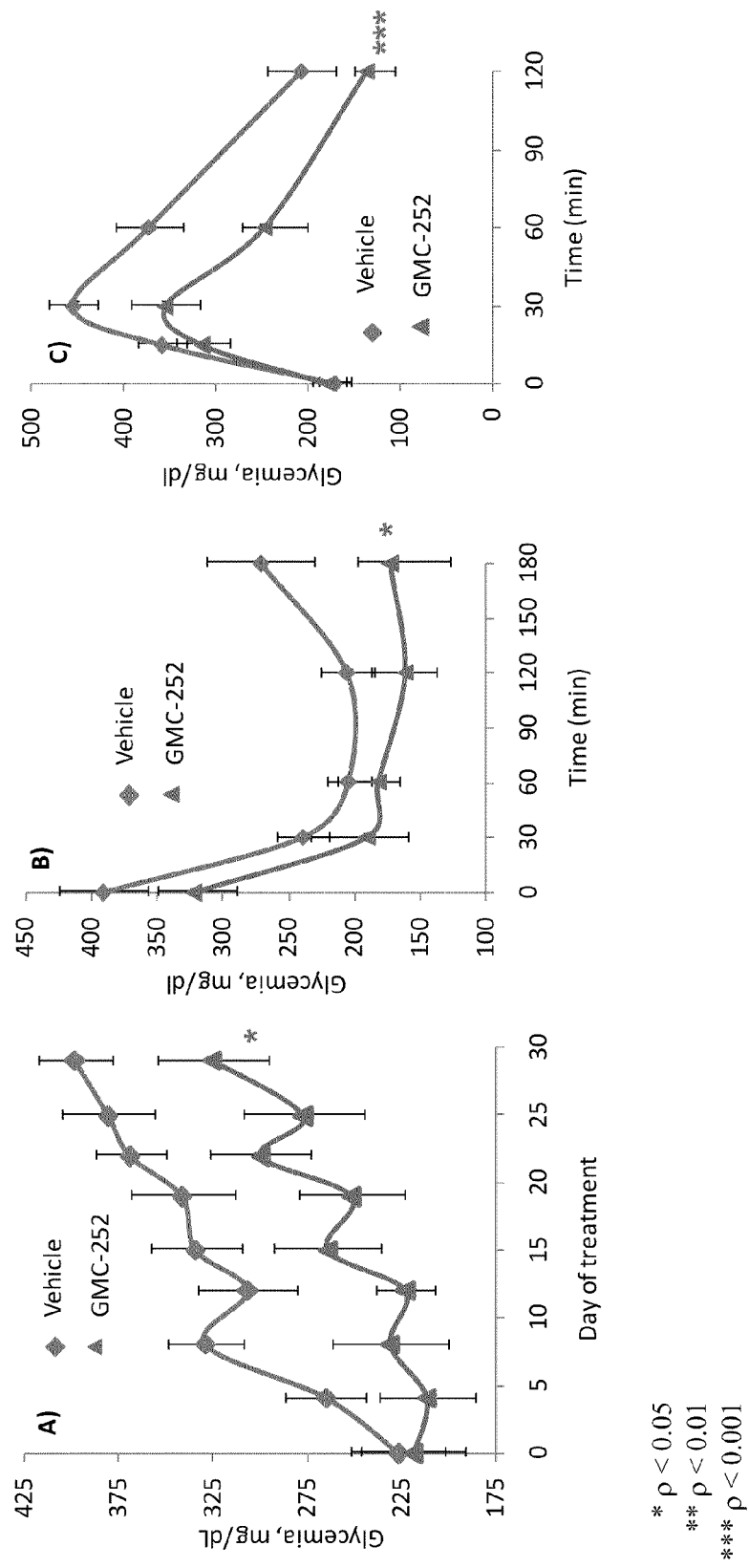
FIG. 19 is a graphical illustration of the effects of the conjugate diflunisal-NAC at reducing glycemia in db/db mice (oral administration).
Figure 20:
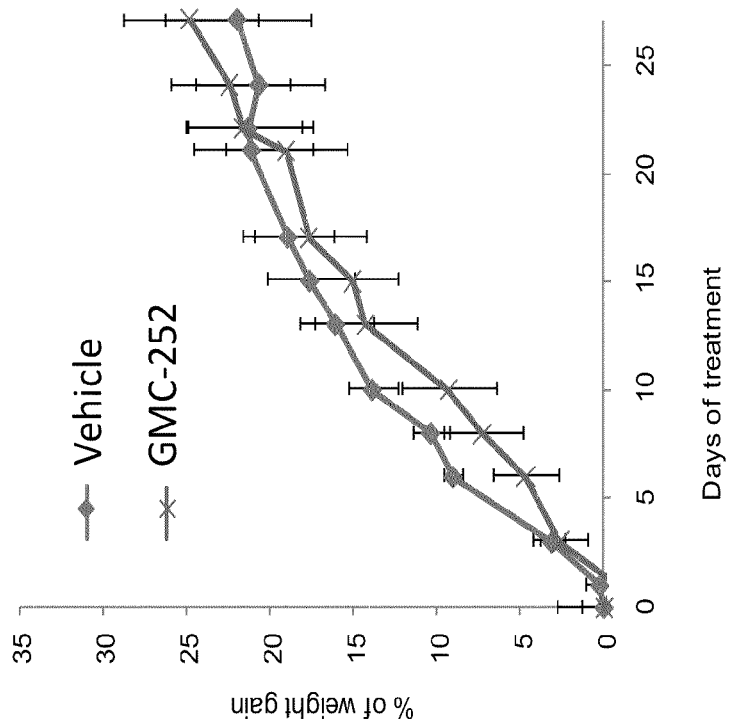
FIG. 20 is a graphical illustration of the effects of the conjugate diflunisal-NAC on weight gain in mice following chronic oral administration.
Figure 22:
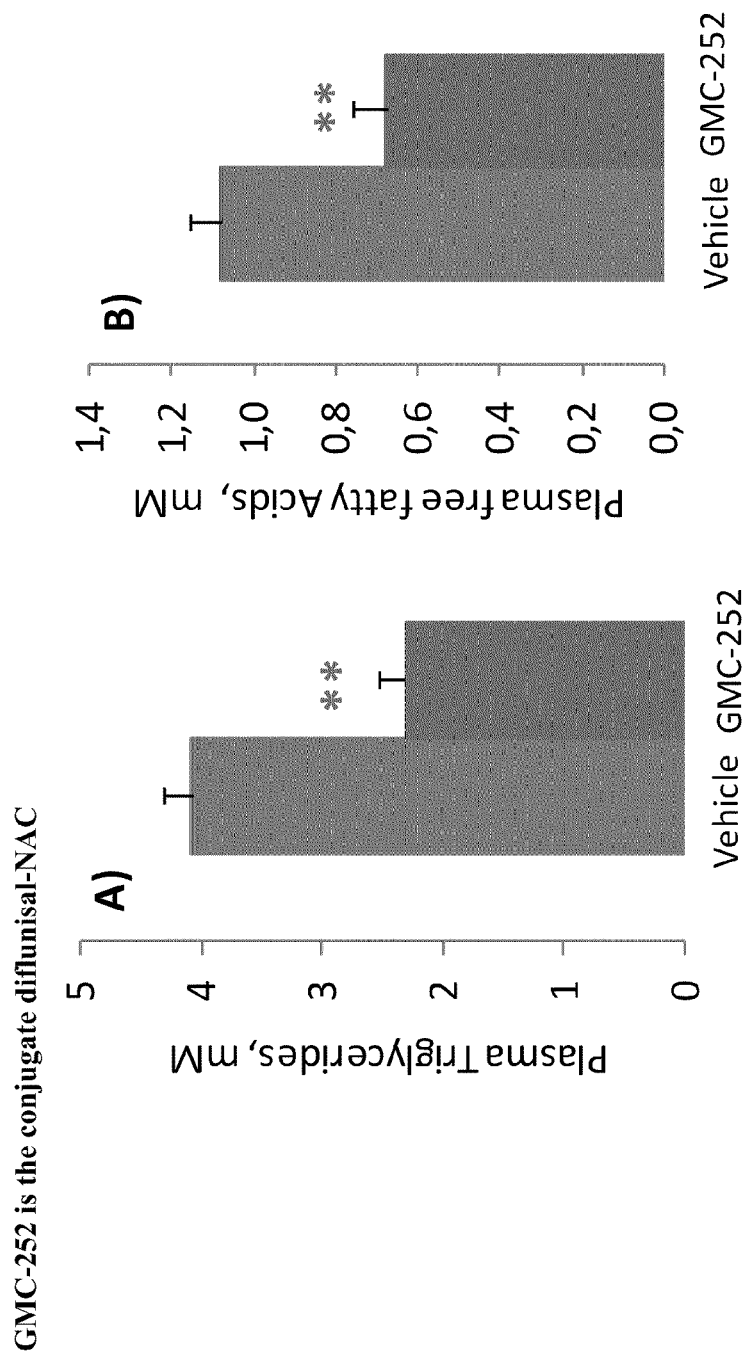
FIG. 22 is a graphical illustration of the effects of the conjugate diflunisal-NAC at reducing Free Fatty Acids and Triglycerides in db/db mice after four weeks of oral administration (0.5 mmol/kg/day).
Figure 23:
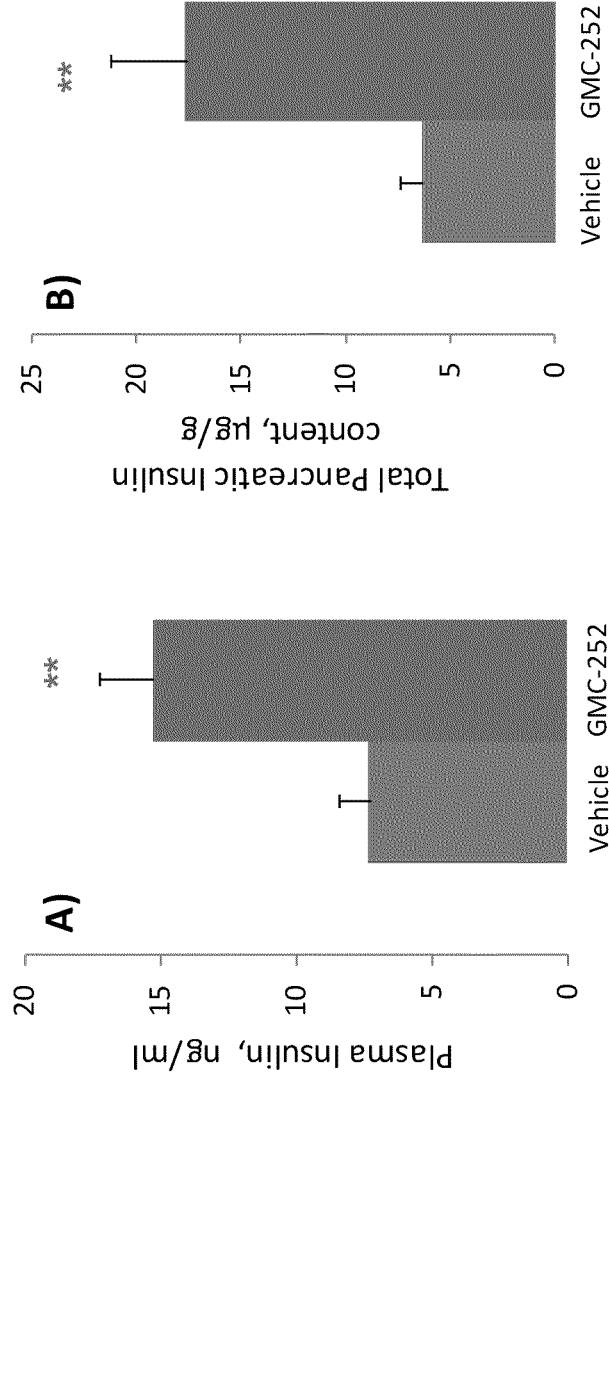
FIG. 23 is a graphical illustration of the effects of the conjugate diflunisal-NAC at increasing both plasma insulin and total pancreatic insulin in db/db mice after four weeks of oral administration (0.5 mmol/kg/day).
Figure 24:
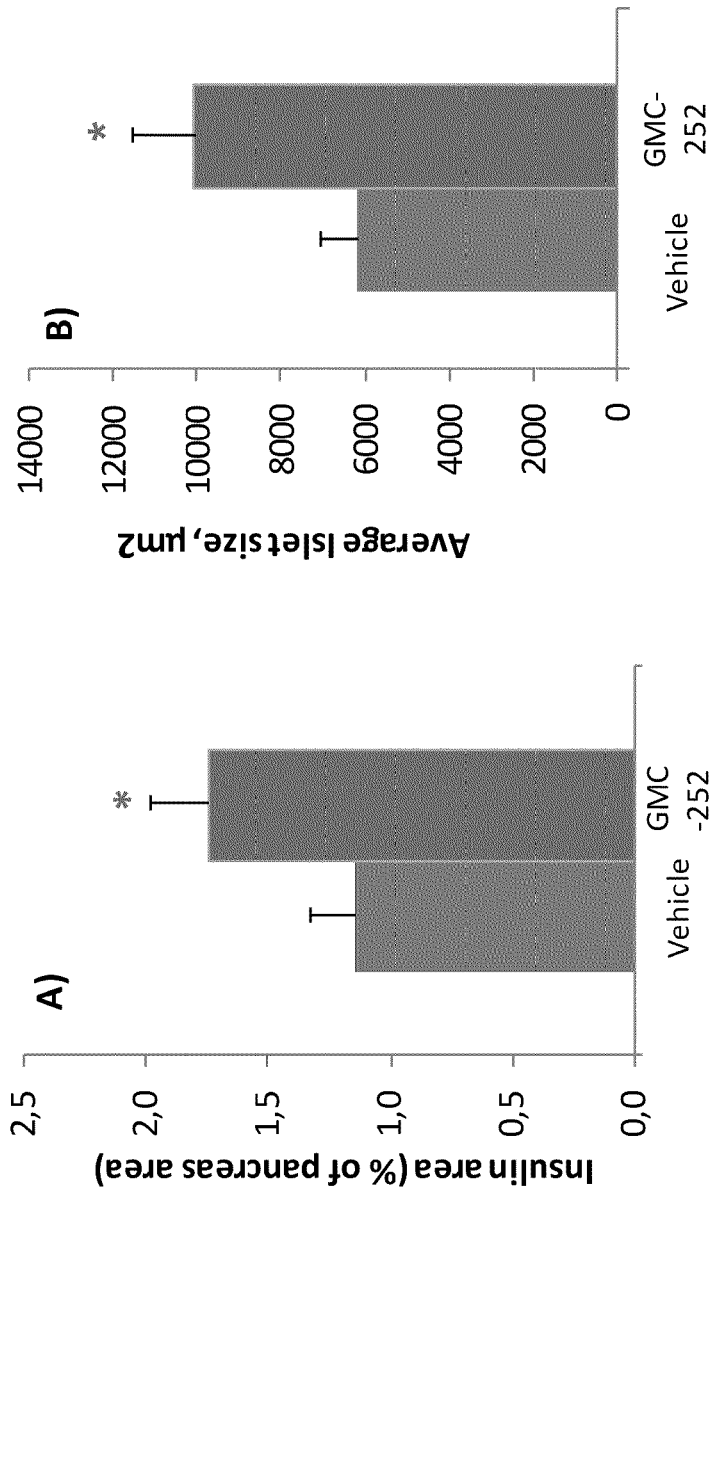
FIG. 24 is a graphical administration of the effects of the conjugate diflunisal-NAC at increasing both insulin expression and islet size without affecting pancreatic weight in db/db mice after four weeks of oral administration (0.5 mmol/kg/day).

Chronic oral administration of the diflunisal-NAC conjugate (GMC-252, 200 mg/kg/day) was shown to significantly reduce glycemia in db/db mice over 30 days of treatment, shown in FIG. 19. In addition, this conjugate showed reduced glycemia during an insulin tolerance (ITT) test and during s glucose tolerance test. Similarly, weight gain improvements were detected in these mice over 25 days of chronic adminisrtation (shown in FIG. 20). This treatment was also found to reduce plasma triglcerides and free fatty acids, as shown in FIG. 22, and was found to increase plasma insulin levels in these mice as well (FIGS. 23 and 24). These results were achieved wherein both insulin expression and islet size were increased without affecting pancreatic weight.

Figure 21:
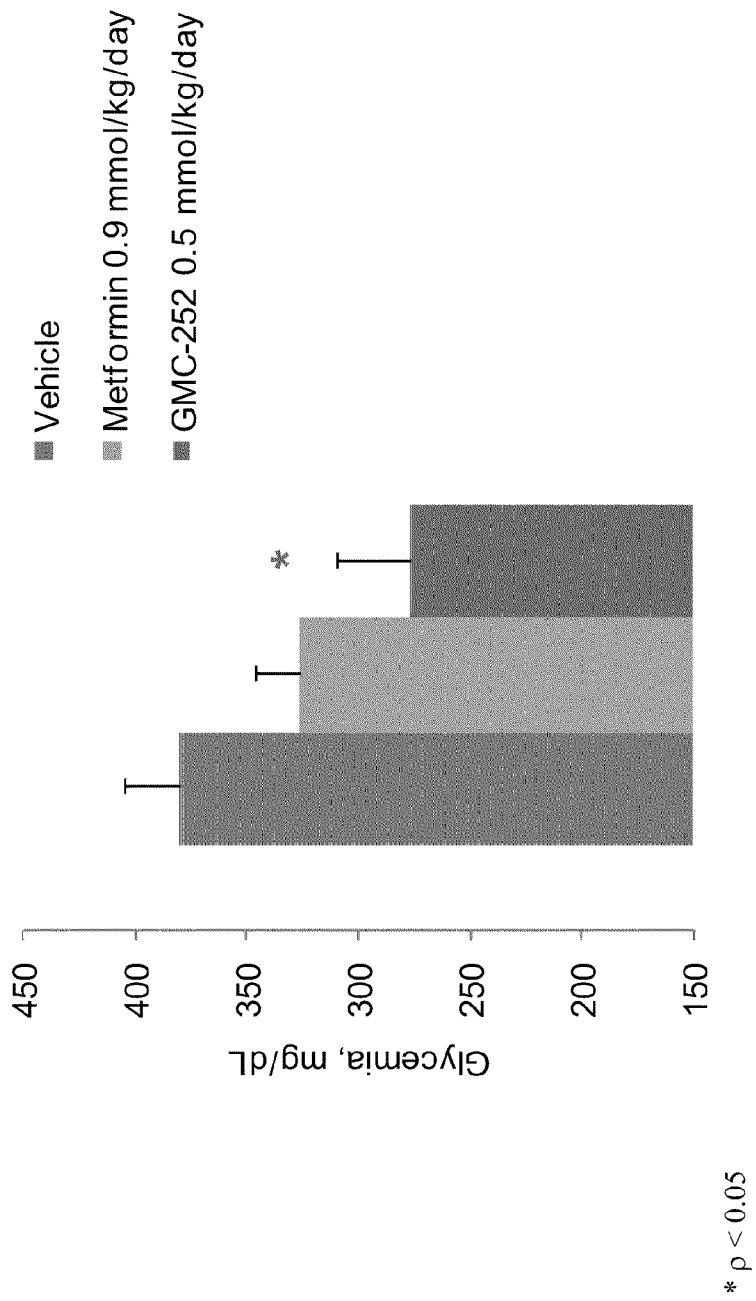
FIG. 21 is a graphical illustration comparing the glycemic effects of the conjugate diflunisal-NAC to metformin in db/db mice (oral administration).

The effects of diflunisal-NAC (GMC-252) oral administration on glycemia were compared with the effects on metformin, a conventional Type II Diabetes drug. As shown in FIG. 21, the diflunisal-NAC conjugate (GMC-252) showed a statistically-significant lowering of plasma glycemia compared with this conventional Type II Diabetes drug.

Figure 25:
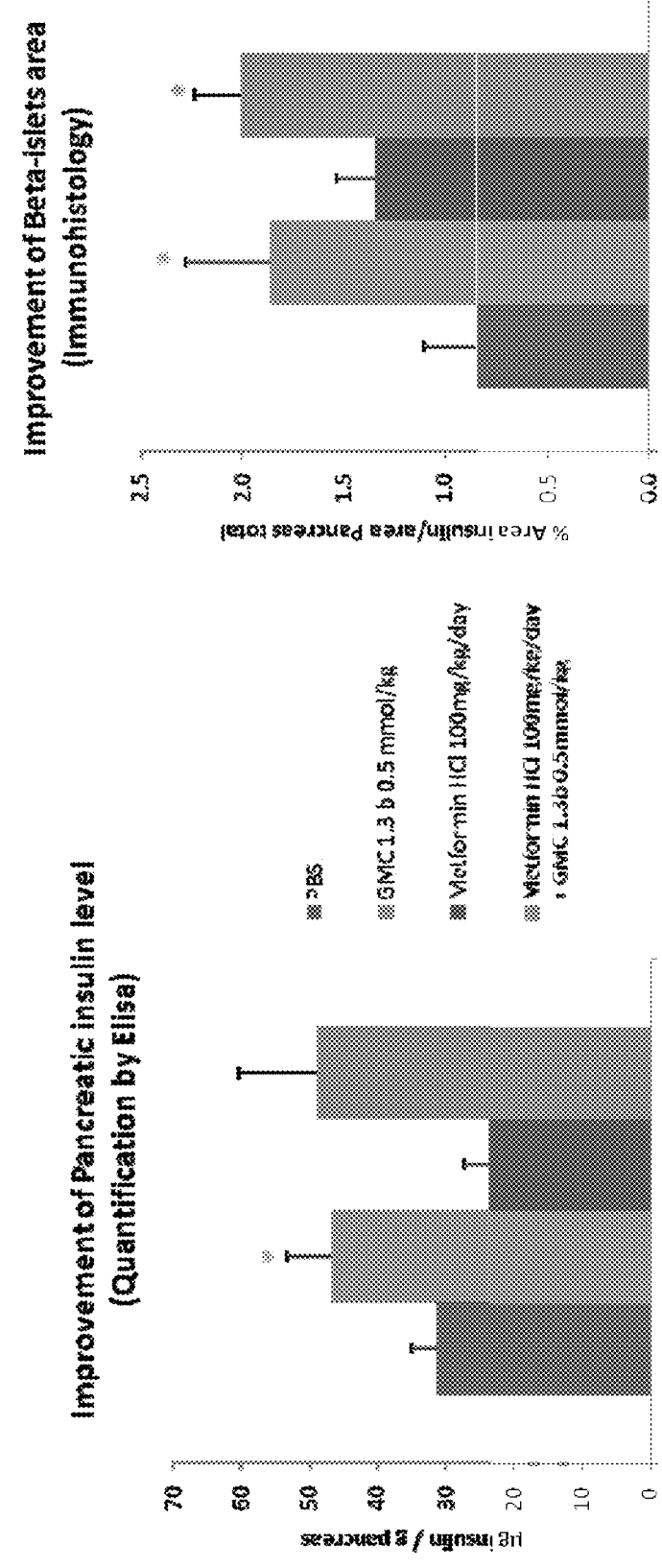
FIG. 25 is a graphical illustration comparing the effects of the conjugate diflunisal-NAC (0.5 mmol/kg/day) to metformin HCl (100 mg/kg/day) at increasing both pancreatic insulin levels and islet size in db/db mice after four weeks of oral administration (0.5 mmol/kg/day).
Figure 26:
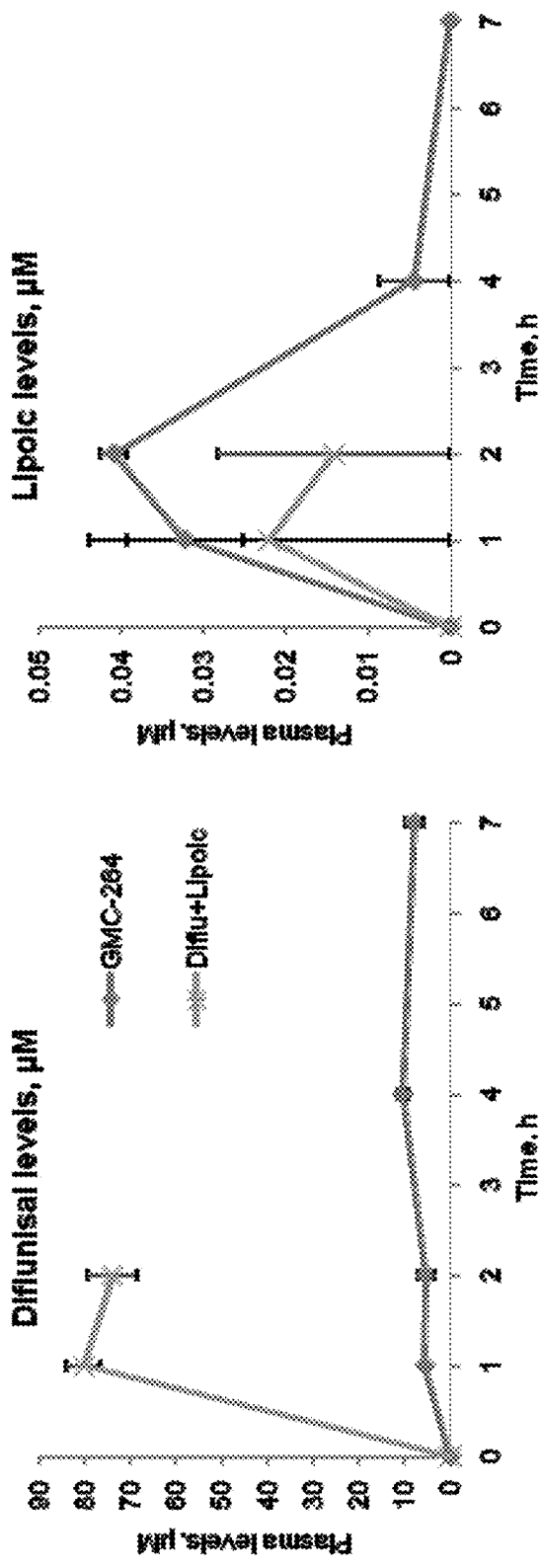
FIG. 26 is a graphical illustration of the cleavage efficiency for the conjugate diflunisal-lipoic acid in vivo in rats.
Figure 27:
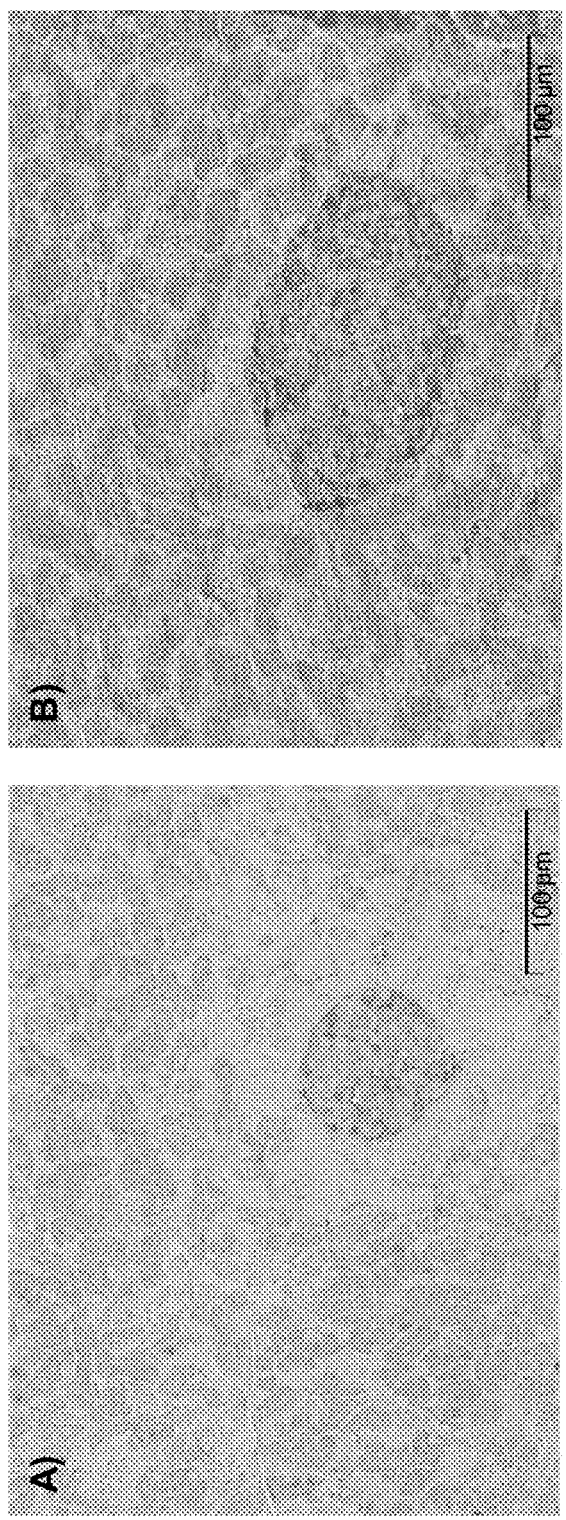
FIG. 27 is a graphical illustration of insulin islet sizes following oral administration of diflunsal-NAC conjugate in db/db mice. A and B are representative islets from the vehicle group (A) and the treated group (B). Also, diflunsal-NAC conjugate did not affect the weight of the treated db/db, a good index of health state (FIG. 20 in) nor the epididimal adipose tissue weight (respectively 1.7±0.09 and 1.8±0.07 g. In a preliminary experiment with control animals, the same oral dose of diflunsal-NAC conjugate (0.5 mmol/kg) did not affect these two parameters. Finally, it is important to note that diflunsal-NAC conjugate treatment did not induce any macroscopic lesions of the gastro intestinal system.

The effects of the combination of metformin HCl (100 mg/kg/day) administration and administration of a diflunical-NAC conjugate (0.5 mmol/kg/day) are shown in FIG. 25, wherein beta-cell areas in the pancreas increased as assayed by immunohistochemistry and islet cell function improved as assayed by ELISA for pancreatic insulin.

Several parameters of certain conjugates of the invention were assayed and the results of these assays shown in FIG. 15.

The data above shows the beneficial effects of compounds of the present invention, including salnacedin, in Type 2 diabetic animal models as compared to control or to animals treated with salicylate or an antioxidant alone (e.g. salicylic acid alone or N-acetylcysteine alone). The data described herein further provides that conjugates of Formula (I), such as salicylate-NAC and diflusinal-NAC, possess strong hypolipidemic and anti-diabetic effects as well as antioxidant properties in different animal models of diabetes useful in preventing the development of β-cell failure and aggravation of the diabetic status leading to cardiovascular complications. This data supports the therapeutic utility of conjugates comprising an antioxidant agent and an anti-inflammatory agent, such as salicylate-NAC and diflusinal-NAC.

Moreover the additive and/or synergism effects of these conjugates allow for the decrease dosing of each independent active ingredient. These additive and/or synergistic effects reduce the liability of side effects associated with a salicylate agent, gastric bleeding, or an antioxidant, tinnitus, given to a patient alone.

We claim:

1. A method for treating a metabolic disorder selected from type I diabetes, type II diabetes, Latent Autoimmune Diabetes of Adulthood (LADA), hyperglycemia, elevated free fatty acids, elevated triglycerides and insulin resistance in a mammal or patient comprising administering to the mammal or patient in need of such treatment a therapeutically effective amount of (R)-2-acetamido-3-(2',4'-difluoro-4-hydroxybiphenylcarbonylthio)propanoic acid or a pharmaceutically acceptable salt thereof.

2. A method of treating Latent Autoimmune Diabetes of Adulthood (LADA), in a mammal or patient comprising administering to the mammal or patient in need of such treatment a therapeutically effective amount of a pharmaceutical composition comprising (R)-2-acetamido-3-(2',4'-difluoro-4-hydroxybiphenylcarbonylthio)propanoic acid or a pharmaceutically acceptable salt thereof and at least one pharmaceutically acceptable carrier.

3. The method according to claim 1, wherein the metabolic disorder is Latent Autoimmune Diabetes of Adulthood (LADA).

4. The method according to claim 1, wherein the method provides beta cell protection.

5. The method according to claim 1, wherein the metabolic disorder is type II diabetes.

6. The method according to claim 1 wherein the metabolic disorder is hyperglycemia.

7. The method according to claim 1, wherein the metabolic disorder is elevated free fatty acids.

8. The method according to claim 1, wherein the metabolic disorder is elevated triglycerides.

9. The method according to claim 1, wherein the metabolic disorder is insulin resistance.

10. The method according to claim 1, wherein the (R)-2-acetamido-3-(2',4'-difluoro-4-hydroxybiphenylcarbonylthio)propanoic acid is administered as a pharmaceutically acceptable salt.

11. The method according to claim 1, wherein the (R)-2-acetamido-3-(2',4'-difluoro-4-hydroxybiphenylcarbonylthio)propanoic acid is administered as a L-lysine salt.

12. The method according to claim 1, wherein the (R)-2-acetamido-3-(2',4'-difluoro-4-hydroxybiphenylcarbonylthio)propanoic acid is administered as a pharmaceutical composition comprising (R)-2-acetamido-3-(2',4'-difluoro-4-hydroxybiphenylcarbonylthio)propanoic acid or a pharmaceutically acceptable salt thereof and at least one pharmaceutically acceptable carrier.

* * * * *